United States Patent
Grammenos et al.

(10) Patent No.: US 10,053,432 B2
(45) Date of Patent: Aug. 21, 2018

(54) SUBSTITUTED [1,2,4]TRIAZOLE AND IMIDAZOLE COMPOUNDS

(71) Applicant: BASF SE, Ludwigshafen (DE)

(72) Inventors: Wassilios Grammenos, Ludwigshafen (DE); Nadege Boudet, Hirschberg (DE); Bernd Müller, Frankenthal (DE); Maria Angelica Quintero Palomar, Mannheim (DE); Ana Escribano Cuesta, Mannheim (DE); Erica May Cambeis, Wachenheim (DE); Jan Klaas Lohmann, Lambsheim (DE); Thomas Grote, Wachenheim (DE); Manuel Kretschmer, Mannheim (DE); Ian Robert Craig, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/103,529

(22) PCT Filed: Dec. 5, 2014

(86) PCT No.: PCT/EP2014/076749
§ 371 (c)(1),
(2) Date: Jun. 10, 2016

(87) PCT Pub. No.: WO2015/086462
PCT Pub. Date: Jun. 18, 2015

(65) Prior Publication Data
US 2016/0318880 A1  Nov. 3, 2016

(30) Foreign Application Priority Data

Dec. 12, 2013 (WO) ............... PCT/EP2013/076315
Feb. 20, 2014 (EP) ..................... 14155978
Jun. 10, 2014 (EP) ..................... 14171814

(51) Int. Cl.
A01N 43/653 (2006.01)
A01N 43/50 (2006.01)
A01N 47/02 (2006.01)
C07D 249/08 (2006.01)

(52) U.S. Cl.
CPC ........... *C07D 249/08* (2013.01); *A01N 43/50* (2013.01); *A01N 43/653* (2013.01); *A01N 47/02* (2013.01)

(58) Field of Classification Search
None
See application file for complete search history.

(56) References Cited

U.S. PATENT DOCUMENTS 4,609,668 A * 9/1986 Schaub ................. A01N 43/50
514/184
5,143,932 A 9/1992 Jautelat et al.

FOREIGN PATENT DOCUMENTS

| DE | 3430833 A1 | 3/1985 |
|---|---|---|
| EP | 0 123 160 | 10/1984 |
| EP | 0 440 950 | 8/1991 |
| EP | 0 470 466 | 2/1992 |
| FR | 2 535 321 | 5/1984 |
| GB | 2 145 717 | 4/1985 |
| JP | 06329636 | 11/1994 |
| WO | WO-2013/007767 | 1/2013 |
| WO | WO-2013/024076 | 2/2013 |
| WO | WO-2013/024082 | 2/2013 |
| WO | WO-2013/092224 | 6/2013 |
| WO | WO-2013/113715 | 8/2013 |
| WO | WO-2013/124250 | 8/2013 |
| WO | WO-2013/135671 | 9/2013 |
| WO | WO-2013/135672 | 9/2013 |
| WO | WO-2014/003908 | 1/2014 |
| WO | WO-2014/009137 | 1/2014 |
| WO | WO-2014/009293 | 1/2014 |
| WO | WO-2014/056780 | 4/2014 |
| WO | WO-2014/061197 | 4/2014 |
| WO | WO-2014/082871 | 6/2014 |
| WO | WO-2014/082872 | 6/2014 |
| WO | WO-2014/082879 | 6/2014 |
| WO | WO-2014/082880 | 6/2014 |

(Continued)

OTHER PUBLICATIONS

Hiraoka et al., "A Molecular Ball Bearing Mediated by Multiligand Exchange in Concert," *Angewandte Chemie, International Edition*, 2004, vol. 43, pp. 3814-3818.

(Continued)

*Primary Examiner* — Alton N Pryor
(74) *Attorney, Agent, or Firm* — Brinks Gilson & Lione

(57) ABSTRACT

The present invention relates to compounds of the formula I

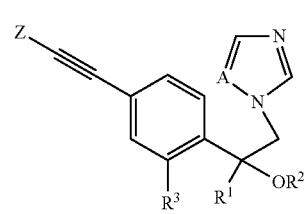

and the N-oxides and the salts thereof for combating phytopathogenic fungi, and to the use and methods for combating phytopathogenic fungi and to seeds coated with at least one such compound. The invention also relates to processes for preparing these compounds, intermediates, processes for preparing such intermediates, and to compositions comprising at least one compound I.

23 Claims, No Drawings

(56) References Cited

FOREIGN PATENT DOCUMENTS

| | | |
|---|---|---|
| WO | WO-2014/082881 | 6/2014 |
| WO | WO-2014/086601 | 6/2014 |
| WO | WO-2014/095249 | 6/2014 |
| WO | WO-2014/095381 | 6/2014 |
| WO | WO-2014/095534 | 6/2014 |
| WO | WO-2014/095547 | 6/2014 |
| WO | WO-2014/095548 | 6/2014 |
| WO | WO-2014/095555 | 6/2014 |
| WO | WO-2014/095637 | 6/2014 |
| WO | WO-2014/095655 | 6/2014 |
| WO | WO-2014/095672 | 6/2014 |
| WO | WO-2014/095932 | 6/2014 |
| WO | WO-2014/095994 | 6/2014 |
| WO | WO-2014/108286 | 6/2014 |
| WO | WO-2014/108288 | 7/2014 |
| WO | WO-2014/108299 | 7/2014 |
| WO | WO-2014/124850 | 8/2014 |
| WO | WO-2014/184236 | 11/2014 |
| WO | WO-2014/184309 | 11/2014 |
| WO | WO-2014/198553 | 12/2014 |
| WO | WO-2014/198557 | 12/2014 |
| WO | WO-2014/202421 | 12/2014 |
| WO | WO-2014/202703 | 12/2014 |
| WO | WO-2014/207052 | 12/2014 |
| WO | WO-2014/207071 | 12/2014 |
| WO | WO-2015/014733 | 2/2015 |
| WO | WO-2015/036058 | 3/2015 |
| WO | WO-2015/036059 | 3/2015 |
| WO | WO-2015/086462 | 6/2015 |
| WO | WO-2015/144480 | 10/2015 |
| WO | WO-2015/150135 | 10/2015 |
| WO | WO-2015/150138 | 10/2015 |
| WO | WO-2015/150139 | 10/2015 |
| WO | WO-2015/150170 | 10/2015 |
| WO | WO-2015/150343 | 10/2015 |
| WO | WO-2015/173050 | 11/2015 |
| WO | WO-2015/181035 | 12/2015 |
| WO | WO-2015/185485 | 12/2015 |
| WO | WO-2015/185708 | 12/2015 |
| WO | WO-2015/189035 | 12/2015 |

OTHER PUBLICATIONS

Ruiz et al., "A Copper- and Amine-Free Sonogashira Reaction of Aryl Halides Catalyzed by 1,3,5-Triaza-7-Phosphaadamantane Palladium Systems," *Organometallics*, 2006, vol. 25, pp. 5768-5773.

Stehmann et al., "Relationship between Chemical Structure and Biological Activity of Triazole Fungicides against Botrytis cinerea," *Pesticidal Science*, 1995, vol. 44, No. 2, pp. 183-195.

Wu et al., Ionic-Liquid-Supported Organocatalyst for the Enantioselective Michael Addition of Ketones to Nitroolefins, *Tetrahedron: Assymetry*, 2007, vol. 18, pp. 2086-2090.

Zou et al., Benzo[e]isoindole-1,3-diones as Potential Inhibitors of Glycogen Synthase Kinase-3 (GSK-3). Synthesis, Kinase Inhibitory Activity, Zebrafish Phenotype, and Modeling of Binding Mode, *Journal of Medicinal Chemistry*, 2010, vol. 53, pp. 994-1003.

International Search Report for PCT/EP2014/076749 dated Feb. 4, 2015.

International Preliminary Report on Patentability for PCT/EP2014/076749 dated Jun. 14, 2016.

\* cited by examiner

SUBSTITUTED [1,2,4]TRIAZOLE AND IMIDAZOLE COMPOUNDS

This application is a National Stage application of International Application No. PCT/EP2014/076749, filed Dec. 5, 2014. This application also claims priority under 35 U.S.C. § 119 to European Patent Application No. 14171814.8, filed Jun. 10, 2014; European Patent Application No. 14155978.1, filed Feb. 20, 2014; and to International Application No. PCT/EP2013/076315, filed Dec. 12, 2013.

The present invention relates to substituted [1,2,4]triazole and imidazole compounds and the N-oxides and the salts thereof for combating phytopathogenic fungi, and to the use and methods for combating phytopathogenic fungi and to seeds coated with at least one such compound. The invention also relates to processes for preparing these compounds, intermediates, processes for preparing such intermediates, and to compositions comprising at least one compound I.

DE 3430833 relates to alpha-(ethynylphenyl)-alpha-hydrocarbyl-1H-azol-1-ethanoles and their use as fungicides. WO 2013/007767 relates to fungicidal substituted 1-[4-phenoxy-2-(halogenalkyl)phenyl]-2-(1,2,4-triazol-1-yl) ethanol compounds. In Pestic. Sci. 1995, 44, 183 to 195, the relationship between chemical structure and biological activity of certain commercial triazole fungicides such as cyproconazole and tebuconazole against *Botrytis cinerea* is discussed.

In many cases, in particular at low application rates, the fungicidal activity of the known fungicidal compounds is unsatisfactory. Based on this, it was an object of the present invention to provide compounds having improved activity and/or a broader activity spectrum against phytopathogenic harmful fungi.

Surprisingly, this object is achieved by the use of the inventive substituted [1,2,4]triazol and imidazole compounds of formula I having favorable fungicidal activity against phytopathogenic fungi.

Accordingly, the present invention relates, to the compounds of the formula I

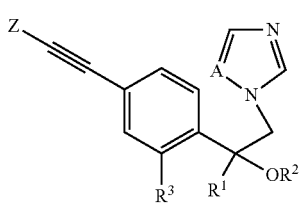

wherein
A is CH or N;
$R^1$ is $C_1$-$C_6$-alkyl, $C_2$-$C_6$-alkenyl, $C_2$-$C_6$-alkynyl, $C_3$-$C_6$-cycloalkyl;
wherein the aliphatic moieties of $R^1$ are not further substituted or carry one, two, three or up to the maximum possible number of identical or different groups $R^{1a}$ which independently of one another are selected from:
$R^{1a}$ halogen, OH, CN, $C_1$-$C_4$-alkoxy, $C_3$-$C_6$-cycloalkyl, $C_3$-$C_6$-halogencycloalkyl and $C_1$-$C_4$-halogenalkoxy;
wherein the cycloalkyl moieties of $R^1$ are not further substituted or carry one, two, three, four, five or up to the maximum number of identical or different groups $R^{1b}$ which independently of one another are selected from:

$R^{1b}$ halogen, OH, CN, $C_1$-$C_4$-alkyl, $C_1$-$C_4$-alkoxy, $C_1$-$C_4$-halogenalkyl, $C_3$-$C_6$-cycloalkyl, $C_3$-$C_6$-halogencycloalkyl and $C_1$-$C_4$-halogenalkoxy;

$R^2$ is hydrogen, $C_1$-$C_4$-alkyl, $C_2$-$C_4$-alkenyl, $C_2$-$C_4$-alkynyl;
wherein the aliphatic moieties of $R^2$ are not further substituted or carry one, two, three or up to the maximum possible number of identical or different groups $R^{2a}$ which independently of one another are selected from:

$R^{2a}$ halogen, OH, CN, $C_1$-$C_4$-alkoxy, $C_3$-$C_6$-cycloalkyl, $C_3$-$C_6$-halogencycloalkyl and $C_1$-$C_4$-halogenalkoxy;

$R^3$ is selected from hydrogen, halogen, CN, $C_1$-$C_4$-alkyl, $C_1$-$C_4$-alkoxy, $C_2$-$C_4$-alkenyl, $C_2$-$C_4$-alkynyl, $C_3$-$C_6$-cycloalkyl, $S(O)_p(C_1$-$C_4$-alkyl), wherein each of $R^3$ is unsubstituted or further substituted by one, two, three or four $R^{3a}$; wherein $R^{3a}$ is independently selected from halogen, CN, OH, $C_1$-$C_4$-alkyl, $C_1$-$C_4$-halogenalkyl, $C_3$-$C_6$-cycloalkyl, $C_3$-$C_6$-halogencycloalkyl, $C_1$-$C_4$-alkoxy and $C_1$-$C_4$-halogenalkoxy;

Z is $C_3$-$C_8$-cycloalkyl or $C_3$-$C_8$-cycloalkenyl, wherein the cycloalkyl or cycloalkenyl is unsubstituted (m=0) or substituted by $(R^4)_m$; wherein
m is 0, 1, 2, 3 or 4; and $R^4$ is in each case independently selected from halogen, CN, $NO_2$, OH, SH, $C_1$-$C_6$-alkyl, $C_1$-$C_6$-alkoxy, $C_2$-$C_6$-alkenyl, $C_2$-$C_6$-alkynyl, $C_3$-$C_6$-cycloalkyl, $C_3$-$C_6$-cycloalkyloxy, $S(O)_p(C_1$-$C_4$-alkyl), $C(=O)(C_1$-$C_4$-alkyl), $C(=O)(OH)$, $C(=O)(O$—$C_1$-$C_4$-alkyl), $C(=O)(NH(C_1$-$C_4$-alkyl))$, $C(=O)(N(C_1$-$C_4$-alkyl)_2)$; wherein each of $R^4$ is unsubstituted or further substituted by one, two, three or four $R^{4a}$ wherein $R^{4a}$ is independently selected from halogen, CN, $NO_2$, OH, $C_1$-$C_4$-alkyl, $C_1$-$C_4$-halogenalkyl, $C_3$-$C_6$-cycloalkyl, $C_3$-$C_6$-halogencycloalkyl, $C_1$-$C_4$-alkoxy and $C_1$-$C_4$-halogenalkoxy;

p is 0, 1 or 2;

and the N-oxides and the agriculturally acceptable salts thereof.

Compounds I can be prepared from halo compounds II using transition metal catalysis in a solvent (such as, e.g. THF, DMF, MeCN, $NEt_3$, $Et(iPr_2)N$, pyrrolidine, piperidine, pyridine, diethylamine) using a base (such as $NEt_3$, $Et(iPr_2)N$, pyrrolidine, piperidine, pyridine, diethylamine and a suitable catalyst like Pd, Cu, Pt, Rh, Ir, Al, Li, $Pd(PPh_3)_4$, $PdCl_2(PPh_3)_2$, $PdCl_2(dppf)$, CuI, CuBr, CuCl, LiCl, $AlCl_3$ or mixtures thereof (see e.g. Tetrahedron: Asymmetry, 18(17), 2086-2090; 2007; Angewandte Chemie, International Edition, 43(29), 3814-3818; 2004; Medicinal Chemistry, 53(3), 994-1003; 2010; Organometallics, 25(24), 5768-5773; 2006)

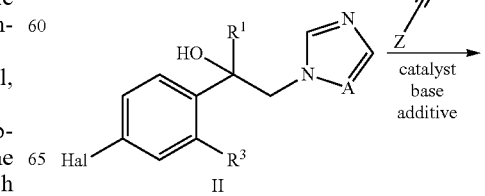

-continued

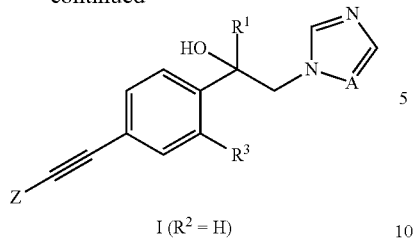

I ($R^2$ = H)

Compounds I, wherein $R^2$ is different from hydrogen can be obtained from alcohol compounds I ($R^2$=H) by reacting the alcohol compound with $R^2$-LG, wherein LG represents a nucleophilically replaceable leaving group, such as halogen, alkylsulfonyl, alkylsulfonyloxy and arylsulfonyloxy, preferably chloro, bromo or iodo, particularly preferably bromo, preferably in the presence of a base. X, Y, $R^2$, $R^3$, $R^4$, n and m are as defined herein.

Halo compounds II can be prepared starting from known molecules. For example a substituted phenyl Grignard is generated and transformed to a ketone IV (in analogy to the compounds in for example WO 2013/07767). Epoxidation followed by reaction with triazole leads to halogen compound II.

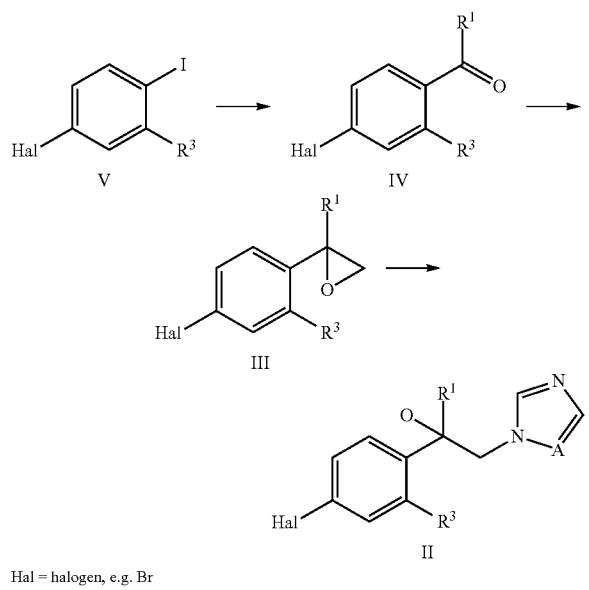

Hal = halogen, e.g. Br

Alternatively, compounds II can be prepared according to the following scheme:

A Grignard is generated and the so obtained acyl compound IVa is chlorinated using a chlorination agent (e.g. $SO_2Cl_2$, NCS, $Cl_2$). Addition of a metal organic species (e.g. a Grignard compound) leads to a chloro alcohol IIIa that can be subsequently transformed into halo compound II.

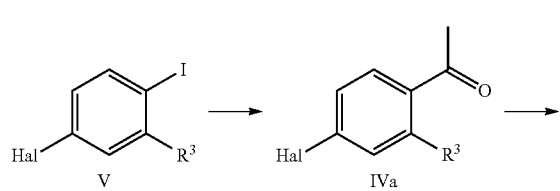

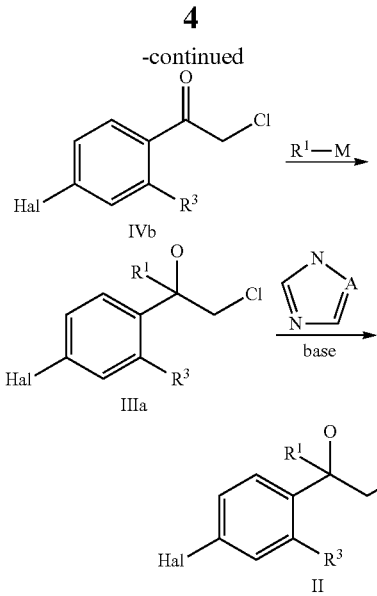

Hal = halogen e.g. Br

The N-oxides may be prepared from the inventive compounds according to conventional oxidation methods, e. g. by treating compounds I with an organic peracid such as metachloroperbenzoic acid (cf. WO 03/64572 or J. Med. Chem. 38(11), 1892-903, 1995); or with inorganic oxidizing agents such as hydrogen peroxide (cf. J. Heterocyc. Chem. 18(7), 1305-8, 1981) or oxone (cf. J. Am. Chem. Soc. 123(25), 5962-5973, 2001). The oxidation may lead to pure mono-N-oxides or to a mixture of different N-oxides, which can be separated by conventional methods such as chromatography.

If the synthesis yields mixtures of isomers, a separation is generally not necessarily required since in some cases the individual isomers can be interconverted during work-up for use or during application (e. g. under the action of light, acids or bases). Such conversions may also take place after use, e. g. in the treatment of plants in the treated plant, or in the harmful fungus to be controlled.

In the following, the intermediate compounds are further described. A skilled person will readily understand that the preferences for the substituents, also in particular the ones given in the tables below for the respective substituents, given herein in connection with compounds I apply for the intermediates accordingly. Thereby, the substituents in each case have independently of each other or more preferably in combination the meanings as defined herein.

The N-oxides may be prepared from the inventive compounds according to conventional oxidation methods, e. g. by treating compounds I with an organic peracid such as metachloroperbenzoic acid (cf. WO 03/64572 or J. Med. Chem. 38(11), 1892-903, 1995); or with inorganic oxidizing agents such as hydrogen peroxide (cf. J. Heterocyc. Chem. 18(7), 1305-8, 1981) or oxone (cf. J. Am. Chem. Soc. 123(25), 5962-5973, 2001). The oxidation may lead to pure mono-N-oxides or to a mixture of different N-oxides, which can be separated by conventional methods such as chromatography.

If the synthesis yields mixtures of isomers, a separation is generally not necessarily required since in some cases the individual isomers can be interconverted during work-up for use or during application (e. g. under the action of light, acids or bases). Such conversions may also take place after use, e. g. in the treatment of plants in the treated plant, or in the harmful fungus to be controlled.

In the following, the intermediate compounds are further described. A skilled person will readily understand that the preferences for the substituents, also in particular the ones given in the tables below for the respective substituents, given herein in connection with compounds I apply for the intermediates accordingly. Thereby, the substituents in each case have independently of each other or more preferably in combination the meanings as defined herein.

Compounds of formula V are at least partially new. Consequently, a further embodiment of the present invention are compounds of formula V (see above), wherein the variables are as defined and preferably defined for formula I herein.

Compounds of formula IV are at least partially new. Consequently, a further embodiment of the present invention are compounds of formula IV (see above), wherein the variables are as defined and preferably defined for formula I herein.

Compounds of formula IVa are at least partially new. Consequently, a further embodiment of the present invention are compounds of formula IVa (see above), wherein the variables are as defined and preferably defined for formula I herein.

Compounds of formula III are at least partially new. Consequently, a further embodiment of the present invention are compounds of formula III (see above), wherein the variables are as defined and preferably defined for formula I herein.

Compounds of formula IIIa are at least partially new. Consequently, a further embodiment of the present invention are compounds of formula IIIa (see above), wherein the variables are as defined and preferably defined for formula I herein.

Compounds of formula II are at least partially new. Consequently, a further embodiment of the present invention are compounds of formula II (see above), wherein the variables are as defined and preferably defined for formula I herein.

Compounds of formula IIa are at least partially new. Consequently, a further embodiment of the present invention are compounds of formula IIa (see above), wherein the variables are as defined and preferably defined for formula I herein.

In the definitions of the variables given above, collective terms are used which are generally representative for the substituents in question. The term "$C_n$-$C_m$" indicates the number of carbon atoms possible in each case in the substituent or substituent moiety in question.

The term "halogen" refers to fluorine, chlorine, bromine and iodine.

The term "$C_1$-$C_6$-alkyl" refers to a straight-chained or branched saturated hydrocarbon group having 1 to 6 carbon atoms, e.g. methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, 1,1-dimethylpropyl, 1,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl. Likewise, the term "$C_2$-$C_4$-alkyl" refers to a straight-chained or branched alkyl group having 2 to 4 carbon atoms, such as ethyl, propyl (n-propyl), 1-methylethyl (iso-propoyl), butyl, 1-methylpropyl (sec.-butyl), 2-methylpropyl (iso-butyl), 1,1-dimethylethyl (tert.-butyl).

The term "$C_1$-$C_6$-haloalkyl" refers to an alkyl group having 1 or 6 carbon atoms as defined above, wherein some or all of the hydrogen atoms in these groups may be replaced by halogen atoms as mentioned above. Examples are "$C_1$-$C_2$-haloalkyl" groups such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl.

The term "$C_1$-$C_6$-hydroxyalkyl" refers to an alkyl group having 1 or 6 carbon atoms as defined above, wherein some or all of the hydrogen atoms in these groups may be replaced by OH groups.

The term "$C_2$-$C_6$-alkenyl" refers to a straight-chain or branched unsaturated hydrocarbon radical having 2 to 6 carbon atoms and a double bond in any position. Examples are "$C_2$-$C_4$-alkenyl" groups, such as ethenyl, 1-propenyl, 2-propenyl (allyl), 1-methylethenyl, 1-butenyl, 2-butenyl, 3-butenyl, 1-methyl-1-propenyl, 2-methyl-1-propenyl, 1-methyl-2-propenyl, 2-methyl-2-propenyl.

The term "$C_2$-$C_6$-alkynyl" refers to a straight-chain or branched unsaturated hydrocarbon radical having 2 to 6 carbon atoms and containing at least one triple bond. Examples are "$C_2$-$C_4$-alkynyl" groups, such as ethynyl, prop-1-ynyl, prop-2-ynyl (propargyl), but-1-ynyl, but-2-ynyl, but-3-ynyl, 1-methyl-prop-2-ynyl.

The term "$C_3$-$C_6$-cycloalkyl" refers to monocyclic saturated hydrocarbon radicals having 3 to 6 carbon ring members, such as cyclopropyl, cyclobutyl, cyclopentyl, cyclohexyl.

The term "$C_3$-$C_6$-cycloalkenyl" refers to a monocyclic partially unsaturated 3-, 4- 5- or 6-membered carbocycle having 3 to 6 carbon ring members and at least one double bond, such as cyclopentenyl, cyclopentadienyl, cyclohexadienyl.

The term "$C_3$-$C_8$-cycloalkyl-$C_1$-$C_4$-alkyl" refers to alkyl having 1 to 4 carbon atoms (as defined above), wherein one hydrogen atom of the alkyl radical is replaced by a cycloalkyl radical having 3 to 8 carbon atoms (as defined above).

The term "$C_1$-$C_6$-alkoxy" refers to a straight-chain or branched alkyl group having 1 to 6 carbon atoms which is bonded via an oxygen, at any position in the alkyl group. Examples are "$C_1$-$C_4$-alkoxy" groups, such as methoxy, ethoxy, n-propoxy, 1-methylethoxy, butoxy, 1-methyl¬propoxy, 2-methylpropoxy or 1,1-dimethylethoxy.

The term "$C_1$-$C_6$-haloalkoxy" refers to a $C_1$-$C_6$-alkoxy radical as defined above, wherein some or all of the hydrogen atoms in these groups may be replaced by halogen atoms as mentioned above. Examples are "$C_1$-$C_4$-haloalkoxy" groups, such as $OCH_2F$, $OCHF_2$, $OCF_3$, $OCH_2Cl$, $OCHCl_2$, $OCCl_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloro¬ethoxy, $OC_2F_5$, 2-fluoropropoxy, 3-fluoropropoxy, 2,2-difluoropropoxy, 2,3-difluoropropoxy, 2 chloropropoxy, 3-chloropropoxy, 2,3-dichloropropoxy, 2-bromo¬propoxy, 3 bromopropoxy, 3,3,3-trifluoropropoxy, 3,3,3-trichloropropoxy, OCH$_2$—C$_2$F$_5$, OCF$_2$—C$_2$F$_5$, 1-fluoromethyl-2-fluoroethoxy, 1-chloromethyl-2-chloroethoxy, 1-bromomethyl-2-bromoethoxy, 4-fluorobutoxy, 4-chlorobutoxy, 4-bromobutoxy or nonafluorobutoxy.

The term "C$_1$-C$_4$-alkoxy-C$_1$-C$_4$-alkyl" refers to alkyl having 1 to 4 carbon atoms (as defined above), wherein one hydrogen atom of the alkyl radical is replaced by a C$_1$-C$_4$-alkoxy group (as defined above). Likewise, the term "C$_1$-C$_6$-alkoxy-C$_1$-C$_4$-alkyl" refers to alkyl having 1 to 4 carbon atoms (as defined above), wherein one hydrogen atom of the alkyl radical is replaced by a C$_1$-C$_6$-alkoxy group (as defined above).

The term "C$_1$-C$_6$-alkylthio" as used herein refers to straight-chain or branched alkyl groups having 1 to 6 carbon atoms (as defined above) bonded via a sulfur atom. Accordingly, the term "C$_1$-C$_6$-haloalkylthio" as used herein refers to straight-chain or branched haloalkyl group having 1 to 6 carbon atoms (as defined above) bonded through a sulfur atom, at any position in the haloalkyl group.

The term "C$_1$-C$_6$-alkylsulfinyl" refers to straight-chain or branched alkyl groups having 1 to 6 carbon atoms (as defined above) bonded through a —S(=O)— moiety, at any position in the alkyl group, for example methylsulfinyl and ethylsulfinyl, and the like. Accordingly, the term "C$_1$-C$_6$-haloalkylsulfinyl" refers to straight-chain or branched haloalkyl group having 1 to 6 carbon atoms (as defined above), bonded through a —S(=O)— moiety, at any position in the haloalkyl group.

The term "C$_1$-C$_6$-alkylsulfonyl" refers to straight-chain or branched alkyl groups having 1 to 6 carbon atoms (as defined above), bonded through a —S(=O)$_2$— moiety, at any position in the alkyl group, for example methylsulfonyl. Accordingly, the term "C$_1$-C$_6$-haloalkylsulfonyl" refers to straight-chain or branched haloalkyl group having 1 to 6 carbon atoms (as defined above), bonded through a —S(=O)$_2$— moiety, at any position in the haloalkyl group.

The term "C$_3$-C$_8$-cycloalkyl-C$_3$-C$_8$-cycloalkyl" refers to a cycloalkyl radical having 3 to 8 carbon atoms (as defined above), which is substituted by a further cycloalkyl radical having 3 to 8 carbon atoms.

The term "C$_3$-C$_8$-cycloalkoxy" refers to a cycloalkyl radical having 3 to 8 carbon atoms (as defined above), which is bonded via an oxygen.

The term "C(=O)—C$_1$-C$_4$-alkyl" refers to a radical which is attached through the carbon atom of the group C(=O) as indicated by the number valence of the carbon atom. The number of valence of carbon is 4, that of nitrogen is 3. Likewise the following terms are to be construed: NH(C$_1$-C$_4$-alkyl), N(C$_1$-C$_4$-alkyl)$_2$, NH(C$_3$-C$_6$-cycloalkyl), N(C$_3$-C$_6$-cycloalkyl)$_2$, C(=O)OH, C(=O)—O—C$_1$-C$_4$-alkyl, C(=O)—NH(C$_1$-C$_4$-alkyl), C(=O)—N(C$_1$-C$_4$-alkyl)$_2$, C(=O)—NH(C$_3$-C$_6$-cycloalkyl), C(=O)—N(C$_3$-C$_6$-cycloalkyl)$_2$.

Agriculturally acceptable salts of the inventive compounds encompass especially the salts of those cations or the acid addition salts of those acids whose cations and anions, respectively, have no adverse effect on the fungicidal action of said compounds. Suitable cations are thus in particular the ions of the alkali metals, preferably sodium and potassium, of the alkaline earth metals, preferably calcium, magnesium and barium, of the transition metals, preferably manganese, copper, zinc and iron, and also the ammonium ion which, if desired, may carry one to four C$_1$-C$_4$-alkyl substituents and/or one phenyl or benzyl substituent, preferably diisopropylammonium, tetramethylammonium, tetrabutylammonium, trimethylbenzylammonium, furthermore phosphonium ions, sulfonium ions, preferably tri(C$_1$-C$_4$-alkyl)sulfonium, and sulfoxonium ions, preferably tri(C$_1$-C$_4$-alkyl)sulfoxonium. Anions of useful acid addition salts are primarily chloride, bromide, fluoride, hydrogensulfate, sulfate, dihydrogenphosphate, hydrogenphosphate, phosphate, nitrate, bicarbonate, carbonate, hexafluorosilicate, hexafluorophosphate, benzoate, and the anions of C$_1$-C$_4$-alkanoic acids, preferably formate, acetate, propionate and butyrate. They can be formed by reacting such inventive compound with an acid of the corresponding anion, preferably of hydrochloric acid, hydrobromic acid, sulfuric acid, phosphoric acid or nitric acid.

The inventive compounds can be present in atropisomers arising from restricted rotation about a single bond of asymmetric groups. They also form part of the subject matter of the present invention.

Depending on the substitution pattern, the compounds of formula I and their N-oxides may have one or more centers of chirality, in which case they are present as pure enantiomers or pure diastereomers or as enantiomer or diastereomer mixtures. Both, the pure enantiomers or diastereomers and their mixtures are subject matter of the present invention.

In the following, particular embodiments of the inventive compounds are described. Therein, specific meanings of the respective substituents are further detailed, wherein the meanings are in each case on their own but also in any combination with one another, particular embodiments of the present invention.

Furthermore, in respect of the variables, generally, the embodiments of the compounds I also apply to the intermediates.

A according to the invention is N or CH. According to one embodiment A is N. According to a further embodiment A is CH.

R$^1$ according to the invention is C$_1$-C$_6$-alkyl, C$_2$-C$_6$-alkenyl, C$_2$-C$_6$-alkynyl or C$_3$-C$_6$-cycloalkyl; wherein the aliphatic moieties of R$^1$ are not further substituted or carry one, two, three or up to the maximum possible number of identical or different groups R$^{1a}$ which independently of one another are selected from R$^{1a}$ halogen, OH, CN, C$_1$-C$_4$-alkoxy, C$_3$-C$_8$-cycloalkyl, C$_3$-C$_8$-halocycloalkyl and C$_1$-C$_4$-halogenalkoxy; and wherein the cycloalkyl moieties of R$^1$ are not further substituted or carry one, two, three, four, five or up to the maximum number of identical or different groups R$^{1b}$ which independently of one another are selected from halogen, OH, CN, C$_1$-C$_4$-alkyl, C$_1$-C$_4$-alkoxy, C$_1$-C$_4$-halogenalkyl, C$_3$-C$_8$-cycloalkyl, C$_3$-C$_8$-halocycloalkyl and C$_1$-C$_4$-halogenalkoxy.

According to a further embodiment of the invention, R$^1$ is selected from C$_1$-C$_6$-alkyl, C$_2$-C$_6$-alkenyl, C$_2$-C$_6$-alkynyl, C$_3$-C$_6$-cycloalkyl and C$_3$-C$_6$-cycloalkyl-C$_1$-C$_4$-alkyl, wherein the R$^1$ are in each case unsubstituted or are substituted by R$^{1a}$ and/or R$^{1b}$ as defined and preferably defined herein. Specific embodiments thereof can be found in the below Table P1.

According to one particular embodiment, R$^1$ is C$_1$-C$_6$-alkyl, in particular C$_1$-C$_4$-alkyl, such as CH$_3$, C$_2$H$_5$, CH(CH$_3$)$_2$ or C(CH$_3$)$_3$. A further embodiment relates to compounds, wherein R$^1$ is C$_1$-C$_6$-alkyl, in particular C$_1$-C$_4$-alkyl that is substituted by one, two or three or up to the maximum possible number of identical or different groups R$^{1a}$, as defined and preferably defined herein. According to a specific embodiment thereof, R$^1$ is C$_1$-C$_6$-haloalkyl, in particular C$_1$-C$_4$-haloalkyl, more particularly C$_1$-C$_2$-haloalkyl such as CF$_3$ or CHF$_2$. According to a further specific embodiment thereof, R$^1$ is C$_1$-C$_4$-alkoxy-C$_1$-C$_6$-alkyl, in particular $C_1$-$C_4$-alkoxy-$C_1$-$C_4$-alkyl, such as $CH_2$—$OCH_3$. Further specific embodiments thereof can be found in the below Table P1.

According to still another embodiment, $R^1$ is $C_3$-$C_8$-cycloalkyl-$C_1$-$C_6$-alkyl, in particular $C_3$-$C_6$-cycloalkyl-$C_1$-$C_4$-alkyl. A further embodiment relates to compounds, wherein $R^1$ is $C_3$-$C_8$-cycloalkyl-$C_1$-$C_6$-alkyl, in particular $C_3$-$C_6$-cycloalkyl-$C_1$-$C_4$-alkyl, that is substituted by one, two or three or up to the maximum possible number of identical or different groups $R^{1a}$ in the alkyl moiety and/or substituted by one, two, three four or five or up to the maximum possible number of identical or different groups $R^{1b}$ in the cycloalkyl moiety. $R^{1a}$ are in each case as defined and preferably defined herein. Specific embodiments thereof can be found in the below Table P1.

According to another embodiment, $R^1$ is $C_2$-$C_6$-alkenyl, in particular $C_2$-$C_4$-alkenyl, such as $CH$=$CH_2$, $CH_2CH$=$CH_2$, $CH$=$CHCH_3$ or $C(CH_3)$=$CH_2$. A further embodiment relates to compounds, wherein $R^1$ is $C_2$-$C_6$-alkenyl, in particular $C_2$-$C_4$-alkenyl that is substituted by one, two or three or up to the maximum possible number of identical or different groups $R^{1a}$ as defined and preferably defined herein. According to a specific embodiment thereof, $R^1$ is $C_2$-$C_6$-haloalkenyl, in particular $C_2$-$C_4$-haloalkenyl. Further specific embodiments thereof can be found in the below Table P1.

According to still another embodiment, $R^1$ is $C_2$-$C_6$-alkynyl, in particular $C_2$-$C_4$-alkynyl, such as $C$≡$CH$, $C$≡$CCH_3$, $CH_2$—$C$≡$C$—$H$ or $CH_2$—$C$≡$C$—$CH_3$.

A further embodiment relates to compounds, wherein $R^1$ is $C_2$-$C_6$-alkynyl, in particular $C_2$-$C_4$-alkynyl that is substituted by one, two or three or up to the maximum possible number of identical or different groups $R^{1a}$, as defined and preferably defined herein. According to a specific embodiment thereof, $R^1$ is $C_2$-$C_6$-haloalkynyl, in particular $C_2$-$C_4$-haloalkynyl. According to a further specific embodiment thereof, $R^1$ is $C_3$-$C_6$-cycloalkyl-$C_2$-$C_6$-alkynyl or $C_3$-$C_6$-halocycloalkyl-$C_2$-$C_6$-alkynyl, in particular $C_3$-$C_6$-cycloalkyl-$C_2$-$C_4$-alkynyl or $C_3$-$C_6$-halocycloalkyl-$C_2$-$C_4$-alkynyl. Further specific embodiments thereof can be found in the below Table P1.

According to still another embodiment, $R^1$ is $C_3$-$C_6$-cycloalkyl, such as $C_3H_5$ (cyclopropyl), $C_4H_7$ (cyclobutyl), cyclopentyl or cyclohexyl. A further embodiment relates to compounds, wherein $R^1$ is $C_3$-$C_6$-cycloalkyl, such as $C_3H_5$ (cyclopropyl) or $C_4H_7$ (cyclobutyl), that is substituted by one, two, three four or five or up to the maximum possible number of identical or different groups $R^{1b}$ as defined and preferably defined herein. According to a specific embodiment thereof, $R^1$ is $C_3$-$C_6$-halocycloalkyl, such as halocyclopropyl, in particular 1-F-cyclopropyl or 1-Cl-cyclopropyl. According to a further specific embodiment thereof, $R^1$ $C_3$-$C_6$-cycloalkyl-$C_3$-$C_6$-cycloalkyl, wherein each of said cycloalkyl-cycloalkyl moieties is unsubstituted or carries one, two or three $R^{1b}$ as defined and preferably defined herein, such as 1-cyclopropyl-cyclopropyl or 2-cyclopropyl-cyclopropyl. Specific embodiments thereof can be found in the below Table P1.

Specifically, it may be preferred, if $R^1$ is selected from $C_1$-$C_4$-alkyl, such as methyl, ethyl, n-propyl, iso-propyl, tert-butyl, $CH_2C(CH_3)_3$ and $CH_2CH(CH_3)_2$, $C_1$-$C_4$-haloalkyl, such as $CF_3$, $C_2$-$C_6$-alkenyl, $C_2$-$C_6$-alkynyl, such as $C$≡$CCH_3$, and $C_3$-$C_6$-cycloalkyl, such as cyclopropyl.

Particularly preferred embodiments of $R^1$ according to the invention are in Table P1 below, wherein each line of lines P1-1 to P1-139 corresponds to one particular embodiment of the invention, wherein P1-1 to P1-139 are also in any combination a preferred embodiment of the present invention.

TABLE P1

| line | $R^1$ |
|---|---|
| P1-1 | $CH_3$ |
| P1-2 | $CH_2CH_3$ |
| P1-3 | $CH_2CH_2CH_3$ |
| P1-4 | $CH(CH_3)_2$ |
| P1-5 | $C(CH_3)_3$ |
| P1-6 | $CH(CH_3)CH_2CH_3$ |
| P1-7 | $CH_2CH(CH_3)_2$ |
| P1-8 | $CH_2CH_2CH_2CH_3$ |
| P1-9 | $CF_3$ |
| P1-10 | $CHF_2$ |
| P1-11 | $CH_2F$ |
| P1-12 | $CHCl_2$ |
| P1-13 | $CH_2Cl$ |
| P1-14 | $CH_2OH$ |
| P1-15 | $CH_2CH_2OH$ |
| P1-16 | $CH_2CH_2CH_2OH$ |
| P1-17 | $CH(CH_3)CH_2OH$ |
| P1-18 | $CH_2CH(CH_3)OH$ |
| P1-19 | $CH_2CH_2CH_2CH_2OH$ |
| P1-20 | $CH(CH_3)CN$ |
| P1-21 | $CH_2CH_2CN$ |
| P1-22 | $CH_2CN$ |
| P1-23 | $CH_2CH_2CN$ |
| P1-24 | $CH_2CH_2CH_2CN$, |
| P1-25 | $CH(CH_3)CH_2CN$ |
| P1-26 | $CH_2CH(CH_3)CN$ |
| P1-27 | $CH_2CH_2CH_2CH_2CN$ |
| P1-28 | $CH_2OCH_3$ |
| P1-29 | $CH_2OCH_2CH_3$ |
| P1-30 | $CH(CH_3)OCH_3$ |
| P1-31 | $CH(CH_3)OCH_2CH_3$ |
| P1-32 | $CH_2CH_2OCH_2CH_3$ |
| P1-33 | $CH_2OCF_3$ |
| P1-34 | $CH_2CH_2OCF_3$ |
| P1-35 | $CH_2OCCl_3$ |
| P1-36 | $CH_2CH_2OCCl_3$ |
| P1-37 | $CH$=$CH_2$ |
| P1-38 | $CH_2CH$=$CH_2$ |
| P1-39 | $CH_2CH$=$CHCH_3$ |
| P1-40 | $CH_2C(CH_3)$=$CH_2$ |
| P1-41 | $CH_2C(CH_3)$=$CHCH_3$ |
| P1-42 | $CH_2C(CH_3)$=$C(CH_3)_2$ |
| P1-43 | $CH$=$CHCH_3$ |
| P1-44 | $C(CH_3)$=$CH_2$ |
| P1-45 | $CH$=$C(CH_3)_2$ |
| P1-46 | $C(CH_3)$=$C(CH_3)_2$ |
| P1-47 | $C(CH_3)$=$CH(CH_3)$ |
| P1-48 | $C(Cl)$=$CH_2$ |
| P1-49 | $C(H)$=$CHCl$ |
| P1-50 | $C(Cl)$=$CHCl$ |
| P1-51 | $CH$=$CCl_2$ |
| P1-52 | $C(Cl)$=$CCl_2$ |
| P1-53 | $C(H)$=$CH(F)$ |
| P1-54 | $C(H)$=$CF_2$ |
| P1-55 | $C(F)$=$CF_2$ |
| P1-56 | $C(F)$=$CHF$ |
| P1-57 | $CH$=$CHCH_2OH$ |
| P1-58 | $CH$=$CHOCH_3$ |
| P1-59 | $CH$=$CHCH_2OCH_3$ |
| P1-60 | $CH$=$CHCH_2OCF_3$ |
| P1-61 | $CH$=$CHCH_2OCCl_3$ |
| P1-62 | $CH$=$CH(C_3H_5)$ |
| P1-63 | $CH$=$CH(C_4H_7)$ |
| P1-64 | $CH$=$CH(1$-$Cl$—$C_3H_4)$ |
| P1-65 | $CH$=$CH(1$-$F$—$C_3H_4)$ |
| P1-66 | $CH$=$CH(1$-$Cl$—$C_4H_6)$ |
| P1-67 | $CH$=$CH(1$-$F$—$C_4H_6)$ |
| P1-68 | $C$≡$CH$ |
| P1-69 | $C$≡$CCH_3$ |
| P1-70 | $CH_2C$≡$CCH_3$ |
| P1-71 | $CH_2C$≡$CH$ |
| P1-72 | $CH_2C$≡$CCH_2CH_3$ |
| P1-73 | $C$≡$CCH(CH_3)_2$ |

TABLE P1-continued

| line | $R^1$ |
|---|---|
| P1-74 | C≡CC(CH$_3$)$_3$ |
| P1-75 | C≡C(C$_3$H$_5$) |
| P1-76 | C≡C(C$_4$H$_7$) |
| P1-77 | C≡C(1-Cl—C$_3$H$_4$) |
| P1-78 | C≡C(1-Cl—C$_4$H$_6$) |
| P1-79 | C≡CCl |
| P1-80 | C≡CBr |
| P1-81 | C≡C—I |
| P1-82 | CH$_2$C≡CCl |
| P1-83 | CH$_2$C≡CBr |
| P1-84 | CH$_2$C≡C—I |
| P1-85 | C≡CCH$_2$OCH$_3$ |
| P1-86 | C≡CCH(OH)CH$_3$ |
| P1-87 | C≡CCH(OCH$_3$)CH$_3$ |
| P1-88 | C≡COCH$_3$ |
| P1-89 | CH$_2$C≡COCH$_3$ |
| P1-90 | C≡CCH$_2$OCCl$_3$ |
| P1-91 | C≡CCH$_2$OCF$_3$ |
| P1-92 | C≡CCH$_2$(C$_3$H$_5$) |
| P1-93 | C≡CCH$_2$(C$_4$H$_7$) |
| P1-94 | C≡C(1-Cl—C$_3$H$_4$) |
| P1-95 | C≡C(1-F—C$_3$H$_4$) |
| P1-96 | C≡C(1-Cl—C$_4$H$_6$) |
| P1-97 | C≡C(1-F—C$_4$H$_6$) |
| P1-98 | C$_3$H$_5$ (cyclopropyl) |
| P1-99 | C$_4$H$_7$ (cyclobutyl) |
| P1-100 | C$_5$H$_9$ (cyclopentyl) |
| P1-101 | cyclohexyl |
| P1-102 | CH(CH$_3$)—C$_3$H$_5$ (CH(CH$_3$)-cyclopropyl) |
| P1-103 | CH$_2$—C$_3$H$_5$ (CH$_2$-cyclopropyl) |
| P1-104 | 1-(Cl)-cyclopropyl |
| P1-105 | 1-(F)-cyclopropyl |
| P1-106 | 1-(CH$_3$)-cyclopropyl |
| P1-107 | 1-(CN)-cyclopropyl |
| P1-108 | 2-(Cl)-cyclopropyl |
| P1-109 | 2-(F)-cyclopropyl |
| P1-110 | 1-(Cl)-cyclobutyl |
| P1-111 | 1-(F)-cyclobutyl |
| P1-112 | 2-(Cl)-cyclobutyl |
| P1-113 | 3-(Cl)-cyclobutyl |
| P1-114 | 2-(F)-cyclobutyl |
| P1-115 | 3-(F)-cyclobutyl |
| P1-116 | 3,3-Cl$_2$-cyclobutyl |
| P1-117 | 3,3-F$_2$-cyclobutyl |
| P1-118 | 2-(CH$_3$)-cyclopropyl |
| P1-119 | 1-(CH$_3$)-cyclobutyl |
| P1-120 | 2-(CH$_3$)-cyclobutyl |
| P1-121 | 3-(CH$_3$)-cyclobutyl |
| P1-122 | 3,3-(CH$_3$)$_2$-cyclobutyl |
| P1-123 | 2-(CN)-cyclopropyl |
| P1-124 | 1-cyclopropyl-cyclopropyl |
| P1-125 | 2-cyclopropyl-cyclopropyl |
| P1-126 | CH(CH$_3$)(cyclobutyl) |
| P1-127 | CH$_2$-(cyclobutyl) |
| P1-128 | CH$_2$CH$_2$-(cyclopropyl) |
| P1-129 | CH$_2$CH$_2$-(cyclobutyl) |
| P1-130 | CH$_2$-(1-Cl-cyclopropyl) |
| P1-131 | CH$_2$-(1-F-cyclopropyl) |
| P1-132 | CH$_2$-(1-Cl-cyclobutyl) |
| P1-133 | CH$_2$-(1-F-cyclobutyl) |
| P1-134 | CHCH$_3$-(1-Cl-cyclopropyl) |
| P1-135 | C(CH$_3$)$_2$-(1-F-cyclopropyl) |
| P1-136 | CF$_2$CH$_3$ |
| P1-137 | CHFCH$_3$ |
| P1-138 | CF$_2$CF$_3$ |
| P1-139 | CH$_2$OCHF$_2$ |

$R^{1a}$ are the possible substituents for the aliphatic moieties of $R^1$.

$R^{1a}$ according to the invention is independently selected from halogen, OH, CN, $C_1$-$C_4$-alkoxy, $C_3$-$C_6$-cycloalkyl, $C_3$-$C_6$-halocycloalkyl and $C_1$-$C_4$-halogenalkoxy.

According to one embodiment $R^{1a}$ is independently selected from halogen, OH, CN, $C_1$-$C_2$-alkoxy, $C_3$-$C_6$-cycloalkyl, $C_3$-$C_6$-halocycloalkyl and $C_1$-$C_2$-halogenalkoxy. Specifically, $R^{1a}$ is independently selected from F, Cl, OH, CN, $C_1$-$C_2$-alkoxy, cyclopropyl, 1-F-cyclopropyl, 1-Cl-cyclopropyl and $C_1$-$C_2$-halogenalkoxy.

$R^{1b}$ are the possible substituents for the cycloalkyl moieties of $R^1$.

$R^{1b}$ according to the invention is independently selected from halogen, OH, CN, $C_1$-$C_4$-alkyl, $C_1$-$C_4$-alkoxy, $C_1$-$C_4$-halogenalkyl, $C_3$-$C_6$-cycloalkyl, $C_3$-$C_6$-halocycloalkyl and $C_1$-$C_4$-halogenalkoxy.

According to one embodiment thereof $R^{1b}$ is independently selected from halogen, CN, $C_1$-$C_2$-alkyl, $C_1$-$C_2$-alkoxy, $C_1$-$C_2$-halogenalkyl, $C_3$-$C_6$-cycloalkyl, $C_3$-$C_6$-halocycloalkyl and $C_1$-$C_2$-halogenalkoxy. Specifically, $R^{1b}$ is independently selected from F, Cl, OH, CN, CH$_3$, OCH$_3$, cyclopropyl, 1-F-cyclopropyl, 1-Cl-cyclopropyl and halogenmethoxy.

According to the invention, $R^2$ is hydrogen, $C_1$-$C_4$-alkyl, $C_2$-$C_4$-alkenyl, $C_2$-$C_4$-alkynyl, wherein the aliphatic moieties of $R^2$ are not further substituted or carry one, two, three or up to the maximum possible number of identical or different groups $R^{2a}$ which independently of one another are selected from halogen, OH, CN, $C_1$-$C_4$-alkoxy, $C_3$-$C_6$-cycloalkyl, $C_3$-$C_6$-halocycloalkyl and $C_1$-$C_4$-halogenalkoxy.

According to one embodiment, $R^2$ is H.

According to a further embodiment of the invention, $R^2$ is selected from $C_1$-$C_4$-alkyl, $C_2$-$C_4$-alkenyl, $C_2$-$C_4$-alkynyl.

According to a further embodiment of the invention, $R^2$ is selected from H, $C_1$-$C_4$-alkyl, in particular methyl or ethyl, $C_2$-$C_4$-alkenyl, in particular CH$_2$CH=CH$_2$, and $C_2$-$C_4$-alkynyl, in particular CH$_2$C≡CH. Specific embodiments thereof can be found in the below Table P2.

According to one particular embodiment, $R^2$ is $C_1$-$C_4$-alkyl, such as CH$_3$, C$_2$H$_5$, CH(CH$_3$)$_2$, CH$_2$CH$_2$CH$_3$, CH$_2$CH$_2$CH$_2$CH$_3$, CH$_2$CH(CH$_3$)$_2$. A further embodiment relates to compounds, wherein $R^2$ is $C_1$-$C_4$-alky, that is substituted by one, two or three or up to the maximum possible number of identical or different groups $R^{2a}$, as defined and preferably defined herein. According to a specific embodiment thereof, $R^2$ is $C_1$-$C_4$-haloalkyl, more particularly $C_1$-$C_2$-haloalkyl. According to a further specific embodiment thereof, $R^2$ is $C_1$-$C_4$-alkoxy-$C_1$-$C_4$-alkyl, such as CH$_2$OCH$_3$ or CH$_2$CH$_2$OCH$_3$. According to still a further specific embodiment thereof, $R^2$ is hydroxyl-$C_1$-$C_4$-alkyl, such as CH$_2$CH$_2$OH. Further specific embodiments thereof can be found in the below Table P2

According to still another embodiment, $R^2$ is $C_3$-$C_6$-cycloalkyl-$C_1$-$C_4$-alkyl. A further embodiment relates to compounds, wherein $R^2$ is $C_3$-$C_6$-cycloalkyl-$C_1$-$C_4$-alkyl, more particularly $C_3$-$C_6$-cycloalkyl-$C_1$-$C_2$-alkyl that is substituted by one, two or three or up to the maximum possible number of identical or different groups $R^{2a}$. A further embodiment relates to compounds, wherein $R^2$ is $C_3$-$C_6$-halocycloalkyl-$C_1$-$C_4$-alkyl, more particularly $C_3$-$C_6$-halocycloalkyl-$C_1$-$C_2$-alkyl. Specific embodiments thereof can be found in the below Table P2.

According to another embodiment, $R^2$ is $C_2$-$C_4$-alkenyl, such as CH$_2$CH=CH$_2$, CH$_2$C(CH$_3$)=CH$_2$ or CH$_2$CH=CHCH$_3$. A further embodiment relates to compounds, wherein $R^2$ is $C_2$-$C_4$-alkenyl that is substituted by one, two or three or up to the maximum possible number of identical or different groups $R^{2a}$ as defined and preferably defined herein. According to a specific embodiment thereof, $R^2$ is $C_2$-$C_4$-haloalkenyl, such as CH$_2$C(Cl)=CH$_2$ and CH$_2$C(H)=CHCl. According to a further specific embodiment thereof, $R^2$ is $C_3$-$C_6$-cycloalkyl-$C_2$-$C_4$-alkenyl or $C_3$-$C_6$-halocycloalkyl-$C_2$-$C_4$-alkenyl. Further specific embodiments thereof can be found in the below Table P2.

According to still another embodiment, $R^2$ is $C_2$-$C_4$-alkynyl, such as $CH_2C{\equiv}CH$ or $CH_2C{\equiv}CCH_3$. A further embodiment relates to compounds, wherein $R^2$ is $C_2$-$C_4$-alkynyl that is substituted by one, two or three or up to the maximum possible number of identical or different groups $R^{2a}$, as defined and preferably defined herein. According to a specific embodiment thereof, $R^2$ is $C_2$-$C_4$-haloalkynyl. According to a further specific embodiment thereof, $R^2$ is $C_3$-$C_6$-cycloalkyl-$C_2$-$C_4$-alkynyl or $C_3$-$C_6$-halocycloalkyl-$C_2$-$C_4$-alkynyl. Specific embodiments thereof can be found in the below Table P2.

Particularly preferred embodiments of $R^2$ according to the invention are in Table P2 below, wherein each line of lines P2-1 to P2-79 corresponds to one particular embodiment of the invention, wherein P2-1 to P2-79 are also in any combination a preferred embodiment of the present invention.

TABLE P2

| line | $R^2$ |
| --- | --- |
| P2-1 | H |
| P2-2 | $CH_3$ |
| P2-3 | $CH_2CH_3$ |
| P2-4 | $CH(CH_3)_2$ |
| P2-5 | $CH_2CH_2CH_3$ |
| P2-6 | $CH_2CH_2CH_2CH_3$ |
| P2-7 | $CH_2CH(CH_3)_2$ |
| P2-8 | $CF_3$ |
| P2-9 | $CHF_2$ |
| P2-10 | $CFH_2$ |
| P2-11 | $CCl_3$ |
| P2-12 | $CHCl_2$ |
| P2-13 | $CClH_2$ |
| P2-14 | $CH_2CF_3$ |
| P2-15 | $CH_2CHF_2$ |
| P2-16 | $CH_2CCl_3$ |
| P2-17 | $CH_2CHCl_2$ |
| P2-18 | $CH_2CH_2OCH_2CH_3$ |
| P2-19 | $CH(CH_3)OCH_2CH_3$ |
| P2-20 | $CH(CH_3)OCH_3$ |
| P2-21 | $CH_2OCH_3$ |
| P2-22 | $CH_2CH_2OCH_3$ |
| P2-23 | $CH_2OCF_3$ |
| P2-24 | $CH_2CH_2OCF_3$ |
| P2-25 | $CH_2OCCl_3$ |
| P2-26 | $CH_2CH_2OCCl_3$ |
| P2-27 | $CH_2CH_2OH$ |
| P2-28 | $CH_2OH$ |
| P2-29 | $CH_2CH_2CH_2OH$, |
| P2-30 | $CH(CH_3)CH_2OH$ |
| P2-31 | $CH_2CH(CH_3)OH$ |
| P2-32 | $CH_2CH_2CH_2CH_2OH$ |
| P2-33 | $CH_2CN$, |
| P2-34 | $CH_2CH_2CN$, |
| P2-35 | $CH_2CH_2CH_2CN$, |
| P2-36 | $CH(CH_3)CH_2CN$, |
| P2-37 | $CH_2CH(CH_3)CN$, |
| P2-38 | $CH_2CH_2CH_2CH_2CN$ |
| P2-39 | $CH{=}CH_2$ |
| P2-40 | $C(CH_3){=}CH_2$ |
| P2-41 | $CH{=}CHCH_3$ |
| P2-42 | $CH_2CH{=}CH_2$ |
| P2-43 | $CH_2CH{=}CHCH_3$ |
| P2-44 | $CH_2C(CH_3){=}CH_2$ |
| P2-45 | $C(CH_3){=}CH(CH_3)$ |
| P2-46 | $CH{=}C(CH_3)_2$ |
| P2-47 | $CH{=}C(Cl)_2$ |
| P2-48 | $C(CH_3){=}CH_2$ |
| P2-49 | $CH_2C(Cl){=}CH_2$ |
| P2-50 | $CH_2C(H){=}CHCl$ |
| P2-51 | $CH{=}CHCH_2OH$ |
| P2-52 | $CH{=}C(CH_3)OH$ |
| P2-53 | $CH{=}CHOCH_3$ |
| P2-54 | $CH{=}CHCH_2OCH_3$ |
| P2-55 | $CH_2CH{=}CHCH_2OCH_3$ |
| P2-56 | $CH{=}CHOCF_3$ |
| P2-57 | $CH{=}CHCH_2OCF_3$ |

TABLE P2-continued

| line | $R^2$ |
| --- | --- |
| P2-58 | $CH{=}CHOCCl_3$ |
| P2-59 | $CH{=}CHCH_2OCCl_3$ |
| P2-60 | $CH_2CH{=}CH(C_3H_5)$ |
| P2-61 | $CH_2CH{=}CH(C_4H_7)$ |
| P2-62 | $CH_2CH{=}CH(1\text{-}Cl{-}C_3H_4)$ |
| P2-63 | $CH_2CH{=}CH(1\text{-}F{-}C_3H_4)$ |
| P2-64 | $CH_2C{\equiv}CH$ |
| P2-65 | $CH_2C{\equiv}CCH_3$ |
| P2-66 | $CH_2C{\equiv}CCl$ |
| P2-67 | $CH_2C{\equiv}CF$ |
| P2-68 | $CH_2C{\equiv}C{-}I$ |
| P2-69 | $CH_2C{\equiv}CCH_2OH$ |
| P2-70 | $CH_2C{\equiv}CCH_2OCH_3$ |
| P2-71 | $CH_2C{\equiv}COCH_3$ |
| P2-72 | $C{\equiv}COCF_3$ |
| P2-73 | $CH_2C{\equiv}COCF_3$ |
| P2-74 | $C{\equiv}COCCl_3$ |
| P2-75 | $CH_2C{\equiv}COCCl_3$ |
| P2-76 | $CH_2\text{-(cyclopropyl)}$ |
| P2-77 | $CH_2\text{-(cyclobutyl)}$ |
| P2-78 | $CH_2\text{-(1-Cl-cyclopropyl)}$ |
| P2-79 | $CH_2\text{-(1-F-cyclopropyl)}$ |

$R^3$ according to the present invention is independently selected from hydrogen, halogen, CN, $C_1$-$C_4$-alkyl, $C_1$-$C_4$-alkoxy, $C_2$-$C_4$-alkenyl, $C_2$-$C_4$-alkynyl, $C_3$-$C_6$-cycloalkyl, $S(O)_p(C_1$-$C_4$-alkyl), wherein each of $R^3$ is unsubstituted or further substituted by one, two, three or four $R^{3a}$; wherein $R^{1a}$ is independently selected from halogen, CN, OH, $C_1$-$C_4$-alkyl, $C_1$-$C_4$-haloalkyl, $C_3$-$C_6$-cycloalkyl, $C_3$-$C_6$-halocycloalkyl, $C_1$-$C_4$-alkoxy and $C_1$-$C_4$-halogenalkoxy, and wherein p is 0, 1 or 2.

$R^3$ according to one embodiment is independently selected from halogen, CN, $C_1$-$C_4$-alkyl, $C_1$-$C_4$-alkoxy, $C_2$-$C_4$-alkenyl, $C_2$-$C_4$-alkynyl, $C_3$-$C_6$-cycloalkyl, $S(O)_p(C_1$-$C_4$-alkyl), wherein each of $R^3$ is unsubstituted or further substituted by one, two, three or four $R^{3a}$; wherein $R^{1a}$ is independently selected from halogen, CN, OH, $C_1$-$C_4$-alkyl, $C_1$-$C_4$-haloalkyl, $C_3$-$C_8$-cycloalkyl, $C_3$-$C_8$-halocycloalkyl, $C_1$-$C_4$-alkoxy and $C_1$-$C_4$-halogenalkoxy, and wherein p is 0, 1 or 2.

According to a further embodiment, $R^3$ is selected from hydrogen, F, Cl, Br, CN, $C_1$-$C_4$-alkyl, $C_1$-$C_4$-haloalkyl, $C_1$-$C_4$-alkoxy, $C_1$-$C_4$-haloalkoxy, $S(C_1$-$C_4$-alkyl), $S(O)(C_1$-$C_4$-alkyl) and $S(O)_2(C_1$-$C_4$-alkyl).

According to a further embodiment, $R^3$ is selected from F, Cl, Br, CN, $C_1$-$C_4$-alkyl, $C_1$-$C_4$-haloalkyl, $C_1$-$C_4$-alkoxy, $C_1$-$C_4$-haloalkoxy, $S(C_1$-$C_4$-alkyl), $S(O)(C_1$-$C_4$-alkyl) and $S(O)_2(C_1$-$C_4$-alkyl).

$R^3$ according to one embodiment is hydrogen.

According to a further embodiment, $R^3$ is selected from hydrogen, Cl, F, Br, CN, $C_1$-$C_2$-alkyl, in particular $CH_3$, $C_1$-$C_2$-haloalkyl, in particular $CF_3$, $C_1$-$C_2$-alkoxy, in particular $OCH_3$, and $C_1$-$C_2$-haloalkoxy, in particular $OCF_3$.

According to still a further embodiment, $R^3$ is selected from Cl, F, Br, CN, $C_1$-$C_2$-alkyl, in particular $CH_3$, $C_1$-$C_2$-haloalkyl, in particular $CF_3$, $C_1$-$C_2$-alkoxy, in particular $OCH_3$, and $C_1$-$C_2$-haloalkoxy, in particular $OCF_3$.

According to a further embodiment, $R^3$ is selected from hydrogen, Cl, F, Br, $C_1$-$C_2$-alkyl, in particular $CH_3$, $C_1$-$C_2$-haloalkyl, in particular $CF_3$, $C_1$-$C_2$-alkoxy, in particular $OCH_3$, and $C_1$-$C_2$-haloalkoxy, in particular $OCF_3$.

According to still a further embodiment, $R^3$ is selected from Cl, F, Br, $C_1$-$C_2$-alkyl, in particular $CH_3$, $C_1$-$C_2$-haloalkyl, in particular $CF_3$, $C_1$-$C_2$-alkoxy, in particular $OCH_3$, and $C_1$-$C_2$-haloalkoxy, in particular $OCF_3$.

According to a further embodiment, $R^3$ is selected from $C_2$-$C_4$-alkenyl, $C_2$-$C_4$-haloalkenyl, $C_2$-$C_4$-alkynyl and $C_2$-$C_4$-haloalkynyl. According to one particular embodiment, $R^3$ is $C_2$-$C_4$-alkenyl or $C_2$-$C_4$-haloalkenyl, such as CH=CH$_2$. According to a further particular embodiment, $R^3$ is $C_2$-$C_4$-alkynyl or $C_2$-$C_4$-haloalkynyl, such as C≡CH.

According to a further embodiment, $R^3$ is selected from $C_3$-$C_6$-cycloalkyl and $C_3$-$C_6$-halocycloalkyl.

According to a further embodiment, $R^3$ is selected from S($C_1$-$C_2$-alkyl), S(O)($C_1$-$C_2$-alkyl) and S(O)$_2$($C_1$-$C_2$-alkyl). According to a particular embodiment thereof, $R^3$ is selected from SCH$_3$, S(O)(CH$_3$) and S(O)$_2$(CH$_3$).

According to one specific embodiment, $R^3$ is halogen, in particular Br, F or Cl, more specifically F or Cl.

According to a further specific embodiment, $R^3$ is CN.

According to a further specific embodiment, $R^3$ is $C_1$-$C_4$-alkyl, such as CH$_3$, or $C_1$-$C_4$-haloalkyl, such as CF$_3$, CHF$_2$, CH$_2$F, CCl$_3$, CHCl$_2$ or CH$_2$Cl.

According to a further specific embodiment, $R^3$ is $C_1$-$C_4$-alkoxy, more specifically $C_1$-$C_2$-alkoxy such as OCH$_3$ or OCH$_2$CH$_3$, or $C_1$-$C_4$-haloalkoxy, more specifically $C_1$-$C_2$-haloalkoxy such as OCF$_3$, OCHF$_2$, OCH$_2$F, OCCl$_3$, OCHCl$_2$ or OCH$_2$Cl, in particular OCF$_3$, OCHF$_2$, OCCl$_3$ or OCHCl$_2$.

$R^{1a}$ is selected from halogen, CN, OH, $C_1$-$C_4$-alkyl, $C_1$-$C_4$-haloalkyl, $C_3$-$C_8$-cycloalkyl, $C_3$-$C_8$-halocycloalkyl, $C_1$-$C_4$-alkoxy and $C_1$-$C_4$-halogenalkoxy, in particular selected from halogen, CN, $C_1$-$C_2$-alkyl, $C_1$-$C_2$-haloalkyl, $C_3$-$C_6$-cycloalkyl, $C_3$-$C_6$-halocycloalkyl, $C_1$-$C_2$-alkoxy and $C_1$-$C_2$-halogenalkoxy. Specifically, $R^{1a}$ is independently selected from F, Cl, CN, OH, CH$_3$, halomethyl, cyclopropyl, halocyclopropyl, OCH$_3$ and halogenmethoxy.

Particularly preferred embodiments of $R^3$ according to the invention are in Table P3 below, wherein each line of lines P3-1 to P5-16 corresponds to one particular embodiment of the invention, wherein P3-1 to P3-16 are also in any combination with one another a preferred embodiment of the present invention. Thereby, for every $R^3$ that is present in the inventive compounds, these specific embodiments and preferences apply independently of the meaning of any other $R^3$ that may be present in the phenyl ring:

TABLE P3

| No. | $R^3$ |
|---|---|
| P3-1 | Cl |
| P3-2 | F |
| P3-3 | CN |
| P3-4 | CH$_3$ |
| P3-5 | CH$_2$CH$_3$ |
| P3-6 | CF$_3$ |
| P3-7 | CHF$_2$ |
| P3-8 | OCH$_3$ |
| P3-9 | OCH$_2$CH$_3$ |
| P3-10 | OCF$_3$ |
| P3-11 | OCHF$_2$ |
| P3-12 | SCH$_3$ |
| P3-13 | SOCH$_3$ |
| P3-14 | SO$_2$CH$_3$ |
| P3-15 | Br |
| P3-16 | H |

Z is $C_3$-$C_8$-cycloalkyl or $C_3$-$C_8$-cycloalkenyl, wherein the cycloalkyl or cycloalkenyl is unsubstituted (m=0) or substituted by $(R^4)_m$; wherein m is 0, 1, 2, 3 or 4; and $R^4$ is in each case independently selected from halogen, CN, NO$_2$, OH, SH, $C_1$-$C_6$-alkyl, $C_1$-$C_6$-alkoxy, $C_2$-$C_6$-alkenyl, $C_2$-$C_6$-alkynyl, $C_3$-$C_6$-cycloalkyl, $C_3$-$C_6$-cycloalkyloxy, S(O)$_p$($C_1$-$C_4$-alkyl), C(=O)($C_1$-$C_4$-alkyl), C(=O)(OH), C(=O)(O—$C_1$-$C_4$-alkyl), C(=O)(NH($C_1$-$C_4$-alkyl)) and C(=O)(N($C_1$-$C_4$-alkyl)$_2$);

wherein each of $R^4$ is unsubstituted or further substituted by one, two, three or four $R^{4a}$ wherein $R^{4a}$ is independently selected from halogen, CN, NO$_2$, OH, $C_1$-$C_4$-alkyl, $C_1$-$C_4$-haloalkyl, $C_3$-$C_6$-cycloalkyl, $C_3$-$C_6$-halocycloalkyl, $C_1$-$C_4$-alkoxy and $C_1$-$C_4$-haloalkoxy; and wherein p is 0, 1 or 2.

According to the invention, there can be zero, one, two, three or four $R^4$ present, namely for m is 0, 1, 2, 3 or 4. In particular, m is 0, 1, 2 or 3. According to one embodiment, m is 0, 1 or 2.

According to one particular embodiment, m is 0.

According to a further embodiment, m is 1, 2 or 3, in particular 1 or 2, more specifically 1. According to one specific embodiment thereof, m is 1, according to a further specific embodiment, m is 2.

According to still a further embodiment, m is 2, 3 or 4.

According to still a further embodiment, m is 3.

For every $R^4$ that is present in the inventive compounds, the following embodiments and preferences apply independently of the meaning of any other $R^4$ that may be present in the phenyl ring. Furthermore, the particular embodiments and preferences given herein for $R^4$ apply independently for each of m=1, m=2, m=3 and m=4.

Each $R^4$ is independently selected from halogen, CN, NO$_2$, OH, SH, $C_1$-$C_6$-alkyl, $C_1$-$C_6$-alkoxy, $C_2$-$C_6$-alkenyl, $C_2$-$C_6$-alkynyl, $C_3$-$C_6$-cycloalkyl, $C_3$-$C_6$-cycloalkyloxy, S(O)$_p$($C_1$-$C_4$-alkyl), C(=O)($C_1$-$C_4$-alkyl), C(=O)(OH), C(=O)(O—$C_1$-$C_4$-alkyl), C(=O)(NH($C_1$-$C_4$-alkyl)) and C(=O)(N($C_1$-$C_4$-alkyl)$_2$); wherein each of $R^4$ is unsubstituted or further substituted by one, two, three or four $R^{4a}$ wherein $R^{4a}$ is independently selected from halogen, CN, NO$_2$, OH, $C_1$-$C_4$-alkyl, $C_1$-$C_4$-haloalkyl, $C_3$-$C_6$-cycloalkyl, $C_3$-$C_6$-halocycloalkyl, $C_1$-$C_4$-alkoxy and $C_1$-$C_4$-haloalkoxy; and wherein p is 0, 1 or 2.

According to one embodiment, $R^4$ is independently selected from halogen, CN, NO$_2$, $C_1$-$C_4$-alkyl, $C_1$-$C_4$-alkoxy, $C_2$-$C_4$-alkenyl, $C_2$-$C_4$-alkynyl, $C_3$-$C_6$-cycloalkyl, $C_3$-$C_6$-cycloalkyloxy, S($C_1$-$C_2$-alkyl), S(O)($C_1$-$C_2$-alkyl), S(O)$_2$($C_1$-$C_2$-alkyl), C(=O)($C_1$-$C_2$-alkyl), C(=O)(OH) and C(=O)(O—$C_1$-$C_2$-alkyl), wherein each of $R^4$ is unsubstituted or further substituted by one, two, three or four independently selected $R^{4a}$, wherein $R^{4a}$ is as defined and preferably defined herein.

According to a further embodiment, $R^4$ is independently selected from halogen, CN, NO$_2$, $C_1$-$C_4$-alkyl, $C_1$-$C_4$-haloalkyl, $C_1$-$C_4$-alkoxy, $C_1$-$C_4$-haloalkoxy, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl, $C_3$-$C_6$-halocycloalkyl, S($C_1$-$C_2$-alkyl), S(O)($C_1$-$C_2$-alkyl), S(O)$_2$($C_1$-$C_2$-alkyl), C(=O)($C_1$-$C_2$-alkyl), C(=O)(OH) and C(=O)(O—$C_1$-$C_2$-alkyl).

According to a further embodiment, $R^4$ is independently selected from halogen, CN, NO$_2$, $C_1$-$C_2$-alkyl, $C_1$-$C_2$-haloalkyl, $C_1$-$C_2$-alkoxy, $C_1$-$C_2$-haloalkoxy, S($C_1$-$C_2$-alkyl), S(O)($C_1$-$C_2$-alkyl), S(O)$_2$($C_1$-$C_2$-alkyl), C(=O)(OH) and C(=O)(O—$C_1$-$C_2$-alkyl).

According to a further embodiment, $R^4$ is independently selected from F, Cl, Br, CN, $C_1$-$C_4$-alkyl, $C_1$-$C_4$-haloalkyl, $C_1$-$C_4$-alkoxy, $C_1$-$C_4$-haloalkoxy, S($C_1$-$C_4$-alkyl), S(O)($C_1$-$C_4$-alkyl) and S(O)$_2$($C_1$-$C_4$-alkyl).

According to a further embodiment, $R^4$ is independently selected from F, Cl, Br, CN, methyl, $C_1$-haloalkyl, methoxy and $C_1$-haloalkoxy, more specifically selected from F, Cl, CN and methyl.

According to still a further specific embodiment, $R^4$ is independently selected from halogen, in particular from Br, F and Cl, more specifically from F and Cl.

According to a further specific embodiment, $R^4$ is CN.

According to a further specific embodiment, $R^4$ is $C_1$-$C_4$-alkyl, such as $CH_3$. Further appropriate alkyls are ethyl, n-propyl, i-propyl, n-butyl, i-butyl and t-butyl.

According to a further specific embodiment, $R^4$ is $C_1$-$C_4$-haloalkyl, such as $CF_3$, $CHF_2$, $CH_2F$, $CCl_3$, $CHCl_2$ or $CH_2Cl$.

According to a further specific embodiment $R^4$ is $C_1$-$C_4$-alkoxy, more specifically $C_1$-$C_2$-alkoxy such as $OCH_3$ or $OCH_2CH_3$.

According to a further specific embodiment, $R^4$ is $C_1$-$C_4$-haloalkoxy, more specifically $C_1$-$C_2$-haloalkoxy such as $OCF_3$, $OCHF_2$, $OCH_2F$, $OCCl_3$, $OCHCl_2$ or $OCH_2Cl$, in particular $OCF_3$, $OCHF_2$, $OCCl_3$ or $OCHCl_2$.

According to still a further embodiment, $R^4$ is $C_2$-$C_6$-alkenyl or $C_2$-$C_6$-haloalkenyl, in particular $C_2$-$C_4$-alkenyl or $C_2$-$C_4$-haloalkenyl, such as $CH=CH_2$, $CH_2CH=CH_2$, $CH=CHCH_3$ or $C(CH_3)=CH_2$.

According to still a further embodiment, $R^4$ is $C_2$-$C_6$-alkynyl or $C_2$-$C_6$-haloalkynyl, in particular $C_2$-$C_4$-alkynyl or $C_2$-$C_4$-haloalkynyl, such as $C\equiv CH$, $CH_2CCH$ or $CH_2CCCH_3$.

According to another embodiment $R^4$ is $C_3$-$C_6$-cycloalkoxy. In a special embodiment $R^4$ is O-cyclopropyl.

According to another embodiment $R^4$ is $C_3$-$C_6$-cycloalkyl, preferably cyclopropyl, cyclobutyl, cyclopentyl or cyclohexyl, in particular cyclopropyl or cyclobutyl. In a special embodiment $R^4$ is cyclopropyl. In a further special embodiment $R^4$ is cyclobutyl. In a further special embodiment $R^4$ is cyclopentyl. In a further special embodiment $R^4$ is cyclohexyl.

According to a specific embodiment $R^4$ is fully or partially halogenated $C_3$-$C_6$-cycloalkyl. In a special embodiment $R^4$ is fully or partially halogenated cyclopropyl. In a further special embodiment $R^4$ is 1-Cl-cyclopropyl. In a further special embodiment $R^4$ is 2-Cl-cyclopropyl. In a further special embodiment $R^4$ is 1-F-cyclopropyl. In a further special embodiment $R^4$ is 2-F-cyclopropyl. In a further special embodiment $R^4$ is fully or partially halogenated cyclobutyl. In a further special embodiment $R^4$ is 1-Cl-cyclobutyl. In a further special embodiment $R^4$ is 1-F-cyclobutyl. In a further special embodiment $R^4$ is 3,3-$Cl_2$-cyclobutyl. In a further special embodiment $R^4$ is 3,3-$F_2$-cyclobutyl. According to a specific embodiment $R^4$ is $C_3$-$C_6$-cycloalkyl substituted by $C_1$-$C_4$-alkyl. In a special embodiment $R^4$ is 1-$CH_3$-cyclopropyl. According to a specific embodiment $R^4$ is $C_3$-$C_6$-cycloalkyl substituted by CN. In a special embodiment $R^4$ is 1-CN-cyclopropyl. According to a further specific embodiment $R^4$ is $C_3$-$C_6$-cycloalkyl-$C_3$-$C_6$-cycloalkyl. In a special embodiment $R^4$ is cyclopropyl-cyclopropyl. In a special embodiment $R^4$ is 2-cyclopropyl-cyclopropyl. According to a further specific embodiment $R^4$ is $C_3$-$C_6$-cycloalkyl-$C_3$-$C_6$-halocycloalkyl.

According to one another embodiment $R^4$ is $C_3$-$C_8$-cycloalkyl-$C_1$-$C_4$-alkyl, preferably $C_3$-$C_6$-cycloalkyl-$C_1$-$C_4$-alkyl. In a special embodiment $R^4$ is $CH(CH_3)$(cyclopropyl). In a further special embodiment $R^4$ is $CH_2$-(cyclopropyl).

According to still a further embodiment, $R^4$ is selected from $C(=O)(C_1$-$C_4$-alkyl), $C(=O)(OH)$, $C(=O)(O$-$C_1$-$C_4$-alkyl), $C(=O)(NH(C_1$-$C_4$-alkyl))$ and $C(=O)(N(C_1$-$C_4$-alkyl)_2)$, in particular selected from $C(=O)(C_1$-$C_2$-alkyl), $C(=O)(OH)$, $C(=O)(O$-$C_1$-$C_2$-alkyl), $C(=O)(NH(C_1$-$C_2$-alkyl))$ and $C(=O)(N(C_1$-$C_2$-alkyl)_2)$. According to one specific embodiment thereof, $R^4$ is $C(=O)(OH)$ or $C(=O)(O$-$C_1$-$C_4$-alkyl), in particular $C(=O)(OCH_3)$.

According to one another embodiment $R^4$ is $C(=O)(C_1$-$C_4$-alkyl). According to a specific embodiment $R^4$ is $C(=O)CH_3$. According to a further specific embodiment $R^4$ is $C(=O)CH_2CH_3$. According to a further specific embodiment $R^4$ is $C(=O)CH_2CH_2CH_3$. According to a further specific embodiment $R^4$ is $C(=O)CH(CH_3)_2$. According to a further specific embodiment $R^4$ is $C(=O)C(CH_3)_3$.

According to one another embodiment $R^4$ is $C(=O)OH$.

According to one another embodiment $R^4$ is $C(=O)(O$-$C_1$-$C_4$-alkyl). According to a specific embodiment $R^4$ is $C(=O)OCH_3$. According to a further specific embodiment $R^4$ is $C(=O)OCH_2CH_3$. According to a further specific embodiment $R^4$ is $C(=O)OCH_2CH_2CH_3$. According to a further specific embodiment $R^4$ is $C(=O)OCH(CH_3)_2$. According to a further specific embodiment $R^4$ is $C(=O)OC(CH_3)_3$.

According to one another embodiment $R^4$ is $C(=O)$—$NH(C_1$-$C_4$-alkyl)$. According to a specific embodiment $R^4$ is $C(=O)NHCH_3$. According to a further specific embodiment $R^4$ is $C(=O)NHCH_2CH_3$. According to a further specific embodiment $R^4$ is $C(=O)NHCH_2CH_2CH_3$. According to a further specific embodiment $R^4$ is $C(=O)NHCH(CH_3)_2$. According to a further specific embodiment $R^{42}$ is $C(=O)NHC(CH_3)_3$.

According to one another embodiment $R^4$ is $C(=O)$—$N(C_1$-$C_4$-alkyl)_2$. According to a specific embodiment $R^4$ is $C(=O)N(CH_3)_2$. According to a further specific embodiment $R^4$ is $C(=O)N(CH_2CH_3)_2$. According to a further specific embodiment $R^4$ is $C(=O)N(CH_2CH_2CH_3)_2$. According to a further specific embodiment $R^4$ is $C(=O)N(CH(CH_3)_2)_2$. According to a further specific embodiment $R^4$ is $C(=O)N(C(CH_3)_3)_2$.

According to still a further embodiment, $R^4$ is selected from $S(C_1$-$C_2$-alkyl)$, $S(O)(C_1$-$C_2$-alkyl)$ and $S(O)_2(C_1$-$C_2$-alkyl)$, in particular $SCH_3$, $S(O)(CH_3)$ and $S(O)_2(CH_3)$. According to a specific embodiment $R^4$ is selected from $S(C_1$-$C_2$-haloalkyl)$, $S(O)(C_1$-$C_2$-haloalkyl)$ and $S(O)_2(C_1$-$C_2$-haloalkyl)$, such as $SO_2CF_3$.

Particularly preferred embodiments of $R^4$ according to the invention are in Table P4 below, wherein each line of lines P4-1 to P4-17 corresponds to one particular embodiment of the invention, wherein P4-1 to P4-17 are also in any combination with one another a preferred embodiment of the present invention. Thereby, for every $R^4$ that is present in the inventive compounds, these specific embodiments and preferences apply independently of the meaning of any other $R^4$ that may be present in the phenyl ring:

TABLE P4

| No. | $R^4$ |
| --- | --- |
| P4-1 | Cl |
| P4-2 | F |
| P4-3 | CN |
| P4-4 | $NO_2$ |
| P4-5 | $CH_3$ |
| P4-6 | $CH_2CH_3$ |
| P4-7 | $CF_3$ |
| P4-8 | $CHF_2$ |
| P4-9 | $OCH_3$ |
| P4-10 | $OCH_2CH_3$ |
| P4-11 | $OCF_3$ |
| P4-12 | $OCHF_2$ |
| P4-13 | $SCH_3$ |
| P4-14 | $SOCH_3$ |
| P4-15 | $SO_2CH_3$ |

TABLE P4-continued

| No. | $R^4$ |
|---|---|
| P4-16 | $CO_2CH_3$ |
| P4-17 | Br |

According to one embodiment, Z is $C_3$-$C_8$-cycloalkyl, wherein said cycloalkyl is unsubstituted or substituted by $(R^4)_m$, wherein m and $R^4$ are defined and preferably defined as given above.

In particular, Z is $C_3$-$C_6$-cycloalkyl, wherein said cycloalkyl is unsubstituted or substituted by $(R^4)_m$, wherein m and $R^4$ are defined and preferably defined as given above.

According to one particular embodiment, Z is cyclopropyl, wherein said cyclopropyl is unsubstituted or substituted by $(R^4)_m$, wherein m and $R^4$ are defined and preferably defined as given above.

According to a further particular embodiment, Z is cyclobutyl, wherein said cyclobutyl is unsubstituted or substituted by $(R^4)_m$, wherein m and $R^4$ are defined and preferably defined as given above.

According to still a further particular embodiment, Z is cyclopentyl, wherein said cyclopentyl is unsubstituted or substituted by $(R^4)_m$, wherein m and $R^4$ are defined and preferably defined as given above.

According to still a further particular embodiment, Z is cyclohexyl, wherein said cyclohexyl is unsubstituted or substituted by $(R^4)_m$, wherein m and $R^4$ are defined and preferably defined as given above.

According to still a further particular embodiment, Z is cycloheptyl, wherein said cycloheptyl is unsubstituted or substituted by $(R^4)_m$, wherein m and $R^4$ are defined and preferably defined as given above.

According to still a further particular embodiment, Z is cyclooctyl, wherein said cyclooctyl is unsubstituted or substituted by $(R^4)_m$, wherein m and $R^4$ are defined and preferably defined as given above.

Particularly preferred embodiments of Z if Z is $C_3$-$C_8$-cycloalkyl according to the invention are in Table Z1 below, wherein each line of lines Z1-1 to Z1-28 corresponds to one particular embodiment of the invention, wherein Z1-1 to Z1-28 are also in any combination a preferred embodiment of the present invention.

TABLE Z1

| No. | $Z$—$(R^4)_m$ |
|---|---|
| Z1-1 | cyclopropyl |
| Z1-2 | 1-Cl-cyclopropyl |
| Z1-3 | 1-F-cyclopropyl |
| Z1-4 | 1-$CH_3$-cyclopropyl |
| Z1-5 | 1-CN-cyclopropyl |
| Z1-6 | 2,2-$Cl_2$-cyclopropyl |
| Z1-7 | 2,2-$CH_3$-cyclopropyl |
| Z1-8 | cyclobutyl |
| Z1-9 | 1-Cl-cyclobutyl |
| Z1-10 | 1-F-cyclobutyl |
| Z1-11 | 1-$CH_3$-cyclobutyl |
| Z1-12 | 1-CN-cyclobutyl |
| Z1-13 | cyclopentyl |
| Z1-14 | 1-Cl-cyclopentyl |
| Z1-15 | 1-F-cyclopentyl |
| Z1-16 | 1-$CH_3$-cyclopentyl |
| Z1-17 | 1-CN-cyclopentyl |
| Z1-18 | cyclohexyl |
| Z1-19 | 1-Cl-cyclohexyl |
| Z1-20 | 1-F-cyclohexyl |
| Z1-21 | 1-$CH_3$-cyclohexyl |
| Z1-22 | 1-CN-cyclohexyl |
| Z1-23 | cycloheptyl |
| Z1-24 | 1-F-cycloheptyl |
| Z1-25 | 1-Cl-cycloheptyl |
| Z1-26 | cyclooctyl |
| Z1-27 | 1-F-cyclooctyl |
| Z1-28 | 1-Cl-cyclooctyl |

According to one further embodiment, Z is $C_3$-$C_8$-cycloalkenyl, wherein said cycloalkenyl is unsubstituted or substituted by $(R^4)_m$, wherein m and $R^4$ are defined and preferably defined as given above. Preferably, the cycloalkenyl contains one or two double bonds in the cycle, in particular one double bond. According to one embodiment, the position of said double bond is adjacent to the attachment carbon atom of Z to the triple bond in the formula I, namely, Z is $C_3$-$C_6$-cycloalken-1-yl.

In particular, Z is $C_3$-$C_6$-cycloalkenyl, wherein said cycloalkenyl is unsubstituted or substituted by $(R^4)_m$, wherein m and $R^4$ are defined and preferably defined as given above. Preferably, the cycloalkenyl contains one or two double bonds in the cycle, in particular one double bond. According to one embodiment, the position of said double bond is adjacent to the attachment carbon atom of Z to the triple bond in the formula I, namely, Z is $C_3$-$C_6$-cycloalken-1-yl.

According to one particular embodiment, Z is cyclopropenyl, more specifically cyclopropen-1-yl, wherein said cyclopropenyl or cyclopropen-1-yl is unsubstituted or substituted by $(R^4)_m$, wherein m and $R^4$ are defined and preferably defined as given above.

According to a further particular embodiment, Z is cyclobutenyl, more specifically cyclobuten-1yl, wherein said cyclobutenyl or cyclobuten-yl is unsubstituted or substituted by $(R^4)_m$, wherein m and $R^4$ are defined and preferably defined as given above.

According to still a further particular embodiment, Z is cyclopentenyl, more specifically cyclopenten-1-yl, wherein said cyclopentenyl or cyclopenten-1-yl is unsubstituted or substituted by $(R^4)_m$, wherein m and $R^4$ are defined and preferably defined as given above.

According to still a further particular embodiment, Z is cyclohexenyl, more specifically cyclohexen-1-yl, wherein said cyclohexenyl or cyclohexen-1-yl is unsubstituted or substituted by $(R^4)_m$, wherein m and $R^4$ are defined and preferably defined as given above.

According to still a further particular embodiment, Z is cycloheptenyl, more specifically cyclohepten-1-yl, wherein said cycloheptenyl or cyclohepten-1-yl is unsubstituted or substituted by $(R^4)_m$, wherein m and $R^4$ are defined and preferably defined as given above.

According to still a further particular embodiment, Z is cyclooctenyl, more specifically cycloocten-1-yl, wherein said cyclooctenyl or cycloocten-1-yl is unsubstituted or substituted by $(R^4)_m$, wherein m and $R^4$ are defined and preferably defined as given above.

Particularly preferred embodiments of Z if Z is $C_3$-$C_8$-cycloalkenyl according to the invention are in Table Z2 below, wherein each line of lines Z2-1 to Z2-16 corresponds to one particular embodiment of the invention, wherein Z2-1 to Z2-16 are also in any combination a preferred embodiment of the present invention.

TABLE Z2

| No. | Z—(R⁴)ₘ |
|---|---|
| Z2-1 | cyclopenten-1-yl |
| Z2-2 | cyclohexen-1-yl |
| Z2-3 | 2-CH₃-cyclopenten-1-yl |
| Z2-4 | 2-CH₃-cyclohexen-1-yl |
| Z2-5 | 2-Cl-cyclopenten-1-yl |
| Z2-6 | 2-Cl-cyclohexen-1-yl |
| Z2-7 | 2-CN-cyclopenten-1-yl |
| Z2-8 | 2-CN-cyclohexen-1-yl |
| Z2-9 | cyclohepten-1-yl |
| Z2-10 | 2-CH₃-cyclohepten-1-yl |
| Z2-11 | 2-Cl-cyclohepten-1-yl |
| Z2-12 | 2-CN-cyclohepten-1-yl |
| Z2-13 | cyloocten-1-yl |
| Z2-14 | 2-CH₃-cyloocten-1-yl |
| Z2-15 | 2-Cl-cyloocten-1-yl |
| Z2-16 | 2-CN-cyloocten-1-yl |

One embodiment relates to compounds I, wherein A is N (I.A).

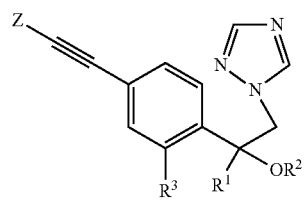

I.A

In one embodiment of I.A, Z is $C_3$-$C_6$-cycloalkyl (compounds I.A1), wherein the cycloalkyl is unsubstituted (m=0) or substituted by $(R^4)_m$.

Specific embodiments thereof are the following I.A1a (A=N, Z=cyclopropyl), I.A1b (A=N, Z=cyclobutyl), I.A1c (A=N, Z=cyclopentyl) and I.A1d (A=N, Z=cyclohexyl):

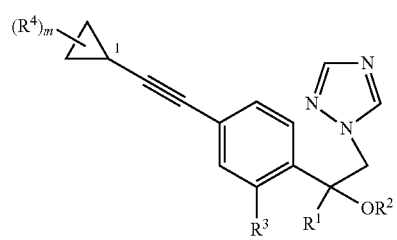

I.A1a

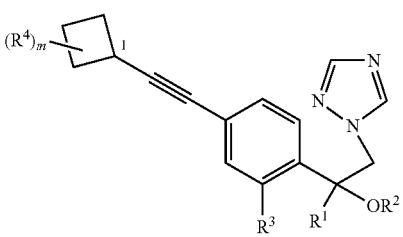

I.A1b

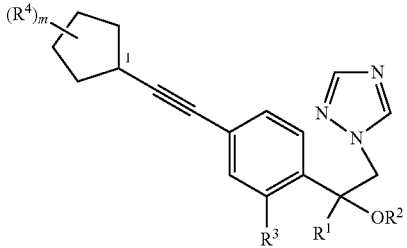

I.A1c

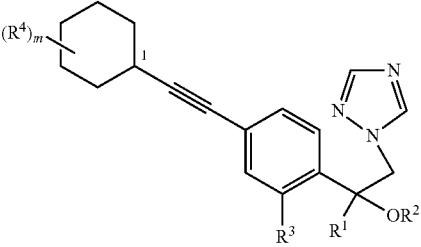

I.A1d

In another embodiment of I.A, Z is $C_3$-$C_6$-cycloalkenyl (compounds I.A2), wherein the cycloalkenyl is unsubstituted (m=0) or substituted by $(R^4)_m$.

Specific embodiments thereof are the following I.A2a (A=N, Z=cyclopropen-1-yl), I.A2b (A=N, Z=cyclobuten-1-yl), I.A2c (A=N, Z=cyclopenten-1-yl) and I.A2d (A=N, Z=cyclohexen-1-yl):

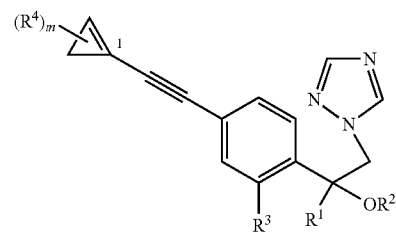

I.A2a

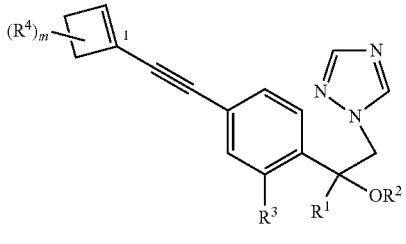

I.A2b

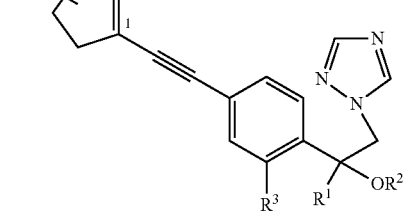

I.A2c

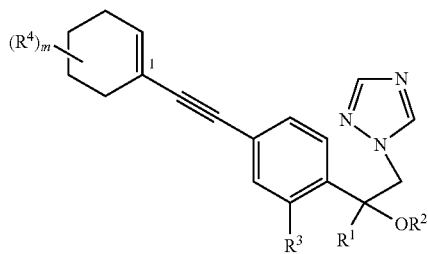

I.A2d

A further embodiment relates to compounds I, wherein A is CH (I.B).

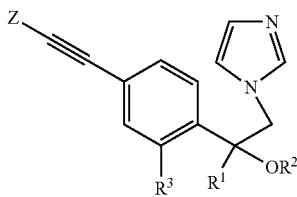

I.B

In one embodiment thereof, Z is $C_3$-$C_6$-cycloalkyl (compounds I.B1), wherein the cycloalkyl is unsubstituted (m=0) or substituted by $(R^4)_m$.

Specific embodiments of I.B are the following I.B1a (A=N, Z=cyclopropyl), I.B1b (A=N, Z=cyclobutyl), I.B1c (A=N, Z=cyclopentyl) and I.B1d (A=N, Z=cyclohexyl):

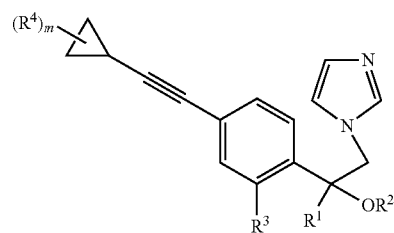

I.B1a

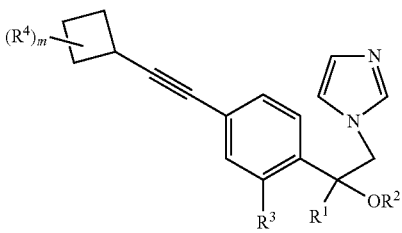

I.B1b

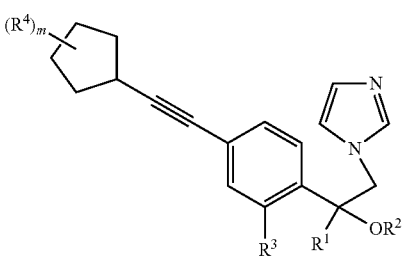

I.B1c

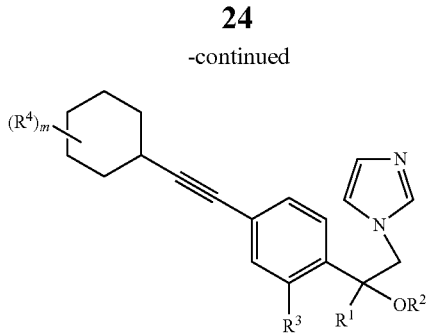

I.B1d

In another embodiment of I.B, Z is $C_3$-$C_6$-cycloalkenyl (compounds I.B2), wherein the cycloalkenyl is unsubstituted (m=0) or substituted by $(R^4)_m$.

Specific embodiments thereof are the following I.B2a (A=N, Z=cyclopropen-1-yl), I.B2b (A=N, Z=cyclobuten-1-yl), I.B2c (A=N, Z=cyclopenten-1-yl) and I.B2d (A=N, Z=cyclohexen-1-yl):

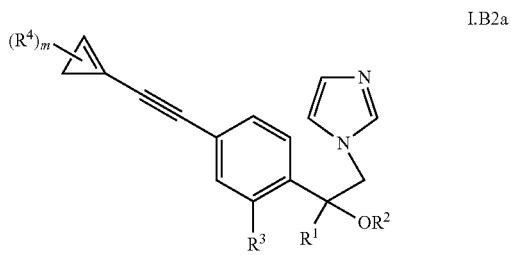

I.B2a

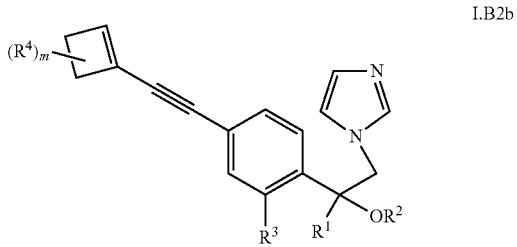

I.B2b

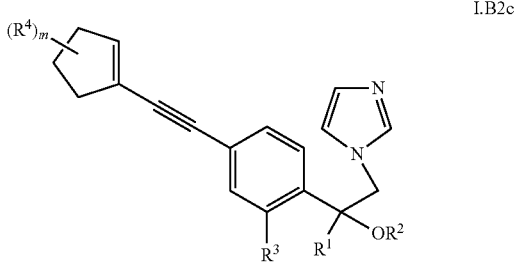

I.B2c

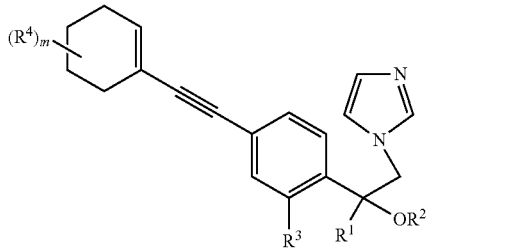

I.B2d

In particular with a view to their use, according to one embodiment, preference is given to the compounds of the formula I.A1 and I.A2 that are compiled in the Tables 1a to 49a, Tables 1b to 49b, Tables 1c to 35c, Tables 1d to 35d, Tables 1e to 7e and Tables 1f to 7f below. Each of the groups mentioned for a substituent in the tables is furthermore per se, independently of the combination in which it is mentioned, a particularly preferred aspect of the substituent in question.

Table 1a Compounds of the formula I.A1a in which m in $(R^4)_m$ is 0 and $R^3$ corresponds to line D1-1 of Table D1 and the meaning for the combination of $R^1$ and $R^2$ for each individual compound corresponds in each case to one line of Table B (compounds I.A1a.D1-1.B1 to I.A1a.D1-1.B455).

Table 2a Compounds of the formula I.A1a in which m in $(R^4)_m$ is 0 and $R^3$ corresponds to line D1-2 of Table D1 and the meaning for the combination of $R^1$ and $R^2$ for each individual compound corresponds in each case to one line of Table B (compounds I.A1a.D1-2.B1 to I.A1a.D1-2.B455).

Table 3a Compounds of the formula I.A1a in which m in $(R^4)_m$ is 0 and $R^3$ corresponds to line D1-3 of Table D1 and the meaning for the combination of $R^1$ and $R^2$ for each individual compound corresponds in each case to one line of Table B (compounds I.A1a.D1-3.B1 to I.A1a.D1-3.B455).

Table 4a Compounds of the formula I.A1a in which m in $(R^4)_m$ is 0 and $R^3$ corresponds to line D1-4 of Table D1 and the meaning for the combination of $R^1$ and $R^2$ for each individual compound corresponds in each case to one line of Table B (compounds I.A1a.D1-4.B1 to I.A1a.D1-4.B455).

Table 5a Compounds of the formula I.A1a in which m in $(R^4)_m$ is 0 and $R^3$ corresponds to line D1-5 of Table D1 and the meaning for the combination of $R^1$ and $R^2$ for each individual compound corresponds in each case to one line of Table B (compounds I.A1a.D1-5.B1 to I.A1a.D1-5.B455).

Table 6a Compounds of the formula I.A1a in which m in $(R^4)_m$ is 0 and $R^3$ corresponds to line D1-6 of Table D1 and the meaning for the combination of $R^1$ and $R^2$ for each individual compound corresponds in each case to one line of Table B (compounds I.A1a.D1-6.B1 to I.A1a.D1-6.B455).

Table 7a Compounds of the formula I.A1a in which m in $(R^4)_m$ is 0 and $R^3$ corresponds to line D1-7 of Table D1 and the meaning for the combination of $R^1$ and $R^2$ for each individual compound corresponds in each case to one line of Table B (compounds I.A1a.D1-7.B1 to I.A1a.D1-7.B455).

Table 8a Compounds of the formula I.A1a in which $(R^4)_m$ is 1-Cl and $R^3$ corresponds to line D1-1 of Table D1 and the meaning for the combination of $R^1$ and $R^2$ for each individual compound corresponds in each case to one line of Table B (compounds I.A1a.D1-1.B1 to I.A1a.D1-1.B455).

Table 9a Compounds of the formula I.A1a in which $(R^4)_m$ is 1-Cl and $R^3$ corresponds to line D1-2 of Table D1 and the meaning for the combination of $R^1$ and $R^2$ for each individual compound corresponds in each case to one line of Table B (compounds I.A1a.D1-2.B1 to I.A1a.D1-2.B455).

Table 10a Compounds of the formula I.A1a in which $(R^4)_m$ is 1-Cl and $R^3$ corresponds to line D1-3 of Table D1 and the meaning for the combination of $R^1$ and $R^2$ for each individual compound corresponds in each case to one line of Table B (compounds I.A1a.D1-3.B1 to I.A1a.D1-3.B455).

Table 11a Compounds of the formula I.A1a in which $(R^4)_m$ is 1-Cl and $R^3$ corresponds to line D1-4 of Table D1 and the meaning for the combination of $R^1$ and $R^2$ for each individual compound corresponds in each case to one line of Table B (compounds I.A1a.D1-4.B1 to I.A1a.D1-4.B455).

Table 12a Compounds of the formula I.A1a in which $(R^4)_m$ is 1-Cl and $R^3$ corresponds to line D1-5 of Table D1 and the meaning for the combination of $R^1$ and $R^2$ for each individual compound corresponds in each case to one line of Table B (compounds I.A1a.D1-5.B1 to I.A1a.D1-5.B455).

Table 13a Compounds of the formula I.A1a in which $(R^4)_m$ is 1-Cl and $R^3$ corresponds to line D1-6 of Table D1 and the meaning for the combination of $R^1$ and $R^2$ for each individual compound corresponds in each case to one line of Table B (compounds I.A1a.D1-6.B1 to I.A1a.D1-6.B455).

Table 14a Compounds of the formula I.A1a in which $(R^4)_m$ is 1-Cl and $R^3$ corresponds to line D1-7 of Table D1 and the meaning for the combination of $R^1$ and $R^2$ for each individual compound corresponds in each case to one line of Table B (compounds I.A1a.D1-7.B1 to I.A1a.D1-7.B455).

Table 15a Compounds of the formula I.A1a in which $(R^4)_m$ is 1-F and $R^3$ corresponds to line D1-1 of Table D1 and the meaning for the combination of $R^1$ and $R^2$ for each individual compound corresponds in each case to one line of Table B (compounds I.A1a.D1-1.B1 to I.A1a.D1-1.B455).

Table 16a Compounds of the formula I.A1a in which $(R^4)_m$ is 1-F and $R^3$ corresponds to line D1-2 of Table D1 and the meaning for the combination of $R^1$ and $R^2$ for each individual compound corresponds in each case to one line of Table B (compounds I.A1a.D1-2.B1 to I.A1a.D1-2.B455).

Table 17a Compounds of the formula I.A1a in which $(R^4)_m$ is 1-F and $R^3$ corresponds to line D1-3 of Table D1 and the meaning for the combination of $R^1$ and $R^2$ for each individual compound corresponds in each case to one line of Table B (compounds I.A1a.D1-3.B1 to I.A1a.D1-3.B455).

Table 18a Compounds of the formula I.A1a in which $(R^4)_m$ is 1-F and $R^3$ corresponds to line D1-4 of Table D1 and the meaning for the combination of $R^1$ and $R^2$ for each individual compound corresponds in each case to one line of Table B (compounds I.A1a.D1-4.B1 to I.A1a.D1-4.B455).

Table 19a Compounds of the formula I.A1a in which $(R^4)_m$ is 1-F and $R^3$ corresponds to line D1-5 of Table D1 and the meaning for the combination of $R^1$ and $R^2$ for each individual compound corresponds in each case to one line of Table B (compounds I.A1a.D1-5.B1 to I.A1a.D1-5.B455).

Table 20a Compounds of the formula I.A1a in which $(R^4)_m$ is 1-F and $R^3$ corresponds to line D1-6 of Table D1 and the meaning for the combination of $R^1$ and $R^2$ for each individual compound corresponds in each case to one line of Table B (compounds I.A1a.D1-6.B1 to I.A1a.D1-6.B455).

Table 21a Compounds of the formula I.A1a in which $(R^4)_m$ is 1-F and $R^3$ corresponds to line D1-7 of Table D1 and the meaning for the combination of $R^1$ and $R^2$ for each individual compound corresponds in each case to one line of Table B (compounds I.A1a.D1-7.B1 to I.A1a.D1-7.B455).

Table 22a Compounds of the formula I.A1a in which $(R^4)_m$ is 1-$CH_3$ and $R^3$ corresponds to line D1-1 of Table D1 and the meaning for the combination of $R^1$ and $R^2$ for each individual compound corresponds in each case to one line of Table B (compounds I.A1a.D1-1.B1 to I.A1a.D1-1.B455).

Table 23a Compounds of the formula I.A1a in which $(R^4)_m$ is 1-$CH_3$ and $R^3$ corresponds to line D1-2 of Table D1 and the meaning for the combination of $R^1$ and $R^2$ for each individual compound corresponds in each case to one line of Table B (compounds I.A1a.D1-2.B1 to I.A1a.D1-2.B455).

Table 24a Compounds of the formula I.A1a in which $(R^4)_m$ is 1-$CH_3$ and $R^3$ corresponds to line D1-3 of Table D1 and the meaning for the combination of $R^1$ and $R^2$ for each individual compound corresponds in each case to one line of Table B (compounds I.A1a.D1-3.B1 to I.A1a.D1-3.B455).

Table 25a Compounds of the formula I.A1a in which $(R^4)_m$ is 1-$CH_3$ and $R^3$ corresponds to line D1-4 of Table D1 and the meaning for the combination of $R^1$ and $R^2$ for each individual compound corresponds in each case to one line of Table B (compounds I.A1a.D1-4.B1 to I.A1a.D1-4.B455).

Table 26a Compounds of the formula I.A1a in which $(R^4)_m$ is 1-$CH_3$ and $R^3$ corresponds to line D1-5 of Table D1 and the meaning for the combination of $R^1$ and $R^2$ for each individual compound corresponds in each case to one line of Table B (compounds I.A1a.D1-5.B1 to I.A1a.D1-5.B455).

Table 27a Compounds of the formula I.A1a in which $(R^4)_m$ is 1-CH$_3$ and R$^3$ corresponds to line D1-6 of Table D1 and the meaning for the combination of R$^1$ and R$^2$ for each individual compound corresponds in each case to one line of Table B (compounds I.A1a.D1-6.B1 to I.A1a.D1-6.B455).

Table 28a Compounds of the formula I.A1a in which $(R^4)_m$ is 1-CH$_3$ and R$^3$ corresponds to line D1-7 of Table D1 and the meaning for the combination of R$^1$ and R$^2$ for each individual compound corresponds in each case to one line of Table B (compounds I.A1a.D1-7.B1 to I.A1a.D1-7.B455).

Table 29a Compounds of the formula I.A1a in which $(R^4)_m$ is 1-CN and R$^3$ corresponds to line D1-1 of Table D1 and the meaning for the combination of R$^1$ and R$^2$ for each individual compound corresponds in each case to one line of Table B (compounds I.A1a.D1-1.B1 to I.A1a.D1-1.B455).

Table 30a Compounds of the formula I.A1a in which $(R^4)_m$ is 1-CN and R$^3$ corresponds to line D1-2 of Table D1 and the meaning for the combination of R$^1$ and R$^2$ for each individual compound corresponds in each case to one line of Table B (compounds I.A1a.D1-2.B1 to I.A1a.D1-2.B455).

Table 31a Compounds of the formula I.A1a in which $(R^4)_m$ is 1-CN and R$^3$ corresponds to line D1-3 of Table D1 and the meaning for the combination of R$^1$ and R$^2$ for each individual compound corresponds in each case to one line of Table B (compounds I.A1a.D1-3.B1 to I.A1a.D1-3.B455).

Table 32a Compounds of the formula I.A1a in which $(R^4)_m$ is 1-CN and R$^3$ corresponds to line D1-4 of Table D1 and the meaning for the combination of R$^1$ and R$^2$ for each individual compound corresponds in each case to one line of Table B (compounds I.A1a.D1-4.B1 to I.A1a.D1-4.B455).

Table 33a Compounds of the formula I.A1a in which $(R^4)_m$ is 1-CN and R$^3$ corresponds to line D1-5 of Table D1 and the meaning for the combination of R$^1$ and R$^2$ for each individual compound corresponds in each case to one line of Table B (compounds I.A1a.D1-5.B1 to I.A1a.D1-5.B455).

Table 34a Compounds of the formula I.A1a in which $(R^4)_m$ is 1-CN and R$^3$ corresponds to line D1-6 of Table D1 and the meaning for the combination of R$^1$ and R$^2$ for each individual compound corresponds in each case to one line of Table B (compounds I.A1a.D1-6.B1 to I.A1a.D1-6.B455).

Table 35a Compounds of the formula I.A1a in which $(R^4)_m$ is 1-CN and R$^3$ corresponds to line D1-7 of Table D1 and the meaning for the combination of R$^1$ and R$^2$ for each individual compound corresponds in each case to one line of Table B (compounds I.A1a.D1-7.B1 to I.A1a.D1-7.B455).

Table 36a Compounds of the formula I.A1a in which $(R^4)_m$ is 2,2-Cl$_2$ and R$^3$ corresponds to line D1-1 of Table D1 and the meaning for the combination of R$^1$ and R$^2$ for each individual compound corresponds in each case to one line of Table B (compounds I.A1a.D1-1.B1 to I.A1a.D1-1.B455).

Table 37a Compounds of the formula I.A1a in which $(R^4)_m$ is 2,2-Cl$_2$ and R$^3$ corresponds to line D1-2 of Table D1 and the meaning for the combination of R$^1$ and R$^2$ for each individual compound corresponds in each case to one line of Table B (compounds I.A1a.D1-2.B1 to I.A1a.D1-2.B455).

Table 38a Compounds of the formula I.A1a in which $(R^4)_m$ is 2,2-Cl$_2$ and R$^3$ corresponds to line D1-3 of Table D1 and the meaning for the combination of R$^1$ and R$^2$ for each individual compound corresponds in each case to one line of Table B (compounds I.A1a.D1-3.B1 to I.A1a.D1-3.B455).

Table 39a Compounds of the formula I.A1a in which $(R^4)_m$ is 2,2-Cl$_2$ and R$^3$ corresponds to line D1-4 of Table D1 and the meaning for the combination of R$^1$ and R$^2$ for each individual compound corresponds in each case to one line of Table B (compounds I.A1a.D1-4.B1 to I.A1a.D1-4.B455).

Table 40a Compounds of the formula I.A1a in which $(R^4)_m$ is 2,2-Cl$_2$ and R$^3$ corresponds to line D1-5 of Table D1 and the meaning for the combination of R$^1$ and R$^2$ for each individual compound corresponds in each case to one line of Table B (compounds I.A1a.D1-5.B1 to I.A1a.D1-5.B455).

Table 41a Compounds of the formula I.A1a in which $(R^4)_m$ is 2,2-Cl$_2$ and R$^3$ corresponds to line D1-6 of Table D1 and the meaning for the combination of R$^1$ and R$^2$ for each individual compound corresponds in each case to one line of Table B (compounds I.A1a.D1-6.B1 to I.A1a.D1-6.B455).

Table 42a Compounds of the formula I.A1a in which $(R^4)_m$ is 2,2-Cl$_2$ and R$^3$ corresponds to line D1-7 of Table D1 and the meaning for the combination of R$^1$ and R$^2$ for each individual compound corresponds in each case to one line of Table B (compounds I.A1a.D1-7.B1 to I.A1a.D1-7.B455).

Table 43a Compounds of the formula I.A1a in which $(R^4)_m$ is 2,2-(CH$_3$)$_2$ and R$^3$ corresponds to line D1-1 of Table D1 and the meaning for the combination of R$^1$ and R$^2$ for each individual compound corresponds in each case to one line of Table B (compounds I.A1a.D1-1.B1 to I.A1a.D1-1.B455).

Table 44a Compounds of the formula I.A1a in which $(R^4)_m$ is 2,2-(CH$_3$)$_2$ and R$^3$ corresponds to line D1-2 of Table D1 and the meaning for the combination of R$^1$ and R$^2$ for each individual compound corresponds in each case to one line of Table B (compounds I.A1a.D1-2.B1 to I.A1a.D1-2.B455).

Table 45a Compounds of the formula I.A1a in which $(R^4)_m$ is 2,2-(CH$_3$)$_2$ and R$^3$ corresponds to line D1-3 of Table D1 and the meaning for the combination of R$^1$ and R$^2$ for each individual compound corresponds in each case to one line of Table B (compounds I.A1a.D1-3.B1 to I.A1a.D1-3.B455).

Table 46a Compounds of the formula I.A1a in which $(R^4)_m$ is 2,2-(CH$_3$)$_2$ and R$^3$ corresponds to line D1-4 of Table D1 and the meaning for the combination of R$^1$ and R$^2$ for each individual compound corresponds in each case to one line of Table B (compounds I.A1a.D1-4.B1 to I.A1a.D1-4.B455).

Table 47a Compounds of the formula I.A1a in which $(R^4)_m$ is 2,2-(CH$_3$)$_2$ and R$^3$ corresponds to line D1-5 of Table D1 and the meaning for the combination of R$^1$ and R$^2$ for each individual compound corresponds in each case to one line of Table B (compounds I.A1a.D1-5.B1 to I.A1a.D1-5.B455).

Table 48a Compounds of the formula I.A1a in which $(R^4)_m$ is 2,2-(CH$_3$)$_2$ and R$^3$ corresponds to line D1-6 of Table D1 and the meaning for the combination of R$^1$ and R$^2$ for each individual compound corresponds in each case to one line of Table B (compounds I.A1a.D1-6.B1 to I.A1a.D1-6.B455).

Table 49a Compounds of the formula I.A1a in which $(R^4)_m$ is 2,2-(CH$_3$)$_2$ and R$^3$ corresponds to line D1-7 of Table D1 and the meaning for the combination of R$^1$ and R$^2$ for each individual compound corresponds in each case to one line of Table B (compounds I.A1a.D1-7.B1 to I.A1a.D1-7.B455).

Table 1b Compounds of the formula I.A1b in which m in $(R^4)_m$ is 0 and R$^3$ corresponds to line D1-1 of Table D1 and the meaning for the combination of R$^1$ and R$^2$ for each individual compound corresponds in each case to one line of Table B (compounds I.A1b.D1-1.B1 to I.A1b.D1-1.B455).

Table 2b Compounds of the formula I.A1b in which m in $(R^4)_m$ is 0 and R$^3$ corresponds to line D1-2 of Table D1 and the meaning for the combination of R$^1$ and R$^2$ for each individual compound corresponds in each case to one line of Table B (compounds I.A1b.D1-2.B1 to I.A1b.D1-2.B455).

Table 3b Compounds of the formula I.A1b in which m in $(R^4)_m$ is 0 and R$^3$ corresponds to line D1-3 of Table D1 and the meaning for the combination of $R^1$ and $R^2$ for each individual compound corresponds in each case to one line of Table B (compounds I.A1b.D1-3.B1 to I.A1b.D1-3.B455).

Table 4b Compounds of the formula I.A1 b in which m in $(R^4)_m$ is 0 and $R^3$ corresponds to line D1-4 of Table D1 and the meaning for the combination of $R^1$ and $R^2$ for each individual compound corresponds in each case to one line of Table B (compounds I.A1b.D1-4.B1 to I.A1b.D1-4.B455).

Table 5b Compounds of the formula I.A1 b in which m in $(R^4)_m$ is 0 and $R^3$ corresponds to line D1-5 of Table D1 and the meaning for the combination of $R^1$ and $R^2$ for each individual compound corresponds in each case to one line of Table B (compounds I.A1b.D1-5.B1 to I.A1b.D1-5.B455).

Table 6b Compounds of the formula I.A1 b in which m in $(R^4)_m$ is 0 and $R^3$ corresponds to line D1-6 of Table D1 and the meaning for the combination of $R^1$ and $R^2$ for each individual compound corresponds in each case to one line of Table B (compounds I.A1b.D1-6.B1 to I.A1b.D1-6.B455).

Table 7b Compounds of the formula I.A1 b in which m in $(R^4)_m$ is 0 and $R^3$ corresponds to line D1-7 of Table D1 and the meaning for the combination of $R^1$ and $R^2$ for each individual compound corresponds in each case to one line of Table B (compounds I.A1b.D1-7.B1 to I.A1 b.D1-7.B455).

Table 8b Compounds of the formula I.A1b in which $(R^4)_m$ is 1-Cl and $R^3$ corresponds to line D1-1 of Table D1 and the meaning for the combination of $R^1$ and $R^2$ for each individual compound corresponds in each case to one line of Table B (compounds I.A1b.D1-1.B1 to I.A1b.D1-1.B455).

Table 9b Compounds of the formula I.A1 b in which $(R^4)_m$ is 1-Cl and $R^3$ corresponds to line D1-2 of Table D1 and the meaning for the combination of $R^1$ and $R^2$ for each individual compound corresponds in each case to one line of Table B (compounds I.A1b.D1-2.B1 to I.A1b.D1-2.B455).

Table 10b Compounds of the formula I.A1b in which $(R^4)_m$ is 1-Cl and $R^3$ corresponds to line D1-3 of Table D1 and the meaning for the combination of $R^1$ and $R^2$ for each individual compound corresponds in each case to one line of Table B (compounds I.A1b.D1-3.B1 to I.A1b.D1-3.B455).

Table 11 b Compounds of the formula I.A1 b in which $(R^4)_m$ is 1-Cl and $R^3$ corresponds to line D1-4 of Table D1 and the meaning for the combination of $R^1$ and $R^2$ for each individual compound corresponds in each case to one line of Table B (compounds I.A1b.D1-4.B1 to I.A1b.D1-4.B455).

Table 12b Compounds of the formula I.A1 b in which $(R^4)_m$ is 1-Cl and $R^3$ corresponds to line D1-5 of Table D1 and the meaning for the combination of $R^1$ and $R^2$ for each individual compound corresponds in each case to one line of Table B (compounds I.A1b.D1-5.B1 to I.A1b.D1-5.B455).

Table 13b Compounds of the formula I.A1 b in which $(R^4)_m$ is 1-Cl and $R^3$ corresponds to line D1-6 of Table D1 and the meaning for the combination of $R^1$ and $R^2$ for each individual compound corresponds in each case to one line of Table B (compounds I.A1b.D1-6.B1 to I.A1b.D1-6.B455).

Table 14b Compounds of the formula I.A1b in which $(R^4)_m$ is 1-Cl and $R^3$ corresponds to line D1-7 of Table D1 and the meaning for the combination of $R^1$ and $R^2$ for each individual compound corresponds in each case to one line of Table B (compounds I.A1b.D1-7.B1 to I.A1b.D1-7.B455).

Table 15b Compounds of the formula I.A1b in which $(R^4)_m$ is 1-F and $R^3$ corresponds to line D1-1 of Table D1 and the meaning for the combination of $R^1$ and $R^2$ for each individual compound corresponds in each case to one line of Table B (compounds I.A1b.D1-1.B1 to I.A1b.D1-1.B455).

Table 16b Compounds of the formula I.A1 b in which $(R^4)_m$ is 1-F and $R^3$ corresponds to line D1-2 of Table D1 and the meaning for the combination of $R^1$ and $R^2$ for each individual compound corresponds in each case to one line of Table B (compounds I.A1b.D1-2.B1 to I.A1b.D1-2.B455).

Table 17b Compounds of the formula I.A1 b in which $(R^4)_m$ is 1-F and $R^3$ corresponds to line D1-3 of Table D1 and the meaning for the combination of $R^1$ and $R^2$ for each individual compound corresponds in each case to one line of Table B (compounds I.A1b.D1-3.B1 to I.A1b.D1-3.B455).

Table 18b Compounds of the formula I.A1 b in which $(R^4)_m$ is 1-F and $R^3$ corresponds to line D1-4 of Table D1 and the meaning for the combination of $R^1$ and $R^2$ for each individual compound corresponds in each case to one line of Table B (compounds I.A1b.D1-4.B1 to I.A1b.D1-4.B455).

Table 19b Compounds of the formula I.A1 b in which $(R^4)_m$ is 1-F and $R^3$ corresponds to line D1-5 of Table D1 and the meaning for the combination of $R^1$ and $R^2$ for each individual compound corresponds in each case to one line of Table B (compounds I.A1b.D1-5.B1 to I.A1b.D1-5.B455).

Table 20b Compounds of the formula I.A1 b in which $(R^4)_m$ is 1-F and $R^3$ corresponds to line D1-6 of Table D1 and the meaning for the combination of $R^1$ and $R^2$ for each individual compound corresponds in each case to one line of Table B (compounds I.A1b.D1-6.B1 to I.A1b.D1-6.B455).

Table 21 b Compounds of the formula I.A1 b in which $(R^4)_m$ is 1-F and $R^3$ corresponds to line D1-7 of Table D1 and the meaning for the combination of $R^1$ and $R^2$ for each individual compound corresponds in each case to one line of Table B (compounds I.A1b.D1-7.B1 to I.A1b.D1-7.B455).

Table 22b Compounds of the formula I.A1b in which $(R^4)_m$ is 1-$CH_3$ and $R^3$ corresponds to line D1-1 of Table D1 and the meaning for the combination of $R^1$ and $R^2$ for each individual compound corresponds in each case to one line of Table B (compounds I.A1b.D1-1.B1 to I.A1b.D1-1.B455).

Table 23b Compounds of the formula I.A1 b in which $(R^4)_m$ is 1-$CH_3$ and $R^3$ corresponds to line D1-2 of Table D1 and the meaning for the combination of $R^1$ and $R^2$ for each individual compound corresponds in each case to one line of Table B (compounds I.A1b.D1-2.B1 to I.A1 b.D1-2.B455).

Table 24b Compounds of the formula I.A1 b in which $(R^4)_m$ is 1-$CH_3$ and $R^3$ corresponds to line D1-3 of Table D1 and the meaning for the combination of $R^1$ and $R^2$ for each individual compound corresponds in each case to one line of Table B (compounds I.A1b.D1-3.B1 to I.A1 b.D1-3.B455).

Table 25b Compounds of the formula I.A1 b in which $(R^4)_m$ is 1-$CH_3$ and $R^3$ corresponds to line D1-4 of Table D1 and the meaning for the combination of $R^1$ and $R^2$ for each individual compound corresponds in each case to one line of Table B (compounds I.A1b.D1-4.B1 to I.A1b.D1-4.B455).

Table 26b Compounds of the formula I.A1 b in which $(R^4)_m$ is 1-$CH_3$ and $R^3$ corresponds to line D1-5 of Table D1 and the meaning for the combination of $R^1$ and $R^2$ for each individual compound corresponds in each case to one line of Table B (compounds I.A1b.D1-5.B1 to I.A1 b.D1-5.B455).

Table 27b Compounds of the formula I.A1 b in which $(R^4)_m$ is 1-$CH_3$ and $R^3$ corresponds to line D1-6 of Table D1 and the meaning for the combination of $R^1$ and $R^2$ for each individual compound corresponds in each case to one line of Table B (compounds I.A1b.D1-6.B1 to I.A1 b.D1-6.B455).

Table 28b Compounds of the formula I.A1 b in which $(R^4)_m$ is 1-$CH_3$ and $R^3$ corresponds to line D1-7 of Table D1 and the meaning for the combination of $R^1$ and $R^2$ for each individual compound corresponds in each case to one line of Table B (compounds I.A1b.D1-7.B1 to I.A1b.D1-7.B455).

Table 29b Compounds of the formula I.A1 b in which $(R^4)_m$ is 1-CN and $R^3$ corresponds to line D1-1 of Table D1 and the meaning for the combination of $R^1$ and $R^2$ for each individual compound corresponds in each case to one line of Table B (compounds I.A1b.D1-1.B1 to I.A1b.D1-1.B455).

Table 30b Compounds of the formula I.A1 b in which $(R^4)_m$ is 1-CN and $R^3$ corresponds to line D1-2 of Table D1 and the meaning for the combination of $R^1$ and $R^2$ for each individual compound corresponds in each case to one line of Table B (compounds I.A1b.D1-2.B1 to I.A1 b.D1-2.B455).

Table 31 b Compounds of the formula I.A1 b in which $(R^4)_m$ is 1-CN and $R^3$ corresponds to line D1-3 of Table D1 and the meaning for the combination of $R^1$ and $R^2$ for each individual compound corresponds in each case to one line of Table B (compounds I.A1b.D1-3.B1 to I.A1 b.D1-3.B455).

Table 32b Compounds of the formula I.A1 b in which $(R^4)_m$ is 1-CN and $R^3$ corresponds to line D1-4 of Table D1 and the meaning for the combination of $R^1$ and $R^2$ for each individual compound corresponds in each case to one line of Table B (compounds I.A1b.D1-4.B1 to I.A1b.D1-4.B455).

Table 33b Compounds of the formula I.A1 b in which $(R^4)_m$ is 1-CN and $R^3$ corresponds to line D1-5 of Table D1 and the meaning for the combination of $R^1$ and $R^2$ for each individual compound corresponds in each case to one line of Table B (compounds I.A1b.D1-5.B1 to I.A1 b.D1-5.B455).

Table 34b Compounds of the formula I.A1 b in which $(R^4)_m$ is 1-CN and $R^3$ corresponds to line D1-6 of Table D1 and the meaning for the combination of $R^1$ and $R^2$ for each individual compound corresponds in each case to one line of Table B (compounds I.A1b.D1-6.B1 to I.A1b.D1-6.B455).

Table 35b Compounds of the formula I.A1 b in which $(R^4)_m$ is 1-CN and $R^3$ corresponds to line D1-7 of Table D1 and the meaning for the combination of $R^1$ and $R^2$ for each individual compound corresponds in each case to one line of Table B (compounds I.A1b.D1-7.B1 to I.A1b.D1-7.B455).

Table 36b Compounds of the formula I.A1b in which $(R^4)_m$ is 3,3-$Cl_2$ and $R^3$ corresponds to line D1-1 of Table D1 and the meaning for the combination of $R^1$ and $R^2$ for each individual compound corresponds in each case to one line of Table B (compounds I.A1b.D1-1.B1 to I.A1b.D1-1.B455).

Table 37b Compounds of the formula I.A1 b in which $(R^4)_m$ is 3,3-$Cl_2$ and $R^3$ corresponds to line D1-2 of Table D1 and the meaning for the combination of $R^1$ and $R^2$ for each individual compound corresponds in each case to one line of Table B (compounds I.A1b.D1-2.B1 to I.A1b.D1-2.B455).

Table 38b Compounds of the formula I.A1 b in which $(R^4)_m$ is 3,3-$Cl_2$ and $R^3$ corresponds to line D1-3 of Table D1 and the meaning for the combination of $R^1$ and $R^2$ for each individual compound corresponds in each case to one line of Table B (compounds I.A1b.D1-3.B1 to I.A1 b.D1-3.B455).

Table 39b Compounds of the formula I.A1 b in which $(R^4)_m$ is 3,3-$Cl_2$ and $R^3$ corresponds to line D1-4 of Table D1 and the meaning for the combination of $R^1$ and $R^2$ for each individual compound corresponds in each case to one line of Table B (compounds I.A1b.D1-4.B1 to I.A1 b.D1-4.B455).

Table 40b Compounds of the formula I.A1 b in which $(R^4)_m$ is 3,3-$Cl_2$ and $R^3$ corresponds to line D1-5 of Table D1 and the meaning for the combination of $R^1$ and $R^2$ for each individual compound corresponds in each case to one line of Table B (compounds I.A1b.D1-5.B1 to I.A1 b.D1-5.B455).

Table 41b Compounds of the formula I.A1b in which $(R^4)_m$ is 3,3-$Cl_2$ and $R^3$ corresponds to line D1-6 of Table D1 and the meaning for the combination of $R^1$ and $R^2$ for each individual compound corresponds in each case to one line of Table B (compounds I.A1b.D1-6.B1 to I.A1 b.D1-6.B455).

Table 42b Compounds of the formula I.A1 b in which $(R^4)_m$ is 3,3-$Cl_2$ and $R^3$ corresponds to line D1-7 of Table D1 and the meaning for the combination of $R^1$ and $R^2$ for each individual compound corresponds in each case to one line of Table B (compounds I.A1b.D1-7.B1 to I.A1 b.D1-7.B455).

Table 43b Compounds of the formula I.A1 b in which $(R^4)_m$ is 3,3-$(CH_3)_2$ and $R^3$ corresponds to line D1-1 of Table D1 and the meaning for the combination of $R^1$ and $R^2$ for each individual compound corresponds in each case to one line of Table B (compounds I.A1b.D1-1.B1 to I.A1b.D1-1.B455).

Table 44b Compounds of the formula I.A1 b in which $(R^4)_m$ is 3,3-$(CH_3)_2$ and $R^3$ corresponds to line D1-2 of Table D1 and the meaning for the combination of $R^1$ and $R^2$ for each individual compound corresponds in each case to one line of Table B (compounds I.A1b.D1-2.B1 to I.A1b.D1-2.B455).

Table 45b Compounds of the formula I.A1 b in which $(R^4)_m$ is 3,3-$(CH_3)_2$ and $R^3$ corresponds to line D1-3 of Table D1 and the meaning for the combination of $R^1$ and $R^2$ for each individual compound corresponds in each case to one line of Table B (compounds I.A1b.D1-3.B1 to I.A1 b.D1-3.B455).

Table 46b Compounds of the formula I.A1 b in which $(R^4)_m$ is 3,3-$(CH_3)_2$ and $R^3$ corresponds to line D1-4 of Table D1 and the meaning for the combination of $R^1$ and $R^2$ for each individual compound corresponds in each case to one line of Table B (compounds I.A1b.D1-4.B1 to I.A1 b.D1-4.B455).

Table 47b Compounds of the formula I.A1 b in which $(R^4)_m$ is 3,3-$(CH_3)_2$ and $R^3$ corresponds to line D1-5 of Table D1 and the meaning for the combination of $R^1$ and $R^2$ for each individual compound corresponds in each case to one line of Table B (compounds I.A1b.D1-5.B1 to I.A1 b.D1-5.B455).

Table 48b Compounds of the formula I.A1 b in which $(R^4)_m$ is 3,3-$(CH_3)_2$ and $R^3$ corresponds to line D1-6 of Table D1 and the meaning for the combination of $R^1$ and $R^2$ for each individual compound corresponds in each case to one line of Table B (compounds I.A1b.D1-6.B1 to I.A1 b.D1-6.B455).

Table 49b Compounds of the formula I.A1 b in which $(R^4)_m$ is 3,3-$(CH_3)_2$ and $R^3$ corresponds to line D1-7 of Table D1 and the meaning for the combination of $R^1$ and $R^2$ for each individual compound corresponds in each case to one line of Table B (compounds I.A1b.D1-7.B1 to I.A1b.D1-7.B455).

Table 1c Compounds of the formula I.A1c in which m in $(R^4)_m$ is 0 and $R^3$ corresponds to line D1-1 of Table D1 and the meaning for the combination of $R^1$ and $R^2$ for each individual compound corresponds in each case to one line of Table B (compounds I.A1c.D1-1.B1 to I.A1c.D1-1.B455).

Table 2c Compounds of the formula I.A1c in which m in $(R^4)_m$ is 0 and $R^3$ corresponds to line D1-2 of Table D1 and the meaning for the combination of $R^1$ and $R^2$ for each individual compound corresponds in each case to one line of Table B (compounds I.A1c.D1-2.B1 to I.A1c.D1-2.B455).

Table 3c Compounds of the formula I.A1c in which m in $(R^4)_m$ is 0 and $R^3$ corresponds to line D1-3 of Table D1 and the meaning for the combination of $R^1$ and $R^2$ for each individual compound corresponds in each case to one line of Table B (compounds I.A1c.D1-3.B1 to I.A1c.D1-3.B455).

Table 4c Compounds of the formula I.A1c in which m in $(R^4)_m$ is 0 and $R^3$ corresponds to line D1-4 of Table D1 and the meaning for the combination of $R^1$ and $R^2$ for each individual compound corresponds in each case to one line of Table B (compounds I.A1c.D1-4.B1 to I.A1c.D1-4.B455).

Table 5c Compounds of the formula I.A1c in which m in $(R^4)_m$ is 0 and $R^3$ corresponds to line D1-5 of Table D1 and the meaning for the combination of $R^1$ and $R^2$ for each individual compound corresponds in each case to one line of Table B (compounds I.A1c.D1-5.B1 to I.A1c.D1-5.B455).

Table 6c Compounds of the formula I.A1c in which m in $(R^4)_m$ is 0 and $R^3$ corresponds to line D1-6 of Table D1 and the meaning for the combination of $R^1$ and $R^2$ for each individual compound corresponds in each case to one line of Table B (compounds I.A1c.D1-6.B1 to I.A1c.D1-6.B455).

Table 7c Compounds of the formula I.A1c in which m in $(R^4)_m$ is 0 and $R^3$ corresponds to line D1-7 of Table D1 and the meaning for the combination of $R^1$ and $R^2$ for each individual compound corresponds in each case to one line of Table B (compounds I.A1c.D1-7.B1 to I.A1c.D1-7.B455).

Table 8c Compounds of the formula I.A1c in which $(R^4)_m$ is 1-Cl and $R^3$ corresponds to line D1-1 of Table D1 and the meaning for the combination of $R^1$ and $R^2$ for each individual compound corresponds in each case to one line of Table B (compounds I.A1c.D1-1.B1 to I.A1c.D1-1.B455).

Table 9c Compounds of the formula I.A1c in which $(R^4)_m$ is 1-Cl and $R^3$ corresponds to line D1-2 of Table D1 and the meaning for the combination of $R^1$ and $R^2$ for each individual compound corresponds in each case to one line of Table B (compounds I.A1c.D1-2.B1 to I.A1c.D1-2.B455).

Table 10c Compounds of the formula I.A1c in which $(R^4)_m$ is 1-Cl and $R^3$ corresponds to line D1-3 of Table D1 and the meaning for the combination of $R^1$ and $R^2$ for each individual compound corresponds in each case to one line of Table B (compounds I.A1c.D1-3.B1 to I.A1c.D1-3.B455).

Table 11c Compounds of the formula I.A1c in which $(R^4)_m$ is 1-Cl and $R^3$ corresponds to line D1-4 of Table D1 and the meaning for the combination of $R^1$ and $R^2$ for each individual compound corresponds in each case to one line of Table B (compounds I.A1c.D1-4.B1 to I.A1c.D1-4.B455).

Table 12c Compounds of the formula I.A1c in which $(R^4)_m$ is 1-Cl and $R^3$ corresponds to line D1-5 of Table D1 and the meaning for the combination of $R^1$ and $R^2$ for each individual compound corresponds in each case to one line of Table B (compounds I.A1c.D1-5.B1 to I.A1c.D1-5.B455).

Table 13c Compounds of the formula I.A1c in which $(R^4)_m$ is 1-Cl and $R^3$ corresponds to line D1-6 of Table D1 and the meaning for the combination of $R^1$ and $R^2$ for each individual compound corresponds in each case to one line of Table B (compounds I.A1c.D1-6.B1 to I.A1c.D1-6.B455).

Table 14c Compounds of the formula I.A1c in which $(R^4)_m$ is 1-Cl and $R^3$ corresponds to line D1-7 of Table D1 and the meaning for the combination of $R^1$ and $R^2$ for each individual compound corresponds in each case to one line of Table B (compounds I.A1c.D1-7.B1 to I.A1c.D1-7.B455).

Table 15c Compounds of the formula I.A1c in which $(R^4)_m$ is 1-F and $R^3$ corresponds to line D1-1 of Table D1 and the meaning for the combination of $R^1$ and $R^2$ for each individual compound corresponds in each case to one line of Table B (compounds I.A1c.D1-1.B1 to I.A1c.D1-1.B455).

Table 16c Compounds of the formula I.A1c in which $(R^4)_m$ is 1-F and $R^3$ corresponds to line D1-2 of Table D1 and the meaning for the combination of $R^1$ and $R^2$ for each individual compound corresponds in each case to one line of Table B (compounds I.A1c.D1-2.B1 to I.A1c.D1-2.B455).

Table 17c Compounds of the formula I.A1c in which $(R^4)_m$ is 1-F and $R^3$ corresponds to line D1-3 of Table D1 and the meaning for the combination of $R^1$ and $R^2$ for each individual compound corresponds in each case to one line of Table B (compounds I.A1c.D1-3.B1 to I.A1c.D1-3.B455).

Table 18c Compounds of the formula I.A1c in which $(R^4)_m$ is 1-F and $R^3$ corresponds to line D1-4 of Table D1 and the meaning for the combination of $R^1$ and $R^2$ for each individual compound corresponds in each case to one line of Table B (compounds I.A1c.D1-4.B1 to I.A1c.D1-4.B455).

Table 19c Compounds of the formula I.A1c in which $(R^4)_m$ is 1-F and $R^3$ corresponds to line D1-5 of Table D1 and the meaning for the combination of $R^1$ and $R^2$ for each individual compound corresponds in each case to one line of Table B (compounds I.A1c.D1-5.B1 to I.A1c.D1-5.B455).

Table 20c Compounds of the formula I.A1c in which $(R^4)_m$ is 1-F and $R^3$ corresponds to line D1-6 of Table D1 and the meaning for the combination of $R^1$ and $R^2$ for each individual compound corresponds in each case to one line of Table B (compounds I.A1c.D1-6.B1 to I.A1c.D1-6.B455).

Table 21c Compounds of the formula I.A1c in which $(R^4)_m$ is 1-F and $R^3$ corresponds to line D1-7 of Table D1 and the meaning for the combination of $R^1$ and $R^2$ for each individual compound corresponds in each case to one line of Table B (compounds I.A1c.D1-7.B1 to I.A1c.D1-7.B455).

Table 22c Compounds of the formula I.A1c in which $(R^4)_m$ is 1-$CH_3$ and $R^3$ corresponds to line D1-1 of Table D1 and the meaning for the combination of $R^1$ and $R^2$ for each individual compound corresponds in each case to one line of Table B (compounds I.A1c.D1-1.B1 to I.A1c.D1-1.B455).

Table 23c Compounds of the formula I.A1c in which $(R^4)_m$ is 1-$CH_3$ and $R^3$ corresponds to line D1-2 of Table D1 and the meaning for the combination of $R^1$ and $R^2$ for each individual compound corresponds in each case to one line of Table B (compounds I.A1c.D1-2.B1 to I.A1c.D1-2.B455).

Table 24c Compounds of the formula I.A1c in which $(R^4)_m$ is 1-$CH_3$ and $R^3$ corresponds to line D1-3 of Table D1 and the meaning for the combination of $R^1$ and $R^2$ for each individual compound corresponds in each case to one line of Table B (compounds I.A1c.D1-3.B1 to I.A1c.D1-3.B455).

Table 25c Compounds of the formula I.A1c in which $(R^4)_m$ is 1-$CH_3$ and $R^3$ corresponds to line D1-4 of Table D1 and the meaning for the combination of $R^1$ and $R^2$ for each individual compound corresponds in each case to one line of Table B (compounds I.A1c.D1-4.B1 to I.A1c.D1-4.B455).

Table 26c Compounds of the formula I.A1c in which $(R^4)_m$ is 1-$CH_3$ and $R^3$ corresponds to line D1-5 of Table D1 and the meaning for the combination of $R^1$ and $R^2$ for each individual compound corresponds in each case to one line of Table B (compounds I.A1c.D1-5.B1 to I.A1c.D1-5.B455).

Table 27c Compounds of the formula I.A1c in which $(R^4)_m$ is 1-$CH_3$ and $R^3$ corresponds to line D1-6 of Table D1 and the meaning for the combination of $R^1$ and $R^2$ for each individual compound corresponds in each case to one line of Table B (compounds I.A1c.D1-6.B1 to I.A1c.D1-6.B455).

Table 28c Compounds of the formula I.A1c in which $(R^4)_m$ is 1-$CH_3$ and $R^3$ corresponds to line D1-7 of Table D1 and the meaning for the combination of $R^1$ and $R^2$ for each individual compound corresponds in each case to one line of Table B (compounds I.A1c.D1-7.B1 to I.A1c.D1-7.B455).

Table 29c Compounds of the formula I.A1c in which $(R^4)_m$ is 1-CN and $R^3$ corresponds to line D1-1 of Table D1 and the meaning for the combination of $R^1$ and $R^2$ for each individual compound corresponds in each case to one line of Table B (compounds I.A1c.D1-1.B1 to I.A1c.D1-1.B455).

Table 30c Compounds of the formula I.A1c in which $(R^4)_m$ is 1-CN and $R^3$ corresponds to line D1-2 of Table D1 and the meaning for the combination of $R^1$ and $R^2$ for each individual compound corresponds in each case to one line of Table B (compounds I.A1c.D1-2.B1 to I.A1c.D1-2.B455).

Table 31c Compounds of the formula I.A1c in which $(R^4)_m$ is 1-CN and $R^3$ corresponds to line D1-3 of Table D1 and the meaning for the combination of $R^1$ and $R^2$ for each individual compound corresponds in each case to one line of Table B (compounds I.A1c.D1-3.B1 to I.A1c.D1-3.B455).

Table 32c Compounds of the formula I.A1c in which $(R^4)_m$ is 1-CN and $R^3$ corresponds to line D1-4 of Table D1 and the meaning for the combination of $R^1$ and $R^2$ for each individual compound corresponds in each case to one line of Table B (compounds I.A1c.D1-4.B1 to I.A1c.D1-4.B455).

Table 33c Compounds of the formula I.A1c in which $(R^4)_m$ is 1-CN and $R^3$ corresponds to line D1-5 of Table D1 and the meaning for the combination of $R^1$ and $R^2$ for each individual compound corresponds in each case to one line of Table B (compounds I.A1c.D1-5.B1 to I.A1c.D1-5.B455).

Table 34c Compounds of the formula I.A1c in which $(R^4)_m$ is 1-CN and $R^3$ corresponds to line D1-6 of Table D1 and the meaning for the combination of $R^1$ and $R^2$ for each individual compound corresponds in each case to one line of Table B (compounds I.A1c.D1-6.B1 to I.A1c.D1-6.B455).

Table 35c Compounds of the formula I.A1c in which $(R^4)_m$ is 1-CN and $R^3$ corresponds to line D1-7 of Table D1 and the meaning for the combination of $R^1$ and $R^2$ for each individual compound corresponds in each case to one line of Table B (compounds I.A1c.D1-7.B1 to I.A1c.D1-7.B455).

Table 1d Compounds of the formula I.A1d in which m in $(R^4)_m$ is 0 and $R^3$ corresponds to line D1-1 of Table D1 and the meaning for the combination of $R^1$ and $R^2$ for each individual compound corresponds in each case to one line of Table B (compounds I.A1d.D1-1.B1 to I.A1d.D1-1.B455).

Table 2d Compounds of the formula I.A1d in which m in $(R^4)_m$ is 0 and $R^3$ corresponds to line D1-2 of Table D1 and the meaning for the combination of $R^1$ and $R^2$ for each individual compound corresponds in each case to one line of Table B (compounds I.A1d.D1-2.B1 to I.A1d.D1-2.B455).

Table 3d Compounds of the formula I.A1d in which m in $(R^4)_m$ is 0 and $R^3$ corresponds to line D1-3 of Table D1 and the meaning for the combination of $R^1$ and $R^2$ for each individual compound corresponds in each case to one line of Table B (compounds I.A1d.D1-3.B1 to I.A1d.D1-3.B455).

Table 4d Compounds of the formula I.A1d in which m in $(R^4)_m$ is 0 and $R^3$ corresponds to line D1-4 of Table D1 and the meaning for the combination of $R^1$ and $R^2$ for each individual compound corresponds in each case to one line of Table B (compounds I.A1d.D1-4.B1 to I.A1 d.D1-4.B455).

Table 5d Compounds of the formula I.A1d in which m in $(R^4)_m$ is 0 and $R^3$ corresponds to line D1-5 of Table D1 and the meaning for the combination of $R^1$ and $R^2$ for each individual compound corresponds in each case to one line of Table B (compounds I.A1d.D1-5.B1 to I.A1 d.D1-5.B455).

Table 6d Compounds of the formula I.A1d in which m in $(R^4)_m$ is 0 and $R^3$ corresponds to line D1-6 of Table D1 and the meaning for the combination of $R^1$ and $R^2$ for each individual compound corresponds in each case to one line of Table B (compounds I.A1d.D1-6.B1 to I.A1 d.D1-6.B455).

Table 7d Compounds of the formula I.A1d in which m in $(R^4)_m$ is 0 and $R^3$ corresponds to line D1-7 of Table D1 and the meaning for the combination of $R^1$ and $R^2$ for each individual compound corresponds in each case to one line of Table B (compounds I.A1d.D1-7.B1 to I.A1 d.D1-7.B455).

Table 8d Compounds of the formula I.A1d in which $(R^4)_m$ is 1-Cl and $R^3$ corresponds to line D1-1 of Table D1 and the meaning for the combination of $R^1$ and $R^2$ for each individual compound corresponds in each case to one line of Table B (compounds I.A1d.D1-1.B1 to I.A1d.D1-1.B455).

Table 9d Compounds of the formula I.A1d in which $(R^4)_m$ is 1-Cl and $R^3$ corresponds to line D1-2 of Table D1 and the meaning for the combination of $R^1$ and $R^2$ for each individual compound corresponds in each case to one line of Table B (compounds I.A1d.D1-2.B1 to I.A1d.D1-2.B455).

Table 10d Compounds of the formula I.A1d in which $(R^4)_m$ is 1-Cl and $R^3$ corresponds to line D1-3 of Table D1 and the meaning for the combination of $R^1$ and $R^2$ for each individual compound corresponds in each case to one line of Table B (compounds I.A1d.D1-3.B1 to I.A1d.D1-3.B455).

Table 11d Compounds of the formula I.A1 d in which $(R^4)_m$ is 1-Cl and $R^3$ corresponds to line D1-4 of Table D1 and the meaning for the combination of $R^1$ and $R^2$ for each individual compound corresponds in each case to one line of Table B (compounds I.A1d.D1-4.B1 to I.A1d.D1-4.B455).

Table 12d Compounds of the formula I.A1d in which $(R^4)_m$ is 1-Cl and $R^3$ corresponds to line D1-5 of Table D1 and the meaning for the combination of $R^1$ and $R^2$ for each individual compound corresponds in each case to one line of Table B (compounds I.A1d.D1-5.B1 to I.A1d.D1-5.B455).

Table 13d Compounds of the formula I.A1d in which $(R^4)_m$ is 1-Cl and $R^3$ corresponds to line D1-6 of Table D1 and the meaning for the combination of $R^1$ and $R^2$ for each individual compound corresponds in each case to one line of Table B (compounds I.A1d.D1-6.B1 to I.A1d.D1-6.B455).

Table 14d Compounds of the formula I.A1d in which $(R^4)_m$ is 1-Cl and $R^3$ corresponds to line D1-7 of Table D1 and the meaning for the combination of $R^1$ and $R^2$ for each individual compound corresponds in each case to one line of Table B (compounds I.A1d.D1-7.B1 to I.A1d.D1-7.B455).

Table 15d Compounds of the formula I.A1d in which $(R^4)_m$ is 1-F and $R^3$ corresponds to line D1-1 of Table D1 and the meaning for the combination of $R^1$ and $R^2$ for each individual compound corresponds in each case to one line of Table B (compounds I.A1d.D1-1.B1 to I.A1d.D1-1.B455).

Table 16d Compounds of the formula I.A1d in which $(R^4)_m$ is 1-F and $R^3$ corresponds to line D1-2 of Table D1 and the meaning for the combination of $R^1$ and $R^2$ for each individual compound corresponds in each case to one line of Table B (compounds I.A1d.D1-2.B1 to I.A1 d.D1-2.B455).

Table 17d Compounds of the formula I.A1d in which $(R^4)_m$ is 1-F and $R^3$ corresponds to line D1-3 of Table D1 and the meaning for the combination of $R^1$ and $R^2$ for each individual compound corresponds in each case to one line of Table B (compounds I.A1d.D1-3.B1 to I.A1d.D1-3.B455).

Table 18d Compounds of the formula I.A1d in which $(R^4)_m$ is 1-F and $R^3$ corresponds to line D1-4 of Table D1 and the meaning for the combination of $R^1$ and $R^2$ for each individual compound corresponds in each case to one line of Table B (compounds I.A1d.D1-4.B1 to I.A1d.D1-4.B455).

Table 19d Compounds of the formula I.A1d in which $(R^4)_m$ is 1-F and $R^3$ corresponds to line D1-5 of Table D1 and the meaning for the combination of $R^1$ and $R^2$ for each individual compound corresponds in each case to one line of Table B (compounds I.A1d.D1-5.B1 to I.A1d.D1-5.B455).

Table 20d Compounds of the formula I.A1d in which $(R^4)_m$ is 1-F and $R^3$ corresponds to line D1-6 of Table D1 and the meaning for the combination of $R^1$ and $R^2$ for each individual compound corresponds in each case to one line of Table B (compounds I.A1d.D1-6.B1 to I.A1d.D1-6.B455).

Table 21d Compounds of the formula I.A1d in which $(R^4)_m$ is 1-F and $R^3$ corresponds to line D1-7 of Table D1 and the meaning for the combination of $R^1$ and $R^2$ for each individual compound corresponds in each case to one line of Table B (compounds I.A1d.D1-7.B1 to I.A1d.D1-7.B455).

Table 22d Compounds of the formula I.A1d in which $(R^4)_m$ is 1-CH$_3$ and $R^3$ corresponds to line D1-1 of Table D1 and the meaning for the combination of $R^1$ and $R^2$ for each individual compound corresponds in each case to one line of Table B (compounds I.A1d.D1-1.B1 to I.A1d.D1-1.B455).

Table 23d Compounds of the formula I.A1d in which $(R^4)_m$ is 1-CH$_3$ and $R^3$ corresponds to line D1-2 of Table D1 and the meaning for the combination of $R^1$ and $R^2$ for each individual compound corresponds in each case to one line of Table B (compounds I.A1d.D1-2.B1 to I.A1 d.D1-2.B455).

Table 24d Compounds of the formula I.A1d in which $(R^4)_m$ is 1-CH$_3$ and $R^3$ corresponds to line D1-3 of Table D1 and the meaning for the combination of $R^1$ and $R^2$ for each individual compound corresponds in each case to one line of Table B (compounds I.A1d.D1-3.B1 to I.A1d.D1-3.B455).

Table 25d Compounds of the formula I.A1d in which $(R^4)_m$ is 1-$CH_3$ and $R^3$ corresponds to line D1-4 of Table D1 and the meaning for the combination of $R^1$ and $R^2$ for each individual compound corresponds in each case to one line of Table B (compounds I.A1d.D1-4.B1 to I.A1d.D1-4.B455).

Table 26d Compounds of the formula I.A1d in which $(R^4)_m$ is 1-$CH_3$ and $R^3$ corresponds to line D1-5 of Table D1 and the meaning for the combination of $R^1$ and $R^2$ for each individual compound corresponds in each case to one line of Table B (compounds I.A1d.D1-5.B1 to I.A1d.D1-5.B455).

Table 27d Compounds of the formula I.A1d in which $(R^4)_m$ is 1-$CH_3$ and $R^3$ corresponds to line D1-6 of Table D1 and the meaning for the combination of $R^1$ and $R^2$ for each individual compound corresponds in each case to one line of Table B (compounds I.A1d.D1-6.B1 to I.A1d.D1-6.B455).

Table 28d Compounds of the formula I.A1d in which $(R^4)_m$ is 1-$CH_3$ and $R^3$ corresponds to line D1-7 of Table D1 and the meaning for the combination of $R^1$ and $R^2$ for each individual compound corresponds in each case to one line of Table B (compounds I.A1d.D1-7.B1 to I.A1d.D1-7.B455).

Table 29d Compounds of the formula I.A1d in which $(R^4)_m$ is 1-CN and $R^3$ corresponds to line D1-1 of Table D1 and the meaning for the combination of $R^1$ and $R^2$ for each individual compound corresponds in each case to one line of Table B (compounds I.A1d.D1-1.B1 to I.A1d.D1-1.B455).

Table 30d Compounds of the formula I.A1d in which $(R^4)_m$ is 1-CN and $R^3$ corresponds to line D1-2 of Table D1 and the meaning for the combination of $R^1$ and $R^2$ for each individual compound corresponds in each case to one line of Table B (compounds I.A1d.D1-2.B1 to I.A1d.D1-2.B455).

Table 31d Compounds of the formula I.A1d in which $(R^4)_m$ is 1-CN and $R^3$ corresponds to line D1-3 of Table D1 and the meaning for the combination of $R^1$ and $R^2$ for each individual compound corresponds in each case to one line of Table B (compounds I.A1d.D1-3.B1 to I.A1d.D1-3.B455).

Table 32d Compounds of the formula I.A1d in which $(R^4)_m$ is 1-CN and $R^3$ corresponds to line D1-4 of Table D1 and the meaning for the combination of $R^1$ and $R^2$ for each individual compound corresponds in each case to one line of Table B (compounds I.A1d.D1-4.B1 to I.A1d.D1-4.B455).

Table 33d Compounds of the formula I.A1d in which $(R^4)_m$ is 1-CN and $R^3$ corresponds to line D1-5 of Table D1 and the meaning for the combination of $R^1$ and $R^2$ for each individual compound corresponds in each case to one line of Table B (compounds I.A1d.D1-5.B1 to I.A1d.D1-5.B455).

Table 34d Compounds of the formula I.A1d in which $(R^4)_m$ is 1-CN and $R^3$ corresponds to line D1-6 of Table D1 and the meaning for the combination of $R^1$ and $R^2$ for each individual compound corresponds in each case to one line of Table B (compounds I.A1d.D1-6.B1 to I.A1d.D1-6.B455).

Table 35d Compounds of the formula I.A1d in which $(R^4)_m$ is 1-CN and $R^3$ corresponds to line D1-7 of Table D1 and the meaning for the combination of $R^1$ and $R^2$ for each individual compound corresponds in each case to one line of Table B (compounds I.A1d.D1-7.B1 to I.A1d.D1-7.B455).

Table 1e Compounds of the formula I.A2c in which m in $(R^4)_m$ is 0 and $R^3$ corresponds to line D1-1 of Table D1 and the meaning for the combination of $R^1$ and $R^2$ for each individual compound corresponds in each case to one line of Table B (compounds I.A2c.D1-1.B1 to I.A2c.D1-1.B455).

Table 2e Compounds of the formula I.A2c in which m in $(R^4)_m$ is 0 and $R^3$ corresponds to line D1-2 of Table D1 and the meaning for the combination of $R^1$ and $R^2$ for each individual compound corresponds in each case to one line of Table B (compounds I.A2c.D1-2.B1 to I.A2c.D1-2.B455).

Table 3e Compounds of the formula I.A2c in which m in $(R^4)_m$ is 0 and $R^3$ corresponds to line D1-3 of Table D1 and the meaning for the combination of $R^1$ and $R^2$ for each individual compound corresponds in each case to one line of Table B (compounds I.A2c.D1-3.B1 to I.A2c.D1-3.B455).

Table 4e Compounds of the formula I.A2c in which m in $(R^4)_m$ is 0 and $R^3$ corresponds to line D1-4 of Table D1 and the meaning for the combination of $R^1$ and $R^2$ for each individual compound corresponds in each case to one line of Table B (compounds I.A2c.D1-4.B1 to I.A2c.D1-4.B455).

Table 5e Compounds of the formula I.A2c in which m in $(R^4)_m$ is 0 and $R^3$ corresponds to line D1-5 of Table D1 and the meaning for the combination of $R^1$ and $R^2$ for each individual compound corresponds in each case to one line of Table B (compounds I.A2c.D1-5.B1 to I.A2c.D1-5.B455).

Table 6e Compounds of the formula I.A2c in which m in $(R^4)_m$ is 0 and $R^3$ corresponds to line D1-6 of Table D1 and the meaning for the combination of $R^1$ and $R^2$ for each individual compound corresponds in each case to one line of Table B (compounds I.A2c.D1-6.B1 to I.A2c.D1-6.B455).

Table 7e Compounds of the formula I.A2c in which m in $(R^4)_m$ is 0 and $R^3$ corresponds to line D1-7 of Table D1 and the meaning for the combination of $R^1$ and $R^2$ for each individual compound corresponds in each case to one line of Table B (compounds I.A2c.D1-7.B1 to I.A2c.D1-7.B455).

Table 1f Compounds of the formula I.A2d in which m in $(R^4)_m$ is 0 and $R^3$ corresponds to line D1-1 of Table D1 and the meaning for the combination of $R^1$ and $R^2$ for each individual compound corresponds in each case to one line of Table B (compounds I.A2d.D1-1.B1 to I.A2d.D1-1.B455).

Table 2f Compounds of the formula I.A2d in which m in $(R^4)_m$ is 0 and $R^3$ corresponds to line D1-2 of Table D1 and the meaning for the combination of $R^1$ and $R^2$ for each individual compound corresponds in each case to one line of Table B (compounds I.A2d.D1-2.B1 to I.A2d.D1-2.B455).

Table 3f Compounds of the formula I.A2d in which m in $(R^4)_m$ is 0 and $R^3$ corresponds to line D1-3 of Table D1 and the meaning for the combination of $R^1$ and $R^2$ for each individual compound corresponds in each case to one line of Table B (compounds I.A2d.D1-3.B1 to I.A2d.D1-3.B455).

Table 4f Compounds of the formula I.A2d in which m in $(R^4)_m$ is 0 and $R^3$ corresponds to line D1-4 of Table D1 and the meaning for the combination of $R^1$ and $R^2$ for each individual compound corresponds in each case to one line of Table B (compounds I.A2d.D1-4.B1 to I.A2d.D1-4.B455).

Table 5f Compounds of the formula I.A2d in which m in $(R^4)_m$ is 0 and $R^3$ corresponds to line D1-5 of Table D1 and the meaning for the combination of $R^1$ and $R^2$ for each individual compound corresponds in each case to one line of Table B (compounds I.A2d.D1-5.B1 to I.A2d.D1-5.B455).

Table 6f Compounds of the formula I.A2d in which m in $(R^4)_m$ is 0 and $R^3$ corresponds to line D1-6 of Table D1 and the meaning for the combination of $R^1$ and $R^2$ for each individual compound corresponds in each case to one line of Table B (compounds I.A2d.D1-6.B1 to I.A2d.D1-6.B455).

Table 7f Compounds of the formula I.A2d in which m in $(R^4)_m$ is 0 and $R^3$ corresponds to line D1-7 of Table D1 and the meaning for the combination of $R^1$ and $R^2$ for each individual compound corresponds in each case to one line of Table B (compounds I.A2d.D1-7.B1 to I.A2d.D1-7.B455).

A further embodiment of the invention relates to the compounds of the formula I.B1 that are compiled in the Tables 1g to 49g below. Each of the groups mentioned for a substituent in the tables is furthermore per se, independently of the combination in which it is mentioned, a particularly preferred aspect of the substituent in question.

Table 1g Compounds of the formula I.B1a in which m in $(R^4)_m$ is 0 and $R^3$ corresponds to line D1-1 of Table D1 and the meaning for the combination of $R^1$ and $R^2$ for each individual compound corresponds in each case to one line of Table B (compounds I.B1a.D1-1.B1 to I.B1a.D1-1.B455).

Table 2g Compounds of the formula I.B1a in which m in $(R^4)_m$ is 0 and $R^3$ corresponds to line D1-2 of Table D1 and the meaning for the combination of $R^1$ and $R^2$ for each individual compound corresponds in each case to one line of Table B (compounds I.B1a.D1-2.B1 to I.B1a.D1-2.B455).

Table 3g Compounds of the formula I.B1a in which m in $(R^4)_m$ is 0 and $R^3$ corresponds to line D1-3 of Table D1 and the meaning for the combination of $R^1$ and $R^2$ for each individual compound corresponds in each case to one line of Table B (compounds I.B1a.D1-3.B1 to I.B1a.D1-3.B455).

Table 4g Compounds of the formula I.B1a in which m in $(R^4)_m$ is 0 and $R^3$ corresponds to line D1-4 of Table D1 and the meaning for the combination of $R^1$ and $R^2$ for each individual compound corresponds in each case to one line of Table B (compounds I.B1a.D1-4.B1 to I.B1a.D1-4.B455).

Table 5g Compounds of the formula I.B1a in which m in $(R^4)_m$ is 0 and $R^3$ corresponds to line D1-5 of Table D1 and the meaning for the combination of $R^1$ and $R^2$ for each individual compound corresponds in each case to one line of Table B (compounds I.B1a.D1-5.B1 to I.B1a.D1-5.B455).

Table 6g Compounds of the formula I.B1a in which m in $(R^4)_m$ is 0 and $R^3$ corresponds to line D1-6 of Table D1 and the meaning for the combination of $R^1$ and $R^2$ for each individual compound corresponds in each case to one line of Table B (compounds I.B1a.D1-6.B1 to I.B1a.D1-6.B455).

Table 7g Compounds of the formula I.B1a in which m in $(R^4)_m$ is 0 and $R^3$ corresponds to line D1-7 of Table D1 and the meaning for the combination of $R^1$ and $R^2$ for each individual compound corresponds in each case to one line of Table B (compounds I.B1a.D1-7.B1 to I.B1a.D1-7.B455).

Table 8g Compounds of the formula I.B1a in which $(R^4)_m$ is 1-Cl and $R^3$ corresponds to line D1-1 of Table D1 and the meaning for the combination of $R^1$ and $R^2$ for each individual compound corresponds in each case to one line of Table B (compounds I.B1a.D1-1.B1 to I.B1a.D1-1.B455).

Table 9g Compounds of the formula I.B1a in which $(R^4)_m$ is 1-Cl and $R^3$ corresponds to line D1-2 of Table D1 and the meaning for the combination of $R^1$ and $R^2$ for each individual compound corresponds in each case to one line of Table B (compounds I.B1a.D1-2.B1 to I.B1a.D1-2.B455).

Table 10g Compounds of the formula I.B1a in which $(R^4)_m$ is 1-Cl and $R^3$ corresponds to line D1-3 of Table D1 and the meaning for the combination of $R^1$ and $R^2$ for each individual compound corresponds in each case to one line of Table B (compounds I.B1a.D1-3.B1 to I.B1a.D1-3.B455).

Table 11g Compounds of the formula I.B1a in which $(R^4)_m$ is 1-Cl and $R^3$ corresponds to line D1-4 of Table D1 and the meaning for the combination of $R^1$ and $R^2$ for each individual compound corresponds in each case to one line of Table B (compounds I.B1a.D1-4.B1 to I.B1a.D1-4.B455).

Table 12g Compounds of the formula I.B1a in which $(R^4)_m$ is 1-Cl and $R^3$ corresponds to line D1-5 of Table D1 and the meaning for the combination of $R^1$ and $R^2$ for each individual compound corresponds in each case to one line of Table B (compounds I.B1a.D1-5.B1 to I.B1a.D1-5.B455).

Table 13g Compounds of the formula I.B1a in which $(R^4)_m$ is 1-Cl and $R^3$ corresponds to line D1-6 of Table D1 and the meaning for the combination of $R^1$ and $R^2$ for each individual compound corresponds in each case to one line of Table B (compounds I.B1a.D1-6.B1 to I.B1a.D1-6.B455).

Table 14g Compounds of the formula I.B1a in which $(R^4)_m$ is 1-Cl and $R^3$ corresponds to line D1-7 of Table D1 and the meaning for the combination of $R^1$ and $R^2$ for each individual compound corresponds in each case to one line of Table B (compounds I.B1a.D1-7.B1 to I.B1a.D1-7.B455).

Table 15g Compounds of the formula I.B1a in which $(R^4)_m$ is 1-F and $R^3$ corresponds to line D1-1 of Table D1 and the meaning for the combination of $R^1$ and $R^2$ for each individual compound corresponds in each case to one line of Table B (compounds I.B1a.D1-1.B1 to I.B1a.D1-1.B455).

Table 16g Compounds of the formula I.B1a in which $(R^4)_m$ is 1-F and $R^3$ corresponds to line D1-2 of Table D1 and the meaning for the combination of $R^1$ and $R^2$ for each individual compound corresponds in each case to one line of Table B (compounds I.B1a.D1-2.B1 to I.B1a.D1-2.B455).

Table 17g Compounds of the formula I.B1a in which $(R^4)_m$ is 1-F and $R^3$ corresponds to line D1-3 of Table D1 and the meaning for the combination of $R^1$ and $R^2$ for each individual compound corresponds in each case to one line of Table B (compounds I.B1a.D1-3.B1 to I.B1a.D1-3.B455).

Table 18g Compounds of the formula I.B1a in which $(R^4)_m$ is 1-F and $R^3$ corresponds to line D1-4 of Table D1 and the meaning for the combination of $R^1$ and $R^2$ for each individual compound corresponds in each case to one line of Table B (compounds I.B1a.D1-4.B1 to I.B1a.D1-4.B455).

Table 19g Compounds of the formula I.B1a in which $(R^4)_m$ is 1-F and $R^3$ corresponds to line D1-5 of Table D1 and the meaning for the combination of $R^1$ and $R^2$ for each individual compound corresponds in each case to one line of Table B (compounds I.B1a.D1-5.B1 to I.B1a.D1-5.B455).

Table 20g Compounds of the formula I.B1a in which $(R^4)_m$ is 1-F and $R^3$ corresponds to line D1-6 of Table D1 and the meaning for the combination of $R^1$ and $R^2$ for each individual compound corresponds in each case to one line of Table B (compounds I.B1a.D1-6.B1 to I.B1a.D1-6.B455).

Table 21g Compounds of the formula I.B1a in which $(R^4)_m$ is 1-F and $R^3$ corresponds to line D1-7 of Table D1 and the meaning for the combination of $R^1$ and $R^2$ for each individual compound corresponds in each case to one line of Table B (compounds I.B1a.D1-7.B1 to I.B1a.D1-7.B455).

Table 22g Compounds of the formula I.B1a in which $(R^4)_m$ is 1-$CH_3$ and $R^3$ corresponds to line D1-1 of Table D1 and the meaning for the combination of $R^1$ and $R^2$ for each individual compound corresponds in each case to one line of Table B (compounds I.B1a.D1-1.B1 to I.B1a.D1-1.B455).

Table 23g Compounds of the formula I.B1a in which $(R^4)_m$ is 1-$CH_3$ and $R^3$ corresponds to line D1-2 of Table D1 and the meaning for the combination of $R^1$ and $R^2$ for each individual compound corresponds in each case to one line of Table B (compounds I.B1a.D1-2.B1 to I.B1a.D1-2.B455).

Table 24g Compounds of the formula I.B1a in which $(R^4)_m$ is 1-$CH_3$ and $R^3$ corresponds to line D1-3 of Table D1 and the meaning for the combination of $R^1$ and $R^2$ for each individual compound corresponds in each case to one line of Table B (compounds I.B1a.D1-3.B1 to I.B1a.D1-3.B455).

Table 25g Compounds of the formula I.B1a in which $(R^4)_m$ is 1-$CH_3$ and $R^3$ corresponds to line D1-4 of Table D1 and the meaning for the combination of $R^1$ and $R^2$ for each individual compound corresponds in each case to one line of Table B (compounds I.B1a.D1-4.B1 to I.B1a.D1-4.B455).

Table 26g Compounds of the formula I.B1a in which $(R^4)_m$ is 1-$CH_3$ and $R^3$ corresponds to line D1-5 of Table D1 and the meaning for the combination of $R^1$ and $R^2$ for each individual compound corresponds in each case to one line of Table B (compounds I.B1a.D1-5.B1 to I.B1a.D1-5.B455).

Table 27g Compounds of the formula I.B1a in which $(R^4)_m$ is 1-$CH_3$ and $R^3$ corresponds to line D1-6 of Table D1 and the meaning for the combination of $R^1$ and $R^2$ for each individual compound corresponds in each case to one line of Table B (compounds I.B1a.D1-6.B1 to I.B1a.D1-6.B455).

Table 28g Compounds of the formula I.B1a in which $(R^4)_m$ is 1-$CH_3$ and $R^3$ corresponds to line D1-7 of Table D1 and the meaning for the combination of $R^1$ and $R^2$ for each individual compound corresponds in each case to one line of Table B (compounds I.B1a.D1-7.B1 to I.B1a.D1-7.B455).

Table 29g Compounds of the formula I.B1a in which $(R^4)_m$ is 1-CN and $R^3$ corresponds to line D1-1 of Table D1 and the meaning for the combination of $R^1$ and $R^2$ for each individual compound corresponds in each case to one line of Table B (compounds I.B1a.D1-1.B1 to I.B1a.D1-1.B455).

Table 30g Compounds of the formula I.B1a in which $(R^4)_m$ is 1-CN and $R^3$ corresponds to line D1-2 of Table D1 and the meaning for the combination of $R^1$ and $R^2$ for each individual compound corresponds in each case to one line of Table B (compounds I.B1a.D1-2.B1 to I.B1a.D1-2.B455).

Table 31g Compounds of the formula I.B1a in which $(R^4)_m$ is 1-CN and $R^3$ corresponds to line D1-3 of Table D1 and the meaning for the combination of $R^1$ and $R^2$ for each individual compound corresponds in each case to one line of Table B (compounds I.B1a.D1-3.B1 to I.B1a.D1-3.B455).

Table 32g Compounds of the formula I.B1a in which $(R^4)_m$ is 1-CN and $R^3$ corresponds to line D1-4 of Table D1 and the meaning for the combination of $R^1$ and $R^2$ for each individual compound corresponds in each case to one line of Table B (compounds I.B1a.D1-4.B1 to I.B1a.D1-4.B455).

Table 33g Compounds of the formula I.B1a in which $(R^4)_m$ is 1-CN and $R^3$ corresponds to line D1-5 of Table D1 and the meaning for the combination of $R^1$ and $R^2$ for each individual compound corresponds in each case to one line of Table B (compounds I.B1a.D1-5.B1 to I.B1a.D1-5.B455).

Table 34g Compounds of the formula I.B1a in which $(R^4)_m$ is 1-CN and $R^3$ corresponds to line D1-6 of Table D1 and the meaning for the combination of $R^1$ and $R^2$ for each individual compound corresponds in each case to one line of Table B (compounds I.B1a.D1-6.B1 to I.B1a.D1-6.B455).

Table 35g Compounds of the formula I.B1a in which $(R^4)_m$ is 1-CN and $R^3$ corresponds to line D1-7 of Table D1 and the meaning for the combination of $R^1$ and $R^2$ for each individual compound corresponds in each case to one line of Table B (compounds I.B1a.D1-7.B1 to I.B1a.D1-7.B455).

Table 36g Compounds of the formula I.B1a in which $(R^4)_m$ is 2,2-$Cl_2$ and $R^3$ corresponds to line D1-1 of Table D1 and the meaning for the combination of $R^1$ and $R^2$ for each individual compound corresponds in each case to one line of Table B (compounds I.B1a.D1-1.B1 to I.B1a.D1-1.B455).

Table 37g Compounds of the formula I.B1a in which $(R^4)_m$ is 2,2-$Cl_2$ and $R^3$ corresponds to line D1-2 of Table D1 and the meaning for the combination of $R^1$ and $R^2$ for each individual compound corresponds in each case to one line of Table B (compounds I.B1a.D1-2.B1 to I.B1a.D1-2.B455).

Table 38g Compounds of the formula I.B1a in which $(R^4)_m$ is 2,2-$Cl_2$ and $R^3$ corresponds to line D1-3 of Table D1 and the meaning for the combination of $R^1$ and $R^2$ for each individual compound corresponds in each case to one line of Table B (compounds I.B1a.D1-3.B1 to I.B1a.D1-3.B455).

Table 39g Compounds of the formula I.B1a in which $(R^4)_m$ is 2,2-$Cl_2$ and $R^3$ corresponds to line D1-4 of Table D1 and the meaning for the combination of $R^1$ and $R^2$ for each individual compound corresponds in each case to one line of Table B (compounds I.B1a.D1-4.B1 to I.B1a.D1-4.B455).

Table 40g Compounds of the formula I.B1a in which $(R^4)_m$ is 2,2-$Cl_2$ and $R^3$ corresponds to line D1-5 of Table D1 and the meaning for the combination of $R^1$ and $R^2$ for each individual compound corresponds in each case to one line of Table B (compounds I.B1a.D1-5.B1 to I.B1a.D1-5.B455).

Table 41g Compounds of the formula I.B1a in which $(R^4)_m$ is 2,2-$Cl_2$ and $R^3$ corresponds to line D1-6 of Table D1 and the meaning for the combination of $R^1$ and $R^2$ for each individual compound corresponds in each case to one line of Table B (compounds I.B1a.D1-6.B1 to I.B1a.D1-6.B455).

Table 42g Compounds of the formula I.B1a in which $(R^4)_m$ is 2,2-$Cl_2$ and $R^3$ corresponds to line D1-7 of Table D1 and the meaning for the combination of $R^1$ and $R^2$ for each individual compound corresponds in each case to one line of Table B (compounds I.B1a.D1-7.B1 to I.B1a.D1-7.B455).

Table 43g Compounds of the formula I.B1a in which $(R^4)_m$ is 2,2-$(CH_3)_2$ and $R^3$ corresponds to line D1-1 of Table D1 and the meaning for the combination of $R^1$ and $R^2$ for each individual compound corresponds in each case to one line of Table B (compounds I.B1a.D1-1.B1 to I.B1a.D1-1.B455).

Table 44g Compounds of the formula I.B1a in which $(R^4)_m$ is 2,2-$(CH_3)_2$ and $R^3$ corresponds to line D1-2 of Table D1 and the meaning for the combination of $R^1$ and $R^2$ for each individual compound corresponds in each case to one line of Table B (compounds I.B1a.D1-2.B1 to I.B1a.D1-2.B455).

Table 45g Compounds of the formula I.B1a in which $(R^4)_m$ is 2,2-$(CH_3)_2$ and $R^3$ corresponds to line D1-3 of Table D1 and the meaning for the combination of $R^1$ and $R^2$ for each individual compound corresponds in each case to one line of Table B (compounds I.B1a.D1-3.B1 to I.B1a.D1-3.B455).

Table 46g Compounds of the formula I.B1a in which $(R^4)_m$ is 2,2-$(CH_3)_2$ and $R^3$ corresponds to line D1-4 of Table D1 and the meaning for the combination of $R^1$ and $R^2$ for each individual compound corresponds in each case to one line of Table B (compounds I.B1a.D1-4.B1 to I.B1a.D1-4.B455).

Table 47g Compounds of the formula I.B1a in which $(R^4)_m$ is 2,2-$(CH_3)_2$ and $R^3$ corresponds to line D1-5 of Table D1 and the meaning for the combination of $R^1$ and $R^2$ for each individual compound corresponds in each case to one line of Table B (compounds I.B1a.D1-5.B1 to I.B1a.D1-5.B455).

Table 48g Compounds of the formula I.B1a in which $(R^4)_m$ is 2,2-$(CH_3)_2$ and $R^3$ corresponds to line D1-6 of Table D1 and the meaning for the combination of $R^1$ and $R^2$ for each individual compound corresponds in each case to one line of Table B (compounds I.B1a.D1-6.B1 to I.B1a.D1-6.B455).

Table 49g Compounds of the formula I.B1a in which $(R^4)_m$ is 2,2-$(CH_3)_2$ and $R^3$ corresponds to line D1-7 of Table D1 and the meaning for the combination of $R^1$ and $R^2$ for each individual compound corresponds in each case to one line of Table B (compounds I.B1a.D1-7.B1 to I.B1a.D1-7.B455).

TABLE D1

| line | $R^3$ |
|---|---|
| D1-1 | H |
| D1-2 | Cl |
| D1-3 | F |
| D1-4 | Br |
| D1-5 | $CF_3$ |
| D1-6 | $CH_3$ |
| D1-7 | $OCH_3$ |

TABLE B

| line | R¹ | R² |
|---|---|---|
| B-1 | CH₃ | H |
| B-2 | CH₂CH₃ | H |
| B-3 | CH₂CH₂CH₃ | H |
| B-4 | CH(CH₃)₂ | H |
| B-5 | C(CH₃)₃ | H |
| B-6 | CH(CH₃)CH₂CH₃ | H |
| B-7 | CH₂CH(CH₃)₂ | H |
| B-8 | CH₂CH₂CH₂CH₃ | H |
| B-9 | CF₃ | H |
| B-10 | CHF₂ | H |
| B-11 | CH₂F | H |
| B-12 | CHCl₂ | H |
| B-13 | CH₂Cl | H |
| B-14 | CF₂CH₃ | H |
| B-15 | CHFCH₃ | H |
| B-16 | CF₂CF₃ | H |
| B-17 | CH₂OH | H |
| B-18 | CH₂CH₂OH | H |
| B-19 | CH₂CH₂CH₂OH | H |
| B-20 | CH(CH₃)CH₂OH | H |
| B-21 | CH₂CH(CH₃)OH | H |
| B-22 | n-C₄H₈OH | H |
| B-23 | CH₂OCH₃ | H |
| B-24 | CH₂OCH₂CH₃ | H |
| B-25 | CH(CH₃)OCH₃ | H |
| B-26 | CH₂OCF₃ | H |
| B-27 | CH₂CH₂OCF₃ | H |
| B-28 | CH₂OCCl₃ | H |
| B-29 | CH₂CH₂OCCl₃ | H |
| B-30 | CH=CH₂ | H |
| B-31 | CH₂CH=CH₂ | H |
| B-32 | CH₂CH=CHCH₃ | H |
| B-33 | CH₂C(CH₃)=CH₂ | H |
| B-34 | CH=CHCH₃ | H |
| B-35 | C(CH₃)=CH₂ | H |
| B-36 | CH=C(CH₃)₂ | H |
| B-37 | C(CH₃)=C(CH₃)₂ | H |
| B-38 | C(CH₃)=CH(CH₃) | H |
| B-39 | C(Cl)=CH₂ | H |
| B-40 | C(H)=CHCl | H |
| B-41 | C(Cl)=CHCl | H |
| B-42 | CH=CCl₂ | H |
| B-43 | C(Cl)=CCl₂ | H |
| B-44 | C(H)=CH(F) | H |
| B-45 | C(H)=CF₂ | H |
| B-46 | C(F)=CF₂ | H |
| B-47 | C(F)=CHF | H |
| B-48 | CH=CHCH₂OH | H |
| B-49 | CH=CHOCH₃ | H |
| B-50 | CH=CHCH₂OCH₃ | H |
| B-51 | CH=CHCH₂OCF₃ | H |
| B-52 | CH=CH(C₃H₅) | H |
| B-53 | C≡CH | H |
| B-54 | C≡CCH₃ | H |
| B-55 | CH₂C≡CCH₃ | H |
| B-56 | CH₂C≡CH | H |
| B-57 | CH₂C≡CCH₂CH₃ | H |
| B-58 | C≡CCH(CH₃)₂ | H |
| B-59 | C≡CC(CH₃)₃ | H |
| B-60 | C≡C(C₃H₅) | H |
| B-61 | C≡C(C₄H₇) | H |
| B-62 | C≡C(1-Cl—C₃H₄) | H |
| B-63 | C≡C(1-Cl—C₄H₆) | H |
| B-64 | C≡C—Cl | H |
| B-65 | C≡C—Br | H |
| B-66 | C≡C—I | H |
| B-67 | CH₂C≡C—Cl | H |
| B-68 | CH₂C≡C—Br | H |
| B-69 | CH₂C≡C—I | H |
| B-70 | C≡CCH₂OCH₃ | H |
| B-71 | C≡CCH(OH)CH₃ | H |
| B-72 | C≡COCH₃ | H |
| B-73 | CH₂C≡COCH₃ | H |
| B-74 | C≡CCH₂OCCl₃ | H |
| B-75 | C≡CCH₂OCF₃ | H |
| B-76 | C≡CCH₂(C₃H₅) | H |
| B-77 | C≡C(1-Cl—C₃H₄) | H |
| B-78 | C≡C(1-F—C₃H₄) | H |
| B-79 | C₃H₅ (cyclopropyl) | H |
| B-80 | CH(CH₃)—C₃H₅ | H |
| B-81 | CH₂—C₃H₅ | H |
| B-82 | 1-(Cl)—C₃H₄ | H |
| B-83 | 1-(F)—C₃H₄ | H |
| B-84 | 1-(CH₃)—C₃H₄ | H |
| B-85 | 1-(CN)—C₃H₄ | H |
| B-86 | 2-(Cl)—C₃H₄ | H |
| B-87 | 2-(F)—C₃H₄ | H |
| B-88 | 1-C₃H₅—C₃H₅₄ | H |
| B-89 | 2-C₃H₅—C₃H₄ | H |
| B-90 | CH₂-(1-Cl—C₃H₄) | H |
| B-91 | CH₂-(1-F—C₃H₄) | H |
| B-92 | CH₃ | CH₃ |
| B-93 | CH₂CH₃ | CH₃ |
| B-94 | CH₂CH₂CH₃ | CH₃ |
| B-95 | CH(CH₃)₂ | CH₃ |
| B-96 | C(CH₃)₃ | CH₃ |
| B-97 | CH(CH₃)CH₂CH₃ | CH₃ |
| B-98 | CH₂CH(CH₃)₂ | CH₃ |
| B-99 | CH₂CH₂CH₂CH₃ | CH₃ |
| B-100 | CF₃ | CH₃ |
| B-101 | CHF₂ | CH₃ |
| B-102 | CH₂F | CH₃ |
| B-103 | CHCl₂ | CH₃ |
| B-104 | CH₂Cl | CH₃ |
| B-105 | CF₂CH₃ | CH₃ |
| B-106 | CHFCH₃ | CH₃ |
| B-107 | CF₂CF₃ | CH₃ |
| B-108 | CH₂OH | CH₃ |
| B-109 | CH₂CH₂OH | CH₃ |
| B-110 | CH₂CH₂CH₂OH | CH₃ |
| B-111 | CH(CH₃)CH₂OH | CH₃ |
| B-112 | CH₂CH(CH₃)OH | CH₃ |
| B-113 | n-C₄H₈OH | CH₃ |
| B-114 | CH₂OCH₃ | CH₃ |
| B-115 | CH₂OCH₂CH₃ | CH₃ |
| B-116 | CH(CH₃)OCH₃ | CH₃ |
| B-117 | CH₂OCF₃ | CH₃ |
| B-118 | CH₂CH₂OCF₃ | CH₃ |
| B-119 | CH₂OCCl₃ | CH₃ |
| B-120 | CH₂CH₂OCCl₃ | CH₃ |
| B-121 | CH=CH₂ | CH₃ |
| B-122 | CH₂CH=CH₂ | CH₃ |
| B-123 | CH₂CH=CHCH₃ | CH₃ |
| B-124 | CH₂C(CH₃)=CH₂ | CH₃ |
| B-125 | CH=CHCH₃ | CH₃ |
| B-126 | C(CH₃)=CH₂ | CH₃ |
| B-127 | CH=C(CH₃)₂ | CH₃ |
| B-128 | C(CH₃)=C(CH₃)₂ | CH₃ |
| B-129 | C(CH₃)=CH(CH₃) | CH₃ |
| B-130 | C(Cl)=CH₂ | CH₃ |
| B-131 | C(H)=CHCl | CH₃ |
| B-132 | C(Cl)=CHCl | CH₃ |
| B-133 | CH=CCl₂ | CH₃ |
| B-134 | C(Cl)=CCl₂ | CH₃ |
| B-135 | C(H)=CH(F) | CH₃ |
| B-136 | C(H)=CF₂ | CH₃ |
| B-137 | C(F)=CF₂ | CH₃ |
| B-138 | C(F)=CHF | CH₃ |
| B-139 | CH=CHCH₂OH | CH₃ |
| B-140 | CH=CHOCH₃ | CH₃ |
| B-141 | CH=CHCH₂OCH₃ | CH₃ |
| B-142 | CH=CHCH₂OCF₃ | CH₃ |
| B-143 | CH=CH(C₃H₅) | CH₃ |
| B-144 | C≡CH | CH₃ |
| B-145 | C≡CCH₃ | CH₃ |
| B-146 | CH₂C≡CCH₃ | CH₃ |
| B-147 | CH₂C≡CH | CH₃ |
| B-148 | CH₂C≡CCH₂CH₃ | CH₃ |
| B-149 | C≡CCH(CH₃)₂ | CH₃ |
| B-150 | C≡CC(CH₃)₃ | CH₃ |
| B-151 | C≡C(C₃H₅) | CH₃ |
| B-152 | C≡C(C₄H₇) | CH₃ |
| B-153 | C≡C(1-Cl—C₃H₄) | CH₃ |
| B-154 | C≡C(1-Cl—C₄H₆) | CH₃ |
| B-155 | C≡CCl | CH₃ |
| B-156 | C≡CBr | CH₃ |

TABLE B-continued

| line | R¹ | R² |
|---|---|---|
| B-157 | C≡C—I | CH₃ |
| B-158 | CH₂C≡CCl | CH₃ |
| B-159 | CH₂C≡CBr | CH₃ |
| B-160 | CH₂C≡C—I | CH₃ |
| B-161 | C≡CCH₂OCH₃ | CH₃ |
| B-162 | C≡CCH(OH)CH₃ | CH₃ |
| B-163 | C≡COCH₃ | CH₃ |
| B-164 | CH₂C≡COCH₃ | CH₃ |
| B-165 | C≡CCH₂OCCl₃ | CH₃ |
| B-166 | C≡CCH₂OCF₃ | CH₃ |
| B-167 | C≡CCH₂(C₃H₅) | CH₃ |
| B-168 | C≡C(1-Cl—C₃H₄) | CH₃ |
| B-169 | C≡C(1-F—C₃H₄) | CH₃ |
| B-170 | C₃H₅ (cyclopropyl) | CH₃ |
| B-171 | CH(CH₃)—C₃H₅ | CH₃ |
| B-172 | CH₂—C₃H₅ | CH₃ |
| B-173 | 1-(Cl)—C₃H₄ | CH₃ |
| B-174 | 1-(F)—C₃H₄ | CH₃ |
| B-175 | 1-(CH₃)—C₃H₄ | CH₃ |
| B-176 | 1-(CN)—C₃H₄ | CH₃ |
| B-177 | 2-(Cl)—C₃H₄ | CH₃ |
| B-178 | 2-(F)—C₃H₄ | CH₃ |
| B-179 | 1-C₃H₅—C₃H₄ | CH₃ |
| B-180 | 2-C₃H₅—C₃H₄ | CH₃ |
| B-181 | CH₂-(1-Cl—C₃H₄) | CH₃ |
| B-182 | CH₂-(1-F—C₃H₄) | CH₃ |
| B-183 | CH₃ | C₂H₅ |
| B-184 | CH₂CH₃ | C₂H₅ |
| B-185 | CH₂CH₂CH₃ | C₂H₅ |
| B-186 | CH(CH₃)₂ | C₂H₅ |
| B-187 | C(CH₃)₃ | C₂H₅ |
| B-188 | CH(CH₃)CH₂CH₃ | C₂H₅ |
| B-189 | CH₂CH(CH₃)₂ | C₂H₅ |
| B-190 | CH₂CH₂CH₂CH₃ | C₂H₅ |
| B-191 | CF₃ | C₂H₅ |
| B-192 | CHF₂ | C₂H₅ |
| B-193 | CH₂F | C₂H₅ |
| B-194 | CHCl₂ | C₂H₅ |
| B-195 | CH₂Cl | C₂H₅ |
| B-196 | CF₂CH₃ | C₂H₅ |
| B-197 | CHFCH₃ | C₂H₅ |
| B-198 | CF₂CF₃ | C₂H₅ |
| B-199 | CH₂OH | C₂H₅ |
| B-200 | CH₂CH₂OH | C₂H₅ |
| B-201 | CH₂CH₂CH₂OH | C₂H₅ |
| B-202 | CH(CH₃)CH₂OH | C₂H₅ |
| B-203 | CH₂CH(CH₃)OH | C₂H₅ |
| B-204 | n-C₄H₈OH | C₂H₅ |
| B-205 | CH₂OCH₃ | C₂H₅ |
| B-206 | CH₂OCH₂CH₃ | C₂H₅ |
| B-207 | CH(CH₃)OCH₃ | C₂H₅ |
| B-208 | CH₂OCF₃ | C₂H₅ |
| B-209 | CH₂CH₂OCF₃ | C₂H₅ |
| B-210 | CH₂OCCl₃ | C₂H₅ |
| B-211 | CH₂CH₂OCCl₃ | C₂H₅ |
| B-212 | CH=CH₂ | C₂H₅ |
| B-213 | CH₂CH=CH₂ | C₂H₅ |
| B-214 | CH₂CH=CHCH₃ | C₂H₅ |
| B-215 | CH₂C(CH₃)=CH₂ | C₂H₅ |
| B-216 | CH=CHCH₃ | C₂H₅ |
| B-217 | C(CH₃)=CH₂ | C₂H₅ |
| B-218 | CH=C(CH₃)₂ | C₂H₅ |
| B-219 | C(CH₃)=C(CH₃)₂ | C₂H₅ |
| B-220 | C(CH₃)=CH(CH₃) | C₂H₅ |
| B-221 | C(Cl)=CH₂ | C₂H₅ |
| B-222 | C(H)=CHCl | C₂H₅ |
| B-223 | C(Cl)=CHCl | C₂H₅ |
| B-224 | CH=CCl₂ | C₂H₅ |
| B-225 | C(Cl)=CCl₂ | C₂H₅ |
| B-226 | C(H)=CH(F) | C₂H₅ |
| B-227 | C(H)=CF₂ | C₂H₅ |
| B-228 | C(F)=CF₂ | C₂H₅ |
| B-229 | C(F)=CHF | C₂H₅ |
| B-230 | CH=CHCH₂OH | C₂H₅ |
| B-231 | CH=CHOCH₃ | C₂H₅ |
| B-232 | CH=CHCH₂OCH₃ | C₂H₅ |
| B-233 | CH=CHCH₂OCF₃ | C₂H₅ |
| B-234 | CH=CH(C₃H₅) | C₂H₅ |
| B-235 | C≡CH | C₂H₅ |
| B-236 | C≡CCH₃ | C₂H₅ |
| B-237 | CH₂C≡CCH₃ | C₂H₅ |
| B-238 | CH₂C≡CH | C₂H₅ |
| B-239 | CH₂C≡CCH₂CH₃ | C₂H₅ |
| B-240 | C≡CCH(CH₃)₂ | C₂H₅ |
| B-241 | C≡CC(CH₃)₃ | C₂H₅ |
| B-242 | C≡C(C₃H₅) | C₂H₅ |
| B-243 | C≡C(C₄H₇) | C₂H₅ |
| B-244 | C≡C(1-Cl—C₃H₄) | C₂H₅ |
| B-245 | C≡C(1-Cl—C₄H₆) | C₂H₅ |
| B-246 | C≡CCl | C₂H₅ |
| B-247 | C≡CBr | C₂H₅ |
| B-248 | C≡C—I | C₂H₅ |
| B-249 | CH₂C≡CCl | C₂H₅ |
| B-250 | CH₂C≡CBr | C₂H₅ |
| B-251 | CH₂C≡C—I | C₂H₅ |
| B-252 | C≡CCH₂OCH₃ | C₂H₅ |
| B-253 | C≡CCH(OH)CH₃ | C₂H₅ |
| B-254 | C≡COCH₃ | C₂H₅ |
| B-255 | CH₂C≡COCH₃ | C₂H₅ |
| B-256 | C≡CCH₂OCCl₃ | C₂H₅ |
| B-257 | C≡CCH₂OCF₃ | C₂H₅ |
| B-258 | C≡CCH₂(C₃H₅) | C₂H₅ |
| B-259 | C≡C(1-Cl—C₃H₄) | C₂H₅ |
| B-260 | C≡C(1-F—C₃H₄) | C₂H₅ |
| B-261 | C₃H₅ (cyclopropyl) | C₂H₅ |
| B-262 | CH(CH₃)—C₃H₅ | C₂H₅ |
| B-263 | CH₂—C₃H₅ | C₂H₅ |
| B-264 | 1-(Cl)—C₃H₄ | C₂H₅ |
| B-265 | 1-(F)—C₃H₄ | C₂H₅ |
| B-266 | 1-(CH₃)—C₃H₄ | C₂H₅ |
| B-267 | 1-(CN)—C₃H₄ | C₂H₅ |
| B-268 | 2-(Cl)—C₃H₄ | C₂H₅ |
| B-269 | 2-(F)—C₃H₄ | C₂H₅ |
| B-270 | 1-C₃H₅—C₃H₄ | C₂H₅ |
| B-271 | 2-C₃H₅—C₃H₄ | C₂H₅ |
| B-272 | CH₂-(1-Cl—C₃H₄) | C₂H₅ |
| B-273 | CH₂-(1-F—C₃H₄) | C₂H₅ |
| B-274 | CH₃ | CH₂CH=CH₂ |
| B-275 | CH₂CH₃ | CH₂CH=CH₂ |
| B-276 | CH₂CH₂CH₃ | CH₂CH=CH₂ |
| B-277 | CH(CH₃)₂ | CH₂CH=CH₂ |
| B-278 | C(CH₃)₃ | CH₂CH=CH₂ |
| B-279 | CH(CH₃)CH₂CH₃ | CH₂CH=CH₂ |
| B-280 | CH₂CH(CH₃)₂ | CH₂CH=CH₂ |
| B-281 | CH₂CH₂CH₂CH₃ | CH₂CH=CH₂ |
| B-282 | CF₃ | CH₂CH=CH₂ |
| B-283 | CHF₂ | CH₂CH=CH₂ |
| B-284 | CH₂F | CH₂CH=CH₂ |
| B-285 | CHCl₂ | CH₂CH=CH₂ |
| B-286 | CF₂CH₃ | CH₂CH=CH₂ |
| B-287 | CHFCH₃ | CH₂CH=CH₂ |
| B-288 | CF₂CF₃ | CH₂CH=CH₂ |
| B-289 | CH₂Cl | CH₂CH=CH₂ |
| B-290 | CH₂OH | CH₂CH=CH₂ |
| B-291 | CH₂CH₂OH | CH₂CH=CH₂ |
| B-292 | CH₂CH₂CH₂OH | CH₂CH=CH₂ |
| B-293 | CH(CH₃)CH₂OH | CH₂CH=CH₂ |
| B-294 | CH₂CH(CH₃)OH | CH₂CH=CH₂ |
| B-295 | n-C₄H₈OH | CH₂CH=CH₂ |
| B-296 | CH₂OCH₃ | CH₂CH=CH₂ |
| B-297 | CH₂OCH₂CH₃ | CH₂CH=CH₂ |
| B-298 | CH(CH₃)OCH₃ | CH₂CH=CH₂ |
| B-299 | CH₂OCF₃ | CH₂CH=CH₂ |
| B-300 | CH₂CH₂OCF₃ | CH₂CH=CH₂ |
| B-301 | CH₂OCCl₃ | CH₂CH=CH₂ |
| B-302 | CH₂CH₂OCCl₃ | CH₂CH=CH₂ |
| B-303 | CH=CH₂ | CH₂CH=CH₂ |
| B-304 | CH₂CH=CH₂ | CH₂CH=CH₂ |
| B-305 | CH₂CH=CHCH₃ | CH₂CH=CH₂ |
| B-306 | CH₂C(CH₃)=CH₂ | CH₂CH=CH₂ |
| B-307 | CH=CHCH₃ | CH₂CH=CH₂ |
| B-308 | C(CH₃)=CH₂ | CH₂CH=CH₂ |
| B-309 | CH=C(CH₃)₂ | CH₂CH=CH₂ |
| B-310 | C(CH₃)=C(CH₃)₂ | CH₂CH=CH₂ |
| B-311 | C(CH₃)=CH(CH₃) | CH₂CH=CH₂ |
| B-312 | C(Cl)=CH₂ | CH₂CH=CH₂ |

TABLE B-continued

| line | R¹ | R² |
|---|---|---|
| B-313 | C(H)=CHCl | CH$_2$CH=CH$_2$ |
| B-314 | C(Cl)=CHCl | CH$_2$CH=CH$_2$ |
| B-315 | CH=CCl$_2$ | CH$_2$CH=CH$_2$ |
| B-316 | C(Cl)=CCl$_2$ | CH$_2$CH=CH$_2$ |
| B-317 | C(H)=CH(F) | CH$_2$CH=CH$_2$ |
| B-318 | C(H)=CF$_2$ | CH$_2$CH=CH$_2$ |
| B-319 | C(F)=CF$_2$ | CH$_2$CH=CH$_2$ |
| B-320 | C(F)=CHF | CH$_2$CH=CH$_2$ |
| B-321 | CH=CHCH$_2$OH | CH$_2$CH=CH$_2$ |
| B-322 | CH=CHOCH$_3$ | CH$_2$CH=CH$_2$ |
| B-323 | CH=CHCH$_2$OCH$_3$ | CH$_2$CH=CH$_2$ |
| B-324 | CH=CHCH$_2$OCF$_3$ | CH$_2$CH=CH$_2$ |
| B-325 | CH=CH(C$_3$H$_5$) | CH$_2$CH=CH$_2$ |
| B-326 | C≡CH | CH$_2$CH=CH$_2$ |
| B-327 | C≡CCH$_3$ | CH$_2$CH=CH$_2$ |
| B-328 | CH$_2$C≡CCH$_3$ | CH$_2$CH=CH$_2$ |
| B-329 | CH$_2$C≡CH | CH$_2$CH=CH$_2$ |
| B-330 | CH$_2$C≡CCH$_2$CH$_3$ | CH$_2$CH=CH$_2$ |
| B-331 | C≡CCH(CH$_3$)$_2$ | CH$_2$CH=CH$_2$ |
| B-332 | C≡CC(CH$_3$)$_3$ | CH$_2$CH=CH$_2$ |
| B-333 | C≡C(C$_3$H$_5$) | CH$_2$CH=CH$_2$ |
| B-334 | C≡C(C$_4$H$_7$) | CH$_2$CH=CH$_2$ |
| B-335 | C≡C(1-Cl—C$_3$H$_4$) | CH$_2$CH=CH$_2$ |
| B-336 | C≡C(1-Cl—C$_4$H$_6$) | CH$_2$CH=CH$_2$ |
| B-337 | C≡CCl | CH$_2$CH=CH$_2$ |
| B-338 | C≡CBr | CH$_2$CH=CH$_2$ |
| B-339 | C≡C—I | CH$_2$CH=CH$_2$ |
| B-340 | CH$_2$C≡CCl | CH$_2$CH=CH$_2$ |
| B-341 | CH$_2$C≡CBr | CH$_2$CH=CH$_2$ |
| B-342 | CH$_2$C≡C—I | CH$_2$CH=CH$_2$ |
| B-343 | C≡CCH$_2$OCH$_3$ | CH$_2$CH=CH$_2$ |
| B-344 | C≡CCH(OH)CH$_3$ | CH$_2$CH=CH$_2$ |
| B-345 | C≡COCH$_3$ | CH$_2$CH=CH$_2$ |
| B-346 | CH$_2$C≡COCH$_3$ | CH$_2$CH=CH$_2$ |
| B-347 | C≡CCH$_2$OCCl$_3$ | CH$_2$CH=CH$_2$ |
| B-348 | C≡CCH$_2$OCF$_3$ | CH$_2$CH=CH$_2$ |
| B-349 | C≡CCH$_2$(C$_3$H$_5$) | CH$_2$CH=CH$_2$ |
| B-350 | C≡C(1-Cl—C$_3$H$_4$) | CH$_2$CH=CH$_2$ |
| B-351 | C≡C(1-F—C$_3$H$_4$) | CH$_2$CH=CH$_2$ |
| B-352 | C$_3$H$_5$ (cyclopropyl) | CH$_2$CH=CH$_2$ |
| B-353 | CH(CH$_3$)—C$_3$H$_5$ | CH$_2$CH=CH$_2$ |
| B-354 | CH$_2$—C$_3$H$_5$ | CH$_2$CH=CH$_2$ |
| B-355 | 1-(Cl)—C$_3$H$_4$ | CH$_2$CH=CH$_2$ |
| B-356 | 1-(F)—C$_3$H$_4$ | CH$_2$CH=CH$_2$ |
| B-357 | 1-(CH$_3$)—C$_3$H$_4$ | CH$_2$CH=CH$_2$ |
| B-358 | 1-(CN)—C$_3$H$_4$ | CH$_2$CH=CH$_2$ |
| B-359 | 2-(Cl)—C$_3$H$_4$ | CH$_2$CH=CH$_2$ |
| B-360 | 2-(F)—C$_3$H$_4$ | CH$_2$CH=CH$_2$ |
| B-361 | 1-C$_3$H$_5$—C$_3$H$_4$ | CH$_2$CH=CH$_2$ |
| B-362 | 2-C$_3$H$_5$—C$_3$H$_4$ | CH$_2$CH=CH$_2$ |
| B-363 | CH$_2$-(1-Cl—C$_3$H$_4$) | CH$_2$CH=CH$_2$ |
| B-364 | CH$_2$-(1-F—C$_3$H$_4$) | CH$_2$CH=CH$_2$ |
| B-365 | CH$_3$ | CH$_2$C≡CH |
| B-366 | CH$_2$CH$_3$ | CH$_2$C≡CH |
| B-367 | CH$_2$CH$_2$CH$_3$ | CH$_2$C≡CH |
| B-368 | CH(CH$_3$)$_2$ | CH$_2$C≡CH |
| B-369 | C(CH$_3$)$_3$ | CH$_2$C≡CH |
| B-370 | CH(CH$_3$)CH$_2$CH$_3$ | CH$_2$C≡CH |
| B-371 | CH$_2$CH(CH$_3$)$_2$ | CH$_2$C≡CH |
| B-372 | CH$_2$CH$_2$CH$_2$CH$_3$ | CH$_2$C≡CH |
| B-373 | CF$_3$ | CH$_2$C≡CH |
| B-374 | CHF$_2$ | CH$_2$C≡CH |
| B-375 | CH$_2$F | CH$_2$C≡CH |
| B-376 | CHCl$_2$ | CH$_2$C≡CH |
| B-377 | CF$_2$CH$_3$ | CH$_2$C≡CH |
| B-378 | CHFCH$_3$ | CH$_2$C≡CH |
| B-379 | CF$_2$CF$_3$ | CH$_2$C≡CH |
| B-380 | CH$_2$Cl | CH$_2$C≡CH |
| B-381 | CH$_2$OH | CH$_2$C≡CH |
| B-382 | CH$_2$CH$_2$OH | CH$_2$C≡CH |
| B-383 | CH$_2$CH$_2$CH$_2$OH | CH$_2$C≡CH |
| B-384 | CH(CH$_3$)CH$_2$OH | CH$_2$C≡CH |
| B-385 | CH$_2$CH(CH$_3$)OH | CH$_2$C≡CH |
| B-386 | n-C$_4$H$_8$OH | CH$_2$C≡CH |
| B-387 | CH$_2$OCH$_3$ | CH$_2$C≡CH |
| B-388 | CH$_2$OCH$_2$CH$_3$ | CH$_2$C≡CH |
| B-389 | CH(CH$_3$)OCH$_3$ | CH$_2$C≡CH |
| B-390 | CH$_2$OCF$_3$ | CH$_2$C≡CH |
| B-391 | CH$_2$CH$_2$OCF$_3$ | CH$_2$C≡CH |
| B-392 | CH$_2$OCCl$_3$ | CH$_2$C≡CH |
| B-393 | CH$_2$CH$_2$OCCl$_3$ | CH$_2$C≡CH |
| B-394 | CH=CH$_2$ | CH$_2$C≡CH |
| B-395 | CH$_2$CH=CH$_2$ | CH$_2$C≡CH |
| B-396 | CH$_2$CH=CHCH$_3$ | CH$_2$C≡CH |
| B-397 | CH$_2$C(CH$_3$)=CH$_2$ | CH$_2$C≡CH |
| B-398 | CH=CHCH$_3$ | CH$_2$C≡CH |
| B-399 | C(CH$_3$)=CH$_2$ | CH$_2$C≡CH |
| B-400 | CH=C(CH$_3$)$_2$ | CH$_2$C≡CH |
| B-401 | C(CH$_3$)=C(CH$_3$)$_2$ | CH$_2$C≡CH |
| B-402 | C(CH$_3$)=CH(CH$_3$) | CH$_2$C≡CH |
| B-403 | C(Cl)=CH$_2$ | CH$_2$C≡CH |
| B-404 | C(H)=CHCl | CH$_2$C≡CH |
| B-405 | C(Cl)=CHCl | CH$_2$C≡CH |
| B-406 | CH=CCl$_2$ | CH$_2$C≡CH |
| B-407 | C(Cl)=CCl$_2$ | CH$_2$C≡CH |
| B-408 | C(H)=CH(F) | CH$_2$C≡CH |
| B-409 | C(H)=CF$_2$ | CH$_2$C≡CH |
| B-410 | C(F)=CF$_2$ | CH$_2$C≡CH |
| B-411 | C(F)=CHF | CH$_2$C≡CH |
| B-412 | CH=CHCH$_2$OH | CH$_2$C≡CH |
| B-413 | CH=CHOCH$_3$ | CH$_2$C≡CH |
| B-414 | CH=CHCH$_2$OCH$_3$ | CH$_2$C≡CH |
| B-415 | CH=CHCH$_2$OCF$_3$ | CH$_2$C≡CH |
| B-416 | CH=CH(C$_3$H$_5$) | CH$_2$C≡CH |
| B-417 | C≡CH | CH$_2$C≡CH |
| B-418 | C≡CCH$_3$ | CH$_2$C≡CH |
| B-419 | CH$_2$C≡CCH$_3$ | CH$_2$C≡CH |
| B-420 | CH$_2$C≡CH | CH$_2$C≡CH |
| B-421 | CH$_2$C≡CCH$_2$CH$_3$ | CH$_2$C≡CH |
| B-422 | C≡CCH(CH$_3$)$_2$ | CH$_2$C≡CH |
| B-423 | C≡CC(CH$_3$)$_3$ | CH$_2$C≡CH |
| B-424 | C≡C(C$_3$H$_5$) | CH$_2$C≡CH |
| B-425 | C≡C(C$_4$H$_7$) | CH$_2$C≡CH |
| B-426 | C≡C(1-Cl—C$_3$H$_4$) | CH$_2$C≡CH |
| B-427 | C≡C(1-Cl—C$_4$H$_6$) | CH$_2$C≡CH |
| B-428 | C≡CCl | CH$_2$C≡CH |
| B-429 | C≡CBr | CH$_2$C≡CH |
| B-430 | C≡C—I | CH$_2$C≡CH |
| B-431 | CH$_2$C≡CCl | CH$_2$C≡CH |
| B-432 | CH$_2$C≡CBr | CH$_2$C≡CH |
| B-433 | CH$_2$C≡C—I | CH$_2$C≡CH |
| B-434 | C≡CCH$_2$OCH$_3$ | CH$_2$C≡CH |
| B-435 | C≡CCH(OH)CH$_3$ | CH$_2$C≡CH |
| B-436 | C≡COCH$_3$ | CH$_2$C≡CH |
| B-437 | CH$_2$C≡COCH$_3$ | CH$_2$C≡CH |
| B-438 | C≡CCH$_2$OCCl$_3$ | CH$_2$C≡CH |
| B-439 | C≡CCH$_2$OCF$_3$ | CH$_2$C≡CH |
| B-440 | C≡CCH$_2$(C$_3$H$_5$) | CH$_2$C≡CH |
| B-441 | C≡C(1-Cl—C$_3$H$_4$) | CH$_2$C≡CH |
| B-442 | C≡C(1-F—C$_3$H$_4$) | CH$_2$C≡CH |
| B-443 | C$_3$H$_5$ (cyclopropyl) | CH$_2$C≡CH |
| B-444 | CH(CH$_3$)—C$_3$H$_5$ | CH$_2$C≡CH |
| B-445 | CH$_2$—C$_3$H$_5$ | CH$_2$C≡CH |
| B-446 | 1-(Cl)—C$_3$H$_4$ | CH$_2$C≡CH |
| B-447 | 1-(F)—C$_3$H$_4$ | CH$_2$C≡CH |
| B-448 | 1-(CH$_3$)—C$_3$H$_4$ | CH$_2$C≡CH |
| B-449 | 1-(CN)—C$_3$H$_4$ | CH$_2$C≡CH |
| B-450 | 2-(Cl)—C$_3$H$_4$ | CH$_2$C≡CH |
| B-451 | 2-(F)—C$_3$H$_4$ | CH$_2$C≡CH |
| B-452 | 1-C$_3$H$_5$—C$_3$H$_4$ | CH$_2$C≡CH |
| B-453 | 2-C$_3$H$_5$—C$_3$H$_4$ | CH$_2$C≡CH |
| B-454 | CH$_2$-(1-Cl—C$_3$H$_4$) | CH$_2$C≡CH |
| B-455 | CH$_2$-(1-F—C$_3$H$_4$) | CH$_2$C≡CH |

The compounds I and the compositions according to the invention, respectively, are suitable as fungicides.

Consequently, according to a further aspect, the present invention relates to the use of compounds of formula I, the N-oxides and the agriculturally acceptable salts thereof or of the compositions of the invention for combating phytopathogenic fungi.

Accordingly, the present invention also encompasses a method for combating harmful fungi, comprising treating the fungi or the materials, plants, the soil or seeds to be protected against fungal attack with an effective amount of at least one compound of formula I or with a composition comprising according to the invention.

The compounds I and the compositions according to the invention, respectively, are suitable as fungicides. They are distinguished by an outstanding effectiveness against a broad spectrum of phytopathogenic fungi, including soil-borne fungi, which derive especially from the classes of the Plasmodiophoromycetes, Peronosporomycetes (syn. Oomycetes), Chytridiomycetes, Zygomycetes, Ascomycetes, Basidiomycetes and Deuteromycetes (syn. Fungi imperfecti). Some are systemically effective and they can be used in crop protection as foliar fungicides, fungicides for seed dressing and soil fungicides. Moreover, they are suitable for controlling harmful fungi, which inter alia occur in wood or roots of plants.

The compounds I and the compositions according to the invention are particularly important in the control of a multitude of phytopathogenic fungi on various cultivated plants, such as cereals, e. g. wheat, rye, barley, triticale, oats or rice; beet, e. g. sugar beet or fodder beet; fruits, such as pomes, stone fruits or soft fruits, e. g. apples, pears, plums, peaches, almonds, cherries, strawberries, raspberries, blackberries or gooseberries; leguminous plants, such as lentils, peas, alfalfa or soybeans; oil plants, such as rape, mustard, olives, sunflowers, coconut, cocoa beans, castor oil plants, oil palms, ground nuts or soybeans; cucurbits, such as squashes, cucumber or melons; fiber plants, such as cotton, flax, hemp or jute; citrus fruit, such as oranges, lemons, grapefruits or mandarins; vegetables, such as spinach, lettuce, asparagus, cabbages, carrots, onions, tomatoes, potatoes, cucurbits or paprika; lauraceous plants, such as avocados, cinnamon or camphor; energy and raw material plants, such as corn, soybean, rape, sugar cane or oil palm; corn; tobacco; nuts; coffee; tea; bananas; vines (table grapes and grape juice grape vines); hop; turf; sweet leaf (also called Stevia); natural rubber plants or ornamental and forestry plants, such as flowers, shrubs, broad-leaved trees or evergreens, e. g. conifers; and on the plant propagation material, such as seeds, and the crop material of these plants.

Preferably, compounds I and compositions thereof, respectively are used for controlling a multitude of fungi on field crops, such as potatoes sugar beets, tobacco, wheat, rye, barley, oats, rice, corn, cotton, soybeans, rape, legumes, sunflowers, coffee or sugar cane; fruits; vines; ornamentals; or vegetables, such as cucumbers, tomatoes, beans or squashes.

The term "plant propagation material" is to be understood to denote all the generative parts of the plant such as seeds and vegetative plant material such as cuttings and tubers (e. g. potatoes), which can be used for the multiplication of the plant. This includes seeds, roots, fruits, tubers, bulbs, rhizomes, shoots, sprouts and other parts of plants, including seedlings and young plants, which are to be transplanted after germination or after emergence from soil. These young plants may also be protected before transplantation by a total or partial treatment by immersion or pouring.

Preferably, treatment of plant propagation materials with compounds I and compositions thereof, respectively, is used for controlling a multitude of fungi on cereals, such as wheat, rye, barley and oats; rice, corn, cotton and soybeans.

The term "cultivated plants" is to be understood as including plants which have been modified by breeding, mutagenesis or genetic engineering including but not limiting to agricultural biotech products on the market or in development (cf. http://cera-gmc.org/, see GM crop database therein). Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-translational modification of protein(s), oligo- or polypeptides e. g. by glycosylation or polymer additions such as prenylated, acetylated or farnesylated moieties or PEG moieties.

Plants that have been modified by breeding, mutagenesis or genetic engineering, e. g. have been rendered tolerant to applications of specific classes of herbicides, such as auxin herbicides such as dicamba or 2,4-D; bleacher herbicides such as hydroxylphenylpyruvate dioxygenase (HPPD) inhibitors or phytoene desaturase (PDS) inhibitors; acetolactate synthase (ALS) inhibitors such as sulfonyl ureas or imidazolinones; enolpyruvylshikimate-3-phosphate synthase (EPSPS) inhibitors, such as glyphosate; glutamine synthetase (GS) inhibitors such as glufosinate; protoporphyrinogen-IX oxidase inhibitors; lipid biosynthesis inhibitors such as acetyl CoA carboxylase (ACCase) inhibitors; or oxynil (i. e. bromoxynil or ioxynil) herbicides as a result of conventional methods of breeding or genetic engineering. Furthermore, plants have been made resistant to multiple classes of herbicides through multiple genetic modifications, such as resistance to both glyphosate and glufosinate or to both glyphosate and a herbicide from another class such as ALS inhibitors, HPPD inhibitors, auxin herbicides, or ACCase inhibitors. These herbicide resistance technologies are e. g. described in Pest Managem. Sci. 61, 2005, 246; 61, 2005, 258; 61, 2005, 277; 61, 2005, 269; 61, 2005, 286; 64, 2008, 326; 64, 2008, 332; Weed Sci. 57, 2009, 108; Austral. J. Agricult. Res. 58, 2007, 708; Science 316, 2007, 1185; and references quoted therein. Several cultivated plants have been rendered tolerant to herbicides by conventional methods of breeding (mutagenesis), e. g. Clearfield® summer rape (Canola, BASF SE, Germany) being tolerant to imidazolinones, e. g. imazamox, or ExpressSun® sunflowers (DuPont, USA) being tolerant to sulfonyl ureas, e. g. tribenuron. Genetic engineering methods have been used to render cultivated plants such as soybean, cotton, corn, beets and rape, tolerant to herbicides such as glyphosate and glufosinate, some of which are commercially available under the trade names RoundupReady® (glyphosate-tolerant, Monsanto, U.S.A.), Cultivance® (imidazolinone tolerant, BASF SE, Germany) and LibertyLink® (glufosinate-tolerant, Bayer CropScience, Germany).

Furthermore, plants are also covered that are by the use of recombinant DNA techniques capable to synthesize one or more insecticidal proteins, especially those known from the bacterial genus *Bacillus*, particularly from *Bacillus thuringiensis*, such as δ-endotoxins, e. g. CryIA(b), CryIA(c), CryIF, CryIF(a2), CryIIA(b), CryIIIA, CryIIIB(b1) or Cry9c; vegetative insecticidal proteins (VIP), e. g. VIP1, VIP2, VIP3 or VIP3A; insecticidal proteins of bacteria colonizing nematodes, e. g. *Photorhabdus* spp. or *Xenorhabdus* spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilbene synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, e. g. WO 02/015701). Further examples of such toxins or genetically modified plants capable of synthesizing such toxins are disclosed, e. g., in EP-A 374 753, WO 93/007278, WO 95/34656, EP-A 427 529, EP-A 451 878, WO 03/18810 and WO 03/52073. The methods for producing such genetically modified plants are generally known to the person skilled in the art and are described, e. g. in the publications mentioned above. These insecticidal proteins contained in the genetically modified plants impart to the plants producing these proteins tolerance to harmful pests from all taxonomic groups of arthropods, especially to beetles (Coeloptera), two-winged insects (Diptera), and moths (Lepidoptera) and to nematodes (Nematoda). Genetically modified plants capable to synthesize one or more insecticidal proteins are, e. g., described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink® (corn cultivars producing the Cry9c toxin), Herculex® RW (corn cultivars producing Cry34Ab1, Cry35Ab1 and the enzyme phosphinothricin-N-acetyltransferase [PAT]); NuCOTN® 33B (cotton cultivars producing the Cry1Ac toxin), Bollgard® I (cotton cultivars producing the Cry1Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); Bt-Xtra®, NatureGard®, KnockOut®, BiteGard®, Protecta®, Bt11 (e. g. Agrisure® CB) and Bt176 from Syngenta Seeds SAS, France, (corn cultivars producing the Cry1Ab toxin and PAT enzyme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bb1 toxin), IPC 531 from Monsanto Europe S.A., Belgium (cotton cultivars producing a modified version of the Cry1Ac toxin) and 1507 from Pioneer Overseas Corporation, Belgium (corn cultivars producing the Cry1F toxin and PAT enzyme).

Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e. g. EP-A 392 225), plant disease resistance genes (e. g. potato cultivars, which express resistance genes acting against *Phytophthora infestans* derived from the Mexican wild potato *Solanum bulbocastanum*) or T4-lysozym (e. g. potato cultivars capable of synthesizing these proteins with increased resistance against bacteria such as *Erwinia amylvora*). The methods for producing such genetically modified plants are generally known to the person skilled in the art and are described, e. g. in the publications mentioned above.

Furthermore, plants are also covered that are by the use of recombinant DNA techniques capable to synthesize one or more proteins to increase the productivity (e. g. bio mass production, grain yield, starch content, oil content or protein content), tolerance to drought, salinity or other growth-limiting environmental factors or tolerance to pests and fungal, bacterial or viral pathogens of those plants.

Furthermore, plants are also covered that contain by the use of recombinant DNA techniques a modified amount of substances of content or new substances of content, specifically to improve human or animal nutrition, e. g. oil crops that produce health-promoting long-chain omega-3 fatty acids or unsaturated omega-9 fatty acids (e. g. Nexera® rape, DOW Agro Sciences, Canada).

Furthermore, plants are also covered that contain by the use of recombinant DNA techniques a modified amount of substances of content or new substances of content, specifically to improve raw material production, e. g. potatoes that produce increased amounts of amylopectin (e. g. Amflora® potato, BASF SE, Germany).

The compounds I and compositions thereof, respectively, are particularly suitable for controlling the following plant diseases:

*Albugo* spp. (white rust) on ornamentals, vegetables (e. g. *A. candida*) and sunflowers (e. g. *A. tragopogonis*); *Alternaria* spp. (*Alternaria* leaf spot) on vegetables, rape (*A. brassicola* or *brassicae*), sugar beets (*A. tenuis*), fruits, rice, soybeans, potatoes (e. g. *A. solani* or *A. alternata*), tomatoes (e. g. *A. solani* or *A. alternata*) and wheat; *Aphanomyces* spp. on sugar beets and vegetables; *Ascochyta* spp. on cereals and vegetables, e. g. *A. tritici* (anthracnose) on wheat and *A. hordei* on barley; *Bipolaris* and *Drechslera* spp. (teleomorph: *Cochliobolus* spp.), e. g. Southern leaf blight (*D. maydis*) or Northern leaf blight (*B. zeicola*) on corn, e. g. spot blotch (*B. sorokiniana*) on cereals and e. g. *B. oryzae* on rice and turfs; *Blumeria* (formerly *Erysiphe*) *graminis* (powdery mildew) on cereals (e. g. on wheat or barley); *Botrytis cinerea* (teleomorph: *Botryotinia fuckeliana*: grey mold) on fruits and berries (e. g. strawberries), vegetables (e. g. lettuce, carrots, celery and cabbages), rape, flowers, vines, forestry plants and wheat; *Bremia lactucae* (downy mildew) on lettuce; *Ceratocystis* (syn. *Ophiostoma*) spp. (rot or wilt) on broad-leaved trees and evergreens, e. g. *C. ulmi* (Dutch elm disease) on elms; *Cercospora* spp. (*Cercospora* leaf spots) on corn (e. g. Gray leaf spot: *C. zeae-maydis*), rice, sugar beets (e. g. *C. beticola*), sugar cane, vegetables, coffee, soybeans (e. g. *C. sojina* or *C. kikuchii*) and rice; *Cladosporium* spp. on tomatoes (e. g. *C. fulvum*: leaf mold) and cereals, e. g. *C. herbarum* (black ear) on wheat; *Claviceps purpurea* (ergot) on cereals; *Cochliobolus* (anamorph: *Helminthosporium* of *Bipolaris*) spp. (leaf spots) on corn (*C. carbonum*), cereals (e. g. *C. sativus*, anamorph: *B. sorokiniana*) and rice (e. g. *C. miyabeanus*, anamorph: *H. oryzae*); *Colletotrichum* (teleomorph: *Glomerella*) spp. (anthracnose) on cotton (e. g. *C. gossypii*), corn (e. g. *C. graminicola*: Anthracnose stalk rot), soft fruits, potatoes (e. g. *C. coccodes*: black dot), beans (e. g. *C. lindemuthianum*) and soybeans (e. g. *C. truncatum* or *C. gloeosporioides*); *Corticium* spp., e. g. *C. sasakii* (sheath blight) on rice; *Corynespora cassiicola* (leaf spots) on soybeans and ornamentals; *Cycloconium* spp., e. g. *C. oleaginum* on olive trees; *Cylindrocarpon* spp. (e. g. fruit tree canker or young vine decline, teleomorph: *Nectria* or *Neonectria* spp.) on fruit trees, vines (e. g. *C. liriodendri*, teleomorph: *Neonectria liriodendri*: Black Foot Disease) and ornamentals; *Dematophora* (teleomorph: *Rosellinia*) necatrix (root and stem rot) on soybeans; *Diaporthe* spp., e. g. *D. phaseolorum* (damping off) on soybeans; *Drechslera* (syn. *Helminthosporium*, teleomorph: *Pyrenophora*) spp. on corn, cereals, such as barley (e. g. *D. teres*, net blotch) and wheat (e. g. *D. tritici-repentis*: tan spot), rice and turf; *Esca* (dieback, apoplexy) on vines, caused by *Formitiporia* (syn. *Phellinus*) *punctata, F. mediterranea, Phaeomoniella chlamydospora* (earlier *Phaeoacremonium chlamydosporum*), *Phaeoacremonium aleophilum* and/or *Botryosphaeria obtusa; Elsinoe* spp. on pome fruits (*E. pyri*), soft fruits (*E. veneta*: anthracnose) and vines (*E. ampelina*: anthracnose); *Entyloma oryzae* (leaf smut) on rice; *Epicoccum* spp. (black mold) on wheat; *Etysiphe* spp. (powdery mildew) on sugar beets (*E. betae*), vegetables (e. g. *E. pisi*), such as cucurbits (e. g. *E. cichoracearum*), cabbages, rape (e. g. *E. cruciferarum*); *Eutypa lata* (*Eutypa* canker or dieback, anamorph: *Cytosporina lata*, syn. *Libertella blepharis*) on fruit trees, vines and ornamental woods; *Exserohilum* (syn. *Helminthosporium*) spp. on corn (e. g. *E. turcicum*); *Fusarium* (teleomorph: *Gibberella*) spp. (wilt, root or stem rot) on various plants, such as *F. graminearum* or *F. culmorum* (root rot, scab or head blight) on cereals (e. g. wheat or barley), *F. oxysporum* on tomatoes, *F. solani* (f. sp. *glycines* now syn. *F. virguliforme*) and *F. tucumaniae* and *F. brasiliense* each causing sudden death syndrome on soybeans, and *F. verticillioides* on corn; *Gaeumannomyces graminis* (take-all) on cereals (e. g. wheat or barley) and corn; *Gibberella* spp. on cereals (e. g. *G. zeae*) and rice (e. g. *G. fujikuroi*: Bakanae disease); *Glomerella cingulata* on vines, pome fruits and other plants and *G. gossypii* on cotton; Grainstaining complex on rice; *Guignardia bidwellii* (black rot) on vines; *Gymnosporangium* spp. on rosaceous plants and junipers, e. g. *G. sabinae* (rust) on pears; *Helminthosporium* spp. (syn. *Drechslera*, teleomorph: *Cochliobolus*) on corn, cereals and rice; *Hemileia* spp., e. g. *H. vastatrix* (coffee leaf rust) on coffee; *Isariopsis clavispora* (syn. *Cladosporium vitis*) on vines; *Macrophomina phaseolina* (syn. *phaseoli*) (root and stem rot) on soybeans and cotton; *Microdochium* (syn. *Fusarium*) *nivale* (pink snow mold) on cereals (e. g. wheat or barley); *Microsphaera diffusa* (powdery mildew) on soybeans; *Monilinia* spp., e. g. *M. laxa, M. fructicola* and *M. fructigena* (bloom and twig blight, brown rot) on stone fruits and other rosaceous plants; *Mycosphaerella* spp. on cereals, bananas, soft fruits and ground nuts, such as e. g. *M. graminicola* (anamorph: *Septoria tritici*, *Septoria* blotch) on wheat or *M. fijiensis* (black Sigatoka disease) on bananas; *Peronospora* spp. (downy mildew) on cabbage (e. g. *P. brassicae*), rape (e. g. *P. parasitica*), onions (e. g. *P. destructor*), tobacco (*P. tabacina*) and soybeans (e. g. *P. manshurica*); *Phakopsora pachyrhizi* and *P. meibomiae* (soybean rust) on soybeans; *Phialophora* spp. e. g. on vines (e. g. *P. tracheiphila* and *P. tetraspora*) and soybeans (e. g. *P. gregata*: stem rot); *Phoma lingam* (root and stem rot) on rape and cabbage and *P. betae* (root rot, leaf spot and damping-off) on sugar beets; *Phomopsis* spp. on sunflowers, vines (e. g. *P. viticola*: can and leaf spot) and soybeans (e. g. stem rot: *P. phaseoli*, teleomorph: *Diaporthe phaseolorum*); *Physoderma maydis* (brown spots) on corn; *Phytophthora* spp. (wilt, root, leaf, fruit and stem root) on various plants, such as paprika and cucurbits (e. g. *P. capsici*), soybeans (e. g. *P. megasperma*, syn. *P. sojae*), potatoes and tomatoes (e. g. *P. infestans*: late blight) and broad-leaved trees (e. g. *P. ramorum*: sudden oak death); *Plasmodiophora brassicae* (club root) on cabbage, rape, radish and other plants; *Plasmopara* spp., e. g. *P. viticola* (grapevine downy mildew) on vines and *P. halstedii* on sunflowers; *Podosphaera* spp. (powdery mildew) on rosaceous plants, hop, pome and soft fruits, e. g. *P. leucotricha* on apples; *Polymyxa* spp., e. g. on cereals, such as barley and wheat (*P. graminis*) and sugar beets (*P. betae*) and thereby transmitted viral diseases; *Pseudocercosporella herpotrichoides* (eyespot, teleomorph: *Tapesia yallundae*) on cereals, e. g. wheat or barley; *Pseudoperonospora* (downy mildew) on various plants, e. g. *P. cubensis* on cucurbits or *P. humili* on hop; *Pseudopezicula tracheiphila* (red fire disease or 'rotbrenner', anamorph: *Phialophora*) on vines; *Puccinia* spp. (rusts) on various plants, e. g. *P. triticina* (brown or leaf rust), *P. striiformis* (stripe or yellow rust), *P. hordei* (dwarf rust), *P. graminis* (stem or black rust) or *P. recondita* (brown or leaf rust) on cereals, such as e. g. wheat, barley or rye, *P. kuehnii* (orange rust) on sugar cane and *P. asparagi* on asparagus; *Pyrenophora* (anamorph: *Drechslera*) *tritici-repentis* (tan spot) on wheat or *P. teres* (net blotch) on barley; *Pyricularia* spp., e. g. *P. oryzae* (teleomorph: *Magnaporthe grisea*, rice blast) on rice and *P. grisea* on turf and cereals; *Pythium* spp. (damping-off) on turf, rice, corn, wheat, cotton, rape, sunflowers, soybeans, sugar beets, vegetables and various other plants (e. g. *P. ultimum* or *P. aphanidermatum*); *Ramularia* spp., e. g. *R. collo-cygni* (*Ramularia* leaf spots, Physiological leaf spots) on barley and *R. beticola* on sugar beets; *Rhizoctonia* spp. on cotton, rice, potatoes, turf, corn, rape, potatoes, sugar beets, vegetables and various other plants, e. g. *R. solani* (root and stem rot) on soybeans, *R. solani* (sheath blight) on rice or *R. cerealis* (*Rhizoctonia* spring blight) on wheat or barley; *Rhizopus stolonifer* (black mold, soft rot) on strawberries, carrots, cabbage, vines and tomatoes; *Rhynchosporium secalis* (scald) on barley, rye and triticale; *Sarocladium oryzae* and *S. attenuatum* (sheath rot) on rice; *Sclerotinia* spp. (stem rot or white mold) on vegetables and field crops, such as rape, sunflowers (e. g. *S. sclerotiorum*) and soybeans (e. g. *S. rolfsii* or *S. sclerotiorum*); *Septoria* spp. on various plants, e. g. *S. glycines* (brown spot) on soybeans, *S. tritici* (*Septoria* blotch) on wheat and S. (syn. *Stagonospora*) *nodorum* (*Stagonospora* blotch) on cereals; *Uncinula* (syn. *Erysiphe*) *necator* (powdery mildew, anamorph: *Oidium tucken*) on vines; *Setospaeria* spp. (leaf blight) on corn (e. g. *S. turcicum*, syn. *Helminthosporium turcicum*) and turf; *Sphacelotheca* spp. (smut) on corn, (e. g. *S. reiliana*: head smut), sorghum and sugar cane; *Sphaerotheca fuliginea* (powdery mildew) on cucurbits; *Spongospora subterranea* (powdery scab) on potatoes and thereby transmitted viral diseases; *Stagonospora* spp. on cereals, e. g. *S. nodorum* (*Stagonospora* blotch, teleomorph: *Leptosphaeria* [syn. *Phaeosphaeria*] *nodorum*) on wheat; *Synchytrium endobioticum* on potatoes (potato wart disease); *Taphrina* spp., e. g. *T. deformans* (leaf curl disease) on peaches and *T. pruni* (plum pocket) on plums; *Thielaviopsis* spp. (black root rot) on tobacco, pome fruits, vegetables, soybeans and cotton, e. g. *T. basicola* (syn. *Chalara elegans*); *Tilletia* spp. (common bunt or stinking smut) on cereals, such as e. g. *T. tritici* (syn. *T. caries*, wheat bunt) and *T. controversa* (dwarf bunt) on wheat; *Typhula incamata* (grey snow mold) on barley or wheat; *Urocystis* spp., e. g. *U. occulta* (stem smut) on rye; *Uromyces* spp. (rust) on vegetables, such as beans (e. g. *U. appendiculatus*, syn. *U. phaseoli*) and sugar beets (e. g. *U. betae*); *Ustilago* spp. (loose smut) on cereals (e. g. *U. nuda* and *U. avaenae*), corn (e. g. *U. maydis*: corn smut) and sugar cane; *Venturia* spp. (scab) on apples (e. g. *V. inaequalis*) and pears; and *Verticillium* spp. (wilt) on various plants, such as fruits and ornamentals, vines, soft fruits, vegetables and field crops, e. g. *V. dahliae* on strawberries, rape, potatoes and tomatoes.

The compounds I and compositions thereof, respectively, are also suitable for controlling harmful fungi in the protection of stored products or harvest and in the protection of materials.

The term "protection of materials" is to be understood to denote the protection of technical and non-living materials, such as adhesives, glues, wood, paper and paperboard, textiles, leather, paint dispersions, plastics, cooling lubricants, fiber or fabrics, against the infestation and destruction by harmful microorganisms, such as fungi and bacteria. As to the protection of wood and other materials, the particular attention is paid to the following harmful fungi: Ascomycetes such as *Ophiostoma* spp., *Ceratocystis* spp., *Aureobasidium pullulans, Sclerophoma* spp., *Chaetomium* spp., *Humicola* spp., *Petriella* spp., *Trichurus* spp.; Basidiomycetes such as *Coniophora* spp., *Coriolus* spp., *Gloeophyllum* spp., *Lentinus* spp., *Pleurotus* spp., *Poria* spp., *Serpula* spp. and *Tyromyces* spp., Deuteromycetes such as *Aspergillus* spp., *Cladosporium* spp., *Penicillium* spp., *Trichoderma* spp., *Alternaria* spp., *Paecilomyces* spp. and Zygomycetes such as *Mucor* spp., and in addition in the protection of stored products and harvest the following yeast fungi are worthy of note: *Candida* spp. and *Saccharomyces cerevisae.*

The method of treatment according to the invention can also be used in the field of protecting stored products or harvest against attack of fungi and microorganisms. According to the present invention, the term "stored products" is understood to denote natural substances of plant or animal origin and their processed forms, which have been taken from the natural life cycle and for which long-term protection is desired. Stored products of crop plant origin, such as plants or parts thereof, for example stalks, leafs, tubers, seeds, fruits or grains, can be protected in the freshly harvested state or in processed form, such as pre-dried, moistened, comminuted, ground, pressed or roasted, which process is also known as post-harvest treatment. Also falling under the definition of stored products is timber, whether in the form of crude timber, such as construction timber, electricity pylons and barriers, or in the form of finished articles, such as furniture or objects made from wood. Stored products of animal origin are hides, leather, furs, hairs and the like. The combinations according the present invention can prevent disadvantageous effects such as decay, discoloration or mold. Preferably "stored products" is understood to denote natural substances of plant origin and their processed forms, more preferably fruits and their processed forms, such as pomes, stone fruits, soft fruits and citrus fruits and their processed forms.

The compounds I and compositions thereof, respectively, may be used for improving the health of a plant. The invention also relates to a method for improving plant health by treating a plant, its propagation material and/or the locus where the plant is growing or is to grow with an effective amount of compounds I and compositions thereof, respectively.

The term "plant health" is to be understood to denote a condition of the plant and/or its products which is determined by several indicators alone or in combination with each other such as yield (e. g. increased biomass and/or increased content of valuable ingredients), plant vigor (e. g. improved plant growth and/or greener leaves ("greening effect")), quality (e. g. improved content or composition of certain ingredients) and tolerance to abiotic and/or biotic stress. The above identified indicators for the health condition of a plant may be interdependent or may result from each other.

The compounds of formula I can be present in different crystal modifications whose biological activity may differ. They are likewise subject matter of the present invention.

The compounds I are employed as such or in form of compositions by treating the fungi or the plants, plant propagation materials, such as seeds, soil, surfaces, materials or rooms to be protected from fungal attack with a fungicidally effective amount of the active substances. The application can be carried out both before and after the infection of the plants, plant propagation materials, such as seeds, soil, surfaces, materials or rooms by the fungi.

Plant propagation materials may be treated with compounds I as such or a composition comprising at least one compound I prophylactically either at or before planting or transplanting.

The invention also relates to agrochemical compositions comprising an auxiliary and at least one compound I according to the invention.

An agrochemical composition comprises a fungicidally effective amount of a compound I. The term "effective amount" denotes an amount of the composition or of the compounds I, which is sufficient for controlling harmful fungi on cultivated plants or in the protection of materials and which does not result in a substantial damage to the treated plants. Such an amount can vary in a broad range and is dependent on various factors, such as the fungal species to be controlled, the treated cultivated plant or material, the climatic conditions and the specific compound I used.

The compounds I, their N-oxides and salts can be converted into customary types of agrochemical compositions, e. g. solutions, emulsions, suspensions, dusts, powders, pastes, granules, pressings, capsules, and mixtures thereof. Examples for composition types are suspensions (e. g. SC, OD, FS), emulsifiable concentrates (e. g. EC), emulsions (e. g. EW, EO, ES, ME), capsules (e. g. CS, ZC), pastes, pastilles, wettable powders or dusts (e. g. WP, SP, WS, DP, DS), pressings (e. g. BR, TB, DT), granules (e. g. WG, SG, GR, FG, GG, MG), insecticidal articles (e. g. LN), as well as gel formulations for the treatment of plant propagation materials such as seeds (e. g. GF). These and further compositions types are defined in the "Catalogue of pesticide formulation types and international coding system", Technical Monograph No. 2, 6th Ed. May 2008, CropLife International.

The compositions are prepared in a known manner, such as described by Mollet and Grubemann, Formulation technology, Wiley VCH, Weinheim, 2001; or Knowles, New developments in crop protection product formulation, Agrow Reports DS243, T&F Informa, London, 2005.

Suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, such as mineral oil fractions of medium to high boiling point, e. g. kerosene, diesel oil; oils of vegetable or animal origin; aliphatic, cyclic and aromatic hydrocarbons, e. g. toluene, paraffin, tetrahydronaphthalene, alkylated naphthalenes; alcohols, e. g. ethanol, propanol, butanol, benzyl alcohol, cyclohexanol; glycols; DMSO; ketones, e. g. cyclohexanone; esters, e. g. lactates, carbonates, fatty acid esters, gamma-butyrolactone; fatty acids; phosphonates; amines; amides, e. g. N-methyl pyrrolidone, fatty acid dimethyl amides; and mixtures thereof.

Suitable solid carriers or fillers are mineral earths, e. g. silicates, silica gels, talc, kaolins, limestone, lime, chalk, clays, dolomite, diatomaceous earth, bentonite, calcium sulfate, magnesium sulfate, magnesium oxide; polysaccharides, e. g. cellulose, starch; fertilizers, e. g. ammonium sulfate, ammonium phosphate, ammonium nitrate, ureas; products of vegetable origin, e. g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emulsifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.)

Suitable anionic surfactants are alkali, alkaline earth or ammonium salts of sulfonates, sulfates, phosphates, carboxylates, and mixtures thereof. Examples of sulfonates are alkylaryl sulfonates, diphenyl sulfonates, alpha-olefin sulfonates, lignin sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkyl naphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are home- or copolymers of vinyl pyrrolidone, vinyl alcohols, or vinyl acetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinyl amines or polyethylene amines.

Suitable adjuvants are compounds, which have a negligible or even no pesticidal activity themselves, and which improve the biological performance of the compound I on the target. Examples are surfactants, mineral or vegetable oils, and other auxiliaries. Further examples are listed by Knowles, Adjuvants and additives, Agrow Reports DS256, T&F Informa UK, 2006, chapter 5.

Suitable thickeners are polysaccharides (e. g. xanthan gum, carboxymethyl cellulose), inorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e. g. in red, blue, or green) are pigments of low water solubility and water-soluble dyes. Examples are inorganic colorants (e. g. iron oxide, titan oxide, iron hexacyanoferrate) and organic colorants (e. g. alizarin-, azo- and phthalocyanine colorants).

Suitable tackifiers or binders are polyvinyl pyrrolidones, polyvinyl acetates, polyvinyl alcohols, polyacrylates, biological or synthetic waxes, and cellulose ethers.

Examples for composition types and their preparation are:
i) Water-Soluble Concentrates (SL, LS)
10-60 wt % of a compound I and 5-15 wt % wetting agent (e. g. alcohol alkoxylates) are dissolved in water and/or in a water-soluble solvent (e. g. alcohols) ad 100 wt %. The active substance dissolves upon dilution with water.
ii) Dispersible Concentrates (DC)
5-25 wt % of a compound I and 1-10 wt % dispersant (e. g. polyvinyl pyrrolidone) are dissolved in organic solvent (e. g. cyclohexanone) ad 100 wt %. Dilution with water gives a dispersion.
iii) Emulsifiable Concentrates (EC)
15-70 wt % of a compound I and 5-10 wt % emulsifiers (e. g. calcium dodecylbenzenesulfonate and castor oil ethoxylate) are dissolved in water-insoluble organic solvent (e. g. aromatic hydrocarbon) ad 100 wt %. Dilution with water gives an emulsion.
iv) Emulsions (EW, EO, ES)
5-40 wt % of a compound I and 1-10 wt % emulsifiers (e. g. calcium dodecylbenzenesulfonate and castor oil ethoxylate) are dissolved in 20-40 wt % water-insoluble organic solvent (e. g. aromatic hydrocarbon). This mixture is introduced into water ad 100 wt % by means of an emulsifying machine and made into a homogeneous emulsion. Dilution with water gives an emulsion.
v) Suspensions (SC, OD, FS)
In an agitated ball mill, 20-60 wt % of a compound I are comminuted with addition of 2-10 wt % dispersants and wetting agents (e. g. sodium lignosulfonate and alcohol ethoxylate), 0.1-2 wt % thickener (e. g. xanthan gum) and water ad 100 wt % to give a fine active substance suspension. Dilution with water gives a stable suspension of the active substance. For FS type composition up to 40 wt % binder (e. g. polyvinyl alcohol) is added.
vi) Water-Dispersible Granules and Water-Soluble Granules (WG, SG)
50-80 wt % of a compound I are ground finely with addition of dispersants and wetting agents (e. g. sodium lignosulfonate and alcohol ethoxylate) ad 100 wt % and prepared as water-dispersible or water-soluble granules by means of technical appliances (e. g. extrusion, spray tower, fluidized bed). Dilution with water gives a stable dispersion or solution of the active substance.
vii) Water-Dispersible Powders and Water-Soluble Powders (WP, SP, WS)
50-80 wt % of a compound I are ground in a rotor-stator mill with addition of 1-5 wt % dispersants (e. g. sodium lignosulfonate), 1-3 wt % wetting agents (e. g. alcohol ethoxylate) and solid carrier (e. g. silica gel) ad 100 wt %. Dilution with water gives a stable dispersion or solution of the active substance.
viii) Gel (GW, GF)
In an agitated ball mill, 5-25 wt % of a compound I are comminuted with addition of 3-10 wt % dispersants (e. g. sodium lignosulfonate), 1-5 wt % thickener (e. g. carboxymethyl cellulose) and water ad 100 wt % to give a fine suspension of the active substance. Dilution with water gives a stable suspension of the active substance.

ix) Microemulsion (ME)

5-20 wt % of a compound I are added to 5-30 wt % organic solvent blend (e. g. fatty acid dimethyl amide and cyclohexanone), 10-25 wt % surfactant blend (e. g. alcohol ethoxylate and arylphenol ethoxylate), and water ad 100%. This mixture is stirred for 1 h to produce spontaneously a thermodynamically stable microemulsion.

x) Microcapsules (CS)

An oil phase comprising 5-50 wt % of a compound I, 0-40 wt % water insoluble organic solvent (e. g. aromatic hydrocarbon), 2-15 wt % acrylic monomers (e. g. methylmethacrylate, methacrylic acid and a di- or triacrylate) are dispersed into an aqueous solution of a protective colloid (e. g. polyvinyl alcohol). Radical polymerization results in the formation of poly(meth)acrylate microcapsules. Alternatively, an oil phase comprising 5-50 wt % of a compound I according to the invention, 0-40 wt % water insoluble organic solvent (e. g. aromatic hydrocarbon), and an isocyanate monomer (e. g. diphenylmethene-4,4'-diisocyanatae) are dispersed into an aqueous solution of a protective colloid (e. g. polyvinyl alcohol). The addition of a polyamine (e. g. hexamethylenediamine) results in the formation of polyurea microcapsules. The monomers amount to 1-10 wt %. The wt % relate to the total CS composition.

xi) Dustable Powders (DP, DS)

1-10 wt % of a compound I are ground finely and mixed intimately with solid carrier (e. g. finely divided kaolin) ad 100 wt %.

xii) Granules (GR, FG)

0.5-30 wt % of a compound I is ground finely and associated with solid carrier (e. g. silicate) ad 100 wt %. Granulation is achieved by extrusion, spray-drying or fluidized bed.

xiii) Ultra-Low Volume Liquids (UL)

1-50 wt % of a compound I are dissolved in organic solvent (e. g. aromatic hydrocarbon) ad 100 wt %.

The compositions types i) to xiii) may optionally comprise further auxiliaries, such as 0.1-1 wt % bactericides, 5-15 wt % anti-freezing agents, 0.1-1 wt % anti-foaming agents, and 0.1-1 wt % colorants.

The agrochemical compositions generally comprise between 0.01 and 95%, preferably between 0.1 and 90%, and in particular between 0.5 and 75%, by weight of active substance. The active substances are employed in a purity of from 90% to 100%, preferably from 95% to 100% (according to NMR spectrum).

For the purposes of treatment of plant propagation materials, particularly seeds, solutions for seed treatment (LS), Suspoemulsions (SE), flowable concentrates (FS), powders for dry treatment (DS), water-dispersible powders for slurry treatment (WS), water-soluble powders (SS), emulsions (ES), emulsifiable concentrates (EC), and gels (GF) are usually employed. The compositions in question give, after two-to-tenfold dilution, active substance concentrations of from 0.01 to 60% by weight, preferably from 0.1 to 40%, in the ready-to-use preparations. Application can be carried out before or during sowing. Methods for applying compound I and compositions thereof, respectively, onto plant propagation material, especially seeds, include dressing, coating, pelleting, dusting, and soaking as well as in-furrow application methods. Preferably, compound I or the compositions thereof, respectively, are applied on to the plant propagation material by a method such that germination is not induced, e. g. by seed dressing, pelleting, coating and dusting.

When employed in plant protection, the amounts of active substances applied are, depending on the kind of effect desired, from 0.001 to 2 kg per ha, preferably from 0.005 to 2 kg per ha, more preferably from 0.05 to 0.9 kg per ha, and in particular from 0.1 to 0.75 kg per ha.

In treatment of plant propagation materials such as seeds, e. g. by dusting, coating or drenching seed, amounts of active substance of from 0.1 to 1000 g, preferably from 1 to 1000 g, more preferably from 1 to 100 g and most preferably from 5 to 100 g, per 100 kilogram of plant propagation material (preferably seeds) are generally required.

When used in the protection of materials or stored products, the amount of active substance applied depends on the kind of application area and on the desired effect. Amounts customarily applied in the protection of materials are 0.001 g to 2 kg, preferably 0.005 g to 1 kg, of active substance per cubic meter of treated material.

Various types of oils, wetters, adjuvants, fertilizer, or micronutrients, and further pesticides (e. g. herbicides, insecticides, fungicides, growth regulators, safeners, biopesticides) may be added to the active substances or the compositions comprising them as premix or, if appropriate not until immediately prior to use (tank mix). These agents can be admixed with the compositions according to the invention in a weight ratio of 1:100 to 100:1, preferably 1:10 to 10:1.

A pesticide is generally a chemical or biological agent (such as pestidal active ingredient, compound, composition, virus, bacterium, antimicrobial or disinfectant) that through its effect deters, incapacitates, kills or otherwise discourages pests. Target pests can include insects, plant pathogens, weeds, mollusks, birds, mammals, fish, nematodes (roundworms), and microbes that destroy property, cause nuisance, spread disease or are vectors for disease. The term pesticides includes also plant growth regulators that alter the expected growth, flowering, or reproduction rate of plants; defoliants that cause leaves or other foliage to drop from a plant, usually to facilitate harvest; desiccants that promote drying of living tissues, such as unwanted plant tops; plant activators that activate plant physiology for defense of against certain pests; safeners that reduce unwanted herbicidal action of pesticides on crop plants; and plant growth promoters that affect plant physiology to increase plant growth, biomass, yield or any other quality parameter of the harvestable goods of a crop plant.

Biopesticides have been defined as a form of pesticides based on micro-organisms (bacteria, fungi, viruses, nematodes, etc.) or natural products (compounds, such as metabolites, proteins, or extracts from biological or other natural sources) (U.S. Environmental Protection Agency: http://www.epa.gov/pesticides/biopesticides/).

Biopesticides are typically created by growing and concentrating naturally occurring organisms and/or their metabolites including bacteria and other microbes, fungi, viruses, nematodes, proteins, etc. They are often considered to be important components of integrated pest management (IPM) programs.

Biopesticides fall into two major classes, microbial and biochemical pesticides:

(1) Microbial pesticides consist of bacteria, fungi or viruses (and often include the metabolites that bacteria and fungi produce). Entomopathogenic nematodes are also classed as microbial pesticides, even though they are multi-cellular.

(2) Biochemical pesticides are naturally occurring substances that control pests or provide other crop protection uses as defined below, but are relatively non-toxic to mammals.

The user applies the composition according to the invention usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

According to one embodiment, individual components of the composition according to the invention such as parts of a kit or parts of a binary or ternary mixture may be mixed by the user himself in a spray tank or any other kind of vessel used for applications (e. g. seed treater drums, seed pelleting machinery, knapsack sprayer) and further auxiliaries may be added, if appropriate.

When living microorganisms, such as pesticides from groups L1), L3) and L5), form part of such kit, it must be taken care that choice and amounts of the components (e. g. chemical pesticidal agents) and of the further auxiliaries should not influence the viability of the microbial pesticides in the composition mixed by the user. Especially for bactericides and solvents, compatibility with the respective microbial pesticide has to be taken into account.

Consequently, one embodiment of the invention is a kit for preparing a usable pesticidal composition, the kit comprising a) a composition comprising component 1) as defined herein and at least one auxiliary; and b) a composition comprising component 2) as defined herein and at least one auxiliary; and optionally c) a composition comprising at least one auxiliary and optionally a further active component 3) as defined herein.

Mixing the compounds I or the compositions comprising them in the use form as fungicides with other fungicides results in many cases in an expansion of the fungicidal spectrum of activity being obtained or in a prevention of fungicide resistance development. Furthermore, in many cases, synergistic effects are obtained.

The following list of pesticides II (e. g. pesticidally-active substances and biopesticides), in conjunction with which the compounds I can be used, is intended to illustrate the possible combinations but does not limit them:

A) Respiration Inhibitors

Inhibitors of complex III at $Q_o$ site (e. g. strobilurins): azoxystrobin (A.1.1), coumethoxystrobin (A.1.2), coumoxystrobin (A.1.3), dimoxystrobin (A.1.4), enestroburin (A.1.5), fenaminstrobin (A.1.6), fenoxystrobin/flufenoxystrobin (A.1.7), fluoxastrobin (A.1.8), kresoxim-methyl (A.1.9), mandestrobin (A.1.10), metominostrobin (A.1.11), orysastrobin (A.1.12), picoxystrobin (A.1.13), pyraclostrobin (A.1.14), pyrametostrobin (A.1.15), pyraoxystrobin (A.1.16), trifloxystrobin (A.1.17) and 2-(2-(3-(2,6-dichlorophenyl)-1-methyl-allylidene-aminooxymethyl)-phenyl)-2-methoxyimino-N-methyl-acetamide (A.1.18), pyribencarb (A.1.19), triclopyricarb/chlorodincarb (A.1.20), famoxadone (A.1.21), fenamidone (A.1.21); methyl-N-[2-[(1,4-dimethyl-5-phenyl-pyrazol-3-yl)oxylmethyl]phenyl]-N-methoxy-carbamate (A.1.22), 1-[3-chloro-2-[[1-(4-chlorophenyl)-1H-pyrazol-3-yl]oxymethyl]phenyl]-4-methyl-tetrazol-5-one (A.1.23), 1-[3-bromo-2-[[1-(4-chlorophenyl)pyrazol-3-yl]oxymethyl]phenyl]-4-methyl-tetrazol-5-one (A.1.24), 1-[2-[[1-(4-chlorophenyl)pyrazol-3-yl]oxymethyl]-3-methyl-phenyl]-4-methyl-tetrazol-5-one (A.1.25), 1-[2-[[1-(4-chlorophenyl)pyrazol-3-yl]oxymethyl]-3-fluoro-phenyl]-4-methyl-tetrazol-5-one (A.1.26), 1-[2-[[1-(2,4-dichlorophenyl)pyrazol-3-yl]oxymethyl]-3-fluoro-phenyl]-4-methyl-tetrazol-5-one (A.1.27), 1-[2-[[4-(4-chlorophenyl)thiazol-2-yl]oxymethyl]-3-methyl-phenyl]-4-methyl-tetrazol-5-one (A.1.28), 1-[3-chloro-2-[[4-(p-tolyl)thiazol-2-yl]oxymethyl]phenyl]-4-methyl-tetrazol-5-one (A.1.29), 1-[3-cyclopropyl-2-[[2-methyl-4-(1-methylpyrazol-3-yl)phenoxy]methyl]phenyl]-4-methyl-tetrazol-5-one (A.1.30), 1-[3-(difluoromethoxy)-2-[[2-methyl-4-(1-methylpyrazol-3-yl)phenoxy]methyl]phenyl]-4-methyl-tetrazol-5-one (A.1.31), 1-methyl-4-[3-methyl-2-[[2-methyl-4-(1-methylpyrazol-3-yl)phenoxy]methyl]phenyl]tetrazol-5-one (A.1.32), 1-methyl-4-[3-methyl-2-[[1-[3-(trifluoromethyl)phenyl]-ethylideneamino]oxymethyl]phenyl]tetrazol-5-one (A.1.33), (Z2E)-5-[1-(2,4-dichlorophenyl)pyrazol-3-yl]-oxy-2-methoxyimino-N,3-dimethyl-pent-3-enamide (A.1.34), (Z,2E)-5-[1-(4-chlorophenyl)pyrazol-3-yl]oxy-2-methoxyimino-N,3-dimethyl-pent-3-enamide (A.1.35), (Z,2E)-5-[1-(4-chloro-2-fluoro-phenyl)pyrazol-3-yl]oxy-2-methoxyimino-N,3-dimethyl-pent-3-enamide (A.1.36);

inhibitors of complex III at $Q_i$; site: cyazofamid (A.2.1), amisulbrom (A.2.2), [(3S,6S,7R,8R)-8-benzyl-3-[(3-acetoxy-4-methoxy-pyridine-2-carbonyl)amino]-6-methyl-4,9-dioxo-1,5-dioxonan-7-yl]2-methylpropanoate (A.2.3), [(3S,6S,7R,8R)-8-benzyl-3-[[3-(acetoxymethoxy)-4-methoxy-pyridine-2-carbonyl]amino]-6-methyl-4,9-dioxo-1,5-dioxonan-7-yl] 2-methylpropanoate (A.2.4), [(3S,6S,7R,8R)-8-benzyl-3-[(3-isobutoxycarbonyloxy-4-methoxy-pyridine-2-carbonyl)amino]-6-methyl-4,9-dioxo-1,5-dioxonan-7-yl] 2-methylpropanoate (A.2.5), [(3S,6S,7R,8R)-8-benzyl-3-[[3-(1,3-benzodioxol-5-ylmethoxy)-4-methoxy-pyridine-2-carbonyl]amino]-6-methyl-4,9-dioxo-1,5-dioxonan-7-yl] 2-methylpropanoate (A.2.6); (3S,6S,7R,8R)-3-[[(3-hydroxy-4-methoxy-2-pyridinyl)carbonyl]amino]-6-methyl-4,9-dioxo-8-(phenylmethyl)-1,5-dioxonan-7-yl 2-methylpropanoate (A.2.7), (3S,6S,7R,8R)-8-benzyl-3-[3-[(isobutyryloxy) methoxy]-4-methoxypicolinamido]-6-methyl-4,9-dioxo-1,5-dioxonan-7-yl isobutyrate (A.2.8);

inhibitors of complex II (e. g. carboxamides): benodanil (A.3.1), benzovindiflupyr (A.3.2), bixafen (A.3.3), boscalid (A.3.4), carboxin (A.3.5), fenfuram (A.3.6), fluopyram (A.3.7), flutolanil (A.3.8), fluxapyroxad (A.3.9), furametpyr (A.3.10), isofetamid (A.3.11), isopyrazam (A.3.12), mepronil (A.3.13), oxycarboxin (A.3.14), penflufen (A.3.14), penthiopyrad (A.3.15), sedaxane (A.3.16), tecloftalam (A.3.17), thifluzamide (A.3.18), N-(4'-trifluoromethylthiobiphenyl-2-yl)-3-difluoromethyl-1-methyl-1H-pyrazole-4-carboxamide (A.3.19), N-(2-(1,3,3-trimethyl-butyl)-phenyl)-1,3-dimethyl-5-fluoro-1H-pyrazole-4-carboxamide (A.3.20), 3-(difluoromethyl)-1-methyl-N-(1,1,3-trimethylindan-4-yl)pyrazole-4-carboxamide (A.3.21), 3-(trifluoromethyl)-1-methyl-N-(1,1,3-trimethylindan-4-yl)pyrazole-4-carboxamide (A.3.22), 1,3-dimethyl-N-(1,1,3-trimethylindan-4-yl)pyrazole-4-carboxamide (A.3.23), 3-(trifluoromethyl)-1,5-dimethyl-N-(1,1,3-trimethylindan-4-yl)pyrazole-4-carboxamide (A.3.24), 1,3,5-trimethyl-N-(1,1,3-trimethylindan-4-yl)pyrazole-4-carboxamide (A.3.25), N-(7-fluoro-1,1,3-trimethyl-indan-4-yl)-1,3-dimethyl-pyrazole-4-carboxamide (A.3.26), N-[2-(2,4-dichlorophenyl)-2-methoxy-1-methyl-ethyl]-3-(difluoromethyl)-1-methyl-pyrazole-4-carboxamide (A.3.27);

other respiration inhibitors (e. g. complex I, uncouplers): diflumetorim (A.4.1), (5,8-difluoro-quinazolin-4-yl)-{2-[2-fluoro-4-(4-trifluoromethylpyridin-2-yloxy)-phenyl]-ethyl}-amine (A.4.2); nitrophenyl derivates: binapacryl (A.4.3), dinobuton (A.4.4), dinocap (A.4.5), fluazinam (A.4.6); ferimzone (A.4.7); organometal compounds: fentin salts, such as fentin-acetate (A.4.8), fentin chloride (A.4.9) or fentin hydroxide (A.4.10); ametoctradin (A.4.11); and silthiofam (A.4.12);

B) Sterol Biosynthesis Inhibitors (SBI Fungicides)

C14 demethylase inhibitors (DMI fungicides): triazoles: azaconazole (B.1.1), bitertanol (B.1.2), bromuconazole (B.1.3), cyproconazole (B.1.4), difenoconazole (B.1.5), diniconazole (B.1.6), diniconazole-M (B.1.7), epoxiconazole (B.1.8), fenbuconazole (B.1.9), fluquinconazole (B.1.10), flusilazole (B.1.11), flutriafol (B.1.12), hexaconazole (B.1.13), imibenconazole (B.1.14), ipconazole (B.1.15), metconazole (B.1.17), myclobutanil (B.1.18), oxpoconazole (B.1.19), paclobutrazole (B.1.20), penconazole (B.1.21), propiconazole (B.1.22), prothioconazole (B.1.23), simeconazole (B.1.24), tebuconazole (B.1.25), tetraconazole (B.1.26), triadimefon (B.1.27), triadimenol (B.1.28), triticonazole (B.1.29), uniconazole (B.1.30), 1-[rel-(2S;3R)-3-(2-chlorophenyl)-2-(2,4-difluorophenyl)-oxiranylmethyl]-5-thiocyanato-1H-[1,2,4]triazolo (B.1.31), 2-[rel-(2S;3R)-3-(2-chlorophenyl)-2-(2,4-difluorophenyl)-oxiranylmethyl]-2H-[1,2,4]triazole-3-thiol (B.1.32), 2-[2-chloro-4-(4-chlorophenoxy)phenyl]-1-(1,2,4-triazol-1-yl)pentan-2-ol (B.1.33), 1-[4-(4-chlorophenoxy)-2-(trifluoromethyl)phenyl]-1-cyclopropyl-2-(1,2,4-triazol-1-yl)ethanol (B.1.34), 2-[4-(4-chlorophenoxy)-2-(trifluoromethyl)phenyl]-1-(1,2,4-triazol-1-yl)butan-2-ol (B.1.35), 2-[2-chloro-4-(4-chlorophenoxy)phenyl]-1-(1,2,4-triazol-1-yl)butan-2-ol (B.1.36), 2-[4-(4-chlorophenoxy)-2-(trifluoromethyl)phenyl]-3-methyl-1-(1,2,4-triazol-1-yl)butan-2-ol (B.1.37), 2-[4-(4-chlorophenoxy)-2-(trifluoromethyl)phenyl]-1-(1,2,4-triazol-1-yl)propan-2-ol (B.1.38), 2-[2-chloro-4-(4-chlorophenoxy)phenyl]-3-methyl-1-(1,2,4-triazol-1-yl)butan-2-ol (B.1.39), 2-[4-(4-chlorophenoxy)-2-(trifluoromethyl)phenyl]-1-(1,2,4-triazol-1-yl)pentan-2-ol (B.1.40), 2-[4-(4-fluorophenoxy)-2-(trifluoromethyl)phenyl]-1-(1,2,4-triazol-1-yl)propan-2-ol (B.1.41); imidazoles: imazalil (B.1.42), pefurazoate (B.1.43), prochloraz (B.1.44), triflumizol (B.1.45); pyrimidines, pyridines and piperazines: fenarimol (B.1.46), nuarimol (B.1.47), pyrifenox (B.1.48), triforine (B.1.49), [3-(4-chloro-2-fluoro-phenyl)-5-(2,4-difluoro-phenyl)isoxazol-4-yl]-(3-pyridyl)methanol (B.1.50), 2-[2-chloro-4-(4-chlorophenoxy)phenyl]-1-(1,2,4-triazol-1-yl)pent-3-yn-2-ol (B.1.51);

Delta14-reductase inhibitors: aldimorph (B.2.1), dodemorph (B.2.2), dodemorph-acetate (B.2.3), fenpropimorph (B.2.4), tridemorph (B.2.5), fenpropidin (B.2.6), piperalin (B.2.7), spiroxamine (B.2.8);

Inhibitors of 3-keto reductase: fenhexamid (B.3.1);

C) Nucleic Acid Synthesis Inhibitors phenylamides or acyl amino acid fungicides: benalaxyl (C.1.1), benalaxyl-M (C.1.2), kiralaxyl (C.1.3), metalaxyl (C.1.4), metalaxyl-M (mefenoxam, C.1.5), ofurace (C.1.6), oxadixyl (C.1.7);

others: hymexazole (C.2.1), octhilinone (C.2.2), oxolinic acid (C.2.3), bupirimate (C.2.4), 5-fluorocytosine (C.2.5), 5-fluoro-2-(p-tolylmethoxy)pyrimidin-4-amine (C.2.6), 5-fluoro-2-(4-fluorophenylmethoxy)pyrimidin-4-amine (C.2.7);

D) Inhibitors of Cell Division and Cytoskeleton tubulin inhibitors, such as benzimidazoles, thiophanates: benomyl (D1.1), carbendazim (D1.2), fuberidazole (D1.3), thiabendazole (D1.4), thiophanate-methyl (D1.5); triazolopyrimidines: 5-chloro-7-(4-methylpiperidin-1-yl)-6-(2,4,6-trifluorophenyl)-[1,2,4]triazolo[1,5-a]pyrimidine (D1.6);

other cell division inhibitors: diethofencarb (D2.1), ethaboxam (D2.2), pencycuron (D2.3), fluopicolide (D2.4), zoxamide (D2.5), metrafenone (D2.6), pyriofenone (D2.7);

E) Inhibitors of Amino Acid and Protein Synthesis methionine synthesis inhibitors (anilino-pyrimidines): cyprodinil (E.1.1), mepanipyrim (E.1.2), pyrimethanil (E.1.3);

protein synthesis inhibitors: blasticidin-S (E.2.1), kasugamycin (E.2.2), kasugamycin hydrochloride-hydrate (E.2.3), mildiomycin (E.2.4), streptomycin (E.2.5), oxytetracyclin (E.2.6), polyoxine (E.2.7), validamycin A (E.2.8);

F) Signal Transduction Inhibitors

MAP/histidine kinase inhibitors: fluoroimid (F.1.1), iprodione (F.1.2), procymidone (F.1.3), vinclozolin (F.1.4), fenpiclonil (F.1.5), fludioxonil (F.1.6);

G protein inhibitors: quinoxyfen (F.2.1);

G) Lipid and Membrane Synthesis Inhibitors

Phospholipid biosynthesis inhibitors: edifenphos (G.1.1), iprobenfos (G.1.2), pyrazophos (G.1.3), isoprothiolane (G.1.4);

lipid peroxidation: dicloran (G.2.1), quintozene (G.2.2), tecnazene (G.2.3), tolclofos-methyl (G.2.4), biphenyl (G.2.5), chloroneb (G.2.6), etridiazole (G.2.7);

phospholipid biosynthesis and cell wall deposition: dimethomorph (G.3.1), flumorph (G.3.2), mandipropamid (G.3.3), pyrimorph (G.3.4), benthiavalicarb (G.3.5), iprovalicarb (G.3.6), valifenalate (G.3.7) and N-(1-(1-(4-cyano-phenyl)ethanesulfonyl)-but-2-yl) carbamic acid-(4-fluorophenyl) ester (G.3.8);

compounds affecting cell membrane permeability and fatty acids: propamocarb (G.4.1);

fatty acid amide hydrolase inhibitors: oxathiapiprolin (G.5.1), 2-{3-[2-(1-{[3,5-bis(di-fluoromethyl-1H-pyrazol-1-yl]acetyl}piperidin-4-yl)-1,3-thiazol-4-yl]-4,5-dihydro-1,2-oxazol-5-yl}phenyl methanesulfonate (G.5.2), 2-{3-[2-(1-{[3,5-bis(difluoromethyl)-1H-pyrazol-1-yl]acetyl}piperidin-4-yl) 1,3-thiazol-4-yl]-4,5-dihydro-1,2-oxazol-5-yl}-3-chlorophenyl methanesulfonate (G.5.3);

H) Inhibitors with Multi Site Action inorganic active substances: Bordeaux mixture (H.1.1), copper acetate (H.1.2), copper hydroxide (H.1.3), copper oxychloride (H.1.4), basic copper sulfate (H.1.5), sulfur (H.1.6);

thio- and dithiocarbamates: ferbam (H.2.1), mancozeb (H.2.2), maneb (H.2.3), metam (H.2.4), metiram (H.2.5), propineb (H.2.6), thiram (H.2.7), zineb (H.2.8), ziram (H.2.9);

organochlorine compounds (e. g. phthalimides, sulfamides, chloronitriles): anilazine (H.3.1), chlorothalonil (H.3.2), captafol (H.3.3), captan (H.3.4), folpet (H.3.5), dichlofluanid (H.3.6), dichlorophen (H.3.7), hexachlorobenzene (H.3.8), pentachlorphenole (H.3.9) and its salts, phthalide (H.3.10), tolylfluanid (H.3.11), N-(4-chloro-2-nitro-phenyl)-N-ethyl-4-methyl-benzenesulfonamide (H.3.12);

guanidines and others: guanidine (H.4.1), dodine (H.4.2), dodine free base (H.4.3), guazatine (H.4.4), guazatine-acetate (H.4.5), iminoctadine (H.4.6), iminoctadine-triacetate (H.4.7), iminoctadine-tris(albesilate) (H.4.8), dithianon (H.4.9), 2,6-dimethyl-1H,5H-[1,4]dithiino[2,3-c:5,6-C']dipyrrole-1,3,5,7(2H,6H)-tetraone (H.4.10);

I) Cell Wall Synthesis Inhibitors inhibitors of glucan synthesis: validamycin (I.1.1), polyoxin B (I.1.2);

melanin synthesis inhibitors: pyroquilon (I.2.1), tricyclazole (I.2.2), carpropamid (I.2.3), dicyclomet (I.2.4), fenoxanil (I.2.5);

J) Plant Defence Inducers acibenzolar-S-methyl (J.1.1), probenazole (J.1.2), isotianil (J.1.3), tiadinil (J.1.4), prohexadione-calcium (J.1.5); phosphonates: fosetyl (J.1.6), fosetyl-aluminum (J.1.7), phosphorous acid and its salts (J.1.8), potassium or sodium bicarbonate (J.1.9);

K) Unknown Mode of Action bronopol (K.1.1), chinomethionat (K.1.2), cyflufenamid (K.1.3), cymoxanil (K.1.4), dazomet (K.1.5), debacarb (K.1.6), diclomezine (K.1.7), difenzoquat (K.1.8), difenzoquat-methylsulfate (K.1.9), diphenylamin (K.1.10), fenpyrazamine (K.1.11), flumetover (K.1.12), flusulfamide (K.1.13), flutianil (K.1.14), methasulfocarb (K.1.15), nitrapyrin (K.1.16), nitrothalisopropyl (K.1.18), oxathiapiprolin (K.1.19), tolprocarb (K.1.20), oxin-copper (K.1.21), proquinazid (K.1.22), tebufloquin (K.1.23), tecloftalam (K.1.24), triazoxide (K.1.25), 2-butoxy-6-iodo-3-propylchromen-4-one (K.1.26), 2-[3,5-bis(difluoromethyl)-1H-pyrazol-1-yl]-1-[4-(4-{5-[2-(prop-2-yn-1-yloxy)phenyl]-4,5-dihydro-1,2-oxazol-3-yl}-1,3-thiazol-2-yl)piperidin-1-yl]ethanone (K.1.27), 2-[3,5-bis(difluoromethyl)-1H-pyrazol-1-yl]-1-[4-(4-{5-[2-fluoro-6-(prop-2-yn-1-yloxy)phenyl]-4,5-dihydro-1,2-oxazol-3-yl}-1,3-thiazol-2-yl)piperidin-1-yl]ethanone (K.1.28), 2-[3,5-bis(difluoromethyl)-1H-pyrazol-1-yl]-1-[4-(4-{5-[2-chloro-6-(prop-2-yn-1-yloxy)phenyl]-4,5-dihydro-1,2-oxazol-3-yl}-1,3-thiazol-2-yl)piperidin-1-yl]ethanone (K.1.29), N-(cyclo-propylmethoxyimino-(6-difluoromethoxy-2,3-difluoro-phenyl)-methyl)-2-phenyl acetamide (K.1.30), N'-(4-(4-chloro-3-trifluoromethyl-phenoxy)-2,5-dimethyl-phenyl)-N-ethyl-N-methyl formamidine (K.1.31), N'-(4-(4-fluoro-3-trifluoromethyl-phenoxy)-2,5-dimethyl-phenyl)-N-ethyl-N-methyl formamidine (K.1.32), N'-(2-methyl-5-trifluoromethyl-4-(3-trimethylsilanyl-propoxy)-phenyl)-N-ethyl-N-methyl formamidine (K.1.33), N'-(5-difluoromethyl-2-methyl-4-(3-trimethylsilanyl-propoxy)-phenyl)-N-ethyl-N-methyl formamidine (K.1.34), methoxy-acetic acid 6-tert-butyl-8-fluoro-2,3-dimethyl-quinolin-4-yl ester (K.1.35), 3-[5-(4-methylphenyl)-2,3-dimethyl-isoxazolidin-3-yl]-pyridine (K.1.36), 3-[5-(4-chloro-phenyl)-2,3-dimethyl-isoxazolidin-3-yl]-pyridine (pyrisoxazole) (K.1.37), N-(6-methoxy-pyridin-3-yl) cyclopropanecarboxylic acid amide (K.1.38), 5-chloro-1-(4,6-dimethoxy-pyrimidin-2-yl)-2-methyl-1H-benzoimidazole (K.1.39), 2-(4-chloro-phenyl)-N-[4-(3,4-dimethoxy-phenyl)-isoxazol-5-yl]-2-prop-2-ynyloxy-acetamide, ethyl (Z)-3-amino-2-cyano-3-phenyl-prop-2-enoate (K.1.40), picarbutrazox (K.1.41), pentyl N-[6-[[(Z)-[(1-methyl-tetrazol-5-yl)-phenyl-methylene]amino]oxymethyl]-2-pyridyl]carbamate (K.1.42), 2-[2-[(7,8-difluoro-2-methyl-3-quinolyl)oxy]-6-fluoro-phenyl]propan-2-ol (K.1.43), 2-[2-fluoro-6-[(8-fluoro-2-methyl-3-quinolyl)oxy]phen-yl]propan-2-ol (K.1.44), 3-(5-fluoro-3,3,4,4-tetramethyl-3,4-dihydroisoquinolin-1-yl)quinoline (K.1.45), 3-(4,4-difluoro-3,3-dimethyl-3,4-dihydroisoquinolin-1-yl)quinoline (K.1.46), 3-(4,4,5-trifluoro-3,3-dimethyl-3,4-dihydroisoquinolin-1-yl)quinoline (K.1.47), 9-fluoro-2,2-dimethyl-5-(3-quinolyl)-3H-1,4-benzoxazepine (K.1.48);

L) Biopesticides

L1) Microbial pesticides with fungicidal, bactericidal, viricidal and/or plant defense activator activity: *Ampelomyces quisqualis, Aspergillus flavus, Aureobasidium pullulans, Bacillus amyloliquefaciens, B. mojavensis, B. pumilus, B. simplex, B. solisalsi, B. subtilis, B. subtilis* var. *amyloliquefaciens, Candida oleophila, C. saitoana, Clavibacter michiganensis* (bacteriophages), *Coniothyrium minitans, Cryphonectria parasitica, Cryptococcus albidus, Dilophosphora alopecuri, Fusarium oxysporum, Clonostachys rosea* f. *catenulate* (also named *Gliocladium catenulatum*), *Gliocladium roseum, Lysobacter antibioticus, L. enzymogenes, Metschnikowia fructicola, Microdochium dimerum, Microsphaeropsis ochracea, Muscodor albus, Paenibacillus polymyxa, Pantoea vagans, Phlebiopsis gigantea, Pseudomonas* sp., *Pseudomonas chloraphis, Pseudozyma flocculosa, Pichia anomala, Pythium oligandrum, Sphaerodes mycoparasitica, Streptomyces griseoviridis, S. lydicus, S. violaceusniger, Talaromyces flavus, Trichoderma asperellum, T. atroviride, T. fertile, T. gamsii, T. harmatum, T. harzianum*; mixture of *T. harzianum* and *T. viride*; mixture of *T. polysporum* and *T. harzianum*; *T. stromaticum, T. virens* (also named *Gliocladium virens*), *T. viride, Typhula phacorrhiza, Ulocladium oudemansii, Verticillium dahlia*, zucchini yellow mosaic virus (avirulent strain);

L2) Biochemical pesticides with fungicidal, bactericidal, viricidal and/or plant defense activator activity: chitosan (hydrolysate), harpin protein, laminarin, Menhaden fish oil, natamycin, Plum pox virus coat protein, potassium or sodium bicarbonate, *Reynoutria sachlinensis* extract, salicylic acid, tea tree oil;

L3) Microbial pesticides with insecticidal, acaricidal, molluscidal and/or nematicidal activity: *Agrobacterium radiobacter, Bacillus cereus, B. firmus, B. thuringiensis, B. thuringiensis* ssp. *aizawai, B. t.* ssp. *israelensis, B. t.* ssp. *galleriae, B. t.* ssp. *kurstaki, B. t.* ssp. *tenebrionis, Beauveria bassiana, B. brongniartii, Burkholderia* sp., *Chromobacterium subtsugae, Cydia pomonella* granulosis virus, *Cryptophlebia leucotreta* granulovirus (CrleGV), *Helicoverpa armigera* nucleopolyhedrovirus (HearNPV), *Isaria fumosorosea, Heterorhabditis bacteriophora, Lecanicillium longisporum, L. muscarium* (formerly *Verticillium lecanii*), *Metarhizium anisopliae, M. anisopliae* var. *acridum, Nomuraea rileyi, Paecilomyces fumosoroseus, P. lilacinus, Paenibacillus popilliae, Pasteuria* sp., *P. nishizawae, P. penetrans, P. ramose, P. reneformis, P. thornea, P. usgae, Pseudomonas fluorescens, Spodoptera littoralis* nucleopolyhedrovirus (SpliNPV), *Steinernema carpocapsae, S. feltiae, S. kraussei*;

L4) Biochemical pesticides with insecticidal, acaricidal, molluscidal, pheromone and/or nematicidal activity:

L-carvone, citral, (E,Z)-7,9-dodecadien-1-yl acetate, ethyl formate, (E,Z)-2,4-ethyl decadienoate (pear ester), (Z,Z,E)-7,11,13-hexadecatrienal, heptyl butyrate, isopropyl myristate, lavanulyl senecioate, cis-jasmone, 2-methyl 1-butanol, methyl eugenol, methyl jasmonate, (E,Z)-2,13-octadecadien-1-ol, (E,Z)-2,13-octadecadien-1-ol acetate, (E,Z)-3,13-octadecadien-1-ol, R-1-octen-3-ol, pentatermanone, potassium silicate, sorbitol actanoate, (E,Z,Z)-3,8,11-tetradecatrienyl acetate, (Z,E)-9,12-tetradecadien-1-yl acetate, Z-7-tetradecen-2-one, Z-9-tetradecen-1-yl acetate, Z-11-tetradecenal, Z-11-tetradecen-1-ol, Acacia negra extract, extract of grapefruit seeds and pulp, extract of *Chenopodium ambrosiodes*, Catnip oil, Neem oil, Quillay extract, Tagetes oil;

L5) Microbial pesticides with plant stress reducing, plant growth regulator, plant growth promoting and/or yield enhancing activity: *Azospirillum amazonense, A. brasilense, A. lipoferum, A. irakense, A. halopraeferens, Bradyrhizobium* sp., *B. elkanii, B. japonicum, B. liaoningense, B. lupini, Delftia acidovorans, Glomus intraradices, Mesorhizobium* sp., *Paenibacillus alvei, Penicillium bilaiae, Rhizobium leguminosarum* bv. *phaseoli, R. l.* bv. *trifolii, R. l.* bv. *viciae, R. tropici, Sinorhizobium meliloti*;

L6) Biochemical pesticides with plant stress reducing, plant growth regulator and/or plant yield enhancing activity: abscisic acid, aluminium silicate (kaolin), 3-decen-2-one, formononetin, genistein, hesperetin, homobrassinlide, humates, jasmonic acid or salts or derivatives thereof, lysophosphatidyl ethanolamine, naringenin, polymeric polyhydroxy acid, *Ascophyllum nodosum* (Norwegian kelp, Brown kelp) extract and *Ecklonia maxima* (kelp) extract;

M) Growth Regulators abscisic acid (M.1.1), amidochlor, ancymidol, 6-benzylaminopurine, brassinolide, butralin, chlormequat, chlormequat chloride, choline chloride, cyclanilide, daminozide, dikegulac, dimethipin, 2,6-dimethylpuridine, ethephon, flumetralin, flurprimidol, fluthiacet, forchlorfenuron, gibberellic acid, inabenfide, indole-3-acetic acid, maleic hydrazide, mefluidide, mepiquat, mepiquat chloride, naphthaleneacetic acid, N-6-benzyladenine, paclobutrazol, prohexadione, prohexadione-calcium, prohydrojasmon, thidiazuron, triapenthenol, tributyl phosphorotrithioate, 2,3,5-tri-iodobenzoic acid, trinexapac-ethyl and uniconazole;

N) Herbicides acetamides: acetochlor (N.1.1), alachlor, butachlor, dimethachlor, dimethenamid (N.1.2), flufenacet (N.1.3), mefenacet (N.1.4), metolachlor (N.1.5), metazachlor (N.1.6), napropamide, naproanilide, pethoxamid, pretilachlor, propachlor, thenylchlor;

amino acid derivatives: bilanafos, glyphosate (N.2.1), glufosinate (N.2.2), sulfosate (N.2.3);

aryloxyphenoxypropionates: clodinafop (N.3.1), cyhalofop-butyl, fenoxaprop (N.3.2), fluazifop (N.3.3), haloxyfop (N.3.4), metamifop, propaquizafop, quizalofop, quizalofop-P-tefuryl;

Bipyridyls: diquat, paraquat (N.4.1);

(thio)carbamates: asulam, butylate, carbetamide, desmediphan, dimepiperate, eptam (EPTC), esprocarb, molinate, orbencarb, phenmedipham (N.5.1), prosulfocarb, pyributicarb, thiobencarb, triallate;

cyclohexanediones: butroxydim, clethodim (N.6.1), cycloxydim (N.6.2), profoxydim (N.6.3), sethoxydim (N.6.4), tepraloxydim (N.6.5), tralkoxydim;

dinitroanilines: benfluralin, ethalfluralin, oryzalin, pendimethalin (N.7.1), prodiamine (N.7.2), trifluralin (N.7.3);

diphenyl ethers: acifluorfen (N.8.1), aclonifen, bifenox, diclofop, ethoxyfen, fomesafen, lactofen, oxyfluorfen;

hydroxybenzonitriles: bomoxynil (N.9.1), dichlobenil, ioxynil;

imidazolinones: imazamethabenz, imazamox (N.10.1), imazapic (N.10.2), imazapyr (N.10.3), imazaquin (N.10.4), imazethapyr (N.10.5);

phenoxy acetic acids: clomeprop, 2,4-dichlorophenoxy-acetic acid (2,4-D) (N.11.1), 2,4-DB, dichlorprop, MCPA, MCPA-thioethyl, MCPB, Mecoprop;

pyrazines: chloridazon (N.11.1), flufenpyr-ethyl, fluthiacet, norflurazon, pyridate;

pyridines: aminopyralid, clopyralid (N.12.1), diflufenican, dithiopyr, fluridone, fluroxypyr (N.12.2), picloram (N.12.3), picolinafen (N.12.4), thiazopyr;

sulfonyl ureas: amidosulfuron, azimsulfuron, bensulfuron (N.13.1), chlorimuron-ethyl (N.13.2), chlorsulfuron, cinosulfuron, cyclosulfamuron (N.13.3), ethoxysulfuron, flazasulfuron, flucetosulfuron, flupyrsulfuron, foramsulfuron, halosulfuron, imazosulfuron, iodosulfuron (N.13.4), mesosulfuron (N.13.5), metazosulfuron, metsulfuron-methyl (N.13.6), nicosulfuron (N.13.7), oxasulfuron, primisulfuron, prosulfuron, pyrazosulfuron, rimsulfuron (N.13.8), sulfometuron, sulfosulfuron, thifensulfuron, triasulfuron, tribenuron, trifloxysulfuron, triflusulfuron (N.13.9), tritosulfuron, 1-((2-chloro-6-propyl-imidazo[1,2-b]pyridazin-3-yl)sulfonyl)-3-(4,6-dimethoxy-pyrimidin-2-yl)urea;

triazines: ametryn, atrazine (N.14.1), cyanazine, dimethametryn, ethiozin, hexazinone (N.14.2), metamitron, metribuzin, prometryn, simazine, terbuthylazine, terbutryn, triaziflam;

ureas: chlorotoluron, daimuron, diuron (N.15.1), flumeturon, isoproturon, linuron, methabenzthiazuron, tebuthiuron;

other acetolactate synthase inhibitors: bispyribac-sodium, cloransulam-methyl, diclosulam, florasulam (N.16.1), flucarbazone, flumetsulam, metosulam, ortho-sulfamuron, penoxsulam, propoxycarbazone, pyribambenz-propyl, pyribenzoxim, pyriftalid, pyriminobac-methyl, pyrimisulfan, pyrithiobac, pyroxasulfone (N.16.2), pyroxsulam;

others: amicarbazone, aminotriazole, anilofos, beflubutamid, benazolin, bencarbazone, benfluresate, benzofenap, bentazone (N.17.1), benzobicyclon, bicyclopyrone, bromacil, bromobutide, butafenacil, butamifos, cafenstrole, carfentrazone, cinidon-ethyl (N.17.2), chlorthal, cinmethylin (N.17.3), clomazone (N.17.4), cumyluron, cyprosulfamide, dicamba (N.17.5), difenzoquat, diflufenzopyr (N.17.6), *Drechslera monoceras*, endothal, ethofumesate, etobenzanid, fenoxasulfone, fentrazamide, flumiclorac-pentyl, flumioxazin, flupoxam, flurochloridone, flurtamone, indanofan, isoxaben, isoxaflutole, lenacil, propanil, propyzamide, quinclorac (N.17.7), quinmerac (N.17.8), mesotrione (N.17.9), methyl arsonic acid, naptalam, oxadiargyl, oxadiazon, oxaziclomefone, pentoxazone, pinoxaden, pyraclonil, pyraflufen-ethyl, pyrasulfotole, pyrazoxyfen, pyrazolynate, quinoclamine, saflufenacil (N.17.10), sulcotrione (N.17.11), sulfentrazone, terbacil, tefuryltrione, tembotrione, thiencarbazone, topramezone (N.17.12), (3-[2-chloro-4-fluoro-5-(3-methyl-2,6-dioxo-4-trifluoromethyl-3,6-dihydro-2H-pyrimidin-1-yl)-phenoxy]-pyridin-2-yloxy)-acetic acid ethyl ester, 6-amino-5-chloro-2-cyclopropyl-pyrimidine-4-carboxylic acid methyl ester, 6-chloro-3-(2-cyclopropyl-6-methyl-phenoxy)-pyridazin-4-ol, 4-amino-3-chloro-6-(4-chloro-phenyl)-5-fluoro-pyridine-2-carboxylic acid, 4-amino-3-chloro-6-(4-chloro-2-fluoro-3-methoxy-phenyl)-pyridine-2-carboxylic acid methyl ester, and 4-amino-3-chloro-6-(4-chloro-3-dimethylamino-2-fluoro-phenyl)-pyridine-2-carboxylic acid methyl ester;

O) Insecticides organo(thio)phosphates: acephate (O.1.1), azamethiphos (O.1.2), azinphos-methyl (O.1.3), chlorpyrifos (O.1.4), chlorpyrifos-methyl (O.1.5), chlorfenvinphos (O.1.6), diazinon (O.1.7), dichlorvos (O.1.8), dicrotophos (O.1.9), dimethoate (O.1.10), disulfoton (O.1.11), ethion (O.1.12), fenitrothion (O.1.13), fenthion (O.1.14), isoxathion (O.1.15), malathion (O.1.16), methamidophos (O.1.17), methidathion (O.1.18), methyl-parathion (O.1.19), mevinphos (O.1.20), monocrotophos (O.1.21), oxydemeton-methyl (O.1.22), paraoxon (O.1.23), parathion (O.1.24), phenthoate (O.1.25), phosalone (O.1.26), phosmet (O.1.27), phosphamidon (O.1.28), phorate (O.1.29), phoxim (O.1.30), pirimiphos-methyl (O.1.31), profenofos (O.1.32), prothiofos (O.1.33), sulprophos (O.1.34), tetrachlorvinphos (O.1.35), terbufos (O.1.36), triazophos (O.1.37), trichlorfon (O.1.38);

carbamates: alanycarb (O.2.1), aldicarb (O.2.2), bendiocarb (O.2.3), benfuracarb (O.2.4), carbaryl (O.2.5), carbofuran (O.2.6), carbosulfan (O.2.7), fenoxycarb (O.2.8), furathiocarb (O.2.9), methiocarb (O.2.10), methomyl (O.2.11), oxamyl (O.2.12), pirimicarb (O.2.13), propoxur (O.2.14), thiodicarb (O.2.15), triazamate (O.2.16);

pyrethroids: allethrin (O.3.1), bifenthrin (O.3.2), cyfluthrin (O.3.3), cyhalothrin (O.3.4), cyphenothrin (O.3.5), cypermethrin (O.3.6), alpha-cypermethrin (O.3.7), beta-cypermethrin (O.3.8), zeta-cypermethrin (O.3.9), deltamethrin (O.3.10), esfenvalerate (O.3.11), etofenprox (O.3.11), fenpropathrin (O.3.12), fenvalerate (O.3.13), imiprothrin (O.3.14), lambda-cyhalothrin (O.3.15), permethrin (O.3.16), prallethrin (O.3.17), pyrethrin I and II (O.3.18), resmethrin (O.3.19), silafluofen (O.3.20), tau-fluvalinate (O.3.21), tefluthrin (O.3.22), tetramethrin (O.3.23), tralomethrin (O.3.24), transfluthrin (O.3.25), profluthrin (O.3.26), dimefluthrin (O.3.27);

insect growth regulators: a) chitin synthesis inhibitors: benzoylureas: chlorfluazuron (O.4.1), cyramazin (O.4.2), diflubenzuron (O.4.3), flucycloxuron (O.4.4), flufenoxuron (O.4.5), hexaflumuron (O.4.6), lufenuron (O.4.7), novaluron (O.4.8), teflubenzuron (O.4.9), triflumuron (O.4.10); buprofezin (O.4.11), diofenolan (O.4.12), hexythiazox (O.4.13), etoxazole (O.4.14), clofentazine (O.4.15); b) ecdysone antagonists: halofenozide (O.4.16), methoxyfenozide (O.4.17), tebufenozide (O.4.18), azadirachtin (O.4.19); c) juvenoids: pyriproxyfen (O.4.20), methoprene (O.4.21), fenoxycarb (O.4.22); d) lipid biosynthesis inhibitors: spirodiclofen (O.4.23), spiromesifen (O.4.24), spirotetramat (O.4.24);

nicotinic receptor agonists/antagonists compounds: clothianidin (O.5.1), dinotefuran (O.5.2), flupyradifurone (O.5.3), imidacloprid (O.5.4), thiamethoxam (O.5.5), nitenpyram (O.5.6), acetamiprid (O.5.7), thiacloprid (O.5.8), 1-2-chloro-thiazol-5-ylmethyl)-2-nitrimino-3,5-dimethyl-[1,3,5]triazinane (O.5.9);

GABA antagonist compounds: endosulfan (O.6.19, ethiprole (O.6.2), fipronil (O.6.3), vaniliprole (O.6.4), pyrafluprole (O.6.5), pyriprole (O.6.6), 5-amino-1-(2,6-dichloro-4-methyl-phenyl)-4-sulfinamoyl-1H-pyrazole-3-carbothioic acid amide (O.6.7);

macrocyclic lactone insecticides: abamectin (O.7.1), emamectin (O.7.2), milbemectin (O.7.3), lepimectin (O.7.4), spinosad (O.7.5), spinetoram (O.7.6);

mitochondrial electron transport inhibitor (METI) acaricides: fenazaquin (O.8.1), pyridaben (O.8.2), tebufenpyrad (O.8.3), tolfenpyrad (O.8.4), flufenerim (O.8.5);

METI II and III compounds: acequinocyl (O.9.1), fluacyprim (O.9.2), hydramethylnon (O.9.3);

Uncouplers: chlorfenapyr (O.10.1);

oxidative phosphorylation inhibitors: cyhexatin (O.11.1), diafenthiuron (O.11.2), fenbutatin oxide (O.11.3), propargite (O.11.4);

moulting disruptor compounds: cryomazine (O.12.1);

mixed function oxidase inhibitors: piperonyl butoxide (O.13.1);

sodium channel blockers: indoxacarb (O.14.1), metaflumizone (O.14.2);

ryanodine receptor inhibitors: chlorantraniliprole (O.15.1), cyantraniliprole (O.15.2), flubendiamide (O.15.3), N-[4,6-dichloro-2-[(diethyl-lambda-4-sulfanylidene)carbamoyl]-phenyl]-2-(3-chloro-2-pyridyl)-5-(trifluoromethyl)pyrazole-3-carboxamide (O.15.4); N-[4-chloro-2-[(di-ethyl-lambda-4-sulfanylidene)carbamoyl]-6-methyl-phenyl]-2-(3-chloro-2-pyridyl)-5-(trifluoromethyl)pyrazole-3-carboxamide (O.15.5); N-[4-chloro-2-[(di-2-propyl-lambda-4-sulfanylidene)carbamoyl]-6-methyl-phenyl]-2-(3-chloro-2-pyridyl)-5-(trifluoromethyl)pyrazole-3-carboxamide (O.15.6); N-[4,6-dichloro-2-[(di-2-propyl-lambda-4-sulfanylidene)carbamoyl]-phenyl]-2-(3-chloro-2-pyridyl)-5-(trifluoromethyl)pyrazole-3-carboxamide (O.15.7); N-[4,6-dichloro-2-[(diethyl-lambda-4-sulfanylidene)carbamoyl]-phenyl]-2-(3-chloro-2-pyridyl)-5-(di-fluoromethyl)pyrazole-3-carboxamide (O.15.8); N-[4,6-dibromo-2-[(di-2-propyl-lambda-4-sulfanylidene)carbamoyl]-phenyl]-2-(3-chloro-2-pyridyl)-5-(trifluoromethyl)pyrazole-3-carboxamide (O.15.9); N-[4-chloro-2-[(di-2-propyl-lambda-4-sulfanylidene)carbamoyl]-6-cyano-phenyl]-2-(3-chloro-2-pyridyl)-5-(trifluoromethyl)pyrazole-3-carboxamide (O.15.10); N-[4,6-dibromo-2-[(diethyl-lambda-4-sulfanylidene)carbamoyl]-phenyl]-2-(3-chloro-2-pyridyl)-5-(tri-fluoromethyl)pyrazole-3-carboxamide (O.15.11);

others: benclothiaz (O.16.1), bifenazate (O.16.2), artap (O.16.3), flonicamid (O.16.4), pyridalyl (O.16.5), pymetrozine (O.16.6), sulfur (O.16.7), thiocyclam (O.16.8), cyenopyrafen (O.16.9), flupyrazofos (O.16.10), cyflumetofen (O.16.11), amidoflumet (O.16.12), imicyafos (O.16.13), bistrifluron (O.16.14), pyrifluquinazon (O.16.15) and 1,1'-[(3S,4R,4aR,6S,6aS,12R,12aS,12bS)-4-[[(2-cyclopropylacetyl)oxy]methyl]-1,3,4,4a,5,6,6a,12,12a,12b-decahydro-12-hydroxy-4,6a,12b-trimethyl-11-oxo-9-(3-pyridinyl)-2H,11H-naphtho[2,1-b]pyrano[3,4-e]pyran-3,6-diyl]cyclopropaneacetic acid ester (O.16.16).

The present invention furthermore relates to agrochemical compositions comprising a mixture of at least one compound I (component 1) and at least one further active substance useful for plant protection, e. g. selected from the groups A) to O) (component 2), in particular one further fungicide, e. g. one or more fungicide from the groups A) to K), as described above, and if desired one suitable solvent or solid carrier. Those mixtures are of particular interest, since many of them at the same application rate show higher efficiencies against harmful fungi. Furthermore, combating harmful fungi with a mixture of compounds I and at least one fungicide from groups A) to K), as described above, is more efficient than combating those fungi with individual compounds I or individual fungicides from groups A) to K).

By applying compounds I together with at least one active substance from groups A) to O) a synergistic effect can be obtained, i.e. more then simple addition of the individual effects is obtained (synergistic mixtures).

This can be obtained by applying the compounds I and at least one further active substance simultaneously, either jointly (e. g. as tank-mix) or separately, or in succession, wherein the time interval between the individual applications is selected to ensure that the active substance applied first still occurs at the site of action in a sufficient amount at the time of application of the further active substance(s). The order of application is not essential for working of the present invention.

When applying compound I and a pesticide II sequentially the time between both applications may vary e. g. between 2 hours to 7 days. Also a broader range is possible ranging from 0.25 hour to 30 days, preferably from 0.5 hour to 14 days, particularly from 1 hour to 7 days or from 1.5 hours to 5 days, even more preferred from 2 hours to 1 day. In case of a mixture comprising a pesticide II selected from group L), it is preferred that the pesticide II is applied as last treatment.

According to the invention, the solid material (dry matter) of the biopesticides (with the exception of oils such as Neem oil, Tagetes oil, etc.) are considered as active components (e. g. to be obtained after drying or evaporation of the extraction medium or the suspension medium in case of liquid formulations of the microbial pesticides).

In accordance with the present invention, the weight ratios and percentages used herein for a biological extract such as Quillay extract are based on the total weight of the dry content (solid material) of the respective extract(s).

The total weight ratios of compositions comprising at least one microbial pesticide in the form of viable microbial cells including dormant forms, can be determined using the amount of CFU of the respective microorganism to calculate the total weight of the respective active component with the following equation that $1 \times 10^9$ CFU equals one gram of total weight of the respective active component. Colony forming unit is measure of viable microbial cells, in particular fungal and bacterial cells. In addition, here "CFU" may also be understood as the number of (juvenile) individual nematodes in case of (entomopathogenic) nematode biopesticides, such as *Steinernema feltiae*.

In the binary mixtures and compositions according to the invention the weight ratio of the component 1) and the component 2) generally depends from the properties of the active components used, usually it is in the range of from 1:100 to 100:1, regularly in the range of from 1:50 to 50:1, preferably in the range of from 1:20 to 20:1, more preferably in the range of from 1:10 to 10:1, even more preferably in the range of from 1:4 to 4:1 and in particular in the range of from 1:2 to 2:1.

According to a further embodiments of the binary mixtures and compositions, the weight ratio of the component 1) and the component 2) usually is in the range of from 1000:1 to 1:1, often in the range of from 100:1 to 1:1, regularly in the range of from 50:1 to 1:1, preferably in the range of from 20:1 to 1:1, more preferably in the range of from 10:1 to 1:1, even more preferably in the range of from 4:1 to 1:1 and in particular in the range of from 2:1 to 1:1.

According to a further embodiments of the binary mixtures and compositions, the weight ratio of the component 1) and the component 2) usually is in the range of from 1:1 to 1:1000, often in the range of from 1:1 to 1:100, regularly in the range of from 1:1 to 1:50, preferably in the range of from 1:1 to 1:20, more preferably in the range of from 1:1 to 1:10, even more preferably in the range of from 1:1 to 1:4 and in particular in the range of from 1:1 to 1:2.

In the ternary mixtures, i.e. compositions according to the invention comprising the component 1) and component 2) and a compound III (component 3), the weight ratio of component 1) and component 2) depends from the properties of the active substances used, usually it is in the range of from 1:100 to 100:1, regularly in the range of from 1:50 to 50:1, preferably in the range of from 1:20 to 20:1, more preferably in the range of from 1:10 to 10:1 and in particular in the range of from 1:4 to 4:1, and the weight ratio of component 1) and component 3) usually it is in the range of from 1:100 to 100:1, regularly in the range of from 1:50 to 50:1, preferably in the range of from 1:20 to 20:1, more preferably in the range of from 1:10 to 10:1 and in particular in the range of from 1:4 to 4:1.

Any further active components are, if desired, added in a ratio of from 20:1 to 1:20 to the component 1).

These ratios are also suitable for inventive mixtures applied by seed treatment.

Preference is also given to mixtures comprising as component 2) at least one active substance selected from group A), which is particularly selected from (A.1.1), (A.1.4), (A.1.8), (A.1.9), (A.1.12), (A.1.13), (A.1.14), (A.1.17), (A.1.19), (A.1.21), (A.2.1), (A.2.2), (A.3.2), (A.3.3), (A.3.4), (A.3.7), (A.3.8), (A.3.9), (A.3.12), (A.3.14), (A.3.15), (A.3.16), (A.3.19), (A.3.20), (A.3.21), (A.3.22), (A.3.23), (A.3.24), (A.3.25), (A.3.26), (A.3.27); (A.4.5), (A.4.6), (A.4.8), (A.4.9) and (A.4.11).

Preference is given to mixtures as component 2) at least one active substance selected from group B), which is particularly selected from (B.1.4), (B.1.5), diniconazole (B.1.6), (B.1.8), (B.1.10), (B.1.11), (B.1.12), (B.1.17), (B.1.18), (B.1.21), (B.1.22), (B.1.23), (B.1.25), (B.1.26), (B.1.27), (B.1.28), (B.1.29), uni (B.1.31), (B.1.32), (B.1.33), (B.1.34), (B.1.35), (B.1.36), (B.1.37), (B.1.38), (B.1.39), (B.1.40), (B.1.41), (B.1.42), (B.1.44), (B.1.46), (B.1.49) and (B.1.50; (B.2.2), (B.2.4), (B.2.5), (B.2.6), piperalin (B.2.7), (B.2.8); and (B.3.1).

Preference is given to mixtures comprising as component 2) at least one active substance selected from group C), which is particularly selected from (C.1.4), C.1.5), (C.1.6), and (C.2.4).

Preference is given to mixtures comprising as component 2) at least one active substance selected from group D), which is particularly selected from (D1.1), (D1.2), (D1.4), (D1.5); (D2.2), (D2.4), (D2.5), (D2.6) and (D2.7);

Preference is also given to mixtures comprising as component 2) at least one active substance selected from group E), which is particularly selected from (E.1.1), (E.1.2), and (E.1.3);

Preference is also given to mixtures comprising as component 2) at least one active substance selected from group F), which is particularly selected from (F.1.2), (F.1.4), (F.1.5), (F.1.6) and (F.2.1).

Preference is also given to mixtures as component 2) at least one active substance selected from group G), which is particularly selected from (G.3.1), (G.3.2), (G.3.3), (G.3.4), (G.3.5), (G.3.6), (G.4.1) and (G.5.1).

Preference is also given to mixtures comprising as component 2) at least one active substance selected from group H), which is and particularly selected from (H.1.2), (H.1.3), copper oxychloride (H.1.4), (H.1.5), (H.1.6); (H.2.2), (H.2.5), (H.2.7), (H.3.2), (H.3.3), (H.3.4), (H.3.5), (H.3.6), (H.3.12); (H.4.2), (H.4.6), dithianon (H.4.9) and (H.4.10).

Preference is also given to mixtures comprising as component 2) at least one active substance selected from group I), which is particularly selected from (I.2.3) and (I.2.5).

Preference is also given to mixtures comprising as component 2) at least one active substance selected from group J), which is particularly selected from (J.1.1), (J.1.2), (J.1.3), (J.1.4), (J.1.6), (J.1.7), (J.1.8) and (J.1.9).

Preference is also given to mixtures comprising as component 2) at least one active substance selected from group K), which is particularly selected from (K.1.4), (K.1.5), (K.1.8), (K.1.12), (K.1.14), (K.1.15), (K.1.19) and (K.1.22).

The biopesticides from group L) of pesticides II, their preparation and their pesticidal activity e. g. against harmful fungi or insects are known (e-Pesticide Manual V 5.2 (ISBN 978 1 901396 85 0) (2008-2011); http://www.epa.gov/opp00001/biopesticides/, see product lists therein; http://www.omri.org/omri-lists, see lists therein; Bio-Pesticides Database BPDB http://sitem.herts.ac.uk/aeru/bpdb/, see A to Z link therein).

The biopesticides from group L1) and/or L2) may also have insecticidal, acaricidal, molluscidal, pheromone, nematicidal, plant stress reducing, plant growth regulator, plant growth promoting and/or yield enhancing activity. The biopesticides from group L3) and/or L4) may also have fungicidal, bactericidal, viricidal, plant defense activator, plant stress reducing, plant growth regulator, plant growth promoting and/or yield enhancing activity. The biopesticides from group L5) and/or L6) may also have fungicidal, bactericidal, viricidal, plant defense activator, insecticidal, acaricidal, molluscidal, pheromone and/or nematicidal activity.

Many of these biopesticides are registered and/or are commercially available: aluminium silicate (Screen™ Duo from Certis LLC, USA), *Agrobacterium radiobacter* K1026 (e. g. NoGall® from BASF Agricultural Specialties Pty Ltd, Australia), *A. radiobacter* K84 (Nature 280, 697-699, 1979; e. g. GallTroll® from AG Biochem, Inc., C, USA), *Ampelomyces quisqualis* M-10 (e. g. AQ 10® from Intrachem Bio GmbH & Co. KG, Germany), *Ascophyllum nodosum* (Norwegian kelp, Brown kelp) extract or filtrate (e. g. ORKA GOLD from BASF Agricultural Specialties (Pty) Ltd., South Africa; or Goemar® from Laboratoires Goemar, France), *Aspergillus flavus* NRRL 21882 isolated from a peanut in Georgia in 1991 by USDA, National Peanut Research Laboratory (e. g. in Afla-Guard® from Syngenta, CH), mixtures of *Aureobasidium pullulans* DSM 14940 and DSM 14941 (e. g. blastospores in BlossomProtect® from bio-ferm GmbH, Germany), *Azospirillum amazonense* BR 11140 (SpY2™) (Proc. 9$^{th}$ Int. and 1$^{st}$ Latin American PGPR meeting, Quimara, Medellin, Colombia 2012, p. 60, ISBN 978-958-46-0908-3), *A. brasilense* AZ39 (Eur. J. Soil Biol 45(1), 28-35, 2009), *A. brasilense* XOH (e. g. AZOS from Xtreme Gardening, USA or RTI Reforestation Technologies International; USA), *A. brasilense* BR 11002 (Proc. 9th Int. and 1st Latin American PGPR meeting, Quimara, Medellin, Colombia 2012, p. 60, ISBN 978-958-46-0908-3), *A. brasilense* BR 11005 (SP245; e. g. in GELFIX Gramineas from BASF Agricultural Specialties Ltd., Brazil), *A. lipoferum* BR 11646 (Sp31) (Proc. 9th Int. and 1st Latin American PGPR meeting, Quimara, Medellin, Colombia 2012, p. 60), *Bacillus amyloliquefaciens* FZB42 (e. g. in RhizoVital® 42 from AbiTEP GmbH, Berlin, Germany), *B. amyloliquefaciens* IN937a (J. Microbiol. Biotechnol. 17(2), 280-286, 2007; e. g. in BioYield® from Gustafson LLC, TX, USA), *B. amyloliquefaciens* IT-45 (CNCM I-3800) (e. g. Rhizocell C from ITHEC, France), *B. amyloliquefaciens* ssp. *plantarum* MBI600 (NRRL B-50595, deposited at USDA) (e. g. Integral®, Subtilex® NG from BASF Corp., USA), *B. cereus* CNCM I-1562 (U.S. Pat. No. 6,406,690), *B. firmus* CNCM I-1582 (WO 2009/126473, WO 2009/124707, U.S. Pat. No. 6,406,690; Votivo® from Bayer Crop Science LP, USA), *B. pumilus* GB34 (ATCC 700814; e. g. in YieldShield® from Gustafson LLC, TX, USA), and *Bacillus pumilus* KFP9F (NRRL B-50754) (e. g. in BAC-UP or FUSION-P from BASF Agricultural Specialties (Pty) Ltd., South Africa), *B. pumilus* QST 2808 (NRRL B-30087) (e. g. Sonata® and Ballad® Plus from AgraQuest Inc., USA), *B. subtilis* GB03 (e. g. Kodiak® or BioYield® from Gustafson, Inc., USA; or Companion® from Growth Products, Ltd., White Plains, N.Y. 10603, USA), *B. subtilis* GB07 (Epic® from Gustafson, Inc., USA), *B. subtilis* QST-713 (NRRL B-21661 in Rhapsody®, Serenade® MAX and Serenade® ASO from AgraQuest Inc., USA), *B. subtilis* var. *amyloliquefaciens* FZB24 (e. g. Taegro® from Novozyme Biologicals, Inc., USA), *B. subtilis* var. *amyloliquefaciens* D747 (e. g. Double Nickel 55 from Certis LLC, USA), *B. thuringiensis* ssp. *aizawai* ABTS-1857 (e. g. in XenTari® from BioFa AG, Münsingen, Germany), *B. t.* ssp. *aizawai* SAN 401 I, ABG-6305 and ABG-6346, *Bacillus t.* ssp. *israelensis* AM65-52 (e. g. in VectoBac® from Valent BioSciences, IL, USA), *Bacillus thuringiensis* ssp. *kurstaki* SB4 (NRRL B-50753; e. g. Beta Pro® from BASF Agricultural Specialties (Pty) Ltd., South Africa), *B. t.* ssp. *kurstaki* ABTS-351 identical to HD-1 (ATCC SD-1275; e. g. in Dipel® DF from Valent BioSciences, IL, USA), *B. t.* ssp. *kurstaki* EG 2348 (e. g. in Lepinox® or Rapax® from CBC (Europe) S.r.I., Italy), *B. t.* ssp. *tenebrionis* DSM 2803 (EP 0 585 215 B1; identical to NRRL B-15939; Mycogen Corp.), *B. t.* ssp. *tenebrionis* NB-125 (DSM 5526; EP 0 585 215 B1; also referred to as SAN 418 I or ABG-6479; former production strain of Novo-Nordisk), *B. t.* ssp. *tenebrionis* NB-176 (or NB-176-1; a gamma-irridated, induced high-yielding mutant of strain NB-125; DSM 5480; EP 585 215 B1; Novodor® from Valent BioSciences, Switzerland), *Beauveria bassiana* ATCC 74040 (e. g. in Naturalis® from CBC (Europe) S.r.I., Italy), *B. bassiana* DSM 12256 (US 200020031495; e. g. BioExpert® SC from Live Systems Technology S.A., Colombia), *B. bassiana* GHA (BotaniGard® 22WGP from Laverlam Int. Corp., USA), *B. bassiana* PPRI 5339 (ARSEF number 5339 in the USDA ARS collection of entomopathogenic fungal cultures; NRRL 50757) (e. g. BroadBand® from BASF Agricultural Specialties (Pty) Ltd., South Africa), *B. brongniartii* (e. g. in Melocont® from Agrifutur, Agrianello, Italy, for control of cockchafer; J. Appl. Microbiol. 100(5), 1063-72, 2006), *Bradyrhizobium* sp. (e. g. Vault® from BASF Corp., USA), *B. japonicum* (e. g. VAULT® from BASF Corp., USA), *Candida oleophila* I-182 (NRRL Y-18846; e. g. Aspire® from Ecogen Inc., USA, Phytoparasitica 23(3), 231-234, 1995), *C. oleophila* strain O (NRRL Y-2317; Biological Control 51, 403-408, 2009), *Candida saitoana* (e. g. Biocure® (in mixture with lysozyme) and BioCoat® from Micro Flo Company, USA (BASF SE) and Arysta), chitosan (e. g. Armour-Zen® from BotriZen Ltd., NZ), *Clonostachys rosea* f. *catenulata*, also named *Gliocladium catenulatum* (e. g. isolate J 1446: Prestop® from Verdera Oy, Finland), *Chromobacterium subtsugae* PRAA4-1 isolated from soil under an eastern hemlock (*Tsuga canadensis*) in the Catoctin Mountain region of central Maryland (e. g. in GRANDEVO from Marrone Bio Innovations, USA), *Coniothyrium minitans* CON/M/91-08 (e. g. Contans® WG from Prophyta, Germany), *Cryphonectria parasitica* (e. g. product *Endothia parasitica* from CNICM, France), *Cryptococcus albidus* (e. g. YIELD PLUS® from Anchor Bio-Technologies, South Africa), *Cryptophlebia leucotreta* granulovirus (CrleGV) (e. g. in CRYPTEX from Andermatt Biocontrol, Switzerland), *Cydia pomonella* granulovirus (CpGV) V03 (DSM GV-0006; e. g. in MADEX Max from Andermatt Biocontrol, Switzerland), CpGV V22 (DSM GV-0014; e. g. in MADEX Twin from Andermatt Biocontrol, Switzerland), *Deiftia acidovorans* RAY209 (ATCC PTA-4249; WO 2003/57861; e. g. in BIOBOOST from Brett Young, Winnipeg, Canada), *Dilophosphora alopecuri* (Twist Fungus from BASF Agricultural Specialties Pty Ltd, Australia), *Ecklonia maxima* (kelp) extract (e. g. KELPAK SL from Kelp Products Ltd, South Africa), formononetin (e. g. in MYCONATE from Plant Health Care plc, U.K.), *Fusarium oxysporum* (e. g. BIOFOX® from S.I.A.P.A., Italy, FUSACLEAN® from Natural Plant Protection, France), *Glomus intraradices* (e. g. MYC 4000 from ITHEC, France), *Glomus intraradices* RTI-801 (e. g. MYKOS from Xtreme Gardening, USA or RTI Reforestation Technologies International; USA), grapefruit seeds and pulp extract (e. g. BC-1000 from Chemie S.A., Chile), harpin (alpha-beta) protein (e. g. MESSENGER or HARP-N-Tek from Plant Health Care plc, U.K.; Science 257, 1-132, 1992), *Helicoverpa armigera* nucleopolyhedrovirus (HearNPV) (e.g. in HELICOVEX from Andermatt Biocontrol, Switzerland), *Heterorhabditis bacteriophaga* (e. g. Nemasys® G from BASF Agricultural Specialties Limited, UK), *Isaria fumosorosea* Apopka-97 (ATCC 20874) (PFR-97™ from Certis LLC, USA), cis-jasmone (U.S. Pat. No. 8,221,736), laminarin (e. g. in VACCIPLANT from Laboratoires Goemar, St. Malo, France or Stahler SA, Switzerland), *Lecanicillium longisporum* KV42 and KV71 (e. g. VERTALEC® from Koppert BV, Netherlands), *L. muscarium* KV01 (formerly *Verticillium lecanii*) (e. g. MYCOTAL from Koppert BV, Netherlands), *Lysobacter antibioticus* 13-1 (Biological Control 45, 288-296, 2008), *L. antibioticus* HS124 (Curr. Microbiol. 59(6), 608-615, 2009), *L. enzymogenes* 3.1T8 (Microbiol. Res. 158, 107-115; Biological Control 31(2), 145-154, 2004), *Metarhizium anisopliae* var. *acridum* IMI 330189 (isolated from Ornithacris cavroisi in *Niger*; NRRL 50758) (e. g. GREEN MUSCLE® from BASF Agricultural Specialties (Pty) Ltd., South Africa), *M. a.* var. *acridum* FI-985 (e. g. GREEN GUARD® SC from BASF Agricultural Specialties Pty Ltd, Australia), *M. anisopliae* FI-1045 (e. g. BIO-CANE® from BASF Agricultural Specialties Pty Ltd, Australia), *M. anisopliae* F52 (DSM 3884, ATCC 90448; e. g. MET52® Novozymes Biologicals BioAg Group, Canada), *M. anisopliae* ICIPE 69 (e. g. METATHRIPOL from ICIPE, Nairobe, Kenya), *Metschnikowia fructicola* (NRRL Y-30752; e. g. SHEMER® from Agrogreen, Israel, now distributed by Bayer Crop-Sciences, Germany; U.S. Pat. No. 6,994,849), *Microdochium dimerum* (e. g. ANTIBOT® from Agrauxine, France), *Microsphaeropsis ochracea* P130A (ATCC 74412 isolated from apple leaves from an abandoned orchard, St-Joseph-du-Lac, Quebec, Canada in 1993; Mycologia 94(2), 297-301, 2002), *Muscodor albus* QST 20799 originally isolated from the bark of a cinnamon tree in Honduras (e. g. in development products Muscudor™ or QRD300 from AgraQuest, USA), Neem oil (e. g. TRILOGY®, TRIACT® 70 EC from Certis LLC, USA), *Nomuraea rileyi* strains SA86101, GU87401, SR86151, CG128 and VA9101, *Paecilomyces fumosoroseus* FE 9901 (e. g. NO FLY™ from Natural Industries, Inc., USA), *P. lilacinus* 251 (e. g. in BioAct®/MeloCon® from Prophyta, Germany; Crop Protection 27, 352-361, 2008; originally isolated from infected nematode eggs in the Philippines), *P. lilacinus* DSM 15169 (e. g. NEMATA® SC from Live Systems Technology S.A., Colombia), *P. lilacinus* BCP2 (NRRL 50756; e. g. PL GOLD from BASF Agricultural Specialties (Pty) Ltd., South Africa), mixture of *Paenibacillus alvei* NAS6G6 (NRRL B-50755) and *Bacillus pumilus* (e.g. BAC-UP from BASF Agricultural Specialties (Pty) Ltd., South Africa), *Pantoea vagans* (formerly agglomerans) C9-1 (originally isolated in 1994 from apple stem tissue; BlightBan C9-1® from NuFrams America Inc., USA, for control of fire blight in apple; J. Bacteriol. 192(24) 6486-6487, 2010), *Pasteuria* sp. ATCC PTA-9643 (WO 2010/085795), *Pasteuria* sp. ATCC SD-5832 (WO 2012/064527), *P. nishizawae* (WO 2010/80169), *P. penetrans* (U.S. Pat. No. 5,248,500), *P. ramose* (WO 2010/80619), *P. thornea* (WO 2010/80169), *P. usgae* (WO 2010/80169), *Penicillium bilaiae* (e. g. Jump Start® from Novozymes Biologicals BioAg Group, Canada, originally isolated from soil in southern Alberta; Fertilizer Res. 39, 97-103, 1994), *Phlebiopsis gigantea* (e. g. Rot-Stop® from Verdera Oy, Finland), *Pichia anomala* WRL-076 (NRRL Y-30842; U.S. Pat. No. 8,206,972), potassium bicarbonate (e. g. Amicarb® from Stahler SA, Switzerland), potassium silicate (e. g. Sil-MATRIX™ from Certis LLC, USA), *Pseudozyma flocculosa* PF-A22 UL (e. g. Sporodex® from Plant Products Co. Ltd., Canada), *Pseudomonas* sp. DSM 13134 (WO 2001/40441, e. g. in PRORADIX from Sourcon Padena GmbH & Co. KG, Hechinger Str. 262, 72072 Tübingen, Germany), *P. chloraphis* MA 342 (e. g. in CERALL or CEDEMON from BioAgri AB, Uppsala, Sweden), *P. fluorescens* CL 145A (e. g. in ZEQUANOX from Marrone BioInnovations, Davis, Calif., USA; J. Invertebr. Pathol. 113(1):104-14, 2013), *Pythium oligandrum* DV 74 (ATCC 38472; e. g. POLYVERSUM® from Remeslo SSRO, Biopreparaty, Czech Rep. and GOWAN, USA; US 2013/0035230), *Reynoutria sachlinensis* extract (e. g. REGALIA® SC from Marrone BioInnovations, Davis, Calif., USA), *Rhizobium leguminosarum* bv. *phaseoli* (e. g. RHIZO-STICK from BASF Corp., USA), *R. l.* bv. *trifolii* RP113-7 (e. g. DORMAL from BASF Corp., USA; Appl. Environ. Microbiol. 44(5), 1096-1101), *R. l.* bv. *viciae* P1NP3Cst (also referred to as 1435; New Phytol. 179(1), 224-235, 2008; e. g. in NODULATOR PL Peat Granule from BASF Corp., USA; or in NODULATOR XL PL from BASF Agricultural Specialties Ltd., Canada), *R. l.* bv. *viciae* SU303 (e. g. NODULAID Group E from BASF Agricultural Specialties Pty Ltd, Australia), *R. l.* bv. *viciae* WSM1455 (e. g. NODULAID Group F from BASF Agricultural Specialties Pty Ltd, Australia), *R. tropici* SEMIA 4080 (identical to PRF 81; Soil Biology & Biochemistry 39, 867-876, 2007), *Sinorhizobium meliloti* MSDJ0848 (INRA, France) also referred to as strain 2011 or RCR2011 (Mol. Gen. Genomics 272, 1-17, 2004; e. g. DORMAL ALFALFA from BASF Corp., USA; NITRAGIN® Gold from Novozymes Biologicals BioAg Group, Canada), *Sphaerodes mycoparasitica* IDAC 301008-01 (WO 2011/022809), *Spodoptera littoralis* nucleopolyhedrovirus (SpliNPV) (e.g. in LITTOVIR from Andermatt Biocontrol, Switzerland), *Steinernema carpocapsae* (e. g. MILLENIUM® from BASF Agricultural Specialties Limited, UK), *S. feltiae* (NEMASHIELD® from BioWorks, Inc., USA; NEMASYS® from BASF Agricultural Specialties Limited, UK), *S. kraussei* L137 (NEMASYS® L from BASF Agricultural Specialties Limited, UK), *Streptomyces griseoviridis* K61 (e. g. MYCOSTOP® from Verdera Oy, Espoo, Finland; Crop Protection 25, 468-475, 2006), *S.*

*lydicus* WYEC 108 (e. g. Actinovate® from Natural Industries, Inc., USA, U.S. Pat. No. 5,403,584), *S. violaceusniger* YCED-9 (e. g. DT-9® from Natural Industries, Inc., USA, U.S. Pat. No. 5,968,503), *Talaromyces flavus* V117b (e. g. PROTUS® from Prophyta, Germany), *Trichoderma asperellum* SKT-1 (e. g. ECO-HOPE® from Kumiai Chemical Industry Co., Ltd., Japan), *T. asperellum* ICC 012 (e. g. in TENET WP, REMDIER WP, BIOTEN WP from Isagro NC, USA, BIO-TAM from AgraQuest, USA), *T. atroviride* LC52 (e. g. SENTINEL® from Agrimm Technologies Ltd, NZ), *T. atroviride* CNCM I-1237 (e. g. in Esquive WG from Agrauxine S.A., France, e. g. against pruning wound diseases on vine and plant root pathogens), *T. fertile* JM41R (NRRL 50759; e. g. RICHPLUS™ from BASF Agricultural Specialties (Pty) Ltd., South Africa), *T. gamsii* ICC 080 (e. g. in TENET WP, REMDIER WP, BIOTEN WP from Isagro NC, USA, BIO-TAM from AgraQuest, USA), *T. harzianum* T-22 (e. g. PLANTSHIELD® der Firma BioWorks Inc., USA), *T. harzianum* TH 35 (e. g. ROOT PRO® from Mycontrol Ltd., Israel), *T. harzianum* T-39 (e. g. TRICHODEX® and *TRICHODERMA* 2000® from Mycontrol Ltd., Israel and Makhteshim Ltd., Israel), mixture of *T. harzianum* and *T. viride* (e. g. TRICHOPEL from Agrimm Technologies Ltd, NZ), *T. harzianum* ICC012 and *T. viride* ICC080 (e. g. REMEDIER® WP from Isagro Ricerca, Italy), *T. polysporum* and *T. harzianum* (e. g. BINAB® from BINAB Bio-Innovation AB, Sweden), *T. stromaticum* (e. g. TRICO-VAB® from C.E.P.L.A.C., Brazil), *T. virens* GL-21 (e. g. SOILGARD® from Certis LLC, USA), *T. viride* (e. g. TRIECO® from Ecosense Labs. (India) Pvt. Ltd., Indien, B10-CURE® F from T. Stanes & Co. Ltd., Indien), *T. viride* TV1 (e. g. *T. viride* TV1 from Agribiotec srl, Italy) and *Ulocladium oudemansii* HRU3 (e. g. in BOTRY-ZEN® from Botry-Zen Ltd, NZ).

Strains can be sourced from genetic resource and deposition centers: American Type Culture Collection, 10801 University Blvd., Manassas, Va. 20110-2209, USA (strains with ATCC prefic); CABI Europe—International Mycological Institute, Bakeham Lane, Egham, Surrey, TW20 9TYN-RRL, UK (strains with prefices CABI and IMI); Centraalbureau voor Schimmelcultures, Fungal Biodiversity Centre, Uppsalaan 8, PO Box 85167, 3508 AD Utrecht, Netherlands (strains with prefic CBS); Division of Plant Industry, CSIRO, Canberra, Australia (strains with prefix CC); Collection Nationale de Cultures de Microorganismes, Institut Pasteur, 25 rue du Docteur Roux, F-75724 PARIS Cedex 15 (strains with prefix CNCM); Leibniz-Institut DSMZ-Deutsche Sammlung von Mikroorganismen und Zellkulturen GmbH, Inhoffenstraβe 7 B, 38124 Braunschweig, Germany (strains with prefix DSM); International Depositary Authority of Canada Collection, Canada (strains with prefix IDAC); International Collection of Micro-organisms from Plants, Landcare Research, Private Bag 92170, Auckland Mail Centre, Auckland 1142, New Zealand (strains with prefix ICMP); IITA, PMB 5320, Ibadan, Nigeria (strains with prefix IITA); The National Collections of Industrial and Marine Bacteria Ltd., Torry Research Station, P.O. Box 31, 135 Abbey Road, Aberdeen, AB9 8DG, Scotland (strains with prefix NCIMB); ARS Culture Collection of the National Center for Agricultural Utilization Research, Agricultural Research Service, U.S. Department of Agriculture, 1815 North University Street, Peoria, Ill. 61604, USA (strains with prefix NRRL); Department of Scientific and Industrial Research Culture Collection, Applied Biochemistry Division, Palmerston North, New Zealand (strains with prefix NZP); FEPAGRO-Fundação Estadual de Pesquisa Agropecuária, Rua Gonçalves Dias, 570, Bairro Menino Deus, Porto Alegre/RS, Brazil (strains with prefix SEMIA); SARDI, Adelaide, South Australia (strains with prefix SRDI); U.S. Department of Agriculture, Agricultural Research Service, Soybean and Alfalfa Research Laboratory, BARC-West, 10300 Baltimore Boulevard, Building 011, Beltsville, Md. 20705, USA (strains with prefix USDA: Beltsville Rhizob. Culture Coll. Catalog March 1987 USDA-ARS ARS-30: http://pdf.usaid.gov/pdf docs/PNAAW891.pdf); and Murdoch University, Perth, Western Australia (strains with prefix WSM). Further strains may be found at the Global catalogue of Microorganisms: http://gcm.wfcc.info/ and http://www.landcareresearch.co.nz/resources/collections/icmp and further references to strain collections and their prefixes at http://refs.wdcm.org/collections.htm.

*Bacillus amyloliquefaciens* ssp. *plantarum* MBI600 (NRRL B-50595) is deposited under accession number NRRL B-50595 with the strain designation *Bacillus subtilis* 1430 (and identical to NCIMB 1237). Recently, MBI 600 has been re-classified as *Bacillus amyloliquefaciens* ssp. *plantarum* based on polyphasic testing which combines classical microbiological methods relying on a mixture of traditional tools (such as culture-based methods) and molecular tools (such as genotyping and fatty acids analysis). Thus, *Bacillus subtilis* MBI600 (or MBI 600 or MBI-600) is identical to *Bacillus amyloliquefaciens* ssp. *plantarum* MBI600, formerly *Bacillus subtilis* MBI600. MBI600 is known as plant growth-promoting rice seed treatment from Int. J. Microbiol. Res. 3(2) (2011), 120-130 and further described e. g. in US 2012/0149571 A1. The strain MBI600 is e. g. commercially available as liquid formulation product INTEGRAL® (BASF Corp., USA).

*Bacillus subtilis* strain FB17 was originally isolated from red beet roots in North America (System. Appl. Microbiol. 27, 372-379, 2004). FB17 promotes plant health (US 2010/0260735; WO 2011/109395). *B. subtilis* FB17 has also been deposited at ATCC under PTA-11857 on Apr. 26, 2011. FB17 may be referred elsewhere to as UD1022 or UD10-22.

*Bacillus amyloliquefaciens* AP-136 (NRRL B-50614), *B. amyloliquefaciens* AP-188 (NRRL B-50615), *B. amyloliquefaciens* AP-218 (NRRL B-50618), *B. amyloliquefaciens* AP-219 (NRRL B-50619), *B. amyloliquefaciens* AP-295 (NRRL B-50620), *B. japonicum* SEMIA 5079 (e. g. GEL-FIX 5 or ADHERE 60 from BASF Agricultural Specialties Ltd., Brazil), *B. japonicum* SEMIA 5080 (e. g. GELFIX 5 or ADHERE 60 from BASF Agricultural Specialties Ltd., Brazil), *B. mojavensis* AP-209 (NRRL B-50616), *B. solisalsi* AP-217 (NRRL B-50617), *B. pumilus* INR-7 (otherwise referred to as BU-F22 (NRRL B-50153) and BU-F33 (NRRL B-50185)), *B. simplex* ABU 288 (NRRL B-50340) and *B. amyloliquefaciens* ssp. *plantarum* MBI600 (NRRL B-50595) have been mentioned i. a. in US 2012/0149571, U.S. Pat. No. 8,445,255, WO 2012/079073.

Jasmonic acid or salts (jasmonates) or derivatives include without limitation potassium jasmonate, sodium jasmonate, lithium jasmonate, ammonium jasmonate, dimethylammonium jasmonate, isopropylammonium jasmonate, diolammonium jasmonate, diethtriethanolammonium jasmonate, jasmonic acid methyl ester, jasmonic acid amide, jasmonic acid methylamide, jasmonic acid-L-amino acid (amide-linked) conjugates (e. g., conjugates with L-isoleucine, L-valine, L-leucine, or L-phenylalanine), 12-oxo-phytodienoic acid, coronatine, coronafacoyl-L-serine, coronafacoyl-L-threonine, methyl esters of 1-oxo-indanoyl-isoleucine, methyl esters of 1-oxo-indanoyl-leucine, coronalon (2-[[(6-ethyl-1-oxo-indane-4-carbonyl)amino]-3-methylpentanoic acid methyl ester), linoleic acid or derivatives thereof and cis-jasmone, or combinations of any of the above.

Humates are humic and fulvic acids extracted from a form of lignite coal and clay, known as leonardite. Humic acids are organic acids that occur in humus and other organically derived materials such as peat and certain soft coal. They have been shown to increase fertilizer efficiency in phosphate and micro-nutrient uptake by plants as well as aiding in the development of plant root systems.

According to one embodiment of the inventive mixtures, the at least one pesticide II is selected from the groups L1) to L6):

L1) Microbial pesticides with fungicidal, bactericidal, viricidal and/or plant defense activator activity: *Ampelomyces quisqualis* M-10 (L.1.1), *Aspergillus flavus* NRRL 21882 (L1.2), *Aureobasidium pullulans* DSM 14940 (L1.3), *A. pullulans* DSM 14941 (L.1.4), *Bacillus amyloliquefaciens* AP-136 (NRRL B-50614) (L.1.5), *B. amyloliquefaciens* AP-188 (NRRL B-50615) (L.1.6), *B. amyloliquefaciens* AP-218 (NRRL B-50618) (L.1.7), *B. amyloliquefaciens* AP-219 (NRRL B-50619) (L.1.8), *B. amyloliquefaciens* AP-295 (NRRL B-50620) (L.1.9), *B. amyloliquefaciens* FZB42 (L.1.10), *B. amyloliquefaciens* IN937a (L.1.11), *B. amyloliquefaciens* IT-45 (CNCM I-3800) (L.1.12), *B. amyloliquefaciens* ssp. *plantarum* MBI600 (NRRL B-50595) (L.1.13), *B. mojavensis* AP-209 (NRRL B-50616) (L.1.15), *B. pumilus* INR-7 (NRRL B-50153; NRRL B-50185) (L.1.14), *B. pumilus* KFP9F (L.1.15), *B. pumilus* QST 2808 (NRRL B-30087) (L.1.16), *B. pumilus* GHA 181 (L.1.17), *B. simplex* ABU 288 (NRRL B-50340) (L.1.18), *B. solisalsi* AP-217 (NRRL B-50617) (L.1.19), *B. subtilis* CX-9060 (L.1.20), *B. subtilis* FB17 (L.1.74), *B. subtilis* GB03 (L.1.21), *B. subtilis* GB07 (L.1.22), *B. subtilis* QST-713 (NRRL B-21661) (L.1.23), *B. subtilis* var. *amyloliquefaciens* FZB24 (L.1.24), *B. subtilis* var. *amyloliquefaciens* D747 (L.1.25), *Candida oleophila* I-82 (L.1.26), *C. oleophila* O (L.1.27), *C. saitoana* (L.1.28), *Clavibacter michiganensis* (bacteriophages) (L.1.29), *Coniothyrium minitans* CON/M/91-08 (L.1.30), *Cryphonectria parasitica* (L.1.31), *Cryptococcus albidus* (L.1.32), *Dilophosphora alopecuri* (L.1.33), *Fusarium oxysporum* (L.1.34), *Clonostachys rosea* f. *catenulata* J1446 (L.1.35), *Gliocladium roseum* 321U (L.1.36), *Metschnikowia fructicola* NRRL Y-30752 (L.1.37), *Microdochium dimerum* (L.1.38), *Microsphaeropsis ochracea* P130A (L.1.39), *Muscodor albus* QST 20799 (L.1.40), *Paenibacillus polymyxa* PKB1 (ATCC 202127) (L.1.41), *Pantoea vagans* C9-1 (L.1.42), *Phlebiopsis gigantea* (L.1.43), *Pichia anomala* WRL-76 (L.1.44), *Pseudozyma flocculosa* PF-A22 UL (L.1.45), *Pythium oligandrum* DV 74 (L.1.46), *Sphaerodes mycoparasitica* IDAC 301008-01 (L.1.47), *Streptomyces griseoviridis* K61 (L.1.48), *S. lydicus* WYEC 108 (L.1.49), *S. violaceusniger* XL-2 (L.1.50), *S. violaceusniger* YCED-9 (L.1.51), *Talaromyces flavus* V117b (L.1.52), *Trichoderma asperellum* T34 (L.1.53), *T. asperellum* SKT-1 (L.1.54), *T. asperellum* ICC 012 (L.1.55), *T. atroviride* LC52 (L.1.56), *T. atroviride* CNCM I-1237 (L.1.57), *T. fertile* JM41R (L.1.58), *T. gamsii* ICC 080 (L.1.59), *T. harmatum* TH 382 (L.1.60), *T. harzianum* TH-35 (L.1.61), *T. harzianum* T-22 (L.1.62), *T. harzianum* T-39 (L.1.63); mixture of *T. harzianum* ICC012 and *T. viride* ICC080 (L.1.64); mixture of *T. polysporum* and *T. harzianum* (L.1.65); *T. stromaticum* (L.1.66), *T. virens* GL-21 (L.1.67), *T. virens* G41 (L.1.68), *T. viride* TV1 (L.1.69), *Typhula phacorrhiza* 94671 (L.1.70), *Ulocladium oudemansii* HRU3 (L.1.71), *Verticillium dahlia* (L.1.72), zucchini yellow mosaic virus (avirulent strain) (L.1.73);

L2) Biochemical pesticides with fungicidal, bactericidal, viricidal and/or plant defense activator activity: chitosan (hydrolysate) (L.2.1), harpin protein (L.2.2), laminarin (L.2.3), Menhaden fish oil (L.2.4), natamycin (L.2.5), Plum pox virus coat protein (L.2.6), potassium bicarbonate (L.2.7), *Reynoutria sachlinensis* extract (L.2.8), salicylic acid (L.2.9), potassium or sodium bicarbonate (L.2.10), tea tree oil (L.2.11);

L3) Microbial pesticides with insecticidal, acaricidal, molluscidal and/or nematicidal activity: *Agrobacterium radiobacter* K1026 (L.3.1), *A. radiobacter* K84 (L.3.2), *Bacillus firmus* I-1582 (L.3.3); *B. thuringiensis* ssp. *aizawai* strains: ABTS-1857 (L.3.4), SAN 401 I (L.3.5), ABG-6305 (L.3.6) and ABG-6346 (L.3.7); *B. t.* ssp. *israelensis* AM65-52 (L.3.8), *B. t.* ssp. *israelensis* SUM-6218 (L.3.9), *B. t.* ssp. *galleriae* SDS-502 (L.3.10), *B. t.* ssp. *kurstaki* EG 2348 (L.3.11), *B. t.* ssp. *kurstaki* SB4 (L.3.12), *B. t.* ssp. *kurstaki* ABTS-351 (HD-1) (L.3.13), *Beauveria bassiana* ATCC 74040 (L.3.14), *B. bassiana* GHA (L.3.15), *B. bassiana* H123 (L.3.16), *B. bassiana* DSM 12256 (L.3.17), *B. bassiana* PPRI 5339 (L.3.18), *B. brongniartii* (L.3.19), *Burkholderia* sp. A396 (L.3.20), *Chromobacterium subtsugae* PRAA4-1 (L.3.21), *Cydia pomonella* granulosis virus V22 (L.3.22), *Cydia pomonella* granulosis virus V1 (L.3.23), *Cryptophlebia leucotreta* granulovirus (CrleGV) (L.3.57), *Helicoverpa armigera* nucleopolyhedrovirus (HearNPV) (L.3.58), *Isaria fumosorosea* Apopka-97 (L.3.24), *Lecanicillium longisporum* KV42 (L.3.25), *L. longisporum* KV71 (L.3.26), *L. muscarium* KV01 (L.3.27), *Metarhizium anisopliae* FI-985 (L.3.28), *M. anisopliae* FI-1045 (L.3.29), *M. anisopliae* F52 (L.3.30), *M. anisopliae* ICIPE 69 (L.3.31), *M. anisopliae* var. *acridum* IMI 330189 (L.3.32); *Nomuraea rileyi* strains: SA86101 (L.3.33), GU87401 (L.3.34), SR86151 (L.3.35), CG128 (L.3.36) and VA9101 (L.3.37); *Paecilomyces fumosoroseus* FE 9901 (L.3.38), *P. lilacinus* 251 (L.3.39), *P. lilacinus* DSM 15169 (L.3.40), *P. lilacinus* BCP2 (L.3.41), *Paenibacillus popilliae* Dutky-1940 (NRRL B-2309=ATCC 14706) (L.3.42), *P. popilliae* Dutky 1 (L.3.43), *P. popilliae* KLN 3 (L.3.56), *Pasteuria* sp. Ph3 (L.3.44), *Pasteuria* sp. ATCC PTA-9643 (L.3.45), *Pasteuria* sp. ATCC SD-5832 (L.3.46), *P. nishizawae* PN-1 (L.3.46), *P. penetrans* (L.3.47), *P. ramose* (L.3.48), *P. reneformis* Pr-3 (L.3.49), *P. thornea* (L.3.50), *P. usgae* (L.3.51), *Pseudomonas fluorescens* CL 145A (L.3.52), *Spodoptera littoralis* nucleopolyhedrovirus (SpliNPV) (L.3.59), *Steinernema carpocapsae* (L.3.53), *S. feltiae* (L.3.54), *S. kraussei* L137 (L.3.55);

L4) Biochemical pesticides with insecticidal, acaricidal, molluscidal, pheromone and/or nematicidal activity: L-carvone (L.4.1), citral (L.4.2), (E,Z)-7,9-dodecadien-1-yl acetate (L.4.3), ethyl formate (L.4.4), (E,Z)-2,4-ethyl decadienoate (pear ester) (L.4.5), (Z,Z,E)-7,11, 13-hexadecatrienal (L.4.6), heptyl butyrate (L.4.7), isopropyl myristate (L.4.8), cis-jasmone (L.4.9), lavanulyl senecioate (L.4.10), 2-methyl 1-butanol (L.4.11), methyl eugenol (L.4.12), methyl jasmonate (L.4.13), (E,Z)-2,13-octadecadien-1-ol (L.4.14), (E,Z)-2,13-octadecadien-1-ol acetate (L.4.15), (E,Z)-3,13-octadecadien-1-ol (L.4.16), R-1-octen-3-ol (L.4.17), pentatermanone (L.4.18), potassium silicate (L.4.19), sorbitol actanoate (L.4.20), (E,Z,Z)-3,8,11-tetradecatrienyl acetate (L.4.21), (Z,E)-9,12-tetradecadien-1-yl acetate (L.4.22), Z-7-tetradecen-2-one (L.4.23), Z-9-tetradecen-1-yl acetate (L.4.24), Z-11-tetradecenal (L.4.25), Z-11-tetradecen-1-ol (L.4.26), Acacia negra extract (L.4.27), extract of grapefruit seeds and pulp (L.4.28), extract of *Chenopodium ambrosiodes* (L.4.29), Catnip oil (L.4.30), Neem oil (L.4.31), Quillay extract (L.4.32), Tagetes oil (L.4.33);

L5) Microbial pesticides with plant stress reducing, plant growth regulator, plant growth promoting and/or yield enhancing activity: *Azospirillum amazonense* BR 11140 (SpY2T) (L.5.1), *A. brasilense* AZ39 (L.5.2), *A. brasilense* XOH (L.5.3), *A. brasilense* BR 11005 (Sp245) (L.5.4), *A. brasilense* BR 11002 (L.5.5), *A. lipoferum* BR 11646 (Sp31) (L.5.6), *A. irakense* (L.5.7), *A. halopraeferens* (L.5.8), *Bradyrhizobium* sp. PNL01 (L.5.9), *B*. sp. (*Arachis*) CB1015 (L.5.10), *B*. sp. (*Arachis*) USDA 3446 (L.5.11), *B*. sp. (*Arachis*) SEMIA 6144 (L.5.12), *B*. sp. (*Arachis*) SEMIA 6462 (L.5.13), *B*. sp. (*Arachis*) SEMIA 6464 (L.5.14), *B*. sp. (*Vigna*) (L.5.15), *B. elkanii* SEMIA 587 (L.5.16), *B. elkanii* SEMIA 5019 (L.5.17), *B. elkanii* U-1301 (L.5.18), *B. elkanii* U-1302 (L.5.19), *B. elkanii* USDA 74 (L.5.20), *B. elkanii* USDA 76 (L.5.21), *B. elkanii* USDA 94 (L.5.22), *B. elkanii* USDA 3254 (L.5.23), *B. japonicum* 532c (L.5.24), *B. japonicum* CPAC 15 (L.5.25), *B. japonicum* E-109 (L.5.26), *B. japonicum* G49 (L.5.27), *B. japonicum* TA-11 (L.5.28), *B. japonicum* USDA 3 (L.5.29), *B. japonicum* USDA 31 (L.5.30), *B. japonicum* USDA 76 (L.5.31), *B. japonicum* USDA 110 (L.5.32), *B. japonicum* USDA 121 (L.5.33), *B. japonicum* USDA 123 (L.5.34), *B. japonicum* USDA 136 (L.5.35), *B. japonicum* SEMIA 566 (L.5.36), *B. japonicum* SEMIA 5079 (L.5.37), *B. japonicum* SEMIA 5080 (L.5.38), *B. japonicum* WB74 (L.5.39), *B. liaoningense* (L.5.40), *B. lupini* LL13 (L.5.41), *B. lupini* WU425 (L.5.42), *B. lupini* WSM471 (L.5.43), *B. lupini* WSM4024 (L.5.44), *Glomus intraradices* RTI-801 (L.5.45), *Mesorhizobium* sp. WSM1271 (L.5.46), *M*. sp. WSM1497 (L.5.47), *M. ciceri* CC1192 (L.5.48), *M. huakii* (L.5.49), *M. loti* CC829 (L.5.50), *M. loti* SU343 (L.5.51), *Paenibacillus alvei* NAS6G6 (L.5.52), *Penicillium bilaiae* (L.5.53), *Rhizobium leguminosarum* bv. *phaseoli* RG-B10 (L.5.54), *R. l*. bv. *trifolii* RP113-7 (L.5.55), *R. l*. bv. *trifolii* 095 (L.5.63), *R. l*. bv. *trifolii* TA1 (L.5.64), *R. l*. bv. *trifolii* CC283b (L.5.65), *R. l*. bv. *trifolii* CC275e (L.5.66), *R. l*. bv. *trifolii* CB782 (L.5.67), *R. l*. bv. *trifolii* CC1099 (L.5.68), *R. l*. bv. *trifolii* WSM1325 (L.5.69), *R. l*. bv. *viciae* SU303 (L.5.56), *R. l*. bv. *viciae* WSM1455 (L.5.57), *R. l*. bv. *viciae* P1NP3Cst (L.5.58), *R. l*. bv. *viciae* RG-P2 (L.5.70), *R. tropici* SEMIA 4080 (L.5.59), *R. tropici* SEMIA 4077 (L.5.71), *R. tropici* CC511 (L.5.72), *Sinorhizobium meliloti* MSDJ0848 (L.5.60), *S. meliloti* NRG185 (L.5.61), *S. meliloti* RRI128 (L.5.62);

L6) Biochemical pesticides with plant stress reducing, plant growth regulator and/or plant yield enhancing activity: abscisic acid (L.6.1), aluminium silicate (kaolin) (L.6.2), 3-decen-2-one (L.6.3), formononectin (L.6.4), genistein (L.6.5), hesperetin (L.6.6), homobrassinlide (L.6.7), humates (L.6.8), methyl jasmonate (L.6.9), cis-jasmone (L.6.10), lysophosphatidyl ethanlamine (L.6.11), naringenin (L.6.12), polymeric polyhydroxy acid (L.6.13), salicylic acid (L.6.14), *Ascophyllum nodosum* (Norwegian kelp, Brown kelp) extract (L.6.15) and *Ecklonia maxima* (kelp) extract (L.6.16).

The present invention furthermore relates to agrochemical compositions comprising a mixture of (component 1) and at least one biopesticide selected from the group L) (component 2), in particular at least one further fungicidal biopesticide selected from the groups L1) and L2), as described above, and if desired at least one suitable auxiliary.

Preference is also given to mixtures comprising as pesticide II (component 2) a biopesticide from group L1), preferably selected from *Bacillus amyloliquefaciens* AP-136 (NRRL B-50614 and B-50330), *B. amyloliquefaciens* AP-188 (NRRL B-50615 and B-50331), *B. amyloliquefaciens* AP-218 (NRRL B-50618), *B. amyloliquefaciens* AP-219 (NRRL B-50619 and B-50332), *B. amyloliquefaciens* AP-295 (NRRL B-50620 and B-50333), *B. amyloliquefaciens* IT-45 (CNCM I-3800), *B. amyloliquefaciens* ssp. *plantarum* MBI600 (NRRL B-50595), *B. mojavensis* AP-209 (NRRL B-50616), *B. pumilus* INR-7 (NRRL B-50153; NRRL B-50185), *B. pumilus* KFP9F, *B. pumilus* QST 2808 (NRRL B-30087), *B. pumilus* GHA 181, *B. simplex* ABU 288 (NRRL B-50340), *B. solisalsi* AP-217 (NRRL B-50617), *B. subtilis* CX-9060, *B. subtilis* FB17, *B. subtilis* GB03, *B. subtilis* GB07, *B. subtilis* QST-713 (NRRL B-21661), *B. subtilis* var. *amyloliquefaciens* FZB24, *B. subtilis* var. *amyloliquefaciens* D747, *Paenibacillus alvei* NAS6G6, *Paenibacillus polymyxa* PKB1 (ATCC 202127), *Sphaerodes mycoparasitica* IDAC 301008-01 and *Trichoderma fertile* JM41R; even more preferably from *Bacillus amyloliquefaciens* AP-136 (NRRL B-50614), *B. amyloliquefaciens* AP-188 (NRRL B-50615), *B. amyloliquefaciens* AP-218 (NRRL B-50618), *B. amyloliquefaciens* AP-219 (NRRL B-50619), *B. amyloliquefaciens* AP-295 (NRRL B-50620), *B. amyloliquefaciens* IT-45 (CNCM I-3800), *B. amyloliquefaciens* ssp. *plantarum* MBI600 (NRRL B-50595), *B. mojavensis* AP-209 (NRRL B-50616), *B. pumilus* INR-7 (NRRL B-50153; NRRL B-50185), *B. pumilus* QST 2808 (NRRL B-30087), *B. simplex* ABU 288 (NRRL B-50340), *B. subtilis* FB17, *B. subtilis* QST-713 (NRRL B-21661), *Paenibacillus alvei* NAS6G6, *Sphaerodes mycoparasitica* IDAC 301008-01 and *Trichoderma fertile* JM41R.

According to one embodiment of the inventive mixtures, the at least one pesticide II is *Bacillus amyloliquefaciens* ssp. *plantarum* MBI600. These mixtures are particularly suitable in soybean.

According to another embodiment of the inventive mixtures, the at least one pesticide II is *B. pumilus* INR-7. These mixtures are particularly suitable in soybean and corn.

According to a further embodiment, the at least one pesticide II is *Bacillus* simplex, preferably *B. simplex* ABU 288. These mixtures are particularly suitable in soybean and corn.

According to a further embodiment, the at least one pesticide II is *Bacillus subtilis*, preferably *B. subtilis* strain FB17.

According to one embodiment of the inventive mixtures, the at least one pesticide II is selected from *Bacillus amyloliquefaciens* AP-136, *B. amyloliquefaciens* AP-188, *B. amyloliquefaciens* AP-218, *B. amyloliquefaciens* AP-219, *B. amyloliquefaciens* AP-295, *B. amyloliquefaciens* FZB42, *B. amyloliquefaciens* IN937a, *B. amyloliquefaciens* IT-45, *B. amyloliquefaciens* ssp. *plantarum* MBI600, *B. mojavensis* AP-209,

*B. pumilus* GB34, *B. pumilus* INR-7, *B. pumilus* KFP9F, *B. pumilus* QST 2808, *B. pumilus* GHA 181, *B. simplex* ABU 288, *B. solisalsi* AP-217, *B. subtilis* CX-9060, *B. subtilis* FB17, *B. subtilis* GB03, *B. subtilis* GB07, *B. subtilis* QST-713, *B. subtilis* var. *amyloliquefaciens* FZB24 and *B. subtilis* var. *amyloliquefaciens* D747. These mixtures are particularly suitable in soybean and corn, in particular for seed treatment.

According to a further embodiment, the at least one pesticide II is selected from *Streptomyces* spp., preferably from *S. griseoviridis*, *S. lydicus* and *S. violaceusniger*, in particular from strains *S. griseoviridis* K61, *S. lydicus* WYEC 108, *S. violaceusniger* XL-2 and *S. violaceusniger* YCED-9.

According to a further embodiment, the at least one pesticide II is *Sphaerodes mycoparasitica*, preferably *S. mycoparasitica* IDAC 301008-01 (also referred to as strain SMCD2220-01). These mixtures are particularly suitable in soybean, cereals and corn, in particular corn especially to combat *Fusarium* head blight.

The present invention also relates to mixtures wherein the at least one pesticide II is selected from the following yeasts and fungi: *Ampelomyces quisqualis*, in particular strain AQ 10; *Aureobasidium pullulans*, in particular blastospores of strain DSM 14940 or blastospores of strain DSM 14941 or mixtures thereof; *Candida oleophila*, in particular strains I-182 and O; *Coniothyrium minitans*, in particular strain CON/M/91-8; *Dilophosphora alopecuri* which reduces annual ryegrass toxicity (ARGT), a disease of livestock resulting from the ingestion of annual ryegrass seed-heads that have been infected by the toxin producing bacterium *Rathayibacter toxicus*; *Gliocladium catenulatum*, in particular strain J 1446; *Metschnikovia fructicola*, in particular strain NRRL Y-30752, *Microsphaeropsis ochracea*, in particular strain P130A for control of apple scab; *Muscodor albus*, in particular strain QST 20799, *Pichia anomala*, in particular strain WRL-076, *Pseudozyma flocculosa*, in particular strain PF-A22 UL; *Pythium oligandrum*, in particular strain DV74.

The present invention also relates to mixtures wherein the at least one pesticide II is selected from the fungal genus *Trichoderma*, preferably from the strains *T. asperellum* T34, *T. asperellum* SKT-1, *T. asperellum* ICC 012, *T. atroviride* LC52, *T. atroviride* CNCM I-1237, *T. fertile* JM41R, *T. gamsii* ICC 080, *T. harmatum* TH 382, *T. harzianum* TH-35, *T. harzianum* T-22, *T. harzianum* T-39, mixture of *T. harzianum* ICC012 and *T. viride* ICC080; mixture of *T. polysporum* and *T. harzianum; T. stromaticum*, *T. virens* GL-21, *T. virens* G41 and *T. viride* TV1; in particular *T. fertile* JM41R.

The present invention also relates to mixtures wherein the at least one pesticide II is selected from the fungal genus *Ulocladium*, in particular *U. oudemansii* HRU3.

Preference is also given to mixtures comprising as pesticide II (component 2) a biopesticide from group L2), preferably selected from chitosan (hydrolysate), methyl-jasmonate, cis-jasmone, laminarin, *Reynoutria sachlinensis* extract and tea tree oil; even more preferable from methyl jasmonate and laminarin.

Preference is also given to mixtures comprising as pesticide II (component 2) a biopesticide from group L3), preferably selected from *Agrobacterium radiobacter* K1026, *Bacillus firmus* I-1582, *Bacillus thuringiensis* ssp. *kurstaki* SB4, *Beauveria bassiana* GHA, *B. bassiana* H123, *B. bassiana* DSM 12256, *B. bassiana* PPRI 5339, *Metarhizium anisopliae* var. *acridum* IMI 330189, *M. anisopliae* FI-985, *M. anisopliae* FI-1045, *M. anisopliae* F52, *M. anisopliae* ICIPE 69, *Paecilomyces lilacinus* DSM 15169, *P. lilacinus* BCP2, *Paenibacillus popilliae* Dutky-1940 (NRRL B-2309=ATCC 14706), *P. popilliae* KLN 3 and *P. popilliae* Dutky 1; even more preferably from *Bacillus thuringiensis* ssp. *kurstaki* SB4, *B. bassiana* DSM 12256, *B. bassiana* PPRI 5339, *Metarhizium anisopliae* var. *acridum* IMI 330189, *M. anisopliae* FI-985, *M. anisopliae* FI-1045, *Paecilomyces lilacinus* DSM 15169, *P. lilacinus* BCP2, *Paenibacillus popilliae* Dutky-1940, *P. popilliae* KLN 3 and *P. popilliae* Dutky 1.

According to a further embodiment, the at least one pesticide II is *Beauveria bassiana*, preferably selected from *B. bassiana* ATCC 74040, *B. bassiana* GHA, *B. bassiana* H123, *B. bassiana* DSM 12256 and *B. bassiana* PPRI 5339, in particular *B. bassiana* PPRI 5339. These mixtures are particularly suitable for wide range of arthropod pests, such as white flies, *thrips*, mites, aphids, tingids and all their developmental stages (eggs, immature stages, and adults) infesting numerous crops (vegetables, cucurbits, solanaceous fruits, strawberry, flowers and ornamentals, grapevine, citrus, pome, stone fruits, etc.). Recent studies have shown that these antagonistic fungal strains can effectively control also nut-weevils, wireworms (*Agriotes* spp.), and Tephritid flies, such as the Mediterranean fruit fly, *Ceratitis capitata*, the cherry fruit fly, *Rhagoletis cerasi*, and the olive fly, *Bactrocera oleae*. They are also useful in soybean and corn.

According to a further embodiment, the at least one pesticide II is *Beauveria brongniartii*.

According to a further embodiment, the at least one pesticide II is *Metarhizium anisopliae* or *M. anisopliae* var. *acridium*, preferably selected from *M. anisopliae* FI-1045, *M. anisopliae* F52, *M. anisopliae* var. *acridum* strains FI-985 and IMI 330189; in particular strain IM 330189. These mixtures are particularly suitable for control of arthropod pests in soybean and corn.

According to a further embodiment, the at least one pesticide II is *Lecanicillium* sp., preferably selected from *Lecanicillium longisporum* KV42, *L. longisporum* KV71 and *L. muscarium* KV01.

According to a further embodiment, the at least one pesticide II is *Paecilomyces fumosoroseus*, preferably strain FE 9901 especially for white fly control.

According to a further embodiment, the at least one pesticide II is selected from *Nomuraea rileyi*, preferably strains SA86101, GU87401, SR86151, CG128 and VA9101; and *P. lilacinus*, preferably strains 251, DSM 15169 or BCP2, in particular BCP2, which strains especially control the growth of plant-pathogenic nematodes.

According to a further embodiment, the at least one pesticide II is *Bacillus firmus*, preferably spores of strain CNCM I-1582, preferably useful for seed treatment of soybean and corn against nematodes and insects.

According to a further embodiment, the at least one pesticide II is *Bacillus cereus*, preferably spores of CNCM I-1562, preferably useful for seed treatment of soybean and corn against nematodes and insects.

According to a further embodiment, the at least one pesticide II is a mixture of spores of *B. firmus* and *B. cereus*, preferably mixtures spores of above mentioned strains CNCM I-1582 and CNCM I-1562, preferably useful for seed treatment of soybean and corn against nematodes and insects.

According to a further embodiment, the at least one pesticide II is selected from *Bacillus thuringiensis*, preferably *B. thuringiensis* ssp. *aizawai*, even more preferably selected from *B. t.* ssp. *aizawai* strains ABTS-18, SAN 401 I, ABG-6305 and ABG-6346, which are effective against different lepidopteran species including also noctuidae.

According to a further embodiment, the at least one pesticide II is selected from *Bacillus t.* ssp. *israelensis*, preferably AM65-52, SAN 402 I and ABG-6164, which are applied against larvae of various dipteran pests, e. g. mosquitoes and nematoceres.

According to a further embodiment, the at least one pesticide II is selected from *Bacillus t.* ssp. *kurstaki* preferably from strains EG 2348, SB4 and ABTS-351 (HD-1), in particular *B. t.* ssp. *kurstaki* SB4. These strains are used for control of lepidopteran larvae, but without noctuidae.

According to a further embodiment, the at least one pesticide II is selected from *Bacillus t.* ssp. *tenebrionis*, preferably the strains DSM 2803, NB-125 and NB-176, in particular NB-176, which all protect plants e. g. against leaf beetle larvae.

Preference is also given to mixtures comprising as pesticide II (component 2) a biopesticide from group L4), preferably selected from methyl jasmonate, Acacia negra extract, extract of grapefruit seeds and pulp, Catnip oil, Neem oil, Quillay extract and Tagetes oil, in particular methyl jasmonate or water-based Quillay extract.

Preference is also given to mixtures comprising as pesticide II (component 2) a biopesticide from group L5), preferably selected from *Azospirillum amazonense* BR 11140 (SpY2T), *A. brasilense* XOH, *A. brasilense* BR 11005 (Sp245), *A. brasilense* BR 11002, *A. lipoferum* BR 11646 (Sp31), *A. irakense*, *A. halopraeferens*, *Bradyrhizobium* sp. (*Vigna*), *B. japonicum* USDA 3, *B. japonicum* USDA 31, *B. japonicum* USDA 76, *B. japonicum* USDA 110, *B. japonicum* USDA 121, *B. japonicum* TA-11, *B. japonicum* 532c, *Glomus intraradices* RTI-801, *Paenibacillus alvei* NAS6G6, *Penicillium bilaiae*, *Rhizobium leguminosarum* bv. *phaseoli, R. l.* bv. *trifolii, R. l.* bv. *viciae*, and *Sinorhizobium meliloti*; more preferably selected from *Azospirillum brasilense* BR 11005 (Sp245), *Bradyrhizobium* sp. (*Vigna*), *B. japonicum* USDA 3, *B. japonicum* USDA 31, *B. japonicum* USDA 76, *B. japonicum* USDA 110, *B. japonicum* USDA 121, *B. japonicum* TA-11, *B. japonicum* 532c, *Rhizobium leguminosarum* bv. *phaseoli* P1NP3Cst, *R. l.* bv. *phaseoli* RG-B10, *R. l.* bv. *trifolii* RP113-7, *R. l.* bv. *viciae* SU303, *R. l.* bv. *viciae* WSM1455, *R. tropici* SEMIA 4077, *R. tropici* SEMIA 4080 and *Sinorhizobium meliloti*.

According to another embodiment of the inventive mixtures, *Bradyrhizobium* sp. (meaning any *Bradyrhizobium* species and/or strain) as pesticide II is *B. japonicum*. These mixtures are particularly suitable in soybean. *B. japonicum* strains are cultivated using media and fermentation techniques known in the art, e. g. in yeast extract-mannitol broth (YEM) at 27° C. for about 5 days.

The present invention also relates to mixtures, wherein the at least one pesticide II is selected from *B. japonicum* and further comprises a compound III, wherein compound III is selected from jasmonic acid or salts or derivatives thereof including cis-jasmone, preferably methyl-jasmonate or cis-jasmone.

References for various *B. japonicum* strains are given e. g. in U.S. Pat. No. 7,262,151 (*B. japonicum* strains USDA 110 (=IITA 2121, SEMIA 5032, RCR 3427, ARS 1-110, Nitragin 61A89; isolated from *Glycine max* in Florida in 1959, Serogroup 110; Appl Environ Microbiol 60, 940-94, 1994), USDA 31 (=Nitragin 61A164; isolated from *Glycine max* in Wisconsin in 1941, USA, Serogroup 31), USDA 76 (plant passage of strain USDA 74 which has been isolated from *Glycine max* in California, USA, in 1956, Serogroup 76), USDA 121 (isolated from *Glycine max* in Ohio, USA, in 1965), USDA 3 (isolated from *Glycine max* in Virginia, USA, in 1914, Serogroup 6; U.S. Pat. No. 7,262,151), USDA 121 (Crop Science 26(5), 911-916, 1986) and USDA 136 (=CB 1809, SEMIA 586, Nitragin 61A136, RCR 3407; isolated from *Glycine max* in Beltsville, Md. in 1961; Appl. Environ. Microbiol. 60, 940-94, 1994). Further *B. japonicum* strain G49 (INRA, Angers, France; C. R. Acad. Agric. Fr. 73, 163-171, 1987) is especially suitable for soybean grown in Europe, in particular in France. Further suitable *B. japonicum* strain TA-11 (TA11 NOD$^+$) (NRRL B-18466) is i. a. described in U.S. Pat. No. 5,021,076; Appl. Environ. Microbiol. 56, 2399-2403, 1990, and commercially available as liquid inoculant for soybean (VAULT® NP, BASF Corp., USA). Further *B. japonicum* strains as example for pesticide II are described in US2012/0252672A. Further suitable and especially in Canada commercially available strain 532c (The Nitragin Company, Milwaukee, Wis., USA, field isolate from Wisconsin; Nitragin strain collection No. 61A152; Can. J. Plant. Sci. 70, 661-666, 1990) (e. g. in RHIZOFLO, HISTICK, HICOAT Super from BASF Agricultural Specialties Ltd., Canada).

Preferably, *B. japonicum* is selected from strains TA-11 and 532c, more preferably a mixture of *B. japonicum* strains TA-11 and 532c is used.

Other suitable and commercially available *B. japonicum* strains (see e. g. Appl. Environ. Microbiol. 73(8), 2635, 2007) are SEMIA 566 (isolated from North American inoculant in 1966 and used in Brazilian commercial inoculants from 1966 to 1978); SEMIA 586 (=CB 1809; originally isolated in Maryland, USA but received from Australia in 1966 and used in Brazilian inoculants in 1977); CPAC 15 (=SEMIA 5079; a natural variant of SEMIA 566 used in commercial inoculants since 1992); and CPAC 7 (=SEMIA 5080; a natural variant of SEMIA 586 used in commercial inoculants since 1992). These strains are especially suitable for soybean grown in Australia or South America, in particular in Brazil. In particular, mixtures of *B. japonicum* SEMIA 5079 and SEMIA 5080 are suitable. Some of the abovementioned strains have been re-classified as a novel species *B. elkanii*, e. g. strain USDA 76 (Can. J. Microbiol. 38, 501-505, 1992).

Another suitable and commercially available *B. japonicum* strain is E-109 (variant of strain USDA 138, see e. g. Eur. J. Soil Biol. 45, 28-35, 2009; Biol. Fertil. Soils 47, 81-89, 2011; deposited at Agriculture Collection Laboratory of the Instituto de Microbiologia y Zoologia Agricola (IMYZA), Instituto Nacional de Tecnologî a Agropecuaria (INTA), Castelar, Argentina). This strain is especially suitable for soybean grown in South America, in particular in Argentina. Further suitable and commercially available *B. japonicum* strains are WB74 or WB74-1 (e. g. from Stimuplant CC, South Africa or from SoyGro Bio-Fertilizer Ltd, South Africa). These strains are especially suitable for soybean grown in South America and Africa, in particular in South Africa.

The present invention also relates to mixtures, wherein the at least one pesticide II is selected from *Bradyrhizobium elkanii* and *Bradyrhizobium liaoningense*, more preferably from *B. elkanii*. These mixtures are particularly suitable in soybean. *B. elkanii* and *B. liaoningense* are cultivated using media and fermentation techniques known in the art, e. g. in yeast extract-mannitol broth (YEM) at 27° C. for about 5 days.

The present invention also relates to mixtures wherein the at least one pesticide II is selected from selected from *B. elkanii* and *B. liaoningense* and further comprises a compound III, wherein compound III is selected from jasmonic acid or salts or derivatives thereof including cis-jasmone, preferably methyl-jasmonate or cis-jasmone.

Suitable and commercially available *B. elkanii* strains are SEMIA 587 and SEMIA 5019 (=29W) (see e. g. Appl. Environ. Microbiol. 73(8), 2635, 2007) and USDA 3254 and USDA 76 and USDA 94. Preferably, mixtures of *B. elkanii* strains SEMIA 587 and SEMIA 5019 are useful (e. g. in GELFIX 5 from BASF Agricultural Specialties Ltd., Brazil). Further commercially available *B. elkanii* strains are U-1301 and U-1302 (e. g. product Nitroagin® Optimize from Novozymes Bio As S.A., Brazil or NITRASEC for soybean from LAGE y Cia, Brazil). These strains are especially suitable for soybean grown in Australia or South America, in particular in Brazil.

The present invention also relates to mixtures, wherein pesticide II is selected from *Bradyrhizobium* sp. (*Arachis*) which shall describe the cowpea miscellany cross-inoculation group which includes inter alia indigenous cowpea bradyrhizobia on cowpea (*Vigna unguiculata*), siratro (*Macroptilium atropurpureum*), lima bean (*Phaseolus lunatus*), and peanut (*Arachis hypogaea*). This mixture comprising as pesticide II *B.* sp. (*Arachis*) is especially suitable for use in peanut, Cowpea, Mung bean, Moth bean, Dune bean, Rice bean, Snake bean and Creeping *vigna*, in particular peanut.

The present invention also relates to mixtures wherein the at least one pesticide II is selected from *Bradyrhizobium* sp. (*Arachis*) and further comprises a compound III, wherein compound III is selected from jasmonic acid or salts or derivatives thereof including cis-jasmone, preferably methyl-jasmonate or cis-jasmone.

Suitable and commercially available *B.* sp. (*Arachis*) strain is CB1015 (=IITA 1006, USDA 3446 presumably originally collected in India; from Australian Inoculants Research Group; e. g. http://www.qaseeds.com.au/inoculant_applic.php). Another suitable strain is *Bradyrhizobium* sp. PNL01 (BASF Corp., USA; Bisson and Mason, Apr. 29, 2010, Project report, Worcester Polytechnic Institute, Worcester, Mass., USA: http://www.wpi.edu/Pubs/E-project/Available/E-project-042810-163614/). These strains are especially suitable for peanut grown in Australia, North America or South America, in particular in Brazil.

Suitable and commercially available *B.* sp. (*Arachis*) strains especially for cowpea and peanut but also for soybean are strains SEMIA 6144, SEMIA 6462 (=BR 3267) and SEMIA 6464 (=BR 3262; see e. g. FEMS Microbiol. Letters 303(2), 123-131, 2010; Revista Brasileira de Ciencia do Solo 35(3), 739-742, 2011, ISSN 0100-0683).

The present invention also relates to mixtures, wherein the at least one pesticide II is selected from *Bradyrhizobium* sp. (Lupine) (also called *B. lupini*, *B. lupines* or *Rhizobium lupini*). This mixture is especially suitable for use in dry beans and lupins.

The present invention also relates to mixtures wherein the at least one pesticide II is selected from *Bradyrhizobium* sp. (Lupine) (*B. lupini*) and further comprises a compound III, wherein compound III is selected from jasmonic acid or salts or derivatives thereof including cis-jasmone, preferably methyl-jasmonate or cis-jasmone.

Suitable and commercially available *B. lupini* strain is LL13 (isolated from *Lupinus iuteus* nodules from French soils; deposited at INRA, Dijon and Angers, France; http://agriculture.gouv.fr/IMG/pdf/ch20060216.pdf). This strain is especially suitable for lupins grown in Australia, North America or Europe, in particular in Europe.

Further suitable and commercially available *B. lupini* strains WU425 (isolated in Esperance, Western Australia from a non-Australian legume *Ornithopus compressus*), WSM4024 (isolated from lupins in Australia by CRS during a 2005 survey) and WSM471 (isolated from *Ornithopus pinnatus* in Oyster Harbour, Western Australia) are described e. g. in Palta J. A., Berger J. B. (eds), Proceed. 12th International Lupin Conference, 14-18 Sep. 2008, Fremantle, Western Australia, International Lupin Association, Canterbury, New Zealand, 47-50, ISBN 0-86476-153-8: http://www.lupins.org/pdf/conference/2008/Agronomy%20and%20Production/John%20Howieson%20and%20G%20OHara.pdf; Appl. Environ. Microbiol. 71, 7041-7052, 2005; Australian J. Exp. Agricult. 36(1), 63-70, 1996.

The present invention also relates to mixtures, wherein the at least one pesticide II is selected from *Mesorhizobium* sp. (meaning any *Mesorhizobium* species and/or strain), more preferably *Mesorhizobium ciceri*. These mixtures are particularly suitable in cowpea.

The present invention also relates to mixtures wherein the at least one pesticide II is selected from *Mesorhizobium* sp. and further comprises a compound III, wherein compound III is selected from jasmonic acid or salts or derivatives thereof including cis-jasmone, preferably methyl-jasmonate or cis-jasmone.

Suitable and commercially available *Mesorhizobium* sp. strains are e. g. *M. ciceri* CC1192 (=UPM 848, C≡CT 5549; from Horticultural Research Station, Gosford, Australia; collected in Israel from *Cicer arietinum* nodules; Can. J. Microbiol. 48, 279-284, 2002) and *Mesorhizobium* sp. strains WSM1271 (collected in Sardinia, Italy, from plant host Biserrula pelecinus), WSM 1497 (collected in Mykonos, Greece, from plant host Biserrula pelecinus); *M. loti* CC829 (commercial inoculant for *Lotus pedunculatus* and *L. ulginosus* in Australia, isolated from *L. ulginosus* nodules in USA; NZP 2012), *M. loti* SU343 (a commercial inoculant for *Lotus corniculatus* in Australia; isolated from host nodules in USA). For references see e. g. Soil Biol. Biochem. 36(8), 1309-1317, 2004; Plant and Soil 348(1-2), 231-243, 2011. Preferably, *M.* sp. strains are *M. loti* CC829, in particular for treatment of Lotus *pedunculatus*.

The present invention also relates to mixtures wherein the at least one pesticide II is selected from *Mesorhizobium huakuii*, also referred to as *Rhizobium huakuii* (see e. g. Appl. Environ. Microbiol. 77(15), 5513-5516, 2011). These mixtures are particularly suitable in *Astralagus*, e. g. *Astalagus sinicus* (Chinese milkwetch), *Thermopsis*, e. g. *Thermopsis luinoides* (Goldenbanner) and alike.

The present invention also relates to mixtures wherein the at least one pesticide II is selected from *Mesorhizobium huakuii* and further comprises a compound III, wherein compound III is selected from jasmonic acid or salts or derivatives thereof including cis-jasmone, preferably methyl-jasmonate or cis-jasmone.

Suitable and commercially available *M. huakuii* strain is HN3015 which was isolated from *Astralagus sinicus* in a rice-growing field of Southern China (see e. g. World J. Microbiol. Biotechn. 23(6), 845-851, 2007, ISSN 0959-3993).

The present invention also relates to mixtures, wherein the at least one pesticide II is selected from *Azospirillum amazonense, A. brasilense, A. lipoferum, A. irakense* and *A. halopraeferens*, more preferably from *A. brasilense*, in particular selected from *A. brasilense* strains BR 11005 (Sp245) and AZ39 which are both commercially used in Brazil and are obtainable from EMBRAPA-Agribiologia, Brazil. These mixtures are particularly suitable in soybean.

The present invention also relates to mixtures wherein the at least one pesticide II is selected from *A. amazonense, A. brasilense, A. lipoferum, A. irakense* and *A. halopraeferens*, more preferably *A. brasilense*, and further comprises a compound III, wherein compound III is selected from jasmonic acid or salts or derivatives thereof including cis-jasmone, preferably methyl-jasmonate or cis-jasmone.

The present invention also relates to mixtures wherein the at least one pesticide II is selected from *Rhizobium leguminosarum* bv. *phaseoli*, especially strain RG-B10 thereof; *R. l.* bv. *trifolii*, especially strain RP113-7 thereof; *R. l.* bv. *viciae*, in particular strains SU303, WSM1455 and P1NP3Cst thereof; *R. tropici*, especially strains CC511, SEMIA 4077 and SEMIA 4080 thereof; and *Sinorhizobium meliloti*, especially strain MSDJ0848 thereof.

According to a further embodiment, in the inventive mixtures pesticide II is selected from one compound II selected from *Sinorhizobium meliloti* MSDJ0848, *S. meliloti* NRG185, *S. meliloti* RRI128, *S. meliloti* SU277, *Rhizobium leguminosarum* bv. *phaseoli* RG-B10, *R. leguminosarum* bv. *viciae* P1 NP3Cst, *R. l.* bv. *viciae* RG-P2, *R. l.* bv. *viciae* SU303, *R. l.* bv. *viciae* WSM1455, *R. leguminosarum* bv. *trifolii* RP113-7, *R. l.* bv. *trifolii* 095, *R. l.* bv. *trifolii* TA1, *R. l.* bv. *trifolii* CC283b, *R. l.* bv. *trifolii* CB782, *R. l.* bv. *trifolii* CC1099, *R. l.* bv. *trifolii* CC275e, *R. l.* bv. *trifolii* WSM1325, *R. tropici* CC511, *R. tropici* SEMIA 4077, and *R. tropici* SEMIA 4080.

*Sinorhizobium meliloti* is commercially available from BASF Corp., USA, as product Dormal® Alfalfa & Luzerne. *Rhizobium leguminosarum* bv. *phaseoli* is commercially available from BASF Corp., USA, as product RhizoStick. These strains are particularly suitable as inoculants for various legumes such as alfalfa, clover, peas, beans, lentils, soybeans, peanuts and others.

*Rhizobium leguminosarum* bv. *phaseoli*, also called *R. phaseoli* and recently the type I isolates being reclassified as *R. etli*, is commercially available from BASF Corp., USA, as product RhizoStick for dry beans. Particularly suitable strains especially for the legume common bean (*Phaseolus vulgaris*), but also for other crops such as corn and lettuce, are as follows: *R. leguminosarum* bv. *phaseoli* RG-B10 (identical to strain USDA 9041) is commercially available as NODULATOR Dry Bean in Africa, HiStick NT Dry bean in US, and NODULATOR Dry Bean in Canada from BASF Corp., USA, or BASF Agricultural Specialties Ltd., Canada, and is known from Int. J. Syst. Bacteriol. 46(1), 240-244, 1996; Int. J. Syst. Evol. Microbiol. 50, 159-170, 2000.

Further *R. l.* bv. *phaseoli* or *R. etli* strains are e. g. known from the above mentioned references and Appl. Environ. Microbiol. 45(3), 737-742, 1983; ibida 54(5), 1280-1283, 1988.

*R. l.* bv. *viciae* P1NP3Cst (also referred to as 1435) is known from New Phytol. 179(1), 224-235, 2008; and e. g. in NODULATOR PL Peat Granule from BASF Corp., USA; or in NODULATOR XL PL from BASF Agricultural Specialties Ltd., Canada). *R. l.* bv. *viciae* RG-P2 (also called P2) is commercially available as inoculant for pean and lentils as RhizUP peat in Canada from BASF Agricultural Specialties Ltd., Canada. *R. l.* bv. *viciae* WSM1455 is commercially available NODULAID for *faba* beans peat from BASF Agricultural Specialties Pty Ltd, Australia. *R. l.* bv. *viciae* SU303 is commercially available as NODULAID Group E, NODULAID NT peat or NODULATOR granules for peas from BASF Agricultural Specialties Pty Ltd, Australia. *R. l.* bv. *viciae* WSM1455 is commercially available as NODULAID Group F peat, NODULAID NT and NODULATOR granules for *faba* bean from BASF Agricultural Specialties Pty Ltd, Australia, and is also as inoculant for *faba* beans as NODULATOR SA *faba* bean in Canada or as *Faba* Sterile Peat in Europe or as NODULATOR *faba* bean granules in Canada from BASF Agricultural Specialties Ltd., Canada.

*Rhizobium leguminosarum* bv. *trifolii* is commercially available from BASF Corp., USA, as product Nodulator or DORMAL true clover. Suitable strains are especially useful for all kind of clovers, are as follows: *R. l.* bv. *trifolii* strains RP113-7 (also called 113-7) and 095 commercially available from BASF Corp., USA; see also Appl. Environ. Microbiol. 44(5), 1096-1101. Suitable strain *R. l.* bv. *trifolii* TA1 obtained from Australia is known from Appl. Environ. Microbiol. 49(1), 127-131, 1985 and commercially available as NODULAID peat for white clover from BASF Agricultural Specialties Pty Ltd, Australia. *R. l.* bv. *trifolii* CC283b is commercially available as NODULAID peat for Caucasian clover from BASF Agricultural Specialties Pty Ltd, Australia. *R. l.* bv. *trifolii* CC1099 is commercially available as NODULAID peat for sainfoin from BASF Agricultural Specialties Pty Ltd, Australia. *R. l.* bv. *trifolii* CC275e is commercially available as NODULAID peat for NZ white clover from BASF Agricultural Specialties Pty Ltd, Australia. *R. l.* bv. *trifolii* CB782 is commercially available as NODULAID peat for Kenya white clover from BASF Agricultural Specialties Pty Ltd, Australia. *R. l.* bv. *trifolii* strain WSM1325 has been collected in 1993 from the Greek Island of Serifos, is commercially available in NODULAID peat for sub clover and NODULATOR granules for sub clover both from BASF Agricultural Specialties Pty Ltd, Australia, for a broad range of annual clovers of Mediterranean origin, and is known from Stand. Genomic Sci. 2(3), 347-356, 2010. *R. l.* bv. *trifolii* strain WSM2304 has been isolated from *Trifolium polymorphum* in Uruguay in 1998 and is known from Stand. Genomic Sci. 2(1), 66-76, 2010, and is particularly suitable to nodulate its clover host in Uruguay.

*R. tropici* is useful for a range of legume crops especially in tropical regions such as Brazil. Suitable strains are especially useful for all kind of clovers, are as follows: *R. tropici* strain SEMIA 4080 (identical to PRF 81; known from Soil Biology & Biochemistry 39, 867-876, 2007; BMC Microbiol. 12, 84, 2012) is commercially available in NITRAFIX FEIJÃO peat for beans from BASF Agricultural Specialties Ltd., Brazil, and has been used as commercial inoculant for applications to common bean crops in Brazil since 1998, and is deposited with FEPAGRO-Fundação Estadual de Pesquisa Agropecuária, Rua Gonçalves Dias, 570, Bairro Menino Deus, Porto Alegre/RS, Brazil. *R. tropici* is useful for a range of legume crops especially in tropical regions such as Brazil. Suitable strains are especially useful for all kind of clovers, are as follows: *R. tropici* strain SEMIA 4077 (identical to CIAT899; Rev. Ciênc. Agron. 44(4) Fortaleza October/December 2013) is commercially available in NITRAFIX FEIJÃO peat for beans from BASF Agricultural Specialties Ltd., Brazil. *R. tropici* strain CC511 is commercially available as NODULAID peat for common bean from BASF Agricultural Specialties Pty Ltd, Australia, and is known from Agronomy, N.Z. 36, 4-35, 2006.

The present invention also relates to mixtures wherein the at least one pesticide II is selected from *R. leguminosarum* bv. *phaseoli*, *R. l.* bv. *trifolii*, *R. l.* bv. *viciae*, *R. tropici* and *Sinorhizobium meliloti*, and further comprises a compound III, wherein compound III is selected from jasmonic acid or salts or derivatives thereof including cis-jasmone, preferably methyl-jasmonate or cis-jasmone.

According to a further embodiment, the at least one pesticide II is selected from *Deiftia acidovorans*, in particular strain RAY209, especially in soybean and canola.

According to a further embodiment, the at least one pesticide II is selected from *Lysobacter* spp., preferably selected from *L. antibioticus*, in particular strains 13-1 and HS124, preferably in rice or pepper for control of *Phytophthora* or bacterial leaf blight. According to a further embodiment, the at least one pesticide II is selected from *L. enzymogenes*, in particular strain 3.1T8.

According to a further embodiment, the at least one pesticide II is selected from *Pseudomonas* spp., preferably selected from *P. chloraphis* MA 342 and *Pseudomonas* sp. DSM 13134.

According to a further embodiment, the at least one pesticide II is selected from *Penicillium bilaiae*.

Preference is also given to mixtures comprising as pesticide II (component 2) a biopesticide from group L6), preferably selected from abscisic acid, aluminium silicate (kaolin), humates, *Ascophyllum nodosum* (Norwegian kelp, Brown kelp) extract and *Ecklonia maxima* (kelp) extract.

Preference is also given to mixtures comprising as pesticide II a biopesticide selected from the isoflavones formonennitin, hesperetin and naringenin.

Accordingly, the present invention furthermore relates to compositions comprising one compound I (component 1) and one pesticide II (component 2), which pesticide II is selected from the column "Co. 2" of the lines C-1 to C-837 of Table C.

A further embodiment relates to the compositions C-1 to C-837 listed in Table C, where a row of Table C corresponds in each case to a fungicidal composition comprising as active components one of the in the present specification individualized compounds of formula I (component 1) and the respective pesticide II from groups A) to O) (component 2) stated in the row in question. Preferably, the compositions described comprise the active components in synergistically effective amounts.

TABLE C

Compositions comprising as active components one individualized compound I (I) (in Column Co. 1) and as component 2) (in Column Co. 2) one pesticide from groups A) to O) [which is coded e.g. as (A.1.1) for azoxystrobin as defined above].

| Mixt. | Co. 1 | Co. 2 |
|---|---|---|
| C-1 | (I) | (A.1.1) |
| C-2 | (I) | (A.1.2) |
| C-3 | (I) | (A.1.3) |
| C-4 | (I) | (A.1.4) |
| C-5 | (I) | (A.1.5) |
| C-6 | (I) | (A.1.6) |
| C-7 | (I) | (A.1.7) |
| C-8 | (I) | (A.1.8) |
| C-9 | (I) | (A.1.9) |
| C-10 | (I) | (A.1.10) |
| C-11 | (I) | (A.1.11) |
| C-12 | (I) | (A.1.12) |
| C-13 | (I) | (A.1.13) |
| C-14 | (I) | (A.1.14) |
| C-15 | (I) | (A.1.15) |
| C-16 | (I) | (A.1.16) |
| C-17 | (I) | (A.1.17) |
| C-18 | (I) | (A.1.18) |
| C-19 | (I) | (A.1.19) |
| C-20 | (I) | (A.1.20) |
| C-21 | (I) | (A.1.21) |
| C-22 | (I) | (A.2.1) |
| C-23 | (I) | (A.2.2) |
| C-24 | (I) | (A.2.3) |
| C-25 | (I) | (A.2.4) |
| C-26 | (I) | (A.2.5) |
| C-27 | (I) | (A.2.6) |
| C-28 | (I) | (A.2.7) |
| C-29 | (I) | (A.3.1) |
| C-30 | (I) | (A.3.2) |
| C-31 | (I) | (A.3.3) |
| C-32 | (I) | (A.3.4) |
| C-33 | (I) | (A.3.5) |
| C-34 | (I) | (A.3.6) |
| C-35 | (I) | (A.3.7) |
| C-36 | (I) | (A.3.8) |
| C-37 | (I) | (A.3.9) |
| C-38 | (I) | (A.3.10) |
| C-39 | (I) | (A.3.11) |
| C-40 | (I) | (A.3.12) |
| C-41 | (I) | (A.3.13) |
| C-42 | (I) | (A.3.14) |
| C-43 | (I) | (A.3.15) |
| C-44 | (I) | (A.3.16) |
| C-45 | (I) | (A.3.17) |
| C-46 | (I) | (A.3.18) |
| C-47 | (I) | (A.3.19) |
| C-48 | (I) | (A.3.20) |
| C-49 | (I) | (A.3.21) |
| C-50 | (I) | (A.3.22) |
| C-51 | (I) | (A.3.23) |
| C-52 | (I) | (A.3.24) |
| C-53 | (I) | (A.3.25) |
| C-54 | (I) | (A.3.26) |
| C-55 | (I) | (A.3.27) |
| C-56 | (I) | (A.4.1) |
| C-57 | (I) | (A.4.2) |
| C-58 | (I) | (A.4.3) |
| C-59 | (I) | (A.4.4) |
| C-60 | (I) | (A.4.5) |
| C-61 | (I) | (A.4.6) |
| C-62 | (I) | (A.4.7) |
| C-63 | (I) | (A.4.8) |
| C-64 | (I) | (A.4.9) |
| C-65 | (I) | (A.4.10) |
| C-66 | (I) | (A.4.11) |
| C-67 | (I) | (A.4.12) |
| C-68 | (I) | (B.1.1) |
| C-69 | (I) | (B.1.2) |
| C-70 | (I) | (B.1.3) |
| C-71 | (I) | (B.1.4) |
| C-72 | (I) | (B.1.5) |
| C-73 | (I) | (B.1.6) |

TABLE C-continued

Compositions comprising as active components one individualized compound I (I) (in Column Co. 1) and as component 2) (in Column Co. 2) one pesticide from groups A) to O) [which is coded e.g. as (A.1.1) for azoxystrobin as defined above].

| Mixt. | Co. 1 | Co. 2 |
|---|---|---|
| C-74 | (I) | (B.1.7) |
| C-75 | (I) | (B.1.8) |
| C-76 | (I) | (B.1.9) |
| C-77 | (I) | (B.1.10) |
| C-78 | (I) | (B.1.11) |
| C-79 | (I) | (B.1.12) |
| C-80 | (I) | (B.1.13) |
| C-81 | (I) | (B.1.14) |
| C-82 | (I) | (B.1.15) |
| C-83 | (I) | (B.1.16) |
| C-84 | (I) | (B.1.17) |
| C-85 | (I) | (B.1.18) |
| C-86 | (I) | (B.1.19) |
| C-87 | (I) | (B.1.20) |
| C-88 | (I) | (B.1.21) |
| C-89 | (I) | (B.1.22) |
| C-90 | (I) | (B.1.23) |
| C-91 | (I) | (B.1.24) |
| C-92 | (I) | (B.1.25) |
| C-93 | (I) | (B.1.26) |
| C-94 | (I) | (B.1.27) |
| C-95 | (I) | (B.1.28) |
| C-96 | (I) | (B.1.29) |
| C-97 | (I) | (B.1.30) |
| C-98 | (I) | (B.1.31) |
| C-99 | (I) | (B.1.32) |
| C-100 | (I) | (B.1.33) |
| C-101 | (I) | (B.1.34) |
| C-102 | (I) | (B.1.35) |
| C-103 | (I) | (B.1.36) |
| C-104 | (I) | (B.1.37) |
| C-105 | (I) | (B.1.38) |
| C-106 | (I) | (B.1.39) |
| C-107 | (I) | (B.1.40) |
| C-108 | (I) | (B.1.41) |
| C-109 | (I) | (B.1.42) |
| C-110 | (I) | (B.1.43) |
| C-111 | (I) | (B.1.44) |
| C-112 | (I) | (B.1.45) |
| C-113 | (I) | (B.1.46) |
| C-114 | (I) | (B.1.47) |
| C-115 | (I) | (B.1.48) |
| C-116 | (I) | (B.1.49) |
| C-117 | (I) | (B.1.50) |
| C-118 | (I) | (B.1.51) |
| C-119 | (I) | (B.2.1) |
| C-120 | (I) | (B.2.2) |
| C-121 | (I) | (B.2.3) |
| C-122 | (I) | (B.2.4) |
| C-123 | (I) | (B.2.5) |
| C-124 | (I) | (B.2.6) |
| C-125 | (I) | (B.2.7) |
| C-126 | (I) | (B.2.8) |
| C-127 | (I) | (B.3.1) |
| C-128 | (I) | (C.1.1) |
| C-129 | (I) | (C.1.2) |
| C-130 | (I) | (C.1.3) |
| C-131 | (I) | (C.1.4) |
| C-132 | (I) | (C.1.5) |
| C-133 | (I) | (C.1.6) |
| C-134 | (I) | (C.1.7) |
| C-135 | (I) | (C.2.1) |
| C-136 | (I) | (C.2.2) |
| C-137 | (I) | (C.2.3) |
| C-138 | (I) | (C.2.4) |
| C-139 | (I) | (C.2.5) |
| C-140 | (I) | (C.2.6) |
| C-141 | (I) | (C.2.7) |
| C-142 | (I) | (D.1.1) |
| C-143 | (I) | (D.1.2) |
| C-144 | (I) | (D.1.3) |
| C-145 | (I) | (D.1.4) |
| C-146 | (I) | (D.1.5) |
| C-147 | (I) | (D.1.6) |
| C-148 | (I) | (D.2.1) |
| C-149 | (I) | (D.2.2) |
| C-150 | (I) | (D.2.3) |
| C-151 | (I) | (D.2.4) |
| C-152 | (I) | (D.2.5) |
| C-153 | (I) | (D.2.6) |
| C-154 | (I) | (D.2.7) |
| C-155 | (I) | (E.1.1) |
| C-156 | (I) | (E.1.2) |
| C-157 | (I) | (E.1.3) |
| C-158 | (I) | (E.2.1) |
| C-159 | (I) | (E.2.2) |
| C-160 | (I) | (E.2.3) |
| C-161 | (I) | (E.2.4) |
| C-162 | (I) | (E.2.5) |
| C-163 | (I) | (E.2.6) |
| C-164 | (I) | (E.2.7) |
| C-165 | (I) | (E.2.8) |
| C-166 | (I) | (F.1.1) |
| C-167 | (I) | (F.1.2) |
| C-168 | (I) | (F.1.3) |
| C-169 | (I) | (F.1.4) |
| C-170 | (I) | (F.1.5) |
| C-171 | (I) | (F.1.6) |
| C-172 | (I) | (F.2.1) |
| C-173 | (I) | (G.1.1) |
| C-174 | (I) | (G.1.2) |
| C-175 | (I) | (G.1.3) |
| C-176 | (I) | (G.1.4) |
| C-177 | (I) | (G.2.1) |
| C-178 | (I) | (G.2.2) |
| C-179 | (I) | (G.2.3) |
| C-180 | (I) | (G.2.4) |
| C-181 | (I) | (G.2.5) |
| C-182 | (I) | (G.2.6) |
| C-183 | (I) | (G.2.7) |
| C-184 | (I) | (G.3.1) |
| C-185 | (I) | (G.3.2) |
| C-186 | (I) | (G.3.3) |
| C-187 | (I) | (G.3.4) |
| C-188 | (I) | (G.3.5) |
| C-189 | (I) | (G.3.6) |
| C-190 | (I) | (G.3.7) |
| C-191 | (I) | (G.3.8) |
| C-192 | (I) | (G.4.1) |
| C-193 | (I) | (G.5.1) |
| C-194 | (I) | (G.5.2) |
| C-195 | (I) | (G.5.3) |
| C-196 | (I) | (H.1.1) |
| C-197 | (I) | (H.1.2) |
| C-198 | (I) | (H.1.3) |
| C-199 | (I) | (H.1.4) |
| C-200 | (I) | (H.1.5) |
| C-201 | (I) | (H.1.6) |
| C-202 | (I) | (H.2.1) |
| C-203 | (I) | (H.2.2) |
| C-204 | (I) | (H.2.3) |
| C-205 | (I) | (H.2.4) |
| C-206 | (I) | (H.2.5) |
| C-207 | (I) | (H.2.6) |
| C-208 | (I) | (H.2.7) |
| C-209 | (I) | (H.2.8) |
| C-210 | (I) | (H.2.9) |
| C-211 | (I) | (H.3.1) |
| C-212 | (I) | (H.3.2) |
| C-213 | (I) | (H.3.3) |
| C-214 | (I) | (H.3.4) |
| C-215 | (I) | (H.3.5) |
| C-216 | (I) | (H.3.6) |
| C-217 | (I) | (H.3.7) |
| C-218 | (I) | (H.3.8) |
| C-219 | (I) | (H.3.9) |

TABLE C-continued

Compositions comprising as active components one individualized compound I (I) (in Column Co. 1) and as component 2) (in Column Co. 2) one pesticide from groups A) to O) [which is coded e.g. as (A.1.1) for azoxystrobin as defined above].

| Mixt. | Co. 1 | Co. 2 |
|---|---|---|
| C-220 | (I) | (H.3.10) |
| C-221 | (I) | (H.3.11) |
| C-222 | (I) | (H.4.1) |
| C-223 | (I) | (H.4.2) |
| C-224 | (I) | (H.4.3) |
| C-225 | (I) | (H.4.4) |
| C-226 | (I) | (H.4.5) |
| C-227 | (I) | (H.4.6) |
| C-228 | (I) | (H.4.7) |
| C-229 | (I) | (H.4.8) |
| C-230 | (I) | (H.4.9) |
| C-231 | (I) | (H.4.10) |
| C-232 | (I) | (I.1.1) |
| C-233 | (I) | (I.1.2) |
| C-234 | (I) | (I.2.1) |
| C-235 | (I) | (I.2.2) |
| C-236 | (I) | (I.2.3) |
| C-237 | (I) | (I.2.4) |
| C-238 | (I) | (I.2.5) |
| C-239 | (I) | (J.1.1) |
| C-240 | (I) | (J.1.2) |
| C-241 | (I) | (J.1.3) |
| C-242 | (I) | (J.1.4) |
| C-243 | (I) | (J.1.5) |
| C-244 | (I) | (J.1.6) |
| C-245 | (I) | (J.1.7) |
| C-246 | (I) | (J.1.8) |
| C-247 | (I) | (J.1.9) |
| C-248 | (I) | (K.1.1) |
| C-249 | (I) | (K.1.2) |
| C-250 | (I) | (K.1.3) |
| C-251 | (I) | (K.1.4) |
| C-252 | (I) | (K.1.5) |
| C-253 | (I) | (K.1.6) |
| C-254 | (I) | (K.1.7) |
| C-255 | (I) | (K.1.8) |
| C-256 | (I) | (K.1.9) |
| C-257 | (I) | (K.1.10) |
| C-258 | (I) | (K.1.11) |
| C-259 | (I) | (K.1.12) |
| C-260 | (I) | (K.1.13) |
| C-261 | (I) | (K.1.14) |
| C-262 | (I) | (K.1.15) |
| C-263 | (I) | (K.1.16) |
| C-264 | (I) | (K.1.17) |
| C-265 | (I) | (K.1.18) |
| C-266 | (I) | (K.1.19) |
| C-267 | (I) | (K.1.20) |
| C-268 | (I) | (K.1.21) |
| C-269 | (I) | (K.1.22) |
| C-270 | (I) | (K.1.23) |
| C-271 | (I) | (K.1.24) |
| C-272 | (I) | (K.1.25) |
| C-273 | (I) | (K.1.26) |
| C-274 | (I) | (K.1.27) |
| C-275 | (I) | (K.1.28) |
| C-276 | (I) | (K.1.29) |
| C-277 | (I) | (K.1.30) |
| C-278 | (I) | (K.1.31) |
| C-279 | (I) | (K.1.32) |
| C-280 | (I) | (K.1.33) |
| C-281 | (I) | (K.1.34) |
| C-282 | (I) | (K.1.35) |
| C-283 | (I) | (K.1.36) |
| C-284 | (I) | (K.1.37) |
| C-285 | (I) | (K.1.38) |
| C-286 | (I) | (K.1.39) |
| C-287 | (I) | (K.1.40) |
| C-288 | (I) | (K.1.41) |
| C-289 | (I) | (K.1.42) |
| C-290 | (I) | (K.1.43) |
| C-291 | (I) | (K.1.44) |
| C-292 | (I) | (K.1.45) |
| C-293 | (I) | (K.1.46) |
| C-294 | (I) | (K.1.47) |
| C-295 | (I) | (K.1.48) |
| C-296 | (I) | (M.1.1) |
| C-297 | (I) | (M.1.2) |
| C-298 | (I) | (M.1.3) |
| C-299 | (I) | (M.1.4) |
| C-300 | (I) | (M.1.5) |
| C-301 | (I) | (M.1.6) |
| C-302 | (I) | (M.1.7) |
| C-303 | (I) | (M.1.8) |
| C-304 | (I) | (M.1.9) |
| C-305 | (I) | (M.1.10) |
| C-306 | (I) | (M.1.11) |
| C-307 | (I) | (M.1.12) |
| C-308 | (I) | (M.1.13) |
| C-309 | (I) | (M.1.14) |
| C-310 | (I) | (M.1.15) |
| C-311 | (I) | (M.1.16) |
| C-312 | (I) | (M.1.17) |
| C-313 | (I) | (M.1.18) |
| C-314 | (I) | (M.1.19) |
| C-315 | (I) | (M.1.20) |
| C-316 | (I) | (M.1.21) |
| C-317 | (I) | (M.1.22) |
| C-318 | (I) | (M.1.23) |
| C-319 | (I) | (M.1.24) |
| C-320 | (I) | (M.1.25) |
| C-321 | (I) | (M.1.26) |
| C-322 | (I) | (M.1.27) |
| C-323 | (I) | (M.1.28) |
| C-324 | (I) | (M.1.29) |
| C-325 | (I) | (M.1.30) |
| C-326 | (I) | (M.1.31) |
| C-327 | (I) | (M.1.32) |
| C-328 | (I) | (M.1.33) |
| C-329 | (I) | (M.1.34) |
| C-330 | (I) | (M.1.35) |
| C-331 | (I) | (M.1.36) |
| C-332 | (I) | (M.1.37) |
| C-333 | (I) | (M.1.38) |
| C-334 | (I) | (M.1.39) |
| C-335 | (I) | (M.1.40) |
| C-336 | (I) | (M.1.41) |
| C-337 | (I) | (M.1.42) |
| C-338 | (I) | (M.1.43) |
| C-339 | (I) | (M.1.44) |
| C-340 | (I) | (M.1.45) |
| C-341 | (I) | (M.1.46) |
| C-342 | (I) | (M.1.47) |
| C-343 | (I) | (M.1.48) |
| C-344 | (I) | (M.1.49) |
| C-345 | (I) | (M.1.50) |
| C-346 | (I) | (N.1.1) |
| C-347 | (I) | (N.1.2) |
| C-348 | (I) | (N.1.3) |
| C-349 | (I) | (N.1.4) |
| C-350 | (I) | (N.1.5) |
| C-351 | (I) | (N.2.1) |
| C-352 | (I) | (N.2.2) |
| C-353 | (I) | (N.2.3) |
| C-354 | (I) | (N.3.1) |
| C-355 | (I) | (N.3.2) |
| C-356 | (I) | (N.3.3) |
| C-357 | (I) | (N.3.4) |
| C-358 | (I) | (N.4.1) |
| C-359 | (I) | (N.5.1) |
| C-360 | (I) | (N.6.1) |
| C-361 | (I) | (N.6.2) |
| C-362 | (I) | (N.6.3) |
| C-363 | (I) | (N.6.4) |
| C-364 | (I) | (N.6.5) |
| C-365 | (I) | (N.7.1) |

TABLE C-continued

Compositions comprising as active components one individualized compound I (I) (in Column Co. 1) and as component 2) (in Column Co. 2) one pesticide from groups A) to O) [which is coded e.g. as (A.1.1) for azoxystrobin as defined above].

| Mixt. | Co. 1 | Co. 2 |
|---|---|---|
| C-366 | (I) | (N.7.2) |
| C-367 | (I) | (N.7.3) |
| C-368 | (I) | (N.8.1) |
| C-369 | (I) | (N.9.1) |
| C-370 | (I) | (N.10.1) |
| C-371 | (I) | (N.10.2) |
| C-372 | (I) | (N.10.3) |
| C-373 | (I) | (N.10.4) |
| C-374 | (I) | (N.10.5) |
| C-375 | (I) | (N.11.1) |
| C-376 | (I) | (N.12.1) |
| C-377 | (I) | (N.12.2) |
| C-378 | (I) | (N.12.3) |
| C-379 | (I) | (N.12.4) |
| C-380 | (I) | (N.13.1) |
| C-381 | (I) | (N.13.2) |
| C-382 | (I) | (N.13.3) |
| C-383 | (I) | (N.13.4) |
| C-384 | (I) | (N.13.5) |
| C-385 | (I) | (N.13.6) |
| C-386 | (I) | (N.13.7) |
| C-387 | (I) | (N.13.8) |
| C-388 | (I) | (N.13.9) |
| C-389 | (I) | (N.14.1) |
| C-390 | (I) | (N.14.2) |
| C-391 | (I) | (N.15.1) |
| C-392 | (I) | (N.16.1) |
| C-393 | (I) | (N.16.2) |
| C-394 | (I) | (N.17.1) |
| C-395 | (I) | (N.17.2) |
| C-396 | (I) | (N.17.3) |
| C-397 | (I) | (N.17.4) |
| C-398 | (I) | (N.17.5) |
| C-399 | (I) | (N.17.6) |
| C-400 | (I) | (N.17.7) |
| C-401 | (I) | (N.17.8) |
| C-402 | (I) | (N.17.9) |
| C-403 | (I) | (N.17.10) |
| C-404 | (I) | (N.17.11) |
| C-405 | (I) | (N.17.12) |
| C-406 | (I) | (O.1.1) |
| C-407 | (I) | (O.1.2) |
| C-408 | (I) | (O.1.3) |
| C-409 | (I) | (O.1.4) |
| C-410 | (I) | (O.1.5) |
| C-411 | (I) | (O.1.6) |
| C-412 | (I) | (O.1.7) |
| C-413 | (I) | (O.1.8) |
| C-414 | (I) | (O.1.9) |
| C-415 | (I) | (O.1.10) |
| C-416 | (I) | (O.1.11) |
| C-417 | (I) | (O.1.12) |
| C-418 | (I) | (O.1.13) |
| C-419 | (I) | (O.1.14) |
| C-420 | (I) | (O.1.15) |
| C-421 | (I) | (O.1.16) |
| C-422 | (I) | (O.1.17) |
| C-423 | (I) | (O.1.18) |
| C-424 | (I) | (O.1.19) |
| C-425 | (I) | (O.1.20) |
| C-426 | (I) | (O.1.21) |
| C-427 | (I) | (O.1.22) |
| C-428 | (I) | (O.1.23) |
| C-429 | (I) | (O.1.24) |
| C-430 | (I) | (O.1.25) |
| C-431 | (I) | (O.1.26) |
| C-432 | (I) | (O.1.27) |
| C-433 | (I) | (O.1.28) |
| C-434 | (I) | (O.1.29) |
| C-435 | (I) | (O.1.30) |
| C-436 | (I) | (O.1.31) |
| C-437 | (I) | (O.1.32) |
| C-438 | (I) | (O.1.33) |
| C-439 | (I) | (O.1.34) |
| C-440 | (I) | (O.1.35) |
| C-441 | (I) | (O.1.36) |
| C-442 | (I) | (O.1.37) |
| C-443 | (I) | (O.1.38) |
| C-444 | (I) | (O.2.1) |
| C-445 | (I) | (O.2.2) |
| C-446 | (I) | (O.2.3) |
| C-447 | (I) | (O.2.4) |
| C-448 | (I) | (O.2.5) |
| C-449 | (I) | (O.2.6) |
| C-450 | (I) | (O.2.7) |
| C-451 | (I) | (O.2.8) |
| C-452 | (I) | (O.2.9) |
| C-453 | (I) | (O.2.10) |
| C-454 | (I) | (O.2.11) |
| C-455 | (I) | (O.2.12) |
| C-456 | (I) | (O.2.13) |
| C-457 | (I) | (O.2.14) |
| C-458 | (I) | (O.2.15) |
| C-459 | (I) | (O.2.16) |
| C-460 | (I) | (O.3.1) |
| C-461 | (I) | (O.3.2) |
| C-462 | (I) | (O.3.3) |
| C-463 | (I) | (O.3.4) |
| C-464 | (I) | (O.3.5) |
| C-465 | (I) | (O.3.6) |
| C-466 | (I) | (O.3.7) |
| C-467 | (I) | (O.3.8) |
| C-468 | (I) | (O.3.9) |
| C-469 | (I) | (O.3.10) |
| C-470 | (I) | (O.3.11) |
| C-471 | (I) | (O.3.12) |
| C-472 | (I) | (O.3.13) |
| C-473 | (I) | (O.3.14) |
| C-474 | (I) | (O.3.15) |
| C-475 | (I) | (O.3.16) |
| C-476 | (I) | (O.3.17) |
| C-477 | (I) | (O.3.18) |
| C-478 | (I) | (O.3.19) |
| C-479 | (I) | (O.3.20) |
| C-480 | (I) | (O.3.21) |
| C-481 | (I) | (O.3.22) |
| C-482 | (I) | (O.3.23) |
| C-483 | (I) | (O.3.24) |
| C-484 | (I) | (O.3.25) |
| C-485 | (I) | (O.3.26) |
| C-486 | (I) | (O.3.27) |
| C-487 | (I) | (O.4.1) |
| C-488 | (I) | (O.4.2) |
| C-489 | (I) | (O.4.3) |
| C-490 | (I) | (O.4.4) |
| C-491 | (I) | (O.4.5) |
| C-492 | (I) | (O.4.6) |
| C-493 | (I) | (O.4.7) |
| C-494 | (I) | (O.4.8) |
| C-495 | (I) | (O.4.9) |
| C-496 | (I) | (O.4.10) |
| C-497 | (I) | (O.4.11) |
| C-498 | (I) | (O.4.12) |
| C-499 | (I) | (O.4.13) |
| C-500 | (I) | (O.4.14) |
| C-501 | (I) | (O.4.15) |
| C-502 | (I) | (O.4.16) |
| C-503 | (I) | (O.4.17) |
| C-504 | (I) | (O.4.18) |
| C-505 | (I) | (O.4.19) |
| C-506 | (I) | (O.4.20) |
| C-507 | (I) | (O.4.21) |
| C-508 | (I) | (O.4.22) |
| C-509 | (I) | (O.4.23) |
| C-510 | (I) | (O.4.24) |
| C-511 | (I) | (O.5.1) |

TABLE C-continued

Compositions comprising as active components one individualized compound I (I) (in Column Co. 1) and as component 2) (in Column Co. 2) one pesticide from groups A) to O) [which is coded e.g. as (A.1.1) for azoxystrobin as defined above].

| Mixt. | Co. 1 | Co. 2 |
|---|---|---|
| C-512 | (I) | (O.5.2) |
| C-513 | (I) | (O.5.3) |
| C-514 | (I) | (O.5.4) |
| C-515 | (I) | (O.5.5) |
| C-516 | (I) | (O.5.6) |
| C-517 | (I) | (O.5.7) |
| C-518 | (I) | (O.5.8) |
| C-519 | (I) | (O.5.9) |
| C-520 | (I) | (O.6.1) |
| C-521 | (I) | (O.6.2) |
| C-522 | (I) | (O.6.3) |
| C-523 | (I) | (O.6.4) |
| C-524 | (I) | (O.6.5) |
| C-525 | (I) | (O.6.6) |
| C-526 | (I) | (O.6.7) |
| C-527 | (I) | (O.7.1) |
| C-528 | (I) | (O.7.2) |
| C-529 | (I) | (O.7.3) |
| C-530 | (I) | (O.7.4) |
| C-531 | (I) | (O.7.5) |
| C-532 | (I) | (O.7.6) |
| C-533 | (I) | (O.8.1) |
| C-534 | (I) | (O.8.2) |
| C-535 | (I) | (O.8.3) |
| C-536 | (I) | (O.8.4) |
| C-537 | (I) | (O.8.5) |
| C-538 | (I) | (O.9.1) |
| C-539 | (I) | (O.9.2) |
| C-540 | (I) | (O.9.3) |
| C-541 | (I) | (O.10.1) |
| C-542 | (I) | (O.11.1) |
| C-543 | (I) | (O.11.2) |
| C-544 | (I) | (O.11.3) |
| C-545 | (I) | (O.11.4) |
| C-546 | (I) | (O.12.1) |
| C-547 | (I) | (O.13.1) |
| C-548 | (I) | (O.14.1) |
| C-549 | (I) | (O.14.2) |
| C-550 | (I) | (O.15.1) |
| C-551 | (I) | (O.15.2) |
| C-552 | (I) | (O.15.3) |
| C-553 | (I) | (O.15.4) |
| C-554 | (I) | (O.15.5) |
| C-555 | (I) | (O.15.6) |
| C-556 | (I) | (O.15.7) |
| C-557 | (I) | (O.15.8) |
| C-558 | (I) | (O.15.9) |
| C-559 | (I) | (O.15.10) |
| C-560 | (I) | (O.15.11) |
| C-561 | (I) | (O.16.1) |
| C-562 | (I) | (O.16.2) |
| C-563 | (I) | (O.16.3) |
| C-564 | (I) | (O.16.4) |
| C-565 | (I) | (O.16.5) |
| C-566 | (I) | (O.16.6) |
| C-567 | (I) | (L.1.1) |
| C-568 | (I) | (L.1.2) |
| C-569 | (I) | (L.1.3) |
| C-570 | (I) | (L.1.4) |
| C-571 | (I) | (L.1.5) |
| C-572 | (I) | (L.1.6) |
| C-573 | (I) | (L.1.7) |
| C-574 | (I) | (L.1.8) |
| C-575 | (I) | (L.1.9) |
| C-576 | (I) | (L.1.10) |
| C-577 | (I) | (L.1.11) |
| C-578 | (I) | (L.1.12) |
| C-579 | (I) | (L.1.13) |
| C-580 | (I) | (L.1.14) |
| C-581 | (I) | (L.1.15) |
| C-582 | (I) | (L.1.16) |
| C-583 | (I) | (L.1.17) |
| C-584 | (I) | (L.1.18) |
| C-585 | (I) | (L.1.19) |
| C-586 | (I) | (L.1.20) |
| C-587 | (I) | (L.1.21) |
| C-588 | (I) | (L.1.22) |
| C-589 | (I) | (L.1.23) |
| C-590 | (I) | (L.1.24) |
| C-591 | (I) | (L.1.25) |
| C-592 | (I) | (L.1.26) |
| C-593 | (I) | (L.1.27) |
| C-594 | (I) | (L.1.28) |
| C-595 | (I) | (L.1.29) |
| C-596 | (I) | (L.1.30) |
| C-597 | (I) | (L.1.31) |
| C-598 | (I) | (L.1.32) |
| C-599 | (I) | (L.1.33) |
| C-600 | (I) | (L.1.34) |
| C-601 | (I) | (L.1.35) |
| C-602 | (I) | (L.1.36) |
| C-603 | (I) | (L.1.37) |
| C-604 | (I) | (L.1.38) |
| C-605 | (I) | (L.1.39) |
| C-606 | (I) | (L.1.40) |
| C-607 | (I) | (L.1.41) |
| C-608 | (I) | (L.1.42) |
| C-609 | (I) | (L.1.43) |
| C-610 | (I) | (L.1.44) |
| C-611 | (I) | (L.1.45) |
| C-612 | (I) | (L.1.46) |
| C-613 | (I) | (L.1.47) |
| C-614 | (I) | (L.1.48) |
| C-615 | (I) | (L.1.49) |
| C-616 | (I) | (L.1.50) |
| C-617 | (I) | (L.1.51) |
| C-618 | (I) | (L.1.52) |
| C-619 | (I) | (L.1.53) |
| C-620 | (I) | (L.1.54) |
| C-621 | (I) | (L.1.55) |
| C-622 | (I) | (L.1.56) |
| C-623 | (I) | (L.1.57) |
| C-624 | (I) | (L.1.58) |
| C-625 | (I) | (L.1.59) |
| C-626 | (I) | (L.1.60) |
| C-627 | (I) | (L.1.61) |
| C-628 | (I) | (L.1.62) |
| C-629 | (I) | (L.1.63) |
| C-630 | (I) | (L.1.64) |
| C-631 | (I) | (L.1.65) |
| C-632 | (I) | (L.1.66) |
| C-633 | (I) | (L.1.67) |
| C-634 | (I) | (L.1.68) |
| C-635 | (I) | (L.1.69) |
| C-636 | (I) | (L.1.70) |
| C-637 | (I) | (L.1.71) |
| C-638 | (I) | (L.1.72) |
| C-639 | (I) | (L.1.73) |
| C-640 | (I) | (L.1.74) |
| C-641 | (I) | (L.2.1) |
| C-642 | (I) | (L.2.2) |
| C-643 | (I) | (L.2.3) |
| C-644 | (I) | (L.2.4) |
| C-645 | (I) | (L.2.5) |
| C-646 | (I) | (L.2.6) |
| C-647 | (I) | (L.2.7) |
| C-648 | (I) | (L.2.8) |
| C-649 | (I) | (L.2.9) |
| C-650 | (I) | (L.2.10) |
| C-651 | (I) | (L.2.11) |
| C-652 | (I) | (L.3.1) |
| C-653 | (I) | (L.3.2) |
| C-654 | (I) | (L.3.3) |
| C-655 | (I) | (L.3.4) |
| C-656 | (I) | (L.3.5) |
| C-657 | (I) | (L.3.6) |

TABLE C-continued

Compositions comprising as active components one individualized compound I (I) (in Column Co. 1) and as component 2) (in Column Co. 2) one pesticide from groups A) to O) [which is coded e.g. as (A.1.1) for azoxystrobin as defined above].

| Mixt. | Co. 1 | Co. 2 |
|---|---|---|
| C-658 | (I) | (L.3.7) |
| C-659 | (I) | (L.3.8) |
| C-660 | (I) | (L.3.9) |
| C-661 | (I) | (L.3.10) |
| C-662 | (I) | (L.3.11) |
| C-663 | (I) | (L.3.12) |
| C-664 | (I) | (L.3.13) |
| C-665 | (I) | (L.3.14) |
| C-666 | (I) | (L.3.15) |
| C-667 | (I) | (L.3.16) |
| C-668 | (I) | (L.3.17) |
| C-669 | (I) | (L.3.18) |
| C-670 | (I) | (L.3.19) |
| C-671 | (I) | (L.3.20) |
| C-672 | (I) | (L.3.21) |
| C-673 | (I) | (L.3.22) |
| C-674 | (I) | (L.3.23) |
| C-675 | (I) | (L.3.24) |
| C-676 | (I) | (L.3.25) |
| C-677 | (I) | (L.3.26) |
| C-678 | (I) | (L.3.27) |
| C-679 | (I) | (L.3.28) |
| C-680 | (I) | (L.3.29) |
| C-681 | (I) | (L.3.30) |
| C-682 | (I) | (L.3.31) |
| C-683 | (I) | (L.3.32) |
| C-684 | (I) | (L.3.33) |
| C-685 | (I) | (L.3.34) |
| C-686 | (I) | (L.3.35) |
| C-687 | (I) | (L.3.36) |
| C-688 | (I) | (L.3.37) |
| C-689 | (I) | (L.3.38) |
| C-690 | (I) | (L.3.39) |
| C-691 | (I) | (L.3.40) |
| C-692 | (I) | (L.3.41) |
| C-693 | (I) | (L.3.42) |
| C-694 | (I) | (L.3.43) |
| C-695 | (I) | (L.3.44) |
| C-696 | (I) | (L.3.45) |
| C-697 | (I) | (L.3.46) |
| C-698 | (I) | (L.3.47) |
| C-699 | (I) | (L.3.48) |
| C-700 | (I) | (L.3.49) |
| C-701 | (I) | (L.3.50) |
| C-702 | (I) | (L.3.51) |
| C-703 | (I) | (L.3.52) |
| C-704 | (I) | (L.3.53) |
| C-705 | (I) | (L.3.54) |
| C-706 | (I) | (L.3.55) |
| C-707 | (I) | (L.3.56) |
| C-708 | (I) | (L.3.57) |
| C-709 | (I) | (L.3.58) |
| C-710 | (I) | (L.3.59) |
| C-711 | (I) | (L.4.1) |
| C-712 | (I) | (L.4.2) |
| C-713 | (I) | (L.4.3) |
| C-714 | (I) | (L.4.4) |
| C-715 | (I) | (L.4.5) |
| C-716 | (I) | (L.4.6) |
| C-717 | (I) | (L.4.7) |
| C-718 | (I) | (L.4.8) |
| C-719 | (I) | (L.4.9) |
| C-720 | (I) | (L.4.10) |
| C-721 | (I) | (L.4.11) |
| C-722 | (I) | (L.4.12) |
| C-723 | (I) | (L.4.13) |
| C-724 | (I) | (L.4.14) |
| C-725 | (I) | (L.4.15) |
| C-726 | (I) | (L.4.16) |
| C-727 | (I) | (L.4.17) |
| C-728 | (I) | (L.4.18) |
| C-729 | (I) | (L.4.19) |
| C-730 | (I) | (L.4.20) |
| C-731 | (I) | (L.4.21) |
| C-732 | (I) | (L.4.22) |
| C-733 | (I) | (L.4.23) |
| C-734 | (I) | (L.4.24) |
| C-735 | (I) | (L.4.25) |
| C-736 | (I) | (L.4.26) |
| C-737 | (I) | (L.4.27) |
| C-738 | (I) | (L.4.28) |
| C-739 | (I) | (L.4.29) |
| C-740 | (I) | (L.4.30) |
| C-741 | (I) | (L.4.31) |
| C-742 | (I) | (L.4.32) |
| C-743 | (I) | (L.4.33) |
| C-744 | (I) | (L.5.1) |
| C-745 | (I) | (L.5.2) |
| C-746 | (I) | (L.5.3) |
| C-747 | (I) | (L.5.4) |
| C-748 | (I) | (L.5.5) |
| C-749 | (I) | (L.5.6) |
| C-750 | (I) | (L.5.7) |
| C-751 | (I) | (L.5.8) |
| C-752 | (I) | (L.5.9) |
| C-753 | (I) | (L.5.10) |
| C-754 | (I) | (L.5.11) |
| C-755 | (I) | (L.5.12) |
| C-756 | (I) | (L.5.13) |
| C-757 | (I) | (L.5.14) |
| C-758 | (I) | (L.5.15) |
| C-759 | (I) | (L.5.16) |
| C-760 | (I) | (L.5.17) |
| C-761 | (I) | (L.5.18) |
| C-762 | (I) | (L.5.19) |
| C-763 | (I) | (L.5.20) |
| C-764 | (I) | (L.5.21) |
| C-765 | (I) | (L.5.22) |
| C-766 | (I) | (L.5.23) |
| C-767 | (I) | (L.5.24) |
| C-768 | (I) | (L.5.25) |
| C-769 | (I) | (L.5.26) |
| C-770 | (I) | (L.5.27) |
| C-771 | (I) | (L.5.28) |
| C-772 | (I) | (L.5.29) |
| C-773 | (I) | (L.5.30) |
| C-774 | (I) | (L.5.31) |
| C-775 | (I) | (L.5.32) |
| C-776 | (I) | (L.5.33) |
| C-777 | (I) | (L.5.34) |
| C-778 | (I) | (L.5.35) |
| C-779 | (I) | (L.5.36) |
| C-780 | (I) | (L.5.37) |
| C-781 | (I) | (L.5.38) |
| C-782 | (I) | (L.5.39) |
| C-783 | (I) | (L.5.40) |
| C-784 | (I) | (L.5.41) |
| C-785 | (I) | (L.5.42) |
| C-786 | (I) | (L.5.43) |
| C-787 | (I) | (L.5.44) |
| C-788 | (I) | (L.5.45) |
| C-789 | (I) | (L.5.46) |
| C-790 | (I) | (L.5.47) |
| C-791 | (I) | (L.5.48) |
| C-792 | (I) | (L.5.49) |
| C-793 | (I) | (L.5.50) |
| C-794 | (I) | (L.5.51) |
| C-795 | (I) | (L.5.52) |
| C-796 | (I) | (L.5.53) |
| C-797 | (I) | (L.5.54) |
| C-798 | (I) | (L.5.55) |
| C-799 | (I) | (L.5.56) |
| C-800 | (I) | (L.5.57) |
| C-801 | (I) | (L.5.58) |
| C-802 | (I) | (L.5.59) |
| C-803 | (I) | (L.5.60) |

TABLE C-continued

Compositions comprising as active components one individualized compound I (I) (in Column Co. 1) and as component 2) (in Column Co. 2) one pesticide from groups A) to O) [which is coded e.g. as (A.1.1) for azoxystrobin as defined above].

| Mixt. | Co. 1 | Co. 2 |
| --- | --- | --- |
| C-804 | (I) | (L.5.60) |
| C-805 | (I) | (L.5.60) |
| C-806 | (I) | (L.5.60) |
| C-807 | (I) | (L.5.60) |
| C-808 | (I) | (L.5.61) |
| C-809 | (I) | (L.5.62) |
| C-810 | (I) | (L.5.63) |
| C-811 | (I) | (L.5.64) |
| C-812 | (I) | (L.5.65) |
| C-813 | (I) | (L.5.66) |
| C-814 | (I) | (L.5.67) |
| C-815 | (I) | (L.5.67) |
| C-816 | (I) | (L.5.67) |
| C-817 | (I) | (L.5.68) |
| C-818 | (I) | (L.5.69) |
| C-819 | (I) | (L.5.70) |
| C-820 | (I) | (L.5.71) |
| C-821 | (I) | (L.5.72) |
| C-822 | (I) | (L.6.1) |
| C-823 | (I) | (L.6.2) |
| C-824 | (I) | (L.6.3) |
| C-825 | (I) | (L.6.4) |
| C-826 | (I) | (L.6.5) |
| C-827 | (I) | (L.6.6) |
| C-828 | (I) | (L.6.7) |
| C-829 | (I) | (L.6.8) |
| C-830 | (I) | (L.6.9) |
| C-831 | (I) | (L.6.10) |
| C-832 | (I) | (L.6.11) |
| C-833 | (I) | (L.6.12) |
| C-834 | (I) | (L.6.13) |
| C-835 | (I) | (L.6.14) |
| C-836 | (I) | (L.6.15) |
| C-837 | (I) | (L.6.16) |

The active substances referred to as component 2, their preparation and their activity e. g. against harmful fungi is known (cf.: http://www.alanwood.net/pesticides/); these substances are commercially available. The compounds described by IUPAC nomenclature, their preparation and their pesticidal activity are also known (cf. Can. J. Plant Sci. 48(6), 587-94, 1968; EP-A 141 317; EP-A 152 031; EP-A 226 917; EP-A 243 970; EP-A 256 503; EP-A 428 941; EP-A 532 022; EP-A 1 028 125; EP-A 1 035 122; EP-A 1 201 648; EP-A 1 122 244, JP 2002316902; DE 19650197; DE 10021412; DE 102005009458; U.S. Pat. No. 3,296,272; U.S. Pat. No. 3,325,503; WO 98/46608; WO 99/14187; WO 99/24413; WO 99/27783; WO 00/29404; WO 00/46148; WO 00/65913; WO 01/54501; WO 01/56358; WO 02/22583; WO 02/40431; WO 03/10149; WO 03/11853; WO 03/14103; WO 03/16286; WO 03/53145; WO 03/61388; WO 03/66609; WO 03/74491; WO 04/49804; WO 04/83193; WO 05/120234; WO 05/123689; WO 05/123690; WO 05/63721; WO 05/87772; WO 05/87773; WO 06/15866; WO 06/87325; WO 06/87343; WO 07/82098; WO 07/90624, WO 11/028657, WO2012/168188, WO 2007/006670, WO 2011/77514; WO13/047749, WO 10/069882, WO 13/047441, WO 03/16303, WO 09/90181, WO 13/007767, WO 13/010862, WO 13/127704, WO 13/024009, WO 13/024010 and WO 2013/047441).

The mixtures of active substances can be prepared as compositions comprising besides the active ingredients at least one inert ingredient (auxiliary) by usual means, e. g. by the means given for the compositions of compounds I.

Concerning usual ingredients of such compositions reference is made to the explanations given for the compositions containing compounds I.

The mixtures of active substances according to the present invention are suitable as fungicides, as are the compounds of formula I. They are distinguished by an outstanding effectiveness against a broad spectrum of phytopathogenic fungi, especially from the classes of the Ascomycetes, Basidiomycetes, Deuteromycetes and Peronosporomycetes (syn. Oomycetes). In addition, it is referred to the explanations regarding the fungicidal activity of the compounds and the compositions containing compounds I, respectively.

According to one embodiment, the microbial pesticides selected from groups L1), L3) and L5) embrace not only the isolated, pure cultures of the respective micro-organism as defined herein, but also its cell-free extract, its suspensions in a whole broth culture or as a metabolite-containing culture medium or a purified metabolite obtained from a whole broth culture of the microorganism or microorganism strain.

According to a further embodiment, the microbial pesticides selected from groups L1), L3 and L5) embraces not only the isolated, pure cultures of the respective micro-organism as defined herein, but also a cell-free extract thereof or at least one metabolite thereof, and/or a mutant of the respective micro-organism having all the identifying characteristics thereof and also a cell-free extract or at least one metabolite of the mutant.

As used herein, "whole culture broth" refers to a liquid culture of a microorganism containing vegetative cells and/or spores suspended in the culture medium and optionally metabolites produced by the respective microorganism.

As used herein, "culture medium", refers to a medium obtainable by culturing the microorganism in said medium, preferably a liquid broth, and remaining when cells grown in the medium are removed, e. g., the supernatant remaining when cells grown in a liquid broth are removed by centrifugation, filtration, sedimentation, or other means well known in the art; comprising e. g. metabolites produced by the respective microorganism and secreted into the culture medium. The "culture medium" sometimes also referred to as "supernatant" can be obtained e. g. by centrifugation at temperatures of about 2 to 30° C. (more preferably at temperatures of 4 to 20° C.) for about 10 to 60 min (more preferably about 15 to 30 min) at about 5,000 to 20,000×g (more preferably at about 15,000×g).

As used herein, "cell-free extract" refers to an extract of the vegetative cells, spores and/or the whole culture broth of a microorganism comprising cellular metabolites produced by the respective microorganism obtainable by cell disruption methods known in the art such as solvent-based (e. g. organic solvents such as alcohols sometimes in combination with suitable salts), temperature-based, application of shear forces, cell disruption with an ultrasonicator. The desired extract may be concentrated by conventional concentration techniques such as drying, evaporation, centrifugation or alike. Certain washing steps using organic solvents and/or water-based media may also be applied to the crude extract preferably prior to use.

As used herein, the term "metabolite" refers to any component, compound, substance or by-product (including but not limited to small molecule secondary metabolites, polyketides, fatty acid synthase products, non-ribosomal peptides, ribosomal peptides, proteins and enzymes) produced by a microorganism (such as fungi and bacteria, in particular the strains of the invention) that has any beneficial effect as described herein such as pesticidal activity or improvement of plant growth, water use efficiency of the plant, plant health, plant appearance, or the population of beneficial microorganisms in the soil around the plant activity herein.

As used herein, "isolate" refers to a pure microbial culture separated from its natural origin, such an isolate obtained by culturing a single microbial colony. An isolate is a pure culture derived from a heterogeneous, wild population of microorganisms.

As used herein, "strain" refers to isolate or a group of isolates exhibiting phenotypic and/or genotypic traits belonging to the same lineage, distinct from those of other isolates or strains of the same species.

The term "mutant" refers a microorganism obtained by direct mutant selection but also includes microorganisms that have been further mutagenized or otherwise manipulated (e. g., via the introduction of a plasmid). Accordingly, embodiments include mutants, variants, and or derivatives of the respective microorganism, both naturally occurring and artificially induced mutants. For example, mutants may be induced by subjecting the microorganism to known mutagens, such as N-methyl-nitrosoguanidine, using conventional methods.

In the case of mixtures comprising microbial pesticides II selected from groups L1), L3) and L5), the microorganisms as used according to the invention can be cultivated continuously or discontinuously in the batch process or in the fed batch or repeated fed batch process. A review of known methods of cultivation will be found in the textbook by Chmiel (Bioprozesstechnik 1. Einführung in die Bioverfahrenstechnik (Gustav Fischer Verlag, Stuttgart, 1991)) or in the textbook by Storhas (Bioreaktoren and periphere Einrichtungen (Vieweg Verlag, Braunschweig/Wiesbaden, 1994)).

When living microorganisms, such as pesticides II from groups L1), L3) and L5), form part of the compositions, such compositions can be prepared as compositions comprising besides the active ingredients at least one auxiliary (inert ingredient) by usual means (see e. g. H. D. Burges: Formulation of Micobial Biopesticides, Springer, 1998). Suitable customary types of such compositions are suspensions, dusts, powders, pastes, granules, pressings, capsules, and mixtures thereof. Examples for composition types are suspensions (e. g. SC, OD, FS), capsules (e. g. CS, ZC), pastes, pastilles, wettable powders or dusts (e. g. WP, SP, WS, DP, DS), pressings (e. g. BR, TB, DT), granules (e. g. WG, SG, GR, FG, GG, MG), insecticidal articles (e. g. LN), as well as gel formulations for the treatment of plant propagation materials such as seeds (e. g. GF). Herein, it has to be taken into account that each formulation type or choice of auxiliary should not influence the viability of the microorganism during storage of the composition and when finally applied to the soil, plant or plant propagation material. Suitable formulations are e. g. mentioned in WO 2008/002371, U.S. Pat. No. 6,955,912, U.S. Pat. No. 5,422,107.

Examples for suitable auxiliaries are those mentioned earlier herein, wherein it must be taken care that choice and amounts of such auxiliaries should not influence the viability of the microbial pesticides in the composition. Especially for bactericides and solvents, compatibility with the respective microorganism of the respective microbial pesticide has to be taken into account. In addition, compositions with microbial pesticides may further contain stabilizers or nutrients and UV protectants. Suitable stabilizers or nutrients are e. g. alpha-tocopherol, trehalose, glutamate, potassium sorbate, various sugars like glucose, sucrose, lactose and maltodextrine (H. D. Burges: Formulation of Micobial Biopesticides, Springer, 1998). Suitable UV protectants are e. g. inorganic compounds like titan dioxide, zinc oxide and iron oxide pigments or organic compounds like benzophenones, benzotriazoles and phenyltriazines. The compositions may in addition to auxiliaries mentioned for compositions comprising compounds I herein optionally comprise 0.1-80% stabilizers or nutrients and 0.1-10% UV protectants.

When mixtures comprising microbial pesticides are employed in crop protection, the application rates preferably range from about $1 \times 10^6$ to $5 \times 10^{15}$ (or more) CFU/ha. Preferably, the spore concentration is about $1 \times 10^7$ to about $1 \times 10^{11}$ CFU/ha. In the case of (entomopathogenic) nematodes as microbial pesticides (e. g. *Steinernema feltiae*), the application rates preferably range inform about $1 \times 10^5$ to $1 \times 10^{12}$ (or more), more preferably from $1 \times 10^8$ to $1 \times 10^{11}$, even more preferably from $5 \times 10^8$ to $1 \times 10^{10}$ individuals (e. g. in the form of eggs, juvenile or any other live stages, preferably in an infective juvenile stage) per ha.

When mixtures comprising microbial pesticides are employed in seed treatment, the application rates with respect to plant propagation material preferably range from about $1 \times 10^6$ to $1 \times 10^{12}$ (or more) CFU/seed. Preferably, the concentration is about $1 \times 10^6$ to about $1 \times 10^{11}$ CFU/seed. In the case of the microbial pesticides II, the application rates with respect to plant propagation material also preferably range from about $1 \times 10^7$ to $1 \times 10^{14}$ (or more) CFU per 100 kg of seed, preferably from $1 \times 10^9$ to about $1 \times 10^{11}$ CFU per 100 kg of seed.

I. SYNTHESIS EXAMPLES

Example 1

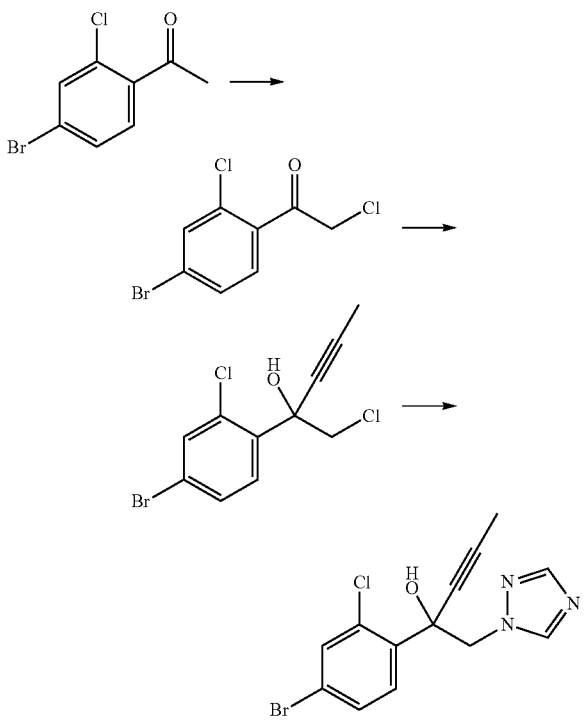

Step 1a Synthesis of
1-(4-bromo-2-chloro-phenyl)-2-chloro-ethanone

To a mixture of 2-chloro-4-bromo acetophenone (500 g), MeOH (137 g) in CH$_2$Cl$_2$ (4 L), SO$_2$Cl$_2$ (578 g in 1 L of CH$_2$Cl$_2$) was added dropwise, maintaining the internal temperature below 30° C. After gas evolution had ceased HPLC indicated full conversion. H$_2$O (3 L) was added carefully and the pH was adjusted to 6.5 using 50% NaOH. The phases were separated and the aqueous phase extracted with CH$_2$Cl$_2$ (2×1 L). The combined organic phases were washed with brine and dried over Na$_2$SO$_4$. The crude compound was obtained as viscous oil (608 g) and was used without further purification. HPLC: $t_R$=3.096 min; $^1$H-NMR (300 MHz, CDCl$_3$): δ=4.65 (2H), 7.40-7.65 (3H).

Step 1b Synthesis of 2-(4-bromo-2-chloro-phenyl)-1-chloro-pent-3-yn-2-ol

A solution of 1-(4-bromo-2-chloro-phenyl)-2-chloro-ethanone (267 g in 500 mL CH$_2$Cl$_2$) was added dropwise to prop-1-inyl magnesium bromide (1915 mL of a 0.5 M solution in THF) at −20° C. and warmed to RT. The reaction mixture was added to sat. aqu. NH$_4$Cl-solution (5 L) and extracted with CH$_2$Cl$_2$ (3×2 L). The combined organic phases were washed with brine, dried over Na$_2$SO$_4$ and evaporated. The crude product was used in the next reaction without any further purification. HPLC: $t_R$=3.271 min; $^1$H-NMR (300 MHz, CDCl$_3$): δ=1.85 (3H), 3.95 (1H), 4.20 (1H), 7.45 (1H), 7.55 (1H), 7.80 (1H).

Step 1c 2-(4-bromo-2-chloro-phenyl)-1-(1,2,4-triazol-1-yl)pent-3-yn-2-ol 2-(4-bromo-2-chloro-phenyl)-1-chloro-pent-3-yn-2-ol (305 g), 1,2,4-triazole (191 g) and NaOH (83.2 g) were stirred in NMP (2 L) at 100° C. for 30 min. HPLC indicated full conversion. The reaction mixture was diluted with sat aqu NH$_4$Cl (2 L) and extracted with MTBE (4×2 L). The combined organic extracts were washed with brine (1 L) and dried over Na$_2$SO$_4$. After evaporation, crystallization from iPr$_2$O furnished the target compound as colorless crystals (322.6 g). HPLC: $t_R$=2.629 min; $^1$H-NMR (300 MHz, CDCl$_3$): δ=1.80 (3H), 4.70 (1H), 4.90 (1H), 7.40 (1H), 7.60 (1H), 7.75 (1H), 7.90 (1H), 8.10 (1H).

Example 2

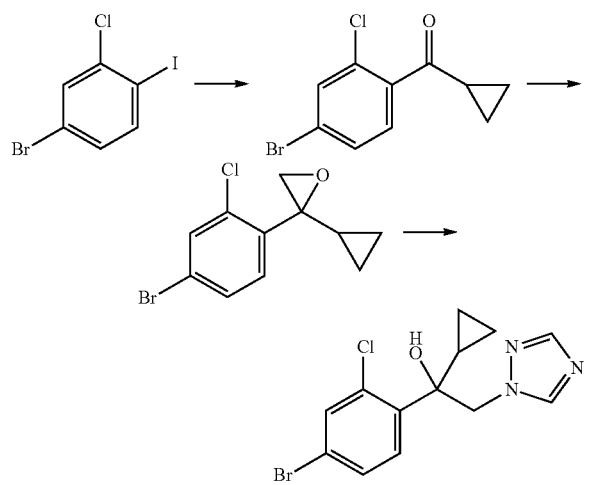

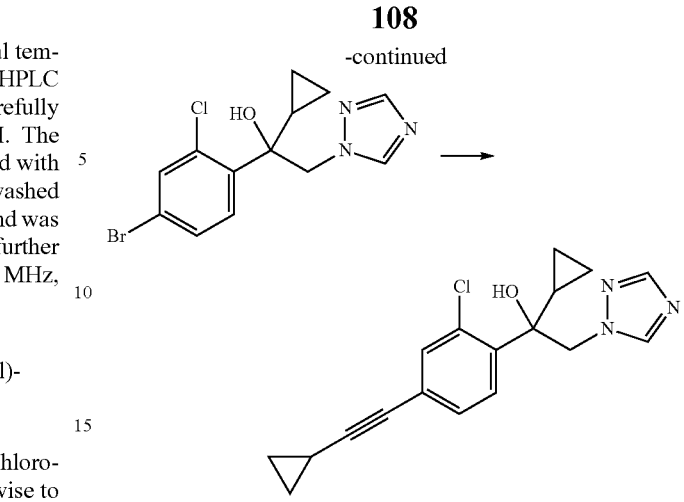

Step 2a Synthesis of (4-bromo-2-chloro-phenyl)-cyclopropyl-methanone

A solution of 4-bromo-2-chloro-1-iodo-benzene (250 g) in 0.5 L THF was cooled to −20° C. and a solution of iPrMgCl (780 mL, 1.3 eq) was added keeping the reaction temperature at −20° C. After HPLC control indicated full conversion, the Grignard solution was transferred to a previously prepared mixture of cyclopropanecarbonyl chloride (107 g), AlCl$_3$ (3.2 g), LiCl (2.0 g) and CuCl (2.34 g) in 1 L THF at 25-35° C. with slight cooling. After HPLC indicated full conversion, the reaction mixture was added to sat aq. NH$_4$Cl (1 L). After extraction with MTBE (3×1 L), the combined organic phases were washed with brine (500 mL) and dried over Na$_2$SO$_4$. After removal of the solvent under reduced pressure, the target compound was isolated and used in the next reaction without further purification. $^1$H-NMR (300 MHz, CDCl$_3$): δ=0.8-1.2 (4H), 2.40 (1H), 7.25-7.60 (3H).

Step 2b Synthesis of 2-(4-bromo-2-chloro-phenyl)-2-cyclopropyl-oxirane

To a suspension of KOtBu (90.4 g) in DMSO (800 mL) was added Me$_3$SI (195 g) in several portions at rt. After stirring for 1 h, a solution of (4-bromo-2-chloro-phenyl)-cyclopropyl-methanone (220 g) was added. After 48 h, the reaction mixture was added to water (3 L) and extracted with EtOAc (3×1 L). The combined organic phases were washed with brine (1 L) and dried over Na$_2$SO$_4$. Removal of the solvent under reduced pressure yielded the title compound which was used without further purification in the next step. $^1$H-NMR (300 MHz, CDCl$_3$): δ=0.4-1.2 (5H), 2.8 (1H), 3.00 (1H), 7.20-7.65 (3H).

Step 2c Synthesis of 1-(4-bromo-2-chloro-phenyl)-1-cyclopropyl-2-(1,2,4-triazol-1-yl)ethanol Crude 2-(4-bromo-2-chloro-phenyl)-2-cyclopropyl-oxirane (211 g), NaOH (62 g) and 1,2,4 triazole (213 g) in NMP (1 L) were heated to 120° C. for 1 h. HPLC indicated full conversion. The reaction mixture was added to a saturated solution of NH$_4$Cl (1 L) and extracted with MTBE (3×1 L). The combined organic phases were washed with brine and dried over Na$_2$SO$_4$. After removal of the solvent under reduced pressure, the crude product was crystallized from iPr$_2$O to yield the product (108 g) as off-white solid.

¹H-NMR (300 MHz, CDCl₃): δ=0.2 (1H), 0.4 (2H), 0.6 (1H), 2.75 (1H), 4.55 (2H), 5.35 (1H), 7.25 (1H), 7.50 (2H), 7.85 (1H), 8.00 (1H).

Step 2d Synthesis of 1-[2-chloro-4-(2-cyclopropylethynyl)phenyl]-1-cyclopropyl-2-(1,2,4-triazol-1-yl)ethanol A mixture of 1-(4-bromo-2-chloro-phenyl)-1-cyclopropyl-2-(1,2,4-triazol-1-yl)ethanol (1.00 g), cyclopropyl acetylene (350 mg), Pd(dppf)Cl₂ (21.0 mg), CuI (50.0 mg), and NEt₃ (320 mg) were heated to reflux in MeCN (5 mL) for 12 h. HPLC indicated full conversion. The reaction mixture was poured onto brine and extracted with MeCN (3×10 mL). The combined organic phases were filtered over a plug of silica and the solvent was removed under reduced pressure. By purification of the residue by column chromatography, the product was obtained as solid (120 mg). HPLC-MS (MSD5): $t_R$=1.054 [M=328 [M⁺]]; ¹H-NMR (500 MHz, CDCl₃): δ=0.10-0.90 (8H), 1.40 (1H), 1.80 (1H), 4.60 (1H), 5.40 (1H), 7.10-7.50 (3H), 7.85 (1H), 8.10 (1H).

With due modification of the starting compounds, the procedures shown in the synthesis examples above were used to obtain further compounds I, in particular triazole compounds I.A1a, wherein A is N and Z is cyclopropyl. The resulting compounds, together with physical data, are listed in Table I below.

TABLE I

| Compound No. | A | R¹ | R² | R³ | Z—(R⁴)ₘ | HPLC-MS (MSD5): $t_R$ (Retention time) [min]** ¹H-NMR |
|---|---|---|---|---|---|---|
| I-1 | N | C₃H₅ (cyclopropyl) | H | Cl | C₃H₅ (cyclopropyl), m = 0 | 1.054 |
| I-2 | N | CH₃ | H | Cl | C₃H₅ (cyclopropyl), m = 0 | 1.071 |
| I-3 | N | C≡C—CH₃ | H | Cl | C₃H₅ (cyclopropyl), m = 0 | 1.093 |
| I-4 | N | C₃H₅ (cyclopropyl) | H | Cl | 1-OH-cyclopentyl | 1.072 |
| I-5 | N | C₃H₅ (cyclopropyl) | H | Cl | 1-cyclooctenyl m = 0 | 1.469 |
| I-6 | N | C₃H₅ (cyclopropyl) | H | Cl | cyclooctyl m = 0 | 1.228 |
| I-7 | N | C₃H₅ (cyclopropyl) | H | Cl | cyclopentyl m = 0 | 1.330 |
| I-8 | N | C(CH₃)₃ | H | H | 1-OH-cyclopentyl | 1.108 |
| I-9 | N | C(CH₃)₃ | H | H | 1-cyclooctenyl m = 0 | 1.482 |
| I-10 | N | C(CH₃)₃ | H | H | cyclooctyl m = 0 | 1.263 |
| I-11 | N | C(CH₃)₃ | H | H | 1-OCH₃-cyclohexyl | 1.341 |
| I-12 | N | C(CH₃)₃ | H | H | cyclopentyl m = 0 | 1.376 |
| I-13 | N | CH₃ | H | CF₃ | cyclooctyl m = 0 | 1.142 |
| I-14 | N | CH₃ | H | CF₃ | 1-OH-cyclopentyl | 0.996 |
| I-15 | N | CH₃ | H | CF₃ | 1-OCH₃-cyclohexyl | 1.261 |
| I-16 | N | CH₃ | H | CF₃ | cyclopentyl m = 0 | 1.258 |
| I-17 | N | C₃H₅ (cyclopropyl) | H | CF₃ | C₃H₅ (cyclopropyl), m = 0 | 1.195 |
| I-18 | N | CH=CH(CH₃) | H | Cl | C₃H₅ (cyclopropyl), m = 0 | 1.144 |
| I-19 | N | C≡C—CH₃ | H | CF₃ | C₃H₅ (cyclopropyl), m = 0 | 1.119 |
| I-20 | N | CH₃ | H | CF₃ | C₃H₅ (cyclopropyl), m = 0 | 1.091 |
| I-21 | N | C(CH₃)₃ | H | H | C₃H₅ (cyclopropyl), m = 0 | 1.204 |
| I-22 | N | CF₂(CH₃) | H | Cl | C₃H₅ (cyclopropyl), m = 0 | 1.164 ¹H-NMR (400 MHz, CDCl₃): δ = 0.70-0.80 (2H), 0.85-1.00 (2H), 1.35-1.55 (4H), 4.75 (1H), 5.60 (1H), 5.80-6.00 (1H), 7.20 (1H), 7.35-7.45 (2H), 7.75 (1H), 8.20 (1H) |
| I-23 | N | 1-F-cyclopropyl | H | Cl | C₃H₅ (cyclopropyl), m = 0 | 1.129 ¹H NMR (400 MHz): δ = 0.55-0.60 (1H), 0.70-0.80 (4H), 0.85-0.95 (4H), 1.35-1.45 (1H), |

TABLE I-continued

| Compound No. | A | R¹ | R² | R³ | Z—(R⁴)ₘ | HPLC-MS (MSD5): $t_R$ (Retention time) [min]** ¹H-NMR |
|---|---|---|---|---|---|---|
| | | | | | | 4.70 (1H), 4.90 (1H), 5.45 (1H), 7.20-7.25 (2H), 7.40 (1H), 7.95 (1H), 8.20 (1H). |
| I-24 | N | CH₂CH₃ | H | Cl | 1-cyclooctenyl m = 0 | 1.455 |
| I-25 | N | CH₂CH₃ | H | Cl | cyclooctyl m = 0 | 1.211 |
| I-26 | N | CH₂CH₃ | H | Cl | 1-OCH₃-cyclohexyl | 1.295 |
| I-27 | N | C(CH₃)₃ | H | H | 1-OH-cyclobutyl | 1.065 |
| I-28 | N | CH₃ | H | CF₃ | 1-OH-cyclobutyl | 0.938 |
| I-29 | N | CH₂CH₃ | H | Cl | C₃H₅ (cyclopropyl), m = 0 | 1.146 |
| I-30 | N | CH₂CH₃ | H | Cl | 1-OH-cyclobutyl | 0.983 |

**HPLC method Data:
Mobile Phase: A: Wasser + 0.1% T FA; B: acetonitrile; Gradient: 5% B to 100% B in 1.5 min; Temperature: 60° C.;
MS-Method: ESI positive; mass area (m/z): 100-700; Flow: 0.8 ml/min to 1.0 ml/min in 1.5 min; Column: Kinetex XB C18 1.7µ 50 × 2.1 mm; Aparatus: Shimadzu Nexera LC-30 LCMS-2020.

II. Examples of the Action Against Harmful Fungi

The fungicidal action of the compounds of the formula I was demonstrated by the following experiments:
Microtest The active compounds were formulated separately as a stock solution having a concentration of 10000 ppm in dimethyl sulfoxide.

M1 Activity Against the Grey Mold *Botrytis cinerea* in the Microtiterplate Test (*Botrci*)

The stock solutions were mixed according to the ratio, pipetted onto a micro titer plate (MTP) and diluted with water to the stated concentrations. A spore suspension of *Botrci cinerea* in an aqueous biomalt or yeast-bactopeptone-sodiumacetate solution was then added. The plates were placed in a water vapor-saturated chamber at a temperature of 18° C. Using an absorption photometer, the MTPs were measured at 405 nm 7 days after the inoculation. Compounds I-1, I-2 and I-3, respectively, showed a growth of 0% at 31 ppm.

M2 Activity Against Rice Blast *Pyricularia Oryzae* in the Microtiterplate Test (Pyrior)

The stock solutions were mixed according to the ratio, pipetted onto a micro titer plate (MTP) and diluted with water to the stated concentrations. A spore suspension of *Pyricularia oryzae* in an aqueous biomalt or yeast-bacto-peptone-glycerine solution was then added. The plates were placed in a water vapor-saturated chamber at a temperature of 18° C. Using an absorption photometer, the MTPs were measured at 405 nm 7 days after the inoculation. Compounds I-1, I-2 and I-3, respectively, showed a growth of 0% at 31 ppm.

M3 Activity Against Leaf Blotch on Wheat Caused by *Septoria tritici* (Septtr)

The stock solutions were mixed according to the ratio, pipetted onto a micro titer plate (MTP) and diluted with water to the stated concentrations. A spore suspension of *Septoria tritici* in an aqueous biomalt or yeast-bactopeptone-glycerine solution was then added. The plates were placed in a water vapor-saturated chamber at a temperature of 18° C. Using an absorption photometer, the MTPs were measured at 405 nm 7 days after the inoculation. Compounds I-1, I-2 and I-3, respectively, showed a growth of 0% at 31 ppm.

The measured parameters were compared to the growth of the active compound-free control variant (100%) and the fungus-free and active compound-free blank value to determine the relative growth in % of the pathogens in the respective active compounds.

The invention claimed is:

1. A compound of the formula I

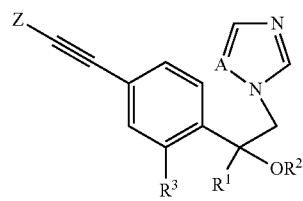

wherein
A is CH or N;
R¹ is $C_1$-$C_6$-alkyl, $C_2$-$C_6$-alkenyl, $C_2$-$C_6$-alkynyl, $C_3$-$C_6$-cycloalkyl;
wherein the aliphatic moieties of R¹ are not further substituted or carry one, two, three or up to the maximum possible number of identical or different groups $R^{1a}$ which independently of one another are selected from:
$R^{1a}$ halogen, OH, CN, $C_1$-$C_4$-alkoxy, $C_3$-$C_6$-cycloalkyl, $C_3$-$C_6$-halogencycloalkyl and $C_1$-$C_4$-halogenalkoxy;
wherein the cycloalkyl moieties of R¹ are not further substituted or carry one, two, three, four, five or up to the maximum number of identical or different groups $R^{1b}$ which independently of one another are selected from:
$R^{1b}$ halogen, OH, CN, $C_1$-$C_4$-alkyl, $C_1$-$C_4$-alkoxy, $C_1$-$C_4$-halogenalkyl, $C_3$-$C_6$-cycloalkyl, $C_3$-$C_6$-halogencycloalkyl and $C_1$-$C_4$-halogenalkoxy;
R² is hydrogen, $C_1$-$C_4$-alkyl, $C_2$-$C_4$-alkenyl, $C_2$-$C_4$-alkynyl;
wherein the aliphatic moieties of R² are not further substituted or carry one, two, three or up to the maximum possible number of identical or different groups $R^{2a}$ which independently of one another are selected from:
$R^{2a}$ halogen, OH, CN, $C_1$-$C_4$-alkoxy, $C_3$-$C_6$-cycloalkyl, $C_3$-$C_6$-halogencycloalkyl and $C_1$-$C_4$-halogenalkoxy;
$R^3$ is selected from hydrogen, halogen, CN, $C_1$-$C_4$-alkyl, $C_1$-$C_4$-alkoxy, $C_2$-$C_4$-alkenyl, $C_2$-$C_4$-alkynyl, $C_3$-$C_6$-cycloalkyl, $S(O)_p(C_1$-$C_4$-alkyl), wherein each of $R^3$ is unsubstituted or further substituted by one, two, three or four $R^{1a}$; wherein
$R^{3a}$ is independently selected from halogen, CN, OH, $C_1$-$C_4$-alkyl, $C_1$-$C_4$-halogenalkyl, $C_3$-$C_6$-cycloalkyl, $C_3$-$C_6$-halogencycloalkyl, $C_1$-$C_4$-alkoxy and $C_1$-$C_4$-halogenalkoxy;
Z is $C_3$-$C_8$-cycloalkyl or $C_3$-$C_8$-cycloalkenyl, wherein the cycloalkyl or cycloalkenyl is unsubstituted (m=0) or substituted by $(R^4)_m$; wherein
m is 0, 1, 2, 3 or 4;
and
$R^4$ is in each case independently selected from halogen, CN, $NO_2$, OH, SH, $C_1$-$C_6$-alkyl, $C_1$-$C_6$-alkoxy, $C_2$-$C_6$-alkenyl, $C_2$-$C_6$-alkynyl, $C_3$-$C_6$-cycloalkyl, $C_3$-$C_6$-cycloalkyloxy, $S(O)_p(C_1$-$C_4$-alkyl), C(=O)($C_1$-$C_4$-alkyl), C(=O)(OH), C(=O)(O$_1$-$C_4$-alkyl), C(=O)(NH($C_1$-$C_4$-alkyl)), C(=O)(N($C_1$-$C_4$-alkyl)$_2$); wherein each of $R^4$ is unsubstituted or further substituted by one, two, three or four $R^{4a}$ wherein
$R^{4a}$ is independently selected from halogen, CN, $NO_2$, OH, $C_1$-$C_4$-alkyl, $C_1$-$C_4$-halogenalkyl, $C_3$-$C_6$-cycloalkyl, $C_3$-$C_6$-halogencycloalkyl, $C_1$-$C_4$-alkoxy and $C_1$-$C_4$-halogenalkoxy;
p is 0, 1 or 2; and the N-oxides and the agriculturally acceptable salts thereof.

2. The compound of claim 1, wherein A is N.
3. The compound of claim 1, wherein Z is $C_3$-$C_8$-cycloalkyl.
4. The compound of claim 1, wherein Z is $C_3$-$C_8$-cycloalkenyl.
5. The compound of claim 1, wherein m is 0.
6. The compound of claim 1, wherein m is 1, 2 or 3.
7. The compound of claim 1, wherein $R^3$ is hydrogen.
8. The compound of claim 1, wherein $R^3$ is F, $C_1$, Br, CN, $C_1$-$C_4$-alkyl, $C_1$-$C_4$-halogenalkyl, $C_1$-$C_4$-alkoxy or S($C_1$-$C_4$-alkyl).
9. The compound of claim 1, wherein $R^2$ is hydrogen.
10. The compound of claim 1, wherein A is N, $R^2$ is hydrogen and:
$R^1$ is cyclopropyl, $R^3$ is $C_1$, m is 0 and Z is cyclopropyl (I-1);
$R^1$ is $CH_3$, $R^3$ is $C_1$, m is 0 and Z is cyclopropyl (I-2);
$R^1$ is C≡C—$CH_3$, $R^3$ is $C_1$, m is 0 and Z is $C_3H_5$ (cyclopropyl) (I-3);
$R^1$ is $C_3H_5$ (cyclopropyl), $R^3$ is Cl and Z—$(R^4)_m$ is 1-OH-cyclopentyl (I-4);
$R^1$ is $C_3H_5$ (cyclopropyl), $R^3$ is $C_1$, m is 0 and Z is 1-cyclooctenyl (I-5);
$R^1$ is $C_3H_5$ (cyclopropyl), $R^3$ is $C_1$, m is 0 and Z is cyclooctyl (I-6);
$R^1$ is $C_3H_5$ (cyclopropyl), $R^3$ is $C_1$, m is 0 and Z is cyclopentyl (I-7);
$R^1$ is $C(CH_3)_3$, $R^3$ is H, Z—$(R^4)_m$ is 1-OH-cyclopentyl (I-8);
$R^1$ is $C(CH_3)_3$, $R^3$ is H; m is 0 and Z is 1-cyclooctenyl (I-9);
$R^1$ is $C(CH_3)_3$; $R^3$ is H; m is 0 and Z is cyclooctyl (I-10);
$R^1$ is $C(CH_3)_3$; $R^3$ is H and Z—$(R^4)_m$ is 1-OCH$_3$-cyclohexyl (I-11);
$R^1$ is $C(CH_3)_3$, $R^3$ is H, m is 0 and Z is cyclopentyl (I-12);
$R^1$ is $CH_3$, $R^3$ is $CF_3$, m is 0 and Z is cyclooctyl (I-13);
$R^1$ is $CH_3$; $R^3$ is $CF_3$ and Z—$(R^4)_m$ is 1-OH-cyclopentyl (I-14);
$R^1$ is $CH_3$, $R^3$ is $CF_3$ and Z—$(R^4)_m$ is 1-OCH$_3$-cyclohexyl (I-15);
$R^1$ is $CH_3$, $R^3$ is $CF_3$, m is 0 and Z is cyclopentyl (I-16);
$R^1$ is $C_3H_5$ (cyclopropyl), $R^3$ is $CF_3$, m is 0 and Z is $C_3H_5$ (cyclopropyl) (I-17);
$R^1$ is CH=CH($CH_3$), $R^3$ is $C_1$, m is 0 and Z is $C_3H_5$ (cyclopropyl) (I-18);
$R^1$ is C≡C—$CH_3$, $R^3$ is $CF_3$, m is 0 and Z is $C_3H_5$ (cyclopropyl) (I-19);
$R^1$ is $CH_3$, $R^3$ is $CF_3$, m is 0 and Z is $C_3H_5$ (cyclopropyl) (I-20);
$R^1$ is $C(CH_3)_3$, $R^3$ is H, m is 0 and Z is $C_3H_5$ (cyclopropyl) (I-21);
$R^1$ is $CF_2(CH_3)$, $R^3$ is $C_1$, m is 0 and Z is $C_3H_5$ (cyclopropyl) (I-22);
$R^1$ is 1-F-cyclopropyl, $R^3$ is $C_1$, m is 0 and Z is $C_3H_5$ (cyclopropyl) (I-23);
$R^1$ is $CH_2CH_3$, $R^3$ is $C_1$, m is 0 and Z is 1-cyclooctenyl (I-24);
$R^1$ is $CH_2CH_3$, $R^3$ is $C_1$, m is 0 and Z is cyclooctyl (I-25);
$R^1$ is $CH_2CH_3$, $R^3$ is Cl and Z—$(R^4)_m$ is 1-OCH$_3$-cyclohexyl (I-26);
$R^1$ is $C(CH_3)_3$, $R^3$ is H, Z—$(R^4)_m$ is 1-OH-cyclobutyl (I-27);
$R^1$ is $CH_3$, $R^3$ is $CF_3$ and Z—$(R^4)_m$ is 1-OH-cyclobutyl (I-28);
$R^1$ is $CH_2CH_3$, $R^3$ is $C_1$, m is 0 and Z is $C_3H_5$ (cyclopropyl) (I-29); or
$R^1CH_2CH_3$, $R^3$ Cl and Z—$(R^4)_m$ is 1-OH-cyclobutyl (I-30).

11. A composition, comprising one compound of formula I, as defined in claim 1, an N-oxide or an agriculturally acceptable salt thereof.
12. Seed, coated with at least one compound of claim 1, and/or an agriculturally acceptable salt thereof, in an amount of from 0.1 to 10 kg per 100 kg of seed.
13. The composition according to claim 11, comprising additionally a further active substance.
14. A method for combating phytopathogenic fungi, comprising treating the fungi or the materials, plants, the soil or seeds to be protected against fungal attack with an effective amount of at least one compound of formula I, as defined in claim 1 or with a composition, as defined in claim 11.
15. The method of claim 14, wherein A is N.
16. The method of claim 14, wherein Z is $C_3$-$C_8$-cycloalkyl.
17. The method of claim 14, wherein Z is $C_3$-$C_8$-cycloalkenyl.
18. The method of claim 14, wherein m is 0.
19. The method of claim 14, wherein m is 1, 2 or 3.
20. The method of claim 14, wherein $R^3$ is hydrogen.
21. The method of claim 14, wherein $R^3$ is F, $C_1$, Br, CN, $C_1$-$C_4$-alkyl, $C_1$-$C_4$-halogenalkyl, $C_1$-$C_4$-alkoxy or S($C_1$-$C_4$-alkyl).
22. The method of claim 14, wherein $R^2$ is hydrogen.
23. The method of claim 14, wherein A is N, $R^2$ is hydrogen and:
$R^1$ is cyclopropyl, $R^3$ is $C_1$, m is 0 and Z is cyclopropyl (I-1);
$R^1$ is $CH_3$, $R^3$ is $C_1$, m is 0 and Z is cyclopropyl (I-2);

$R^1$ is C≡C—CH$_3$, $R^3$ is C$_1$, m is 0 and Z is C$_3$H$_5$ (cyclopropyl) (I-3);

$R^1$ is C$_3$H$_5$ (cyclopropyl), $R^3$ is Cl and Z—(R$^4$)$_m$ is 1-OH-cyclopentyl (I-4);

$R^1$ is C$_3$H$_5$ (cyclopropyl), $R^3$ is C$_1$, m is 0 and Z is 1-cyclooctenyl (I-5);

$R^1$ is C$_3$H$_5$ (cyclopropyl), $R^3$ is C$_1$, m is 0 and Z is cyclooctyl (I-6);

$R^1$ is C$_3$H$_5$ (cyclopropyl), $R^3$ is C$_1$, m is 0 and Z is cyclopentyl (I-7);

$R^1$ is C(CH$_3$)$_3$, $R^3$ is H, Z—(R$^4$)$_m$ is 1-OH-cyclopentyl (I-8);

$R^1$ is C(CH$_3$)$_3$, $R^3$ is H; m is 0 and Z is 1-cyclooctenyl (I-9);

$R^1$ is C(CH$_3$)$_3$; $R^3$ is H; m is 0 and Z is cyclooctyl (I-10);

$R^1$ is C(CH$_3$)$_3$; $R^3$ is H and Z—(R$^4$)$_m$ is 1-OCH$_3$-cyclohexyl (I-11);

$R^1$ is C(CH$_3$)$_3$, $R^3$ is H, m is 0 and Z is cyclopentyl (I-12);

$R^1$ is CH$_3$, $R^3$ is CF$_3$, m is 0 and Z is cyclooctyl (I-13);

$R^1$ is CH$_3$; $R^3$ is CF$_3$ and Z—(R$^4$)$_m$ is 1-OH-cyclopentyl (I-14);

$R^1$ is CH$_3$, $R^3$ is CF$_3$ and Z—(R$^4$)$_m$ is 1-OCH$_3$-cyclohexyl (I-15);

$R^1$ is CH$_3$, $R^3$ is CF$_3$, m is 0 and Z is cyclopentyl (I-16);

$R^1$ is C$_3$H$_5$ (cyclopropyl), $R^3$ is CF$_3$, m is 0 and Z is C$_3$H$_5$ (cyclopropyl) (I-17);

$R^1$ is CH=CH(CH$_3$), $R^3$ is C$_1$, m is 0 and Z is C$_3$H$_5$ (cyclopropyl) (I-18);

$R^1$ is C≡C—CH$_3$, $R^3$ is CF$_3$, m is 0 and Z is C$_3$H$_5$ (cyclopropyl) (I-19);

$R^1$ is CH$_3$, $R^3$ is CF$_3$, m is 0 and Z is C$_3$H$_5$ (cyclopropyl) (I-20);

$R^1$ is C(CH$_3$)$_3$, $R^3$ is H, m is 0 and Z is C$_3$H$_5$ (cyclopropyl) (I-21);

$R^1$ is CF$_2$(CH$_3$), $R^3$ is C$_1$, m is 0 and Z is C$_3$H$_5$ (cyclopropyl) (I-22);

$R^1$ is 1-F-cyclopropyl, $R^3$ is C$_1$, m is 0 and Z is C$_3$H$_5$ (cyclopropyl) (I-23);

$R^1$ is CH$_2$CH$_3$, $R^3$ is C$_1$, m is 0 and Z is 1-cyclooctenyl (I-24);

$R^1$ is CH$_2$CH$_3$, $R^3$ is C$_1$, m is 0 and Z is cyclooctyl (I-25);

$R^1$ is CH$_2$CH$_3$, $R^3$ is Cl and Z—(R$^4$)$_m$ is 1-OCH$_3$-cyclohexyl (I-26);

$R^1$ is C(CH$_3$)$_3$, $R^3$ is H, Z—(R$^4$)$_m$ is 1-OH-cyclobutyl (I-27);

$R^1$ is CH$_3$, $R^3$ is CF$_3$ and Z—(R$^4$)$_m$ is 1-OH-cyclobutyl (I-28);

$R^1$ is CH$_2$CH$_3$, $R^3$ is C$_1$, m is 0 and Z is C$_3$H$_5$ (cyclopropyl) (I-29); or $R^1$CH$_2$CH$_3$, $R^3$ Cl and Z—(R$^4$)$_m$ is 1-OH-cyclobutyl (I-30).

* * * * *